US011237155B2

(12) United States Patent
McGrane et al.

(10) Patent No.: US 11,237,155 B2
(45) Date of Patent: Feb. 1, 2022

(54) SCREENING METHODS USING OLFACTORY RECEPTORS AND NOVEL COMPOUNDS IDENTIFIED USING THE SAME

(71) Applicant: MARS, INCORPORATED, McLean, VA (US)

(72) Inventors: Scott McGrane, Leicestershire (GB); Matthew Ronald Gibbs, Leicestershire (GB)

(73) Assignee: MARS, INCORPORATED, McLean, VA (US)

( * ) Notice: Subject to any disclaimer, the term of this patent is extended or adjusted under 35 U.S.C. 154(b) by 284 days.

(21) Appl. No.: 16/333,899

(22) PCT Filed: Sep. 29, 2017

(86) PCT No.: PCT/US2017/054620
§ 371 (c)(1),
(2) Date: Mar. 15, 2019

(87) PCT Pub. No.: WO2018/064636
PCT Pub. Date: Apr. 5, 2018

(65) Prior Publication Data
US 2019/0212328 A1 Jul. 11, 2019

Related U.S. Application Data

(60) Provisional application No. 62/402,823, filed on Sep. 30, 2016.

(51) Int. Cl.
*G01N 33/50* (2006.01)
*A23K 50/40* (2016.01)

(52) U.S. Cl.
CPC ......... *G01N 33/5038* (2013.01); *A23K 50/40* (2016.05); *G01N 33/5008* (2013.01); *G01N 2333/726* (2013.01)

(58) Field of Classification Search
CPC ................................................ G01N 33/5038
See application file for complete search history.

(56) References Cited

U.S. PATENT DOCUMENTS

| 7,344,845 | B2 | 3/2008 | Han et al. |
|---|---|---|---|
| 2003/0207337 | A1 | 11/2003 | Han et al. |
| 2006/0134693 | A1 | 6/2006 | Servant et al. |
| 2011/0189335 | A1 | 8/2011 | Mussawir-Key et al. |
| 2013/0209625 | A1 | 8/2013 | Brand et al. |

FOREIGN PATENT DOCUMENTS

| WO | WO 2010/018365 A1 | 2/2010 |
|---|---|---|
| WO | WO 2012/013480 A1 | 2/2012 |
| WO | WO 2012/029922 A1 | 3/2012 |
| WO | 2014191047 A1 | 12/2014 |
| WO | WO 2014/199114 A1 | 12/2014 |
| WO | WO 2016/030378 A1 | 3/2016 |
| WO | WO 2016/094702 A2 | 6/2016 |

OTHER PUBLICATIONS

Jaeger et al., A Mendelian Trait for Olfactory Sensitivity Affects Odor Experience and Food Selection. Current Biology 23 (16): 1601-1605, 2013.*
Santos, et al., "Genomic architecture of MHC-linked odorant receptor gene repertoires among 16 vertebrate species," Immunogenetics, Springer, Berlin, DE, vol. 62, No. 9, Aug. 2010, pp. 569-584, XP019841484.
Altschul, et al., "Basic Local Alignment Search Tool", J. Mol. Biol., Oct. 1990, 215, 403-410.
Altschul, et al., "Gapped BLAST and PSI-BLAST: A New Generation of Protein Database Search Programs", Nucleic Acids Research, Sep. 1997, vol. 25, No. 17, pp. 3389-3402.
Benbernou, et al., "cAMP and IP3 Signaling Pathways in HEK293 Cells Transfected with Canine Olfactory Receptor Genes", Journal of Heredity, vol. 102(S1):S47-S61, Jan. 1, 2011.
Castro, et al., "Categorical Dimensions of Human Odor Descriptor Space Revealed by Non-Negative Matrix Factorization", Plos One, 8(9), e73289, 13 pgs. (Sep. 2013).
Cline, "Perspectives for Gene Therapy: Inserting New Genetic Information into Mammalian Cells by Physical Techniques and Viral Vectors", Pharmac. Ther., vol. 29, pp. 69-92, 1985.
Cotten, et al., "Receptor-Mediated Transport of DNA into Eurkaryotic Cells", Methods in Enzymology, vol. 217 (Mar. 1993), pp. 618-644.
Cunningham, et al., "High-Resolution Epitope Mapping of hGH-Receptor Interactions by Alanine-Scanning Mutagenesis", Science, 1989, 244(4908):1081-1085, Abstract only (2 pgs.).
Dravnieks, "Atlas of Odor Character Profiles, American Society for Testing and Materials", 1985, 7 pgs.
Eswar, et al., "Comparative Protein Structure Modeling Using Modeller", Curr Protoc Bioinformatics, Supplement 15, 5.6.1-5.6.30, 47 pages (Oct. 2006).
Fu, et al., "CD-HIT: accelerated for clustering the next-generation sequencing data", Bioinformatics, 28(23):3150-2, Dec. 2012.
Karlin, et al., "Applications and Statistics for Multiple High-Scoring Segments in Molecular Sequences", Proc. Natl. Acad. Sci. USA vol. 90 pp. 5873-5877, Jun. 1993.
Karlin, et al., "Methods for Assessing the Statistical Significance of Molecular Sequence Features by Using General Scoring Schemes", Proc. Natl. Acad. Sci. USA, vol. 87, pp. 2264-2268, Mar. 1990.
Lee et al., "Structural Insights into Ligand Recognition and Selectivity for Class A, B and C GPCR's", Eur. J. Pharmacol., Sep. 2015, 763:196-205.
Loeffler, et al., "Gene Transfer into Primary and Established Mammalian Cell Lines with Lipopolyamine-Coated DNA", Methods in Enzymology, vol. 217 (Mar. 1993), 599-618.
Myers et al., Optimal Alignments in Linear Space, CABIOS, vol. 4(1), 11-17 (Mar. 1988).

(Continued)

*Primary Examiner* — Ruixiang Li
(74) *Attorney, Agent, or Firm* — Baker Botts L.L.P.

(57) ABSTRACT

The presently disclosed subject matter relates to methods of screening raw materials and pet food products to manufacture a palatable pet food product. The presently disclosed subject matter also relates to methods for identifying compounds that modulate the activity and/or expression of an olfactory receptor.

16 Claims, 97 Drawing Sheets

Specification includes a Sequence Listing.

(56) References Cited

OTHER PUBLICATIONS

Niimura, et al., "Corrigendum: Extreme expansion of the olfactory receptor gene repertoire in African elephants and evolutionary dynamics of orthologous gene groups in 13 placental mammals", Gen Research, 24(9) 19485-1496 (Sep. 2014).
Niimura, et al., "Extensive Gains and Losses of Olfactory Receptor Genes in Mammalian Evolution", Plos One, vol. 2, No. 8, Aug. 1, 2007, p. e708, 8 pgs.
Pearson, et al., "Improved Tools for Biological Sequence Comparison", Proc. Natl. Acad. Sci. USA, 85:2444-8, Apr. 1988.
Rasmussen, et al., "Crystal Structure of the Beta Adrenergic Receptor-Gs Protein Complex", Nature, (Jul. 2011) 477: 549-555.
Rice, et al., "EMBOSS: the European Molecular Biology Open Software Suite," Trends Genet., 16(6), 276-7, Jun. 2000.
Torelli, et al., "ADVANCE and ADAM: two algorithms for the analysis of global similarity between homologous informational sequences", Bioinformatics, vol. 10, Issue 1, Feb. 1994, 3-5.
Yang, et al., "The I-TASSER Suite: Protein Structure and Function Prediction", Nat. Methods vol. 12:7-8 (Jan. 2015).

* cited by examiner

Olfactory Receptor Nucleotide Sequences and Corresponding Amino Acid Sequences

HsOR17.1.11 (hOR3A1) nucleotide sequence (SEQ ID NO:1)

ATGCAGCCAGAATCTGGGGCCAATGGAACAGTCATTGCTGAGTTCATCCTGCTGGGCTTGCTGGAGGC
GCCAGGGCTGCAGCCAGTTGTCTTTGTGCTCTTCCTCTTTGCCTACCTGGTCACGGTCAGGGGCAACC
TCAGCATCCTGGCAGCTGTCTTGGTGGAGCCCAAACTCCACACCCCCATGTACTTCTTCCTGGGGAAC
CTATCAGTGCTGGATGTTGGGTGCATCAGCGTCACTGTTCCATCAATGTTGAGTCGTCTCCTGTCCCG
CAAGCGTGCAGTTCCCTGTGGGGCCTGCCTTACCCAGCTCTTCTTCTTCCATCTGTTCGTTGGAGTGG
ACTGCTTCCTGCTGACCGCCATGGCCTATGACCGATTCCTGGCCATCTGCCGGCCCCTCACCTACAGC
ACCCGCATGAGTCAGACAGTCCAGAGGATGTTGGTGGCTGCGTCCTGGGCTTGTGCTTTCACCAACGC
ACTGACCCACACTGTGGCCATGTCCACGCTCAACTTCTGTGGCCCCAATGTGATCAATCACTTCTACT
GTGACCTCCCACAGCTCTTCCAGCTCTCCTGCTCCAGCACCCAACTCAATGAGCTGCTGCTTTTTGCT
GTGGGTTTTATAATGGCAGGTACCCCCATGGCTCTCATTGTCATCTCCTATATCCACGTGGCAGCTGC
AGTCCTGCGAATTCGCTCTGTAGAGGGCAGGAAGAAAGCCTTCTCCACATGTGGCTCCCACCTCACTG
TGGTTGCCATATTCTATGGTTCAGGTATCTTTAACTATATGCGACTGGGTTCAACCAAGCTTTCAGAC
AAGGATAAAGCTGTTGGAATTTTCAACACTGTCATCAATCCCATGCTGAACCCAATCATCTACAGCTT
CAGAAACCCTGATGTGCAGAGTGCCATCTGGAGGATGCTCACAGGGAGGCGGTCACTGGCTTGA

HsOR17.1.11 (hOR3A1) amino acid sequence (SEQ ID NO:31)

MQPESGANGTVIAEFILLGLLEAPGLQPVVFVLFLFAYLVTVRGNLSILAAVLVEPKLHTPMYFFLGN
LSVLDVGCISVTVPSMLSRLLSRKRAVPCGACLTQLFFFHLFVGVDCFLLTAMAYDRFLAICRPLTYS
TRMSQTVQRMLVAASWACAFTNALTHTVAMSTLNFCGPNVINHFYCDLPQLFQLSCSSTQLNELLLFA
VGFIMAGTPMALIVISYIHVAAAVLRIRSVEGRKKAFSTCGSHLTVVAIFYGSGIFNYMRLGSTKLSD
KDKAVGIFNTVINPMLNPIIYSFRNPDVQSAIWRMLTGRRSLA

FIG. 1

HsOR1.4.8 (hOR6P1) nucleotide sequence (SEQ ID NO:2)

ATGAGAAATTTGAGTGGAGGCCATGTCGAGGAGTTTGTCTTGGTGGGTTTCCCTACCACGCCTCCCCT
CCAGCTGCTCCTCTTTGTCCTTTTTTTGCAATTTACCTTCTGACATTGTTGGAGAATGCACTTATTG
TCTTCACAATATGGCTTGCTCCAAGCCTTCATCGTCCCATGTACTTTTTCCTTGGCCATCTCTCTTTC
CTGGAGCTATGGTACATCAATGTCACCATTCCTCGGCTCTTGGCAGCCTTTCTTACCCAGGATGGTAG
AGTCTCCTACGTAGGTTGCATGACCCAACTGTACTTCTTTATTGCCTTAGCCTGTACTGAATGTGTGC
TGTTGGCAGTTATGGCCTATGATCGCTACCTGGCCATCTGTGGACCCCTCCTTTACCCTAGTCTCATG
CCTTCCAGTCTGGCCACTCGCCTTGCTGCTGCCTCTTGGGGCAGTGGCTTCTTCAGCTCCATGATGAA
GCTTCTTTTTATTTCCCAATTGTCCTACTGTGGACCCAACATTATCAACCACTTTTTCTGTGATATTT
CCCCACTACTCAACCTCACCTGCTCTGACAAGGAGCAAGCAGAGCTAGTAGACTTCCTTCTGGCCCTG
GTGATGATTCTACTCCCTCTATTGGCTGTGGTTTCATCATACACTGCCATCATTGCAGCCATCCTGAG
GATCCCTACGTCCAGGGGACGCCACAAAGCCTTTTCCACTTGTGCCGCTCATCTGGCAGTGGTTGTTA
TCTACTACTCCTCCACTCTCTTCACCTATGCACGGCCCCGGGCCATGTACACCTTCAACCACAACAAG
ATTATCTCTGTGCTCTACACTATCATTGTACCATTCTTCAACCCAGCCATCTACTGCCTGAGGAACAA
GGAGGTGAAGGAGGCCTTCAGGAAGACAGTGATGGGCAGATGTCACTATCCTAGGGATGTTCAGGACT
GA

HsOR1.4.8 (hOR6P1) amino acid sequence (SEQ ID NO:32)

MRNLSGGHVEEFVLVGFPTTPPLQLLLFVLFFAIYLLTLLENALIVFTIWLAPSLHRPMYFFLGHLSF
LELWYINVTIPRLLAAFLTQDGRVSYVGCMTQLYFFIALACTECVLLAVMAYDRYLAICGPLLYPSLM
PSSLATRLAAASWGSGFFSSMMKLLFISQLSYCGPNIINHFFCDISPLLNLTCSDKEQAELVDFLLAL
VMILLPLLAVVSSYTAIIAAILRIPTSRGRHKAFSTCAAHLAVVVIYYSSTLFTYARPRAMYTFNHNK
IISVLYTIIVPFFNPAIYCLRNKEVKEAFRKTVMGRCHYPRDVQD*

FIG. 1 Continued

HsOR11.3.14 (hOR51E1) nucleotide sequence (SEQ ID NO:3)

ATGATGGTGGATCCCAATGGCAATGAATCCAGTGCTACATACTTCATCCTAATAGGCCTCCCTGGTTT
AGAAGAGGCTCAGTTCTGGTTGGCCTTCCCATTGTGCTCCCTCTACCTTATTGCTGTGCTAGGTAACT
TGACAATCATCTACATTGTGCGGACTGAGCACAGCCTGCATGAGCCCATGTATATATTTCTTTGCATG
CTTTCAGGCATTGACATCCTCATCTCCACCTCATCCATGCCCAAAATGCTGGCCATCTTCTGGTTCAA
TTCCACTACCATCCAGTTTGATGCTTGTCTGCTACAGATGTTTGCCATCCACTCCTTATCTGGCATGG
AATCCACAGTGCTGCTGGCCATGGCTTTTGACCGCTATGTGGCCATCTGTCACCCACTGCGCCATGCC
ACAGTACTTACGTTGCCTCGTGTCACCAAAATTGGTGTGGCTGCTGTGGTGCGGGGGGCTGCACTGAT
GGCACCCCTTCCTGTCTTCATCAAGCAGCTGCCCTTCTGCCGCTCCAATATCCTTTCCCATTCCTACT
GCCTACACCAAGATGTCATGAAGCTGGCCTGTGATGATATCCGGGTCAATGTCGTCTATGGCCTTATC
GTCATCATCTCCGCCATTGGCCTGGACTCACTTCTCATCTCCTTCTCATATCTGCTTATTCTTAAGAC
TGTGTTGGGCTTGACACGTGAAGCCCAGGCCAAGGCATTTGGCACTTGCGTCTCTCATGTGTGTGCTG
TGTTCATATTCTATGTACCTTTCATTGGATTGTCCATGGTGCATCGCTTTAGCAAGCGGCGTGACTCT
CCGCTGCCCGTCATCTTGGCCAATATCTATCTGCTGGTTCCTCCTGTGCTCAACCCAATTGTCTATGG
AGTGAAGACAAAGGAGATTCGACAGCGCATCCTTCGACTTTTCCATGTGGCCACACACGCTTCAGAGC
CCTA

HsOR11.3.14 (hOR51E1) amino acid sequence (SEQ ID NO:33)

MMVDPNGNESSATYFILIGLPGLEEAQFWLAFPLCSLYLIAVLGNLTIIYIVRTEHSLHEPMYIFLCM
LSGIDILISTSSMPKMLAIFWFNSTTIQFDACLLQMFAIHSLSGMESTVLLAMAFDRYVAICHPLRHA
TVLTLPRVTKIGVAAVVRGAALMAPLPVFIKQLPFCRSNILSHSYCLHQDVMKLACDDIRVNVVYGLI
VIISAIGLDSLLISFSYLLILKTVLGLTREAQAKAFGTCVSHVCAVFIFYVPFIGLSMVHRFSKRRDS
PLPVILANIYLLVPPVLNPIVYGVKTKEIRQRILRLFHVATHASEP*

FIG. 1 Continued

HsOR11.3.40 (hOR51L1) nucleotide sequence (SEQ ID NO:4)

ATGGGAGACTGGAATAACAGTGATGCTGTGGAGCCCATATTTATCCTGAGGGGTTTTCCTGGACTGGA
GTATGTTCATTCTTGGCTCTCCATCCTCTTCTGTCTTGCATATTTGGTAGCATTTATGGGTAATGTTA
CCATCCTGTCTGTCATTTGGATAGAATCCTCTCTCCATCAGCCCATGTATTACTTTATTTCCATCTTA
GCAGTGAATGACCTGGGGATGTCCCTGTCTACACTTCCCACCATGCTTGCTGTGTTATGGTTGGATGC
TCCAGAGATCCAGGCAAGTGCTTGCTATGCTCAGCTGTTCTTCATCCACACATTCACATTCCTGGAGT
CCTCAGTGTTGCTGGCCATGGCCTTTGACCGTTTTGTTGCTATCTGCCATCCACTGCACTACCCCACC
ATCCTCACCAACAGTGTAATTGGCAAAATTGGTTTGGCCTGTTTGCTACGAAGCTTGGGAGTTGTACT
TCCCACACCTTTGCTACTGAGACACTATCACTACTGCCATGGCAATGCCCTCTCTCACGCCTTCTGTT
TGCACCAGGATGTTCTAAGATTATCCTGTACAGATGCCAGGACCAACAGTATTTATGGGCTTTGTGTA
GTCATTGCCACACTAGGTGTGGATTCAATCTTCATACTTCTTTCTTATGTTCTGATTCTTAATACTGT
GCTGGATATTGCATCTCGTGAAGAGCAGCTAAAGGCACTCAACACATGTGTATCCCATATCTGTGTGG
TGCTTATCTTCTTTGTGCCAGTTATTGGGGTGTCAATGGTCCATCGCTTTGGGAAGCATCTGTCTCCC
ATAGTCCACATCCTCATGGCAGACATCTACCTTCTTCTTCCCCCAGTCCTTAACCCTATTGTCTATAG
TGTCAGAACAAAGCAGATTCGTCTAGGAATTCTCCACAAGTTTGTCCTAAGGAGGAGGTTTTAA

HsOR11.3.40 (hOR51L1) amino acid sequence (SEQ ID NO:34)

MGDWNNSDAVEPIFILRGFPGLEYVHSWLSILFCLAYLVAFMGNVTILSVIWIESSLHQPMYYFISIL
AVNDLGMSLSTLPTMLAVLWLDAPEIQASACYAQLFFIHTFTFLESSVLLAMAFDRFVAICHPLHYPT
ILTNSVIGKIGLACLLRSLGVVLPTPLLLRHYHYCHGNALSHAFCLHQDVLRLSCTDARTNSIYGLCV
VIATLGVDSIFILLSYVLILNTVLDIASREEQLKALNTCVSHICVVLIFFVPVIGVSMVHRFGKHLSP
IVHILMADIYLLLPPVLNPIVYSVRTKQIRLGILHKFVLRRRF*

FIG. 1 Continued

HsOR14.1.27 (hOR11H6) nucleotide sequence (SEQ ID NO:5)

atgttctttattattCATTCTTTGGTTACTTCTGTTTTTCTAACAGCTTTGGGACCCCAGAA
CAGAACAATGCATTTTGTGACTGAGTTTGTCCTCCTGGGTTTCCATGGTCAAAGGGAGATGC
AGAGCTGCTTCTTCTCATTCATCCTGGTTCTCTATCTCCTGACACTGCTAGGGAATGGAGCT
ATTGTCTGTGCAGTGAAATTGGACAGGCGGCTCCACACACCCATGTACATCCTTCTGGGAAA
CTTTGCCTTTCTAGAGATCTGGTACATTTCCTCCACTGTCCCAAACATGCTAGTCAATATCC
TCTCTGAGATTAAAACCATCTCCTTCTCTGGTTGCTTCCTGCAATTCTATTTCTTTTTTTCA
CTGGGTACAACAGAGTGTTTCTTTTTATCAGTTATGGCTTATGATCGGTACCTGGCCATCTG
TCGTCCATTACACTACCCCTCCATCATGACTGGGAAGTTCTGTATAATTCTGGTCTGTGTAT
GCTGGGTAGGCGGATTTCTCTGCTATCCAGTCCCTATTGTTCTTATCTCCCAACTTCCCTTC
TGTGGGCCCAACATCATTGACCACTTGGTGTGTGACCCAGGCCCATTGTTTGCACTGGCCTG
CATCTCTGCTCCTTCCACTGAGCTTATCTGTTACACCTTCAACTCGATGATTATCTTTGGGC
CCTTCCTCTCCATCTTGGGATCTTACACTCTGGTCATCAGAGCTGTGCTTTGTATTCCCTCT
GGTGCTGGTCGAACTAAAGCTTTCTCCACATGTGGGTCCCACCTAATGGTGGTGTCTCTATT
CTATGGAACCCTTATGGTGATGTATGTGAGCCCAACATCAGGGAACCCAGCAGGAATGCAGA
AGATCATCACTCTGGTATACACAGCAATGACTCCATTCTTAAATCCCCTTATCTATAGTCTT
CGAAACAAAGACATGAAAGATGCTCTAAAGAGAGTCCTGGGGTTAACAGTTAGCCAAAACTG
A HsOR14.1.27 (hOR11H6) amino acid sequence (SEQ ID NO:35)

MFFIIHSLVTSVFLTALGPQNRTMHFVTEFVLLGFHGQREMQSCFFSFILVLYLLTLLGNGA
IVCAVKLDRRLHTPMYILLGNFAFLEIWYISSTVPNMLVNILSEIKTISFSGCFLQFYFFFS
LGTTECFFLSVMAYDRYLAICRPLHYPSIMTGKFCIILVCVCWVGGFLCYPVPIVLISQLPF
CGPNIIDHLVCDPGPLFALACISAPSTELICYTFNSMIIFGPFLSILGSYTLVIRAVLCIPS
GAGRTKAFSTCGSHLMVVSLFYGTLMVMYVSPTSGNPAGMQKIITLVYTAMTPFLNPLIYSL
RNKDMKDALKRVLGLTVSQN*

FIG. 1 Continued

HsOR11.13.7 (hOR4D6) nucleotide sequence (SEQ ID NO:6)

ATGGACCAGATCAACCACACTAATGTGAAGGAGTTTTTCTTCCTGGAACTTACACGTTCCCGAGAGCT
GGAGTTTTTCTTGTTTGTGGTCTTCTTTGCTGTGTATGTAGCAACAGTCCTGGGAAATGCACTCATTG
TGGTCACTATTACCTGTGAGTCCCGCCTACACACTCCTATGTACTTTCTCCTGCGGAACAAATCAGTC
CTGGACATCGTTTTTTCATCTATCACCGTCCCCAAGTTCCTGGTGGATCTTTTATCAGACAGGAAAAC
CATCTCCTACAATGGCTGCATGGCACAGATCTTTTTCTTCCACTTTGCTGGTGGGGCAGATATTTTTT
TCCTCTCTGTGATGGCCTATGACAGATACCTTGCAATCGCCAAGCCCCTGCACTATGTGACCATGATG
AGGAAAGAGGTGTGGGTGGCCTTGGTGGTGGCTTCTTGGGTGAGTGGTGGTTTGCATTCAATCATCCA
GGTAATTCTGATGCTTCCATTCCCCTTCTGTGGCCCCAACACACTGGATGCCTTCTACTGTTATGTGC
TCCAGGTGGTAAAACTGGCCTGCACTGACACCTTTGCTTTGGAGCTTTTCATGATCTCTAACAACGGA
CTGGTGACCCTGCTCTGGTTCCTCCTGCTCCTGGGCTCCTACACTGTCATTCTGGTGATGCTGAGATC
CCACTCTGGGGAGGGGCGGAACAAGGCCCTCTCCACGTGCACGTCCCACATGCTGGTGGTGACTCTTC
ACTTCGTGCCTTGTGTTTACATCTACTGCCGGCCCTTCATGACGCTGCCCATGGACACAACCATATCC
ATTAATAACACGGTCATTACCCCCATGCTGAACCCCATCATCTATTCCCTGAGAAATCAAGAGATGAA
GTCAGCCATGCAGAGGCTGCAGAGGAGACTTGGGCCTTCCGAGAGCAGAAAATGGGGG

HsOR11.13.7 (hOR4D6) amino acid sequence (SEQ ID NO:36)

MDQINHTNVKEFFFLELTRSRELEFFLFVVFFAVYVATVLGNALIVVTITCESRLHTPMYFLLRNKSV
LDIVFSSITVPKFLVDLLSDRKTISYNGCMAQIFFFHFAGGADIFFLSVMAYDRYLAIAKPLHYVTMM
RKEVWVALVVASWVSGGLHSIIQVILMLPFPFCGPNTLDAFYCYVLQVVKLACTDTFALELFMISNNG
LVTLLWFLLLLGSYTVILVMLRSHSGEGRNKALSTCTSHMLVVTLHFVPCVYIYCRPFMTLPMDTTIS
INNTVITPMLNPIIYSLRNQEMKSAMQRLQRRLGPSESRKWG*

FIG. 1 Continued

HsOR14.2.5 (hOR4E2) nucleotide sequence (SEQ ID NO:7)

atggacagtctaaaccaaacaagagtgactgaatttgtcttcttgggactcactgataaccgggtgct
Ggaaatgctgttttcatggcattctcagccatttatatgctaacgctttcagggaacattctcatca
Tcattgccacagtctttactccaagtctccatacccccatgtatttcttcctgagcaatctgtccttt
Attgacatctgccactcatctgtcactgtgcctaagatgttggagggtttgcttttagaaagaaagac
Catttcctttgacaactgcatcacacagctcttcttcctacatctctttgcctgtgccgagatctttc
Tgctgatcattatggcgtatgatcgttacgtggctatctgcactccactccactaccccaatgtgatg
Aacatgagagtctgtatacagcttgtctttgctctctggttgggggggtactgttcactcactagggca
Gaccttcttgactattcgtctaccttactgtggccccaacattattgacagctacttctgtgatgtgc
Ctcttgttatcaagctggcctgcacagatacatacctcacaggaatactgattgtgaccaatagtgga
Accatctccctcctgtttcttggccgtggtcacctcctatatggtcatcctggtttctcttcgaaa
Acactcagctgaagggcgccgtaaagccctgtctacctgctcggcccacttcatggtggttgccctct
Tctttgggccatgtatcttcatctatactcggccagacaccagcttctccattgacaaggtggtgtct
Gtcttctacacagtggtcaccccttcgctgaatcccttcatttacaccttgaggaatgaggaggtaaa
aagtgccatgaagcagctcaggcagagacaagttttttttcacgaaatcatataca HsOR14.2.5 (hOR4E2) amino acid sequence (SEQ ID NO:37)

MDSLNQTRVTEFVFLGLTDNRVLEMLFFMAFSAIYMLTLSGNILIIIATVFTPSLHTPMYFFLSNLSF
IDICHSSVTVPKMLEGLLLERKTISFDNCITQLFFLHLFACAEIFLLIIMAYDRYVAICTPLHYPNVM
NMRVCIQLVFALWLGGTVHSLGQTFLTIRLPYCGPNIIDSYFCDVPLVIKLACTDTYLTGILIVTNSG
TISLSCFLAVVTSYMVILVSLRKHSAEGRRKALSTCSAHFMVVALFFGPCIFIYTRPDTSFSIDKVVS
VFYTVVTPLLNPFIYTLRNEEVKSAMKQLRQRQVFFTKSYT*

FIG. 1 Continued

HsOR16.1.3 (hOR2C1) nucleotide sequence (SEQ ID NO:8)

ATGGACGGGGTGAATGATAGCTCCTTGCAGGGCTTTGTTCTGATGGGCATATCAGACCATCCCCAGCT
GGAGATGATCTTTTTTATAGCCATCCTCTTCTCCTATTTGCTGACCCTACTTGGGAACTCAACCATCA
TCTTGCTTTCCCGCCTGGAGGCCCGGCTCCATACACCCATGTACTTCTTCCTCAGCAACCTCTCCTCC
TTGGACCTTGCTTTCGCTACTAGTTCAGTCCCCCAAATGCTGATCAATTTATGGGGACCAGGCAAGAC
CATCAGCTATGGTGGCTGCATAACCCAGCTCTATGTCTTCCTTTGGCTGGGGGCCACCGAGTGCATCC
TGCTGGTGGTGATGGCATTTGACCGCTACGTGGCAGTGTGCCGGCCCCTCCGCTACACCGCCATCATG
AACCCCCAGCTCTGCTGGCTGCTGGCTGTGATTGCCTGGCTGGGTGGCTTGGGCAACTCTGTGATCCA
GTCAACATTCACTCTGCAGCTCCCATTGTGTGGGCACCGGAGGGTGGAGGGATTCCTCTGCGAGGTGC
CTGCCATGATCAAACTGGCCTGTGGCGACACAAGTCTCAACCAGGCTGTGCTCAATGGTGTCTGCACC
TTCTTCACTGCAGTCCCACTAAGCATCATCGTGATCTCCTACTGCCTCATTGCTCAGGCAGTGCTGAA
AATCCGCTCTGCAGAGGGGAGGCGAAAGGCGTTCAATACGTGCCTCTCCCATCTGCTGGTGGTGTTCC
TCTTCTATGGCTCAGCCAGCTATGGGTATCTGCTTCCGGCCAAGAACAGCAAACAGGACCAGGGCAAG
TTCATTTCCCTGTTCTACTCGTTGGTCACACCCATGGTGAATCCCCTCATCTACACGCTGCGGAACAT
GGAAGTGAAGGGCGCACTGAGGAGGTTGCTGGGGAAAGGAAGAGAAGTTGGCTGA

HsOR16.1.3 (hOR2C1) amino acid sequence (SEQ ID NO:38)

MDGVNDSSLQGFVLMGISDHPQLEMIFFIAILFSYLLTLLGNSTIILLSRLEARLHTPMYFFLSNLSS
LDLAFATSSVPQMLINLWGPGKTISYGGCITQLYVFLWLGATECILLVVMAFDRYVAVCRPLRYTAIM
NPQLCWLLAVIAWLGGLGNSVIQSTFTLQLPLCGHRRVEGFLCEVPAMIKLACGDTSLNQAVLNGVCT
FFTAVPLSIIVISYCLIAQAVLKIRSAEGRRKAFNTCLSHLLVVFLFYGSASYGYLLPAKNSKQDQGK
FISLFYSLVTPMVNPLIYTLRNMEVKGALRRLLGKGREVG*

FIG. 1 Continued

HsOR11.13.6 (hOR5A1) nucleotide sequence (SEQ ID NO:9)

ATGTCCATAACCAAAGCCTGGAACAGCTCATCAGTGACCATGTTCATCCTCCTGGGATTCACAGACCA
TCCAGAACTCCAGGCCCTCCTCTTTGTGACCTTCCTGGGCATCTATCTTACCACCCTGGCCTGGAACC
TGGCCCTCATTTTTCTGATCAGAGGTGACACCCATCTGCACACACCCATGTACTTCTTCCTAAGCAAC
TTATCTTTCATTGACATCTGCTACTCTTCTGCTGTGGCTCCCAATATGCTCACTGACTTCTTCTGGGA
GCAGAAGACCATATCATTTGTGGGCTGTGCTGCTCAGTTTTTTTTCTTTGTCGGCATGGGTCTGTCTG
AGTGCCTCCTCCTGACTGCTATGGCATACGACCGATATGCAGCCATCTCCAGCCCCCTTCTCTACCCC
ACTATCATGACCCAGGGCCTCTGTACACGCATGGTGGTTGGGGCATATGTTGGTGGCTTCCTGAGCTC
CCTGATCCAGGCCAGCTCCATATTTAGGCTTCACTTTTGCGGACCCAACATCATCAACCACTTCTTCT
GCGACCTCCCACCAGTCCTGGCTCTGTCTTGCTCTGACACCTTCCTCAGTCAAGTGGTGAATTTCCTC
GTGGTGGTCACTGTCGGAGGAACATCGTTCCTCCAACTCCTTATCTCCTATGGTTACATAGTGTCTGC
GGTCCTGAAGATCCCTTCAGCAGAGGGCCGATGGAAAGCCTGCAACACGTGTGCCTCGCATCTGATGG
TGGTGACTCTGCTGTTTGGACAGCCCTTTTCGTGTACTTGCGACCCAGCTCCAGCTACTTGCTAGGC
AGGGACAAGGTGGTGTCTGTTTTCTATTCATTGGTGATCCCCATGCTGAACCCTCTCATTTACAGTTT
GAGGAACAAAGAGATCAAGGATGCCCTGTGGAAGGTGTTGGAAAGGAAGAAAGTGTTTTCTTAG

HsOR11.13.6 (hOR5A1) amino acid sequence (SEQ ID NO:39)

MSITKAWNSSSVTMFILLGFTDHPELQALLFVTFLGIYLTTLAWNLALIFLIRGDTHLHTPMYFFLSN
LSFIDICYSSAVAPNMLTDFFWEQKTISFVGCAAQFFFFVGMGLSECLLLTAMAYDRYAAISSPLLYP
TIMTQGLCTRMVVGAYVGGFLSSLIQASSIFRLHFCGPNIINHFFCDLPPVLALSCSDTFLSQVVNFL
VVVTVGGTSFLQLLISYGYIVSAVLKIPSAEGRWKACNTCASHLMVVTLLFGTALFVYLRPSSSYLLG
RDKVVSVFYSLVIPMLNPLIYSLRNKEIKDALWKVLERKKVFS*

FIG. 1 Continued

HsOR11.18.36 (hOR8B8) nucleotide sequence (SEQ ID NO:10)

ATGGCTGCTGAGAATTCCTCCTTCGTGACACAGTTTATCCTCGCAGGCTTAACTGACCAACC
GGGAGTCCAGATCCCCCTCTTCTTCCTGTTTCTAGGCTTCTACGTGGTCACTGTGGTGGGGA
ACCTGGGCTTGATAACCCTGATAAGGCTCAACTCTCACTTGCACACCCCTATGTACTTCTTC
CTCTATAACTTGTCCTTCATAGATTTCTGCTATTCCAGTGTTATCACTCCCAAAATGCTGAT
GAGCTTTGTCTTAAAGAAGAACAGCATCTCCTACGCAGGGTGTATGACTCAGCTCTTCTTCT
TTCTTTTCTTTGTTGTCTCTGAGTCCTTCATCCTGTCAGCAATGGCGTATGACCGCTATGTG
GCCATCTGTAACCCACTGTTGTACATGGTCACCATGTCTCCCCAGGTGTGTTTTCTCCTTTT
GTTGGGTGTCTATGGGATGGGGTTTGCTGGGGCCATGGCCCACACAGCGTGCATGATGGGTG
TGACCTTCTGTGCCAATAACCTTGTCAACCACTACATGTGTGACATCCTTCCCCTTCTTGAG
TGTGCTTGCACCAGCACCTATGTGAATGAGCTTGTAGTGTTTGTTGTTGTGGGCATTGATAT
TGGTGTGCCCACAGTCACCATCTTCATTTCCTATGCTCTCATTCTCTCCAGCATCTTCCACA
TTGATTCCACGGAGGGCAGGTCCAAAGCCTTCAGCACCTGCAGCTCCCACATAATTGCAGTT
TCTCTGTTCTTTGGGTCAGGAGCATTCATGTACCTCAAACCCTTTTCTCTTTTAGCTATGAA
CCAGGGCAAGGTGTCTTCCCTATTCTATACCACTGTGGTGCCCATGCTCAACCCATTAATTT
ATAGCCTGAGGAATAAGGACGTCAAAGTTGCTCTAAAGAAAATCTTGAACAAAAATGCATTC
TCCTGA

HsOR11.18.36 (hOR8B8) amino acid sequence (SEQ ID NO:40)

MAAENSSFVTQFILAGLTDQPGVQIPLFFLFLGFYVVTVVGNLGLITLIRLNSHLHTPMYFFLYNLSF
IDFCYSSVITPKMLMSFVLKKNSISYAGCMTQLFFFLFFVVSESFILSAMAYDRYVAICNPLLYMVTM
SPQVCFLLLLGVYGMGFAGAMAHTACMMGVTFCANNLVNHYMCDILPLLECACTSTYVNELVVFVVG
IDIGVPTVTIFISYALILSSIFHIDSTEGRSKAFSTCSSHIIAVSLFFGSGAFMYLKPFSLLAMNQGK
VSSLFYTTVVPMLNPLIYSLRNKDVKVALKKILNKNAFS*

FIG. 1 Continued

CafaOR9.2.9 nucleotide sequence (SEQ ID NO:11)

ATGCAGTCAAAATTTGGGGCCAATAGCACAGCCATTACTGAGTTCATCCTGCTGGGCTTGGTGGACAC
ACCAGGGCTACAACCAGTTGTCTTTGTAGTCTTCCTCTTTGCCTACCTGGTCACAGTCGGAGGCAACC
TCAGCATCCTGGCTGCCATCTTGGTGGAACCCAAACTCCACACGCCCATGTACTTCTTCCTGGGGAAC
CTGTCAGTGCTGGATGTTGGGTGCATCACTGTCACTGTTCCCTCAATGTTGGCTCGCCTCTTGTCCCA
CAAACGTACAGTTCCCTACAGAGCCTGCCTCACACAACTCTTCTTCTTCCATCTCTTGGTTGGGGTGG
ACTGCTTCCTGTTGACAGCCATGGCCTATGACCGATTCCTGGCCATCTGCCGGCCCCTCACCTACAGC
ACCCAGATGAGCCAGACAGTCCAGAGAATATTGGTAGTTGTGTCCTGGGCTTTAGCCTTCACCAATGC
ACTGACCCACACAGTAGCCATAGCCACACTCAACTTTTGTGGTCCTAATGTGATCAACCACTTCTACT
GCGACCTCCCACAGCTCTTCCAGCTCTCCTGCTCCAGCACTCAGCTCAATGAGCTGCTGCTCTTTGCT
GTGGGTTTCATAATGGCAGGTACCCCCTTGGCTCTCATCATCACTTCCTATGCACATGTGGCAGCTGC
AGTCCTAAGAATCCGCTCTGCTGAGGGCAGGAAGAAAGCTTTCTCTACATGTGGCTCTCATCTCACTG
TGGTAGCCATATTCTATGGTTCAGGTATATTTAATTACATGCGACTGGGTACAGCCAAGCATTCAGAC
AAGGATAAAGGGGTTGGGGTCTTCAACACTGTCATCAACCCCATGCTGAATCCAATCATTTACAGCCT
CAGGAACCTTGATGTACAGGGTGCCCTCTGGCGGGTGCTCAGGGGAAGGCAGTCACTGGCTTGA

CafaOR9.2.9 amino acid sequence (SEQ ID NO:41)

MQSKFGANSTAITEFILLGLVDTPGLQPVVFVVFLFAYLVTVGGNLSILAAILVEPKLHTPMYFFLGN
LSVLDVGCITVTVPSMLARLLSHKRTVPYRACLTQLFFFHLLVGVDCFLLTAMAYDRFLAICRPLTYS
TQMSQTVQRILVVVSWALAFTNALTHTVAIATLNFCGPNVINHFYCDLPQLFQLSCSSTQLNELLLFA
VGFIMAGTPLALIITSYAHVAAAVLRIRSAEGRKKAFSTCGSHLTVVAIFYGSGIFNYMRLGTAKHSD
KDKGVGVFNTVINPMLNPIIYSLRNLDVQGALWRVLRGRQSLA*

FIG. 1 Continued

CafaOR38.1.21 nucleotide sequence (SEQ ID NO:12)

ATGATGGGAAATTTGAGTGGAGGCCACATAGCAGATTTTATTTTGGTGGGCTTCCCAACCTCTCCACC
CCTCCAGTTACTTCTCTTTGTCCTCTTCTTTGCAATTTACCTGTTGACACTGTTGGAGAATGCACTCA
TCGTTTCCACAATCTGGCTCACTCCAAGCCTTCACCGCCCGATGTACTTTTTCCTTGGCCATCTGTCC
TTCCTGGAGCTGTGGTACATCAATGTCACAGTTCCTCGTCTTTTGGGAGCATTTCTTACCCAGGACCG
TAGAGTCTCCTATGTAGGCTGCATGACCCAGCTCTACTTCTTCATTGCCCTAGCCTGCACCGAATGTG
TCCTGCTGGCAGTCATGGCCTATGACCGCTACCTGGCCATCTGTGAGCCCCTCCGTTATCCTAGTCTC
ATGCCGTCCAGCCTGGCCATTCGCCTTGCTGCTTCCTCTTGGGGTGGTGGCTTCTTCAGCTCCATGAT
GAAGCTTCTTTTCATTTCCCGACTGTCCTACTGTGGGCCCAACATCATCAACCATTTTTTCTGTGATA
TCTCCCCACTACTCAACCTTACCTGCTCTGACAAGGAGCAAGCAGAACTAGTAGACTTCCTGTTGGCC
CTGGTGATGATCCTGCTTCCTCTACTGGCTGTGGTTTCATCATATGCTGCCATCATTGCCACCATCCT
GAGGATCCCTACTGCCCAGGGACGTCGCAAAGCCTTTTCCACCTGTGCCTCTCACCTGGCAGTGGTTG
TCATCTACTACTCCTCCACCCTCTTCACCTATGCAAGGCCCCGGGCCATGTACACCTTCAACCACAAC
AAGATCATCTCTGTGCTCTATACGGTCATTGTACCATTCCTCAATCCAGCCATCTACTGCCTGAGGAA
CAAGGAGGTGAAGGATGCTCTCAGGAAGTTGGTTCTGGGCAGATGCCACTATCCTAGTGATGTCCCAG
ACTGA

CafaOR38.1.21 amino acid sequence (SEQ ID NO:42)

MMGNLSGGHIADFILVGFPTSPPLQLLLFVLFFAIYLLTLLENALIVSTIWLTPSLHRPMYFFLGHLS
FLELWYINVTVPRLLGAFLTQDRRVSYVGCMTQLYFFIALACTECVLLAVMAYDRYLAICEPLRYPSL
MPSSLAIRLAASSWGGGFFSSMMKLLFISRLSYCGPNIINHFFCDISPLLNLTCSDKEQAELVDFLLA
LVMILLPLLAVVSSYAAIIATILRIPTAQGRRKAFSTCASHLAVVVIYYSSTLFTYARPRAMYTFNHN
KIISVLYTVIVPFLNPAIYCLRNKEVKDALRKLVLGRCHYPSDVPD*

FIG. 1 Continued

CafaOR21.2.15 nucleotide sequence (SEQ ID NO:13)

ATGGTGGACCCCAATGGCAATGAATCCAGTGCCACATATTTTATTTTAATAGGCCTCCCAGGCTTGGA
AGAAGCTCAGTTCTGGTTGGCCTTCCCCTTGTGCTCCCTCTACTTTATTGCTGTATTGGGTAACCTGA
CAATCATCTACATTGTGCGGACTGAGCACAGCCTACATGAACCCATGTATGTTTTCTTTGCATGCTT
TCTGGCCTTGACATCCTTATCTCCACCTCATCTATGCCCAAAATGATGGCCATCTTCTGGTTCAATTC
CACTACCATCCAGTTTGATGCTTGTCTACTACAGATGTTTGCCATCCATTCTTTATCTGGCATGGAGT
CCACAGTACTGCTGGCCATGGCCTTTGACCGCTATGTGGCCATTTGCCACCCACTACGCCATGCCACT
GTACTAACATTGCCTCGTGTTATGAAGATTGGCATGGCTGCTGTGGTACGGGGTACTGCACTTATGGC
ACCCCTGCCTGTTTTTATCAAACGACTGCCTTTCTGCCACTCCAACATTCTTTCCCATTCCTACTGCC
TACACCAAGATGTCATGAAGCTGGCTTGTGCTGACATCCGTGTCAATATCATCTATGGCCTCATTGTC
ATCATCTCTGCCATTGGCCTGGACTCACTTCTCATCTCCTTGTCATATCTACTTATCCTCAAGACTGT
GTTGGGCTTGACACGTGAAGCCCAGGCAAAGGCATTTGGCACTTGTGTCTCTCATGTATGTGCTGTTT
TCATATTCTATGTACCTTTCATTGGATTATCTATGGTGCACCGCTTTGGCAAGAGACATGACTCCTTC
CTGCCCATCATTATGGCCAACACCTACCTACTTGTACCTCCTGTGCTCAACCCCATTGTTTATGGAGT
CAAGACAAAGGAGATCTGGCAGCGTATCCTTCGTCTTTTCCATGTGACCAACCATACTTCAGATCTCT
AG

CafaOR21.2.15 amino acid sequence (SEQ ID NO:43)

MVDPNGNESSATYFILIGLPGLEEAQFWLAFPLCSLYFIAVLGNLTIIYIVRTEHSLHEPMYVFLCML
SGLDILISTSSMPKMMAIFWFNSTTIQFDACLLQMFAIHSLSGMESTVLLAMAFDRYVAICHPLRHAT
VLTLPRVMKIGMAAVVRGTALMAPLPVFIKRLPFCHSNILSHSYCLHQDVMKLACADIRVNIIYGLIV
IISAIGLDSLLISLSYLLILKTVLGLTREAQAKAFGTCVSHVCAVFIFYVPFIGLSMVHRFGKRHDSF
LPIIMANTYLLVPPVLNPIVYGVKTKEIWQRILRLFHVTNHTSDL*

FIG. 1 Continued

CafaOR21.2.43 nucleotide sequence (SEQ ID NO:14)

ATGCCAAGGGTCACCATGGTGGTCTGGAATAACAATAACACTCTGGAGCCCATATTTATTCTGAAGGG
ATTTCCTGGGTTGGAGTGTGTTCATTCTTGGTTCTCAATCCCTTTCTGTCTTGCGTACTTGGTAGCAT
TTATTGGTAATGTCACCATCCTCTCTGTCATCTGGATAGAGTCCTCACTCCACCAGCCCATGTATTAC
TTTCTTTCCATCTTGGCACTGACTGACCTAGGCATGTCCATGTCCACACTTCCCACCATGCTTGCTGT
GTTATGGCTGGATGCTAGAGAGATCCAGGCAAGTGCTTGCTATGCTCAGCTCTTCTTCATCCACACAT
TCACATTCCTGGAGTCTTCGGTGCTATTGGCCATGGCCTTCGATCGTTTTGTTGCTATCTGCCGTCCA
CTGCACTACACCACCATCCTTAACAACAGTGTAATAGGCAAGATTGGCTTGGCCTGCTTGCTAAGAAG
CATGGGAGTTGTACTTCCTACACCTTTGCTACTGAGACATTATCACTACTGCCATGTCAATGCCCTTT
CCCATGCCTTCTGTTTGCACCAAGACGTTCTCAAATTGTCCTGTTCAGATGCCAGGATCAGCAGTGTC
TATGGACTGTGTGTAGTCATCACTACACTGGGCATGGATTCAGTCTTCATACTTCTTTCTTATGTCCT
GATTTTGAATGCTGTGCTGGGCATAGCATCTCATGAAGAGCGGCTAAAGGCACTCAACACATGTGTGT
CCCATATCTGCGTGGTGCTCATTTTCTTTGTGCCAGTTATTGGGGTGTCAATGGTCCATCGCTTTGGG
AAACATCTGTCTCCCATAGTTCACATCATCATGGCTGATATTTACTTGCTTTTCCCCCCAGTACTTAA
CCCTATTGTCTATAGTGTCAGGACAAAGCAGATTCGTATAAGAATTTTCCACAAGTTAAGACTAGGGA
GGAGGCTTTAA

CafaOR21.2.43 amino acid sequence (SEQ ID NO:44)

MPRVTMVVWNNNNTLEPIFILKGFPGLECVHSWFSIPFCLAYLVAFIGNVTILSVIWIESSLHQPMYY
FLSILALTDLGMSMSTLPTMLAVLWLDAREIQASACYAQLFFIHTFTFLESSVLLAMAFDRFVAICRP
LHYTTILNNSVIGKIGLACLLRSMGVVLPTPLLLRHYHYCHVNALSHAFCLHQDVLKLSCSDARISSV
YGLCVVITTLGMDSVFILLSYVLILNAVLGIASHEERLKALNTCVSHICVVLIFFVPVIGVSMVHRFG
KHLSPIVHIIMADIYLLFPPVLNPIVYSVRTKQIRIRIFHKLRLGRRL*

FIG. 1 Continued

CafaOR15.2.20 nucleotide sequence (SEQ ID NO:15)

ATGCTCATCATTATTCACTCATTGGTTATCTCTGCTTCTCTAACAGCTTTGGAATCCCAGAACACAAC
AATGCGTTTTGTGTCTGAGTTTGTCCTCCTGGGTTTCCCTGGTCAAAGGGAGATGCAGAACTTTTTCT
TCTCATTCATCCTGGTGATCTATCTCCTCACCCTGCTGGGGAATGGGATTATTGTCTGCATAGTGAAA
TGGGACAAGCAGCTTCACACACCCATGTACATCTTCTTGGGAAACTTTGCCTTCCTAGAGATCTGGTA
CACCTCCTCCACTGTCCCAAGTATGCTGGTCAACATCCTTTCCGAGACCAAGACCATCTCCTTCACTG
GGTGCTTCCTTCAATTCTACTTCTTTTTCTCACTGGGTACAACAGAGTGTTTCTTCTTATCAGTCATG
GCTTATGATCGGTACCTCGCCATCTGTCGCCCACTCCATTACCCCTCCATCATGACTGGGAAGCTCTG
TGTGGCCCTGGTCTGTGTTTGCTGGGTGAGTGGATTTCTCTGCTATCCAGTCCCCATTGTCCTCATCT
CCCAACTTCCATTCTGTGGACCCAACATCATTGATCACTTTGTGTGTGACCCAGGCCCACTGTTCGCA
CTGGCCTGCATCCCTGCTCCTTCCACTGAGCTTCTCTGTTACACCTTCAATTCACTGATTATCTTCGG
GCCCTTCCTCTTCATCCTGGGATCTTACACCCTGGTTCTCAGAGCTGTGCTTCGCATTCCTTCTGGTG
CAGGTCGAACTAAAGCATTCTCCACGTGTGGGTCCCATCTAATGGTGGTGTCTCTATTCTATGGAACC
CTTATGGTGATGTATGTGAGCCCGACATCAGGGAATCCGACGGGAATGCAAAAGATCATCACTCTGGT
ATACTCGGCAGTGACTCCACTCTTAAACCCCCTTATCTATAGTCTCCGAAACAAAGACATGAAAGATG
CCCTAAAGAAAGTCCTAGGATTAAGAAGTAACCAAAACTGA

CafaOR15.2.20 amino acid sequence (SEQ ID NO:45)

MLIIIHSLVISASLTALESQNTTMRFVSEFVLLGFPGQREMQNFFFSFILVIYLLTLLGNGIIVCIVK
WDKQLHTPMYIFLGNFAFLEIWYTSSTVPSMLVNILSETKTISFTGCFLQFYFFFSLGTTECFFLSVM
AYDRYLAICRPLHYPSIMTGKLCVALVCVCWVSGFLCYPVPIVLISQLPFCGPNIIDHFVCDPGPLFA
LACIPAPSTELLCYTFNSLIIFGPFLFILGSYTLVLRAVLRIPSGAGRTKAFSTCGSHLMVVSLFYGT
LMVMYVSPTSGNPTGMQKIITLVYSAVTPLLNPLIYSLRNKDMKDALKKVLGLRSNQN*

FIG. 1 Continued

CafaOR18.3.11 nucleotide sequence (SEQ ID NO:16)

ATGGGCCAGAGCAACCACACCAATGTGAAGGAATTTGTCTTTCTGAAACTCACTCACTTCCACGAGCT
AGAATTGTTCTTGTTTGTGGTCTTCCTTGCTGTATATGTAGCAACTGTGCTGGGCAATGTCCTCATTG
TGGTGACCATCACCTGTGAGTCCCACCTCCACTCTCCCATGTACTTTCTGCTGCGGAACAAATCAGTC
CTGGACATTGTCTTTTCATCTGTCACTGTTCCCAAGTTCCTGGTGGATCTGTTATCAGAGAGAAAAAC
CATCTCCTACAATGGCTGCATGGCACAGATCTTCTTCTTCCACTTCGCTGGTGGGGCAGACATTTTCT
TCCTCTCTGTGATGGCCTATGACAGGTACCTTGCAATCGCCAAACCCCTGCATTATGTGACCATTATG
AGGAGAGAGACGTGGGTGGGCTTGGTGGTGGCTTCCTGGGTGGGTGGTGGTTTGCACTCAATTGTCCA
GGTAACTCTCATGCTTCCACTCCCTTTCTGTGGCCCCAACATCCTGGATGCCTTCTACTGTGATGTGC
CCCAAGTGATTAAGCTGGCCTGTACCAACACCTTTGCCCTGGAGCTTCTCATGATCTCTAACAATGGG
CTGGTGACCCTGCTGTGGTTCCTCCTGCTCCTGGGCTCCTACACTGTCATTCTGGTGATGCTGAGATC
TCACTCTGGGGAGGGGCGGAATAAGGCCCTGTCCACCTGCACTTCCCATATCTTCGTGGTGACCCTGC
ACTTCGTGCCTTGCGTCTACATCTACTGCCGGCCCTTCATCACGCTGCCCATGGACACAGTTGTATCC
ATCAATAACACAGTCATTACCCCCATGCTGAACCCCATGATCTATACACTGAGGAACCAGGAGATGAA
GTCAGCCATGAAAAGACTGCAGAGAAGGCTTGGACCTTCTGAGAGCAGTTAG

CafaOR18.3.11 amino acid sequence (SEQ ID NO:46)

MGQSNHTNVKEFVFLKLTHFHELELFLFVVFLAVYVATVLGNVLIVVTITCESHLHSPMYFLLRNKSV
LDIVFSSVTVPKFLVDLLSERKTISYNGCMAQIFFFHFAGGADIFFLSVMAYDRYLAIAKPLHYVTIM
RRETWVGLVVASWVGGGLHSIVQVTLMLPLPFCGPNILDAFYCDVPQVIKLACTNTFALELLMISNNG
LVTLLWFLLLLGSYTVILVMLRSHSGEGRNKALSTCTSHIFVVTLHFVPCVYIYCRPFITLPMDTVVS
INNTVITPMLNPMIYTLRNQEMKSAMKRLQRRLGPSESS*

FIG. 1 Continued

CafaOR15.3.1 nucleotide sequence (SEQ ID NO:17)

ATGGAGGCTCCGAATCAAACAAGAGTGACTGAGTTTGTCTTCTTGGGGCTCACAGATAACTGGGCGCT
GGGGACGCTACTTTTTGTGGCATTCTCCCTGGCTTATGTGCTCACCCTTCTGGGGAACACTCTCATCA
TAGTGACCACGGCCCTTACCCGGCGCCTCCATACCCCCATGTACTTCTTCCTGAGCAACCTGTCCTTC
ATTGACACCTGCCACTCCTCGGTCACTGTGCCCAAGATGCTGGAGGGCCTGCTTAGGGAGAGAAAGAC
TATTTCCTTTGATGACTGCATTGCGCAGCTCTTCTTCCTACACCTGTTCGCTTGTGCTGAGATCCTTC
TGCTGACCGTCATGGCTTACGACCGCTACGTGGCCATCTGTGCCCCGCTGCGCTACCCCAACGTGATG
AGCATCCGGGTGTGTGTGCAGCTCGTCCTCGCCCTCTGGTGGGGGGGTACCGTTCACTCTCTGGTGCA
GACCCTCCTGACCATTCGTTTGCCCTACTGCGGCCCCAACGTTATCGATAGCTACTTCTGCGATGTGC
CCCCCGTCATCAAGCTGGCCTGCACGGACACCTACCTCACGGGAGTGCTCATTGTCTCCAACAGTGGA
ACCATCTCCCTCACCTGTTTCCTGGCTTTGGTCACCTCTTACACAATCATCCTGGTGTCTCTTAGAAA
ACAGTCTGCTGAAGGGCGCCGGAAAGCTCTGTCTACGTGCTCAGCCCACTTCATGGTGGTCGCCTTCT
TCTTTGGACCATGCATCTTCATCTACACTCGGCCAGACACCAGCTTCTCCATCGACAAGGTGGTATCT
GTCTTCTACACCGTGGTCACCCCTTTGCTAAATCCCCTCATTTACACCTTGAGGAATGAGGAGGTAAA
AAGTGCCATAAAGCATCTCAGACAGAAACAGGTTTTCTCATAA

CafaOR15.3.1 amino acid sequence (SEQ ID NO:47)

MEAPNQTRVTEFVFLGLTDNWALGTLLFVAFSLAYVLTLLGNTLIIVTTALTRRLHTPMYFFLSNLSF
IDTCHSSVTVPKMLEGLLRERKTISFDDCIAQLFFLHLFACAEILLLTVMAYDRYVAICAPLRYPNVM
SIRVCVQLVLALWWGGTVHSLVQTLLTIRLPYCGPNVIDSYFCDVPPVIKLACTDTYLTGVLIVSNSG
TISLTCFLALVTSYTIILVSLRKQSAEGRRKALSTCSAHFMVVAFFFGPCIFIYTRPDTSFSIDKVVS
VFYTVVTPLLNPLIYTLRNEEVKSAIKHLRQKQVFS*

FIG. 1 Continued

CafaOR6.3.1 nucleotide sequence (SEQ ID NO:18)

ATGCCAGAGGCCAACGACAGCTTCCTGGAGGGCTTCATTCTGATGGGTATATCTGACCATCCCCAGCT
GGAGATAATCTTTTTCATGGTCATTCTCTTCTCTTACTTACTGACTCTGCTTGGGAACTCAACCATTA
TCCTGCTTTCCTGGCTGGATGCCCGGCTCCATACTCCCATGTACTTCTTCCTCAGCAACCTCTCCACC
CTGGACCTTGCTTTTACTACTAGCTCAGTCCCCCAAATGCTGATCAACTTATGGGGACCAGATAAGAC
CATAAGCTATGGTGGCTGTGTGACCCAGCTCTATGTTTTCCTCTGGCTAGGGGCCACTGAGTGTATCC
TGCTTGTGGTGATGGCGTTTGACCGCTATGTGGCAGTTTGCCGGCCCCTGCACTACACCACCATCATG
AACCCTCGGCTCTGCTGGCTGCTGGCTGCCATTGCATGGCTGGGTGGCTTGAGCAACTCTGTGATCCA
GTCAACCTTCACTCTGCAGCTCCCCTTATGTGGGCACCGGAGGGTGGACAACTTCCTGTGTGAGGTAC
CTGCCATGATCAAACTGGCCTGTGGAGACACGAGTCTCAATGAGGTTGTGCTCAATGGTGTCTGCACC
TTCTTCACTGCTGTCCCACTAAGTGTCATCCTGATCTCCTACTGCTACATAGCTCAGGCAGTGCTGAA
GATCCACTCAGTAGAGGGACAGAGAAAGGCCTTTAATACGTGCCTCTCACATCTGGTGGTGGTGTTGC
TCTTCTATGGCTCAGCTATCTATGGGTATCTCCTTCCAGCTAAGACCAGCAACCAGGACCAGGGCAAA
TTCATTTCCCTCTTCTACTCTGTGGTCACACCAACGGTGAACCCTCTCATCTACACTCTGAGAAATAG
GGAAGTAAAGGGAGCACTAAGGAGGCTGCTAGGAAAGGGAAGATCACTTGGCTGA

CafaOR6.3.1 amino acid sequence (SEQ ID NO:48)

MPEANDSFLEGFILMGISDHPQLEIIFFMVILFSYLLTLLGNSTIILLSWLDARLHTPMYFFLSNLST
LDLAFTTSSVPQMLINLWGPDKTISYGGCVTQLYVFLWLGATECILLVVMAFDRYVAVCRPLHYTTIM
NPRLCWLLAAIAWLGGLSNSVIQSTFTLQLPLCGHRRVDNFLCEVPAMIKLACGDTSLNEVVLNGVCT
FFTAVPLSVILISYCYIAQAVLKIHSVEGQRKAFNTCLSHLVVVLLFYGSAIYGYLLPAKTSNQDQGK
FISLFYSVVTPTVNPLIYTLRNREVKGALRRLLGKGRSLG*

FIG. 1 Continued

CafaOR18.3.12 nucleotide sequence (SEQ ID NO:19)

ATGTCCACAGTTAAGGCCTGGAACAGCTCTTCAGTGACCATGTTCATCCTCCTGGGATTTGCAGACCA
TCCAGAACTGCAGACTCTTCTCTTTGTGACCTTCCTGAGTATCTATCTTGTGACACTGGCCTGGAACC
TGGCCCTCATCTTTCTGATCAGAAGTGACCCCATCTGCACACACCCATGTACTTCTTCCTCAGCAAC
TTGTCCTTCATTGACATCTGTTATTCTTCCACAGTGGCCCCCAAGATGCTCACTGATTTCTTCCAGGA
GCAAAAGACCATCTCGTTCTTGGGCTGTGCTGCTCAGTTTTTTTTCTTTGTCAGCATGGGTCTCACTG
AGTGCTTCCTTCTGACTGCCATGGCATATGATCGATACGCAGCCATCTCCAACCCCTTGCTCTACACT
GCCATCATGTCCCAGGGCCTCTGTACACGCATGGTGCTGGGGGCATATGTCGGTGGTTTCCTGAGCTC
CTTGATCCAGGCCATCTCTATATTTCAGCTCCACTTCTGTGGACCCAATATCATCAACCATTTCTTCT
GTGACCTTCCACCAGTCCTGGCACTTTCTTGCTCTGACACCTTCCCTAGTCAAGTGGTGAATTTTCTC
ATAGTGATCACTGTTGGGGGAACATCATTCCTCATCCTCCTCATCTCCTACAGTTACATAGGAGCTGC
TGTCTTGAAGATCCGCTCAGTGGAAGGCCGAAGGAAAGCCTTCAACACATGTGCCTCGCATCTGATGG
TGGTGACTCTTCTGTTTGGGACAGCTCTTTTCATGTACCTGCGGCCCAGCTCCAGCTACTCACTTGCC
AGGGACAAGGTGGTGTCTGTCTTCTATTCGCTGGTGATCCCCATGCTGAACCCTCTCATTTACAGTCT
AAGGAACAGAGATATCAAAGACGCCCTGTGGAAGGCATTGGAGAAGAAGAAAGTGTTTTTCCTAGATC
ATGATTGA

CafaOR18.3.12 amino acid sequence (SEQ ID NO:49)

MSTVKAWNSSSVTMFILLGFADHPELQTLLFVTFLSIYLVTLAWNLALIFLIRSDPHLHTPMYFFLSN
LSFIDICYSSTVAPKMLTDFFQEQKTISFLGCAAQFFFFVSMGLTECFLLTAMAYDRYAAISNPLLYT
AIMSQGLCTRMVLGAYVGGFLSSLIQAISIFQLHFCGPNIINHFFCDLPPVLALSCSDTFPSQVVNFL
IVITVGGTSFLILLISYSYIGAAVLKIRSVEGRRKAFNTCASHLMVVTLLFGTALFMYLRPSSSYSLA
RDKVVSVFYSLVIPMLNPLIYSLRNRDIKDALWKALEKKKVFFLDHD*

FIG. 1 Continued

CafaOR5.2.5 nucleotide sequence (SEQ ID NO:20)

ATGCCTTTAGTAAGAATGGCAGCTGAGAATTCCTCTGTGACAGAGTTTATCCTCTCAGGCTTAACCAA
CCAGCCAGGACTCCAGATTCCTCTCTTCTTCCTGTTTCTAGGTTTCTATGTGGTCACGGTGGTAGGGA
ACCTGGGCCTGATAACCCTGATTGGGCTGAATTCTCACCTGCACACCCCCATGTACTTTTTCCTCTTC
AACTTGTCCTTCATAGATTTCTGCTATTCCACTGTTATCACTCCCAAGATGCTGATGAATTTTGTCTT
GAGGAAGAACGTCATCTCCTACGCAGGGTGTATGACTCAGCTCTTCTTCTTTCTCTTCTTTGTTGTAT
CTGAGTCCTTCATCCTGTCAGCAATGGCATATGACCGCTATGCCGCCATCTGTAACCCACTGGTATAC
ACTGCCACCATGTCTCCTCAGGTCTGCTTCCTCCTTCTGTTGGGTGTCTATGTGATGGGGTTTGCTGG
AGCCATGGCCCACACAGTGTGCATGGTAAGACTGACCTTCTGTGCCAACAATCTGGTTGACCACTACA
TGTGCGACATCCTTCCCCTTCTTGAGCGTTCTTGCACCAGCACCTATGTCAATGAGCTGGTAGTTTTT
ATTGTTGTGGGCATTGATATTGGTGTGCCCACAGTTACCATCTTCATTTCTTATGCCCTCATCCTCTC
CAGCATTCTCCGTATTCATTCTACCAAGGGCAGGTCCAAAGCCTTCAGCACCTGCAGCTCCCACATAA
TTGCTGTTTCCCTCTTCTTTGGATCAGGGGCATTTATGTACCTCAAACCATCCTCTCTTTTACCTATG
AATCAGGGGAAAGTGTCCTCTTTGTTCTACACCATCGTTGTGCCCATGCTCAACCCACTAATCTACAG
CTTGAGGAATAAGGATGTCAAAATTGCTCTGAAGAAAACACTGAGCAAGAAACCATTCTCTTGA

CafaOR5.2.5 amino acid sequence (SEQ ID NO:50)

MPLVRMAAENSSVTEFILSGLTNQPGLQIPLFFLFLGFYVVTVVGNLGLITLIGLNSHLHTPMYFFLF
NLSFIDFCYSTVITPKMLMNFVLRKNVISYAGCMTQLFFFLFFVVSESFILSAMAYDRYAAICNPLVY
TATMSPQVCFLLLLGVYVMGFAGAMAHTVCMVRLTFCANNLVDHYMCDILPLLERSCTSTYVNELVVF
IVVGIDIGVPTVTIFISYALILSSILRIHSTKGRSKAFSTCSSHIIAVSLFFGSGAFMYLKPSSLLPM
NQGKVSSLFYTIVVPMLNPLIYSLRNKDVKIALKKTLSKKPFS*

FIG. 1 Continued

E1:13347030-13347977 nucleotide sequence (SEQ ID NO:21)

atgaagtcaaaattTGAGTACAATAGAACAGCCATTACTGAGTTCATCCTGCTGGGCTTAGT
GGAGACACCAGACCTGCGGCCAGTTGTCTTTGTAGTCTTCCTCCTTTCCTACCTGCTCACAG
TTGGGGGCAACCTCAGCATCCTGGCCGCCATCTTGGTGGagcccaaactccacaccccatg
tacttcttcctggggAACCTATCGGTGCTGGACATTGGGTGCATCACAGTCACTATTCCCTC
AATGTTGGCTCGTCTCCTGTCCCACAAGCGTACTGTTCCCTATGGAGCCTGCCTCACACAGC
TTTTCTTCTTTCACCTTCTCGTTGGGGTGGACTGCTTCCTTTTGACAGCCATGGCCTATGAC
CGATTCCTGGCCATCTGCCAGCCCCTCACCTACAGCACCCGAATGAGCCAGACAGTCCAGAG
GATATTGGTGGCTGTGTCCTGGGCTTTAGCCTTCACTAATGCACTGACCCACACAGTAGCCA
TATCCACCCTGAACTTCTGTGGTCCCAATGTGATCAATCACTTCTACTGTGACCTCCCACAG
CTCTTCCAGCTCTCCTGCTCCAGCACCCAACTCAATGAGTTGCTGCTCTTTGCTGTGGGTTT
CATAATGGCAGGTACTCCCCTGGCTCTCATCGTCACCTCCTATGCCCATGTGACAGCTGCAG
TCCTACGAATCCGTTCTGCTGAGGGCAGGAAGAAAGCCTTCTCCACATGTGGCTCTCATCTC
ACTGTGGTTGCCATATTCTACGGTTCAGGTATATTTAATTACATGCGACTGGGTTCAGCCAA
GCTTTCAGACAAGGATAAAGCTTTTGGAATTTTTAACACCGTCATCAACCCCATGCTGAATC
CAATCATCTACAGCCTCAGGAACCCTGACGTGCAGGGTGCCCTCTGGAGAGTGCTCATGGGG
AGGCGGCCACTGGCTTGA E1:13347030-13347977 amino acid sequence (SEQ ID NO:51)

MKSKFEYNRTAITEFILLGLVETPDLRPVVFVVFLLSYLLTVGGNLSILAAILVEPKLHTPM
YFFLGNLSVLDIGCITVTIPSMLARLLSHKRTVPYGACLTQLFFFHLLVGVDCFLLTAMAYD
RFLAICQPLTYSTRMSQTVQRILVAVSWALAFTNALTHTVAISTLNFCGPNVINHFYCDLPQ
LFQLSCSSTQLNELLLFAVGFIMAGTPLALIVTSYAHVTAAVLRIRSAEGRKKAFSTCGSHL
TVVAIFYGSGIFNYMRLGSAKLSDKDKAFGIFNTVINPMLNPIIYSLRNPDVQGALWRVLMG
RRPLA*

FIG. 1 Continued

F1:65134904-65135858 nucleotide sequence (SEQ ID NO:22)

ATGGGAAATTGGAGCAGAGGCCACATAGCAGAGTTCGTGTTGGTGGGCTTCCCTACCTCTCCGCCCCT
CCAGTGCCTCCTCTTTGTCCTCTTCCTGGCAATTTACCTGTTGACATTGTTGGAGAACGCACTCATCG
TTTCCACAGTCTGGCTCACGCCAAGCCTTCACCGCCCGATGTACTTTTTCCTTGGCCATCTCTCCTTC
CTGGAGCTGTGGTACATCAATGTCACAGTTCCCCGGCTTTTGGGAGCATTTCTTACCCAGGAGCGTAG
AGTCTCCTACGTAGGCTGCATGACTCAGCTCTACTTCTTTATTGCCCTAGCCTGCACCGAATGTGTCC
TGCTGGCGgtcatggcctatgaccgctaccTGGCCATCTGTGAGCCCCTCCGTTATCCTAGTCTCATG
CCATCCAGCCTGGCCATTCGCCTCGCTGCTTCCTCTTGGGGTAGTGGCTTCTTGAGCTCCATGATGAA
GCTTCTTTTCATTTCCCGGCTGTCCTACTGTGGACCCAACGTCATCAACCACTTTTTCTGCGATATCT
CCCCACTACTCAACCTCACCTGCTCTGACAAAGAGCAAGCAGAACTAGTAGACTTCCTCTTGGCCCTG
GTGATGATTCTGCTCCCTCTGTTGGCCGTGGTTTCATCATATGCTGCCATAATGGCTGCCATCCTCAG
GATTCCTACTGCCCAGGGACGTCGcaaagccttctccacctgtgccTCTCACCTGGCAGTGGTTGTTA
TCTACTACTCCTCCACCCTCTTCACCTATGCACGGCCCCAGGCCATGTACACCTTCAACCATAACAAG
GTCATCTCTGTGCTCTATACAGTCATTGTACCGTTCCTCAATCCAGCCATCTACTGCCTGAGGAACAA
GGAGGTGAAGGATGCTCTCAGGAAGTCAGTCCTGGGCAGATGCCACTATCCGAGGGACGTCCCAGATT
GA F1:65134904-65135858 amino acid sequence (SEQ ID NO:52)

MGNWSRGHIAEFVLVGFPTSPPLQCLLFVLFLAIYLLTLLENALIVSTVWLTPSLHRPMYFFLGHLSF
LELWYINVTVPRLLGAFLTQERRVSYVGCMTQLYFFIALACTECVLLAVMAYDRYLAICEPLRYPSLM
PSSLAIRLAASSWGSGFLSSMMKLLFISRLSYCGPNVINHFFCDISPLLNLTCSDKEQAELVDFLLAL
VMILLPLLAVVSSYAAIMAAILRIPTAQGRRKAFSTCASHLAVVVIYYSSTLFTYARPQAMYTFNHNK
VISVLYTVIVPFLNPAIYCLRNKEVKDALRKSVLGRCHYPRDVPD*

FIG. 1 Continued

D1:62955839-62956792 nucleotide sequence (SEQ ID NO:23)

ATGGTGGACACCAATGGCAGTGAATCTAGTGCCACATATTTCATTCTAATAGGCCTTCCAGGCTTGGA
AAAAGCTCAGTTCTGGTTGGCCTTCCCGTTATGCTCCCTCTACCTTATTGCTGTGCTAGGTAACCTGA
CAGTCATCTGCATTGTGCGGACTGAGCACAGACTACATGAAcccatgtatattttctttgcatGCTT
TCTGGCCTTGACATACTTATCTCTACTTCATCTATGCCCAGAATGATGGCCATCTTCTGGTTCAATTC
CACTACCATCCAGTTTGATGCTTGTCTTCTACAGATGTTTGCCATCCACTCCTTATCTGGCATGGAGT
CCACTGTACTGCTGGCCATGGCCTttgaccgctatgtggccattTGTCACCCACTACGCCATGCCACT
GTGCTAACATTGCCTCGTGTTACCAAGATTGGCGTGGCTGCTGTGGTACGGGGTACTTCACTTATGGC
ACCCCTGCCTATCTTCATCAAACGGCTGCCTTTCTGCCGCTCCAACATTCTTTCCCATTCCTACTGCC
TACATCAAGATGTCATGAAGCTGGCTTGTGCTGACATCCGTGTCAATATCATCTATGGCCTCATTGTC
ATCATCTCTGCCATTGGCCTGGACTCACTTCTCATCTCCTTGTCATATCTGCTTATCCTCAAGACTGT
GTTGGGCTTGACACGTGAAGCCCAGGCAAAGGCATTTGGCACTTGTGTCTCTCATGTGTGTGCTGTTT
TCATATTCTATGTACCTTTCATTGGGTTATCTATGGTGCACCGCTTTGGGAAGCGGCATGACTCCCTC
CTGCCCATCATTATGGCCAACACCTACTTGCTTGTTCCTCCTGTGCTCAACCCTATTGTTTATGGAGT
GAAGACAAAGGAGATCCGGCAGCGTATCCTTCGTCTTTTCCATGTGACCACCCATACTTCAGATCCCT
AG D1:62955839-62956792 amino acid sequence (SEQ ID NO:53)

MVDTNGSESSATYFILIGLPGLEKAQFWLAFPLCSLYLIAVLGNLTVICIVRTEHRLHEPMYIFLCML
SGLDILISTSSMPRMMAIFWFNSTTIQFDACLLQMFAIHSLSGMESTVLLAMAFDRYVAICHPLRHAT
VLTLPRVTKIGVAAVVRGTSLMAPLPIFIKRLPFCRSNILSHSYCLHQDVMKLACADIRVNIIYGLIV
IISAIGLDSLLISLSYLLILKTVLGLTREAQAKAFGTCVSHVCAVFIFYVPFIGLSMVHRFGKRHDSL
LPIIMANTYLLVPPVLNPIVYGVKTKEIRQRILRLFHVTTHTSDP*

FIG. 1 Continued

D1:63312327-63313289 nucleotide sequence (SEQ ID NO:24)

ATGCCAAGGTTCACCATGGTGGTCTGGAATAACAATAACACCATGGAGCCTATATTTATTCTGAGGGG
ATTTCATGGATTGGAGTGTGTCTATTCTTGGATCTCAGTCCCATTCTGTCTTGCATACTTGGTAGCAT
TTATTGGTAATGTTACCATCCTCTCTGTCATTTGGATAGAGTCATCACTCCATCAGCCCATGTACTAC
TTCCTTTCCATCTTGGCACTGACTGACCTAGGTATGTCTATGTCCACACTTCCCACCATGCTTGCTGT
GTTATGGCTGGATGCTCGGGAGATCCAGGCAAGTGCTTGCTATGCTCAGCTCTTTTTCATCCACACAT
TCACATTCCTGGAGTCTTCGGTGCTACTGGCCATGGCCTTTGACCGTTTTGTTGCTATCTGCCGTCCA
CTGCACTATACTACCATCCTTAACAACAGTGTAATAGGCAAGATTGGTTTGGCCTGCTTGCTAAGAAG
CATGGGAGTTGTACTTCCTACACCTTTGCTACTGAGACATTATCACTACTGCCATGACAATGCCCTTT
CCCATACCTTCTGTTTGCACCAAGACATTCTGAAATTATCCTGTTCAGATGCAAGGATCAGCAGTGTC
TATGGCCTGTGTGTAGTTATTACCACACTTGGTGTGGATTCAGTCTGCATACTTCTTTCTTATATCCT
GATTCTGAATGCTGTGCTGGGGATTGCATCTCATGAAGAGCGGCGGAAGGCACTCAACACATGCATAT
CCCATATCTGTGTTGTGCTCATTTTCTTTGTGCCAGTAATTGGGGTGTCAATGGTCCATCGCTTTGGG
AAACATCTGTCTCCAAGAATTCACATCATCATGGCCGATATTTACCTGCTTTTCCCCCCAGTGCTTAA
CCCTATTGTCTATAGCATCAAAACAAAGCAGATTCGTCTAAGAATTCTCCGCAGGTTTGGACTGCGGA
GGGGGCATTAA

D1:63312327-63313289 amino acid sequence (SEQ ID NO:54)

MPRFTMVVWNNNNTMEPIFILRGFHGLECVYSWISVPFCLAYLVAFIGNVTILSVIWIESSLHQPMYY
FLSILALTDLGMSMSTLPTMLAVLWLDAREIQASACYAQLFFIHTFTFLESSVLLAMAFDRFVAICRP
LHYTTILNNSVIGKIGLACLLRSMGVVLPTPLLLRHYHYCHDNALSHTFCLHQDILKLSCSDARISSV
YGLCVVITTLGVDSVCILLSYILILNAVLGIASHEERRKALNTCISHICVVLIFFVPVIGVSMVHRFG
KHLSPRIHIIMADIYLLFPPVLNPIVYSIKTKQIRLRILRRFGLRRGH*

FIG. 1 Continued

B3:72908295-72909287 nucleotide sequence (SEQ ID NO:25)

ATGTTCATTGTTATTCACTCCTTCGTTACTTCTATTTCTCTAACAGCTTTGGAATCTCAGAACGCAAC
AATGCATTTTGTGACTGAGTTTGTCCTCCTGGGTTTTCCTGGTCAAAGGGAGATGCAgaactttttct
tctcattaatcCTTGTGGTCTATCTCCTCACTCTGCTGGGGAATGGGGTTATTGTCTATGTAGTGAAA
TGGGACAAGCGGCTTCACACACCCATGTACATCCTCTTGGGAAACTTTGCCTTCCTAGAGATCTGGTA
CATCTCCTCCACTGTCCCAAACATGCTGGTCACCATCCTCTCTGAGACCAAGACCATCTCCTTCACTG
GATGCTTcctccaattttatttcttttctcattgggtACAACAGAGTGTTTCTTCTTATCAGTTATG
GCTTATGACCGGTACCTTGCCATCTGTCGCCCACTACATTATCCTTCCATCATGACTGGGAAGCTCTG
TGTGATCCTGGTCTGCGTTTGCTGGGTGAGTGGATTTCTCTGCTATCCAATCCCCATTGTCCTCATCT
CCCAACTTCCCTTCTGTGGACCTAACATCATTGACCACTTCGTGTGTGACCCAGGCCCATTGTTCGCA
CTGGCCTGCATCCCTGCTCCTTCCACTGAACTTATCTGCTATACCTTCAACTCAGTGATTATCTTTGG
GCCCTTCCTTTCTATCTTGGGATCTTACACTCTGGTACTCAGAGCTGTGCTTCGTATTCCTTCTGGTG
CTGGTCAAACTAAAGCTTTCTCCACATGTGGGTCACACCTAATGGTGGTGTCTCTATTCTATGGAACC
CTTATGGTGATGTATGTAAGCCCAACATCAGGAAATCCAGCAGGAATGCAGAAGATCGTCACTTTGGT
ATACTCAGCAGTGACTCCACTCTTAAACCCCCTTATCTATAGTCTTCGAAATAAAGACATGAAAGATG
CCCTAAAGAAACTCCTAGGATTAAGAAGTAACCCAAACTGA B3:72908295-72909287 amino acid sequence (SEQ ID NO:55)

MFIVIHSFVTSISLTALESQNATMHFVTEFVLLGFPGQREMQNFFFSLILVVYLLTLLGNGVIVYVVK
WDKRLHTPMYILLGNFAFLEIWYISSTVPNMLVTILSETKTISFTGCFLQFYFFFSLGTTECFFLSVM
AYDRYLAICRPLHYPSIMTGKLCVILVCVCWVSGFLCYPIPIVLISQLPFCGPNIIDHFVCDPGPLFA
LACIPAPSTELICYTFNSVIIFGPFLSILGSYTLVLRAVLRIPSGAGQTKAFSTCGSHLMVVSLFYGT
LMVMYVSPTSGNPAGMQKIVTLVYSAVTPLLNPLIYSLRNKDMKDALKKLLGLRSNPN*

FIG. 1 Continued

D1:105486528-105487493 nucleotide sequence (SEQ ID NO:26)

ATGGAGGAGGGTGGTCCCAACCATGGCCAGAGCAACCACACCAATGTGAAGGAATTTGTCTT
CCTAGAACTCACTCACTTCCAGGAGCTGGAATGTTTCTTGTTTGTGGCTTTCCTTGCTGTAT
ATGTAACCACCGTGCTGGGCAATGCCCTCATTGTGCTGACCATCACCTATGAGTCCCACCTT
CACACTCCCATGTACTTTCTGCTGCGGAACAAATCGGTCCTGGACATTGTTTTTTCATCTGT
CACTGTTCCCAAGTTCCTGGTGGATCTGTTATCAGAGAGGAAAACCATCTCCTACAATGGCT
GCATGGCACAGatcttcttcttccattttgctGGTGGGGcagatattttcttcctctccgTG
ATGGCCTATGACAGATACCTTGCAATCGCCAAACCCCTGCATTATGTGACCATTATGAAGAG
AGAGGTGTGGGTGGGCTTGGTGGTGGCTTCCTGGGTGGGCGGTGGTTTGCACTCAATTGTCC
AGATAATTCTGATGCTTCCACTCTCCTTCTGTGGCCCCAACATCCTGGATGCCTTCTACTGT
GATGTGCCCCAAGTAGTTAAGCTGGCTTGCACTGATACCTTTGCTCTGGAACTTCTCATGAT
CTCTAACAATGGGTTGGTGACCCTGCTATGGTTCCTCTTGCTCCTGGGATCCTACACCGTTA
TTCTGGTGATGCTGAGATCTCACTCTGGGGCAGGACGGAACAAGGCCCTGTCCACCTGCACC
TCCCATATCCTCGTGGTGACTCTGCACTTTGTGCCTTGTGTCTACATCTACTGCCGGCCCTT
CACTACACTGCCCATGGACACAGCTGTGTCCATCAATAACACGGTCATTACGCCCATGCTGA
ACCCCATGATTTATACCCTGAGGAACCAGGAGATGAAGTCTGCCATGAAAAGACTACACAGA
AGGCTTGGACCTTCTGAGAGCAGTAAGCTGGGGTGA D1:105486528-105487493 amino acid sequence (SEQ ID NO:56)

MEEGGPNHGQSNHTNVKEFVFLELTHFQELECFLFVAFLAVYVTTVLGNALIVLTITYESHLHTPMYF
LLRNKSVLDIVFSSVTVPKFLVDLLSERKTISYNGCMAQIFFFHFAGGADIFFLSVMAYDRYLAIAKP
LHYVTIMKREVWVGLVVASWVGGGLHSIVQIILMLPLSFCGPNILDAFYCDVPQVVKLACTDTFALEL
LMISNNGLVTLLWFLLLLGSYTVILVMLRSHSGAGRNKALSTCTSHILVVTLHFVPCVYIYCRPFTTL
PMDTAVSINNTVITPMLNPMIYTLRNQEMKSAMKRLHRRLGPSESSKLG*

FIG. 1 Continued

B3:74116955-74117893 nucleotide sequence (SEQ ID NO:27)

ATGGATGCTCTAAATCAAACAAGAGTGACTGAATTTGTCTTCTTGGGACTCACTGATAAGTGGGTGCT
GGAGATACTATTTTTTCTGGCATTCTCCGTCACATATGTATTAACCCTTTTGGGAAACACTCTCATTA
TAGTTACTATAGTCTTTACTCCACGCCTCCATAccccatgtatttcttcctgagCAATCTGTCCTTT
ATTGACATCTGCCACTCATCTGTCACTGTGCCCAAGATGCTAGAGGGCTTGCTTTTAGAGATAAAGAC
TATTTCCTTTGATAATTGCATTGCACAGCTCTTCTTCCTACATCTGTTTGCTTGTGCTGAGATCTTTC
TGCTGACCATTATGGCTTATGATCGTTATGTAGCCATCTGTGCTCCATTGCACTATTCTAATGTGATG
AACATGAGGGTCTGTGTACAGCTTGTCTTTGCTCTCTGGTTGGGGGCTACTGTTCACTCTCTGGTGCA
GACCTTCTTGACCATTCGTCTACCTTACTGTGGCCCCAACATTATTGATAGCTACTTCTGCGATGTGC
CCCCTGTCATCAAGCTGGCTTGCACAGATACATACCTCACGGGAATGCTAATTGTGTCTAATAGTGGA
ACCATCTCCCTCACCTGTTTCCTGGCTTTGGTCACCTCTTACACGGTCATCCTGGTTTCTCTTAGAAA
ACAGTCAGCTGAAGGGCGCCGGAAAGCCTTGTCTACCTGTTCAGCCCACTTCATGGTTGTAGCCTTCT
TTTTTGGACCATGTATCTTCATCTACACTCGGCCAGACACTAGCTTCTCCATTGACAAGGTGGTATCT
GTCTTCTACACAGTGGTCACTCCTTTGCTGAATCCTCTCATTTACACCTTGAGAAATGAGGAGGTAAA
AAGTGCCATGAAGCATCTCAGACAGAGAGGTTTTTTCATGAAGTCAGGTACATGA B3:74116955-74117893 amino acid sequence (SEQ ID NO:57)

MDALNQTRVTEFVFLGLTDKWVLEILFFLAFSVTYVLTLLGNTLIIVTIVFTPRLHTPMYFFLSNLSF
IDICHSSVTVPKMLEGLLLEIKTISFDNCIAQLFFLHLFACAEIFLLTIMAYDRYVAICAPLHYSNVM
NMRVCVQLVFALWLGATVHSLVQTFLTIRLPYCGPNIIDSYFCDVPPVIKLACTDTYLTGMLIVSNSG
TISLTCFLALVTSYTVILVSLRKQSAEGRRKALSTCSAHFMVVAFFFGPCIFIYTRPDTSFSIDKVVS
VFYTVVTPLLNPLIYTLRNEEVKSAMKHLRQRGFFMKSGT*

FIG. 1 Continued

E3:40237904-40238842 nucleotide sequence (SEQ ID NO:28)

ATGGCAGAGGCCAACAACAGCTTTTCAGAGGGCTGCATCCTGATGGGTATATCTGACCATCCCCAGCT
GGAGATCGTCTTTTTCATAGTCATTCTCTTCTCTTACTCGCTGACCCTAGTTGGGAATTCGACCACCA
TCCTGCTCTCCTGCCTGGATGCCCggctccacaccccatgtacttcttcctcagcAACCTCTCCTCC
CTGGACCTCGCTTTTACTACCAGCTCGGTCCCCCAAATGCTGACCAACTTATGGGGACCAGATAAGAC
TATAAGCTACGCTGGCTGTGTGATCCAGCTCTATGTTTTCCTCTGGCTAGGGGCCACTGAGTGCATCC
TGCTCGTGGTGATGGCATTCGACCGCCATGTGGCAGTTTGCCAGCCCCTGCGCTACACCGTCATCGTG
AGCCCTCGGCTCTGCCGGCTGCTGGCTGCCATTGCATGGCTGGGCGGCTTGAGCAACTCCATGATCCA
GTCAACGTTCACTCTCCAGCTCCCATTGTGTGGGCACCGGAGGGTGGACAACTTCCTGTGTGAGGTGC
CTGCCATGATCAAACTGGCCTGTGGAGACACAAGTCTCAACGAGGCCGTGCTCAATGGTGTCTGCACC
TTCTTCACTGCCGTCCCGCTGAGCATCATCCTGATCTCCTACTGCTCCATAGCTCGGGCAGTGCTGAA
GATCCGCTCagctgagggacagagaaaggccTTTAATACTTGCCTTTCCCATCTGGTGGTGGTGCTCC
TCTTCTATGGGTCAGCTATCTACGGGTACCTCCTTCCGGCTAAGACCAGCCACCAGGGCCAAGGCAAA
TTCATTTCCCTCTTCTACTCTGTGGTCACGCCAATGGTGAACCCTCTCATCTACACTCTGAGAAACAA
GGAGGTAAAGGCGGCACTGAGGAGGCTccggggaaagggaagagaattcGGCTGA E3:40237904-40238842 amino acid sequence (SEQ ID NO:58)

MAEANNSFSEGCILMGISDHPQLEIVFFIVILFSYSLTLVGNSTTILLSCLDARLHTPMYFFLSNLSS
LDLAFTTSSVPQMLTNLWGPDKTISYAGCVIQLYVFLWLGATECILLVVMAFDRHVAVCQPLRYTVIV
SPRLCRLLAAIAWLGGLSNSMIQSTFTLQLPLCGHRRVDNFLCEVPAMIKLACGDTSLNEAVLNGVCT
FFTAVPLSIILISYCSIARAVLKIRSAEGQRKAFNTCLSHLVVVLLFYGSAIYGYLLPAKTSHQGQGK
FISLFYSVVTPMVNPLIYTLRNKEVKAALRRLRGKGREFG*

FIG. 1 Continued

D1:105462554-105463512 nucleotide sequence (SEQ ID NO:29)

ATGAGAAGCATGTCCACAGCTAAGGCCTGGAATAGCTCTTCAGTAACCATGTTCATCTTCCTGGGATT
TGCAGACCATCCAGAACTCCAGACCCTTCTCTTTGTGACCTTCCTGGGTATCTATCTTGTGACACTGG
CCTGGAACCTGGCCCTCATCTTTTTGATCAGAGGTGACCCCCGTCTGCAcacacccatgtacttcttc
ctcagcAACTTGTCTTTCATCGACATCTGCTACTCTTCTACAGTGGCCCCCAAGATGCTCACTGATTT
CTTCTGGGAGCAAAAGACCATATCATTCTTGGGCTGTGctgctcagttttttttctttgtcagtatGG
GTCTCACTGAGTGCTTCCTCCTGACTGCCATGGCATACGACAGATACGCAGCCATCTCCAATCCCCTG
CTGTACACAGCCATCATGTCCCAAGGCCTCTGCACACGCATGGTGCTTGGGGCATATGTTGGTGGCTT
CCTGAGCTCCCTGATCCAGGCCAGCTCCATATTTCAGCTTCACTTCTGCGGACCCAACATTATCAATC
ATTTCTTCTGTGACCTCCCTCCAGTACTGGCACTTTCTTGCTCTGACACCTTTCCTAGTCAAGTGGTG
AATTTTCTCGTGGTAGTCACTATTGGGGGACATCATTCCTCATCCTCATCATCTCCTACAGTTACAT
AGGAACTGCTGTCTTGAAAATCCGTTCAGTGGAAGGCCGAAAGAAAGCCTTCAGCACATGTGCCTCAC
ACTTGATGGTGGTGACTCTGTTGTTTGGGACGGCCCTTTTCATGTACCTGAGACCCAGCTCCAGCTAC
TCGCTTGGCAGGGACAAGGTAGTGTCTGTGTTCTATTCACTGGTGATCCCCATGCTGAACCCTCTTAT
TTACAgtttgaggaacagagagatcaaAGATGCCCTATGGAAGGTGTTGGAGAAGAAGAAACTGTTTT
CCTAG D1:105462554-105463512 amino acid sequence (SEQ ID NO:59)

MRSMSTAKAWNSSSVTMFIFLGFADHPELQTLLFVTFLGIYLVTLAWNLALIFLIRGDPRLHTPMYFF
LSNLSFIDICYSSTVAPKMLTDFFWEQKTISFLGCAAQFFFFVSMGLTECFLLTAMAYDRYAAISNPL
LYTAIMSQGLCTRMVLGAYVGGFLSSLIQASSIFQLHFCGPNIINHFFCDLPPVLALSCSDTFPSQVV
NFLVVVTIGGTSFLILIISYSYIGTAVLKIRSVEGRKKAFSTCASHLMVVTLLFGTALFMYLRPSSSY
SLGRDKVVSVFYSLVIPMLNPLIYSLRNREIKDALWKVLEKKKLFS*

FIG. 1 Continued

D1:21266824-21267768 nucleotide sequence (SEQ ID NO:30)

ATGCCTTTAATGAGAATGGCAGCTGAGAACTCCTCTGTGACAGAATTTATCCTTGCAGGCTTAACCAA
CCAGCCCGGACTTCGGATGCccctcttcttcctgtttctagGTTTCTATGTGGTCACTGTGATGGGGA
ACCTGGGTCTGATAACCCTGATTGGGCTGAATTCTCACCTgcacaccccccatgtacttcttcctcttc
AACTTGTCCTTCATAGATTTTTGCTATTCCACTGTTATCACTCCCAAGATGCTGATGAGTTTTGTCTC
AAAGAACACCATCGCCTACGCAGGGTGTATGACTcagctcttcttttttcttttctttgttgtctCTG
AGTCCTTCATCCTGTCAGCAATGGCATATGACCGCTACACCGCCATCTGTAACCCACTGGTGTACACA
GCCACCATGTCTCCTCAGGTCTGCTCGCTTCTTCTGTTGGGTGTCTATGTGATGGGGTTTGCTGGGGC
CATGGCCCACACGACATGCATGGTGAGGCTGACCTTCTGTGCCAACAATCTGGTTGACCACTACATGT
GTGACATCCTTCCCCTTCTTGAGCGCTCTTGCACCAGCACCTATGTAAATGAGCTGGTAGTTTTCGTT
GTCGTGGGCATTGATATTGGCGTGCCCACAGTTACCATCTTCATTTCTTATGccctcatcctccaccag
cattcTCCATATTCGTTCCACTGAGGGCAGGTCCAAAGCCTTCAGCACATGCAGCTCTCACATAAttg
ctgtttctcttttctttgggtCAGGGGCATTTATGTACCTCAAACCATCCTCTCTTTTACCTATGAAT
CAGGGGAAAGTGTCCTCCTTGTTCTATACCACCGTTGTGCCCATGCTCAACCCGCTAATCTATAGCTT
AAGAAATAAAGATGTCAAAGTTGCTCTGAAGAAATCATTGAGCAAAAAGACATTCTCTTGA D1:21266824-21267768 amino acid sequence (SEQ ID NO:60)

MPLMRMAAENSSVTEFILAGLTNQPGLRMPLFFLFLGFYVVTVMGNLGLITLIGLNSHLHTPMYFFLF
NLSFIDFCYSTVITPKMLMSFVSKNTIAYAGCMTQLFFFLFFVVSESFILSAMAYDRYTAICNPLVYT
ATMSPQVCSLLLLGVYVMGFAGAMAHTTCMVRLTFCANNLVDHYMCDILPLLERSCTSTYVNELVVFV
VVGIDIGVPTVTIFISYALILTSILHIRSTEGRSKAFSTCSSHIIAVSLFFGSGAFMYLKPSSLLPMN
QGKVSSLFYTTVVPMLNPLIYSLRNKDVKVALKKSLSKKTFS*

FIG. 1 Continued

SEQ ID NOS 41, 51 and 31, respectively, in order of appearance

|  | 1 | 10 | 20 | 30 | 40 | 50 |
|---|---|---|---|---|---|---|
| CafaOR9.2.9 | MQSKFGANSTAITEFILLGLVQTPGLQPVVFVVFLFAYLVTVGGNLSILA | | | | | |
| CatG1 | MKSKFEYNRTAITEFILLGLVETPDLRPVVFVVFLLSYLLTVGGNLSILA | | | | | |
| HsOR17.1.11 | MQPESGANGTVIAEFILLGLLEAPGLQPVVFVLFLFAYLVTVRGNLSILA | | | | | |

|  | 60 | 70 | 80 | 90 | 100 |
|---|---|---|---|---|---|
| CafaOR9.2.9 | AILVEPKLHTPMYFFLGNLSVLDVGCITVTVPSMLARLLSHKRTVPYRAC | | | | |
| CatG1 | AILVEPKLHTPMYFFLGNLSVLDIGCITVTIPSMLARLLSHKRTVPYGAC | | | | |
| HsOR17.1.11 | AVLVEPKLHTPMYFFLGNLSVLDVGCISVTVPSMLSRLLSRKRAVPCGAC | | | | |

|  | 110 | 120 | 130 | 140 | 150 |
|---|---|---|---|---|---|
| CafaOR9.2.9 | LTQLFFFHLLVGVDCFLLTAMAYDRFLAICRPLTYSTQMSQTVQRILVVV | | | | |
| CatG1 | LTQLFFFHLLVGVDCFLLTAMAYDRFLAICQPLTYSTRMSQTVQRILVAV | | | | |
| HsOR17.1.11 | LTQLFFFHLFVGVDCFLLTAMAYDRFLAICRPLTYSTRMSQTVQRMLVAA | | | | |

|  | 160 | 170 | 180 | 190 | 200 |
|---|---|---|---|---|---|
| CafaOR9.2.9 | SWALAFTNALTHTVAIATLNFCGPNVINHFYCDLPQLFQLSCSSTQLNEL | | | | |
| CatG1 | SWALAFTNALTHTVAISTLNFCGPNVINHFYCDLPQLFQLSCSSTQLNEL | | | | |
| HsOR17.1.11 | SWACAFTNALTHTVAMSTLNFCGPNVINHFYCDLPQLFQLSCSSTQLNEL | | | | |

|  | 210 | 220 | 230 | 240 | 250 |
|---|---|---|---|---|---|
| CafaOR9.2.9 | LLFAVGFIMAGTPLALIITSYAHVAAAVLRIRSAEGRKKAFSTCGSHLTV | | | | |
| CatG1 | LLFAVGFIMAGTPLALIVTSYAHVTAAVLRIRSAEGRKKAFSTCGSHLTV | | | | |
| HsOR17.1.11 | LLFAVGFIMAGTPMALIVISYIHVAAAVLRIRSVEGRKKAFSTCGSHLTV | | | | |

|  | 260 | 270 | 280 | 290 | 300 |
|---|---|---|---|---|---|
| CafaOR9.2.9 | VAIFYGSGIFNYMRLGTAKHSDKDKGVGVFNTVINPMLNPIIYSLRNLDV | | | | |
| CatG1 | VAIFYGSGIFNYMRLGSAKLSDKDKAFGIFNTVINPMLNPIIYSLRNPDV | | | | |
| HsOR17.1.11 | VAIFYGSGIFNYMRLGSTKLSDKDKAVGIFNTVINPMLNPIIYSFRNPDV | | | | |

|  | 310 | 320 | 330 | 340 | 350 |
|---|---|---|---|---|---|
| CafaOR9.2.9 | QGALWRVLRGRQSLA | | | | |
| CatG1 | QGALWRVLMGRRPLA | | | | |
| HsOR17.1.11 | QSAIWRMLTGRRSLA | | | | |

FIG. 2A

SEQ ID NOS 52, 32 and 42, respectively, in order of appearance

|            | 1          10         20         30         40         50 |
|------------|------------------------------------------------------------|
| CatG2      | -MGNWSRGHIAEFVLVGFPTSPPLQCLLFVLFLAIYLLTLLENALIVSTV          |
| HsOR1.4.8  | -MRNLSGGHVEEFVLVGFPTTPPLQLLLFVLFFAIYLLTLLENALIVFTI          |
| CafaOR38.1.21 | MMGNLSGGHIADFILVGFPTSPPLQLLLFVLFFAIYLLTLLENALIVSTI       |

|            |           60         70         80         90        100 |
|------------|-----------------------------------------------------------|
| CatG2      | WLTPSLHRPMYFFLGHLSFLELWYINVTVPRLLGAFLTQERRVSYVGCMT         |
| HsOR1.4.8  | WLAPSLHRPMYFFLGHLSFLELWYINVTIPRLLAAFLTQDGRVSYVGCMT         |
| CafaOR38.1.21 | WLTPSLHRPMYFFLGHLSFLELWYINVTVPRLLGAFLTQDRRVSYVGCMT      |

|            |          110        120        130        140        150 |
|------------|-----------------------------------------------------------|
| CatG2      | QLYFFIALACTECVLLAVMAYDRYLAICEPLRYPSLMPSSLAIRLAASSW         |
| HsOR1.4.8  | QLYFFIALACTECVLLAVMAYDRYLAICGPLLYPSLMPSSLATRLAAASW         |
| CafaOR38.1.21 | QLYFFIALACTECVLLAVMAYDRYLAICEPLRYPSLMPSSLAIRLAASSW      |

|            |          160        170        180        190        200 |
|------------|-----------------------------------------------------------|
| CatG2      | GSGFLSSMMKLLFISRLSYCGPNVINHFFCDISPLLNLTCSDKEQAELVD         |
| HsOR1.4.8  | GSGFFSSMMKLLFISQLSYCGPNIINHFFCDISPLLNLTCSDKEQAELVD         |
| CafaOR38.1.21 | GGGFFSSMMKLLFISRLSYCGPNIINHFFCDISPLLNLTCSDKEQAELVD      |

|            |          210        220        230        240        250 |
|------------|-----------------------------------------------------------|
| CatG2      | FLLALVMILLPLLAVVSSYAAIMAAILRIPTAQGRRKAFSTCASHLAVVV         |
| HsOR1.4.8  | FLLALVMILLPLLAVVSSYTAIIAAILRIPTSRGHKAFSTCAAHLAVVV          |
| CafaOR38.1.21 | FLLALVMILLPLLAVVSSYAAIIATILRIPTAQGRRKAFSTCASHLAVVV      |

|            |          260        270        280        290        300 |
|------------|-----------------------------------------------------------|
| CatG2      | IYYSSTLFTYARPQAMYTFNHNKVISVLYTVIVPFLQPAIYCLRNKEVKD         |
| HsOR1.4.8  | IYYSSTLFTYARPRAMYTFNHNKIISVLYTIIVPFFQPAIYCLRNKEVKE         |
| CafaOR38.1.21 | IYYSSTLFTYARPRAMYTFNHNKIISVLYTVIVPFLQPAIYCLRNKEVKD      |

|            |          310        320        330        340        350 |
|------------|-----------------------------------------------------------|
| CatG2      | ALRKSVLGRCHYPRDVPD                                        |
| HsOR1.4.8  | AFRKTVMGRCHYPRDVQD                                        |
| CafaOR38.1.21 | ALRKLVLGRCHYPSDVPD                                     |

FIG. 3A

SEQ ID NOS 43, 53 and 33, respectively, in order of appearance

|              | 1          10         20         30         40         50 |
|--------------|---|
| CafaOR21.2.15 | -MVDPNGNESSATYFILIGLPGLEEAQFWLAFPLCSLYFIAVLGNLTIIY |
| CatG3        | -MVDTNGSESSATYFILIGLPGLEKAQFWLAFPLCSLYLIAVLGNLTVIC |
| HsOR11.3.14  | MMVDPNGNESSATYFILIGLPGLEEAQFWLAFPLCSLYLIAVLGNLTIIY |
|              | 60         70         80         90         100 |
| CafaOR21.2.15 | IVRTEHSLHEPMYVFLCMLSGLDILISTSSMPKMMAIFWFNSTTIQFDAC |
| CatG3        | IVRTEHRLHEPMYIFLCMLSGLDILISTSSMPRMMAIFWFNSTTIQFDAC |
| HsOR11.3.14  | IVRTEHSLHEPMYIFLCMLSGIDILISTSSMPKMLAIFWFNSTTIQFDAC |
|              | 110        120        130        140        150 |
| CafaOR21.2.15 | LLQMFAIHSLSGMESTVLLAMAFDRYVAICHPLRHATVLTLPRVMKIGMA |
| CatG3        | LLQMFAIHSLSGMESTVLLAMAFDRYVAICHPLRHATVLTLPRVTKIGVA |
| HsOR11.3.14  | LLQMFAIHSLSGMESTVLLAMAFDRYVAICHPLRHATVLTLPRVTKIGVA |
|              | 160        170        180        190        200 |
| CafaOR21.2.15 | AVVRGTALMAPLPVFIKRLPFCHSNILSHSYCLHQDVMKLACADIRVNII |
| CatG3        | AVVRGTSLMAPLPIFIKRLPFCRSNILSHSYCLHQDVMKLACADIRVNII |
| HsOR11.3.14  | AVVRGAALMAPLPVFIKQLPFCRSNILSHSYCLHQDVMKLACDDIRVNVV |
|              | 210        220        230        240        250 |
| CafaOR21.2.15 | YGLIVIISAIGLDSLLISLSYLLILKTVLGLTREAQAKAFGTCVSHVCAV |
| CatG3        | YGLIVIISAIGLDSLLISLSYLLILKTVLGLTREAQAKAFGTCVSHVCAV |
| HsOR11.3.14  | YGLIVIISAIGLDSLLISFSYLLILKTVLGLTREAQAKAFGTCVSHVCAV |
|              | 260        270        280        290        300 |
| CafaOR21.2.15 | FIFYVPFIGLSMVHRFGKRHDSFLPIIMANTYLLVPPVLNPIVYGVKTKE |
| CatG3        | FIFYVPFIGLSMVHRFGKRHDSLLPIIMANTYLLVPPVLNPIVYGVKTKE |
| HsOR11.3.14  | FIFYVPFIGLSMVHRFSKRRDSPLPVILANIYLLVPPVLNPIVYGVKTKE |
|              | 310        320        330        340        350 |
| CafaOR21.2.15 | IWQRILRLFHVTNHTSDL |
| CatG3        | IRQRILRLFHVTTHTSDP |
| HsOR11.3.14  | IRQRILRLFHVATHASEP |

FIG. 4A

SEQ ID NOS 34, 44 and 54 respectively, in order of appearance

|  | 1         10        20        30        40        50 |
|---|---|
| HsOR11.3.40 | -----MGDWNNSDAVEPIFILRGFPGLEYVHSWLSILFCLAYLVAFMGNV |
| CafaOR21.2.43 | MPRVTMVVWNNNNTLEPIFILKGFPGLECVHSWFSIPFCLAYLVAFIGNV |
| CatG4 | MPRFTMVVWNNNNTMEPIFILRGFHGLECVHSWISVPFCLAYLVAFIGNV |

|  | 60        70        80        90        100 |
|---|---|
| HsOR11.3.40 | TILSVIWIESSLHQPMYYFISILAVNDLGMSLSTLPTMLAVLWLDAPEIQ |
| CafaOR21.2.43 | TILSVIWIESSLHQPMYYFISILALTDLGMSMSTLPTMLAVLWLDAREIQ |
| CatG4 | TILSVIWIESSLHQPMYYFLSILALTDLGMSMSTLPTMLAVLWLDAREIQ |

|  | 110       120       130       140       150 |
|---|---|
| HsOR11.3.40 | ASACYAQLFFIIHTFTFLESSVLLAMAFDRFVAICHPLHYPTILTNSVIGK |
| CafaOR21.2.43 | ASACYAQLFFIIHTFTFLESSVLLAMAFDRFVAICRPLHYTTILNNSVIGK |
| CatG4 | ASACYAQLFFIIHTFTFLESSVLLAMAFDRFVAICRPLHYTTILNNSVIGK |

|  | 160       170       180       190       200 |
|---|---|
| HsOR11.3.40 | IGLACLLRSLGVVLPTPLLLRHYHYCHGNALSHAFCLHQDVLRLSCTDAR |
| CafaOR21.2.43 | IGLACLLRSMGVVLPTPLLLRHYHYCHVNALSHAFCLHQDVLKLSCSDAR |
| CatG4 | IGLACLLRSMGVVLPTPLLLRHYHYCHDNALSHTFCLHQDILKLSCSDAR |

|  | 210       220       230       240       250 |
|---|---|
| HsOR11.3.40 | TNSIYGLCVVIATLGVDSIFILLSYVLILNTVLDIASREEQLKALNTCVS |
| CafaOR21.2.43 | ISSVYGLCVVITTLGMDSVFILLSYVLILNAVLGIASHEERLKALNTCVS |
| CatG4 | ISSVYGLCVVITTLGVDSVCILLSYILILNAVLGIASHEERRKALNTCIS |

|  | 260       270       280       290       300 |
|---|---|
| HsOR11.3.40 | HICVVLIFFVPVIGVSMVHRFGKHLSPIVHILMADIYLLLPPVLNPIVYS |
| CafaOR21.2.43 | HICVVLIFFVPVIGVSMVHRFGKHLSPIVHIIMADIYLLFPPVLNPIVYS |
| CatG4 | HICVVLIFFVPVIGVSMVHRFGKHLSPRIHIIMADIYLLFPPVLNPIVYS |

|  | 310       320       330       340       350 |
|---|---|
| HsOR11.3.40 | VRTKQIRLGILHKFVLRRRF |
| CafaOR21.2.43 | VRTKQIRIRIFHKLRLGRRL |
| CatG4 | IKTKQIRLRILRRFGLRRGH |

FIG. 5A

SEQ ID NOS 35, 45 and 55, respectively, in order of appearance

|  | 1　　　　　　10　　　　　　20　　　　　　30　　　　　　40　　　　　　50 |
|---|---|
| HsOR14.1.27 | MFFIIHSLVTSVFLTALGPQNRTMHFVTEFVLLGFHGQREMQSCFFSFIL |
| CafaOR15.2.20 | MLIIIHSLVISASLTALESQNTTMRFVSEFVLLGFPGQREMQNFFFSFIL |
| CatGr5 | MFIVIHSFVTSISLTALESQNATMHFVTEFVLLGFPGQREMQNFFFSLIL |
|  | 60　　　　　　70　　　　　　80　　　　　　90　　　　　　100 |
| HsOR14.1.27 | VLYLLTLLGNGAIVCAVKLDRRLHTPMYILLGNFAFLEIWYISSTVPNML |
| CafaOR15.2.20 | VIYLLTLLGNGIIVCIVKWDKQLHTPMYIFLGNFAFLEIWYTSSTVPSML |
| CatGr5 | VVYLLTLLGNGVIVYVVKWDKRLHTPMYILLGNFAFLEIWYISSTVPNML |
|  | 110　　　　　120　　　　　130　　　　　140　　　　　150 |
| HsOR14.1.27 | VNILSEIKTISFSGCFLQFYFFFSLGTTECFFLSVMAYDRYLAICRPLHY |
| CafaOR15.2.20 | VNILSEIKTISFTGCFLQFYFFFSLGTTECFFLSVMAYDRYLAICRPLHY |
| CatGr5 | VTILSETKTISFTGCFLQFYFFFSLGTTECFFLSVMAYDRYLAICRPLHY |
|  | 160　　　　　170　　　　　180　　　　　190　　　　　200 |
| HsOR14.1.27 | PSIMTGKFCIILVCVCWVGGFLCYPVPIVLISQLPFCGPNIIDHLVCDPG |
| CafaOR15.2.20 | PSIMTGKLCVALVCVCWVSGFLCYPVPIVLISQLPFCGPNIIDHFVCDPG |
| CatGr5 | PSIMTGKLCVILVCVCWVSGFLCYPIPIVLISQLPFCGPNIIDHFVCDPG |
|  | 210　　　　　220　　　　　230　　　　　240　　　　　250 |
| HsOR14.1.27 | PLFALACISAPSTELICYTFNSMIIFGPFLSILGSYTLVIRAVLCIPSGA |
| CafaOR15.2.20 | PLFALACIPAPSTELLCYTFNSLIIFGPFLFILGSYTLVLRAVLRIPSGA |
| CatGr5 | PLFALACIPAPSTELICYTFNSVIIFGPFLSILGSYTLVLRAVLRIPSGA |
|  | 260　　　　　270　　　　　280　　　　　290　　　　　300 |
| HsOR14.1.27 | GRTKAFSTCGSHLMVVSLFYGTLMVMYVSPTSGNPAGMQKIITLVYTAMT |
| CafaOR15.2.20 | GRTKAFSTCGSHLMVVSLFYGTLMVMYVSPTSGNPTGMQKIITLVYTAVT |
| CatGr5 | GQTKAFSTCGSHLMVVSLFYGTLMVMYVSPTSGNPAGMQKIVTLVYTAVT |
|  | 310　　　　　320　　　　　330　　　　　340　　　　　350 |
| HsOR14.1.27 | PFLNPLIYSLRNKDMKDALKRVLGLTVSQN |
| CafaOR15.2.20 | PLLNPLIYSLRNKDMKDALKKVLGLRSNQN |
| CatGr5 | PLLNPLIYSLRNKDMKDALKKLLGLRSNPN |

FIG. 6A

SEQ ID NOS 36, 56 and 46, respectively, in order of appearance

|  | 1 | 10 | 20 | 30 | 40 | 50 |
|---|---|---|---|---|---|---|
| HsOR11.13.7 | -------MDQINHTNVKEFFFLELTRSRELEFFLFVVFFAVYVATVLGNA |
| CatGr6 | MEEGGPNHGQSNHTNVKEFVFLELTHFQELECFLFVAFLAVYVTTVLGNA |
| CafaOR18.3.11 | -------MGQSNHTNVKEFVFLKLTHFHELELFLFVVFLAVYVATVLGNV |

|  | 60 | 70 | 80 | 90 | 100 |
|---|---|---|---|---|---|
| HsOR11.13.7 | LIVVTITCESRLHTPMYFLLRNKSVLDIVFSSITVPKFLVDLLSDRKTIS |
| CatGr6 | LIVLTITYESHLHTPMYFLLRNKSVLDIVFSSVTVPKFLVDLLSERKTIS |
| CafaOR18.3.11 | LIVVTITCESHLHSPMYFLLRNKSVLDIVFSSVTVPKFLVDLLSERKTIS |

|  | 110 | 120 | 130 | 140 | 150 |
|---|---|---|---|---|---|
| HsOR11.13.7 | YNGCMAQIFFFHFAGGADIFFLSVMAYDRYLAIAKPLHYVTMMRKEVWVA |
| CatGr6 | YNGCMAQIFFFHFAGGADIFFLSVMAYDRYLAIAKPLHYVTIMKREVWVG |
| CafaOR18.3.11 | YNGCMAQIFFFHFAGGADIFFLSVMAYDRYLAIAKPLHYVTIMRRETWVG |

|  | 160 | 170 | 180 | 190 | 200 |
|---|---|---|---|---|---|
| HsOR11.13.7 | LVVASWVSGGLHSIIQVILMLPFPFCGPNTLDAFYCYVLQVVKLACTDTF |
| CatGr6 | LVVASWVGGGLHSIVQIILMLPLSFCGPNILDAFYCDVPQVVKLACTDTF |
| CafaOR18.3.11 | LVVASWVGGGLHSIVQVTLMLPLPFCGPNILDAFYCDVPQVIKLACTNTF |

|  | 210 | 220 | 230 | 240 | 250 |
|---|---|---|---|---|---|
| HsOR11.13.7 | ALELFMISNNGLVTLLWFLLLLGSYTVILVMLRSHSGEGRNKALSTCTSH |
| CatGr6 | ALELLMISNNGLVTLLWFLLLLGSYTVILVMLRSHSGAGRNKALSTCTSH |
| CafaOR18.3.11 | ALELLMISNNGLVTLLWFLLLLGSYTVILVMLRSHSGEGRNKALSTCTSH |

|  | 260 | 270 | 280 | 290 | 300 |
|---|---|---|---|---|---|
| HsOR11.13.7 | MLVVTLHFVPCVYIYCRPFMTLPMDTTISINNTVITPMLNPIIYSLRNQE |
| CatGr6 | ILVVTLHFVPCVYIYCRPFTTLPMDTAVSINNTVITPMLNPMIYTLRNQE |
| CafaOR18.3.11 | IFVVTLHFVPCVYIYCRPFITLPMDTVVSINNTVITPMLNPMIYTLRNQE |

|  | 310 | 320 | 330 | 340 | 350 |
|---|---|---|---|---|---|
| HsOR11.13.7 | MKSAMQRLQRRLGPSESRKWG |
| CatGr6 | MKSAMKRLHRRLGPSESSKWG |
| CafaOR18.3.11 | MKSAMKRLQRRLGPSESS--- |

FIG. 7A

SEQ ID NOS 47, 37 and 57, respectively, in order of appearance

|  | 1        10        20        30        40        50 |
|---|---|
| CafaOR15.3.1 | MEAPNQTRVTEFVFLGLTDNWALGTLLFVAFSLAYVLTLLGNTLIIVTTA |
| HsOR14.2.5 | MDSLNQTRVTEFVFLGLTDNRVLEMLFFMAFSAIYMLTLSGNILIIIATV |
| CatG7 | MDALNQTRVTEFVFLGLTDKWVLEILFFLAFSVTYVLTLLGNTLIIVTIV |

|  | 60        70        80        90        100 |
|---|---|
| CafaOR15.3.1 | LTRRLHTPMYFFLSNLSFIDTCHSSVTVPKMLEGLLRERKTISFDDCIAQ |
| HsOR14.2.5 | FTPSLHTPMYFFLSNLSFIDICHSSVTVPKMLEGLLLERKTISFDNCITQ |
| CatG7 | FTPRLHTPMYFFLSNLSFIDICHSSVTVPKMLEGLLLEIKTISFDNCIAQ |

|  | 110        120        130        140        150 |
|---|---|
| CafaOR15.3.1 | LFFLHLFACAEILLLTVMAYDRYVAICAPLRYPNVMSIRVCVQLVLALWW |
| HsOR14.2.5 | LFFLHLFACAEIFLLIIMAYDRYVAICTPLHYPNVMNMRVCIQLVFALWL |
| CatG7 | LFFLHLFACAEIFLLTIMAYDRYVAICAPLHYSNVMNMRVCVQLVFALWL |

|  | 160        170        180        190        200 |
|---|---|
| CafaOR15.3.1 | GGTVHSLVQTLLTIRLPYCGPNVIDSYFCDVPPVIKLACTDTYLTGVLIV |
| HsOR14.2.5 | GGTVHSLGQTFLTIRLPYCGPNIIDSYFCDVPLVIKLACTDTYLTGILIV |
| CatG7 | GATVHSLVQTFLTIRLPYCGPNIIDSYFCDVPPVIKLACTDTYLTGMLIV |

|  | 210        220        230        240        250 |
|---|---|
| CafaOR15.3.1 | SNSGTISLTCFLALVTSYTIILVSLRKQSAEGRRKALSTCSAHFMVVAFF |
| HsOR14.2.5 | TNSGTISLSCFLAVVTSYMVILVSLRKHSAEGRRKALSTCSAHFMVVALF |
| CatG7 | SNSGTISLTCFLALVTSYTVILVSLRKQSAEGRRKALSTCSAHFMVVAFF |

|  | 260        270        280        290        300 |
|---|---|
| CafaOR15.3.1 | FGPCIFIYTRPDTSFSIDKVVSVFYTVVTPLLNPLIYTLRNEEVKSAIKH |
| HsOR14.2.5 | FGPCIFIYTRPDTSFSIDKVVSVFYTVVTPLLNPFIYTLRNEEVKSAMKQ |
| CatG7 | FGPCIFIYTRPDTSFSIDKVVSVFYTVVTPLLNPLIYTLRNEEVKSAMKH |

|  | 310        320        330        340        350 |
|---|---|
| CafaOR15.3.1 | LRQKQVFS----- |
| HsOR14.2.5 | LRQRQVFFTKSYT |
| CatG7 | LRQRGFFMKSGT- |

FIG. 8A

SEQ ID NOS 38, 58 and 48, respectively, in order of appearance

|  | 1 10 20 30 40 50 |
|---|---|
| HsOR16.1.3 | MDGVNDSSLQGFVLMGISDHPQLEMIFFIAILFSYLLTLLGNSTIILLSR |
| CatG8 | MAEANNSFSEGCILMGISDHPQLEIVFFIVILFSYSLTLVGNSTTILLSC |
| CafaOR6.3.1 | MPEANDSFLEGFILMGISDHPQLEIIFFMVILFSYLLTLLGNSTIILLSW |

|  | 60 70 80 90 100 |
|---|---|
| HsOR16.1.3 | LEARLHTPMYFFLSNLSSLDLAFATSSVPQMLINLWGPGKTISYGGCITQ |
| CatG8 | LDARLHTPMYFFLSNLSSLDLAFTTSSVPQMLTNLWGPDKTISYAGCVIQ |
| CafaOR6.3.1 | LDARLHTPMYFFLSNLSTLDLAFTTSSVPQMLINLWGPDKTISYGGCVTQ |

|  | 110 120 130 140 150 |
|---|---|
| HsOR16.1.3 | LYVFLWLGATECILLVVMAFDRYVAVCRPLRYTAIMNPQLCWLLAVIAWL |
| CatG8 | LYVFLWLGATECILLVVMAFDRHVAVCQPLRYTVIVSPRLCRLLAAIAWL |
| CafaOR6.3.1 | LYVFLWLGATECILLVVMAFDRYVAVCRPLHYTTIMNPRLCWLLAAIAWL |

|  | 160 170 180 190 200 |
|---|---|
| HsOR16.1.3 | GGLGNSVIQSTFTLQLPLCGHRRVEGFLCEVPAMIKLACGDTSLNQAVLN |
| CatG8 | GGLSNSMIQSTFTLQLPLCGHRRVDNFLCEVPAMIKLACGDTSLNEAVLN |
| CafaOR6.3.1 | GGLSNSVIQSTFTLQLPLCGHRRVDNFLCEVPAMIKLACGDTSLNEVVLN |

|  | 210 220 230 240 250 |
|---|---|
| HsOR16.1.3 | GVCTFFTAVPLSIIVISYCLIAQAVLKIRSAEGRRKAFNTCLSHLLVVFL |
| CatG8 | GVCTFFTAVPLSIILISYCSIARAVLKIRSAEGQRKAFNTCLSHLVVVLL |
| CafaOR6.3.1 | GVCTFFTAVPLSVILISYCYIAQAVLKIHSVEGQRKAFNTCLSHLVVVLL |

|  | 260 270 280 290 300 |
|---|---|
| HsOR16.1.3 | FYGSASYGYLLPAKNSKQDQGKFISLFYSLVTPMVNPLIYTLRNMEVKGA |
| CatG8 | FYGSAIYGYLLPAKTSHQGQGKFISLFYSVVTPMVNPLIYTLRNKEVKAA |
| CafaOR6.3.1 | FYGSAIYGYLLPAKTSNQDQGKFISLFYSVVTPTVNPLIYTLRNREVKGA |

|  | 310 320 330 340 350 |
|---|---|
| HsOR16.1.3 | LRRLLGKGREVG |
| CatG8 | LRRLRGKGREFG |
| CafaOR6.3.1 | LRRLLGKGRSLG |

FIG. 9A

SEQ ID NOS 49, 59 and 39, respectively, in order of appearance

|   | 1 | 10 | 20 | 30 | 40 | 50 |
|---|---|---|---|---|---|---|
| CafaOR18.3.12 | ---MSTVKAWNSSSVTMFILLGFADHPELQTLLFVTFLSIYLVTLAWNLA | | | | | |
| CatG9 | MRSMSTAKAWNSSSVTMFIFLGFADHPELQTLLFVTFLGIYLVTLAWNLA | | | | | |
| HsOR11.13.6 | ---MSITKAWNSSSVTMFILLGFTDHPELQALLFVTFLGIYLTTLAWNLA | | | | | |

|   | 60 | 70 | 80 | 90 | 100 |
|---|---|---|---|---|---|
| CafaOR18.3.12 | LIFLIRSDPHLHTPMYFFLSNLSFIDICYSSTVAPKMLTDFFQEQKTISF | | | | |
| CatG9 | LIFLIRGDPRLHTPMYFFLSNLSFIDICYSSTVAPKMLTDFFWEQKTISF | | | | |
| HsOR11.13.6 | LIFLIRGDTHLHTPMYFFLSNLSFIDICYSSAVAPNMLTDFFWEQKTISF | | | | |

|   | 110 | 120 | 130 | 140 | 150 |
|---|---|---|---|---|---|
| CafaOR18.3.12 | LGCAAQFFFFVSMGLTECFLLTAMAYDRYAAISNPLLYTAIMSQGLCTRM | | | | |
| CatG9 | LGCAAQFFFFVSMGLTECFLLTAMAYDRYAAISNPLLYTAIMSQGLCTRM | | | | |
| HsOR11.13.6 | VGCAAQFFFFVGMGLSECLLLTAMAYDRYAAISSPLLYPTIMTQGLCTRM | | | | |

|   | 160 | 170 | 180 | 190 | 200 |
|---|---|---|---|---|---|
| CafaOR18.3.12 | VLGAYVGGFLSSLIQAISIFQLHFCGPNIINHFFCDLPPVLALSCSDTFP | | | | |
| CatG9 | VLGAYVGGFLSSLIQASSIFQLHFCGPNIINHFFCDLPPVLALSCSDTFP | | | | |
| HsOR11.13.6 | VVGAYVGGFLSSLIQASSIFRLHFCGPNIINHFFCDLPPVLALSCSDTFL | | | | |

|   | 210 | 220 | 230 | 240 | 250 |
|---|---|---|---|---|---|
| CafaOR18.3.12 | SQVVNFLIVITVGGTSFLILLISYSYIGAAVLKIRSVEGRRKAFNTCASH | | | | |
| CatG9 | SQVVNFLVVVTIGGTSFLILIISYSYIGTAVLKIRSVEGRKKAFSTCASH | | | | |
| HsOR11.13.6 | SQVVNFLVVVTVGGTSFLQLLISYGYIVSAVLKIPSAEGRWKACNTCASH | | | | |

|   | 260 | 270 | 280 | 290 | 300 |
|---|---|---|---|---|---|
| CafaOR18.3.12 | LMVVTLLFGTALFMYLRPSSSYSLARDKVVSVFYSLVIPMLNPLIYSLRN | | | | |
| CatG9 | LMVVTLLFGTALFMYLRPSSSYSLGRDKVVSVFYSLVIPMLNPLIYSLRN | | | | |
| HsOR11.13.6 | LMVVTLLFGTALFVYLRPSSSYLLGRDKVVSVFYSLVIPMLNPLIYSLRN | | | | |

|   | 310 | 320 | 330 | 340 | 350 |
|---|---|---|---|---|---|
| CafaOR18.3.12 | RDIKDALWKALEKKKVFFLDHD | | | | |
| CatG9 | REIKDALWKVLEKKKLFS---- | | | | |
| HsOR11.13.6 | KEIKDALWKVLERKKVFS---- | | | | |

FIG. 10A

SEQ ID NOS 60, 3,809, 50 and 40, respectively, in order of appearance

|  | 1 10 20 30 40 50 |
|---|---|
| CatG10 | MPLMRMAAENS-SVTEFILAGLTNQPGLRMPLFFLFLGFYVVTVMGNLGL |
| Olfr145 | -----MATENA-SVPEFILAGLTDQPGLRMPLFFLFLGFYMVTMVGNLGL |
| CafaOR5.2.5 | MPLMRMAAENS-SVTEFILSGLTNQPGLQIPLFFLFLGFYVVTVVGNLGL |
| HsOR11.18.36 | -----MAAENSSFVTQFILAGLTDQPGVQIPLFFLFLGFYVVTVVGNLGL |
|  | 60 70 80 90 100 |
| CatG10 | ITLIGLNSHLHTPMYFFLFNLSFIDFQYSTVITPKMLMSFVS-KNTIAYA |
| Olfr145 | ITLIGLNSHLHTPMYFFLFNLSLIDFQYSTVITPKMLMSFVSKKNIISYS |
| CafaOR5.2.5 | ITLIGLNSHLHTPMYFFLFNLSFIDFQYSTVITPKMLMNFVLRKNVISYA |
| HsOR11.18.36 | ITLIRLNSHLHTPMYFFLYNLSFIDFQYSSVITPKMLMSFVLKKNSISYA |
|  | 110 120 130 140 150 |
| CatG10 | GCMTQLFFFLFFVVSEEFILSAMAYDRYTAICNPLVYTATMSPQVCSLLL |
| Olfr145 | GCMTQLFFFLFFVVSEEFILSAMAYDRYVAICNPLMYTVTMSPQVCLLLL |
| CafaOR5.2.5 | GCMTQLFFFLFFVVSEEFILSAMAYDRYAAICNPLVYTATMSPQVCFLLL |
| HsOR11.18.36 | GCMTQLFFFLFFVVSEEFILSAMAYDRYVAICNPLLYMVTMSPQVCFLLL |
|  | 160 170 180 190 200 |
| CatG10 | LGVYVMGFAGAMAHTTCMVRLTFCANNLVDHYMCDILPLLERSCTSTYVN |
| Olfr145 | LGVYVMGFAGAMAHTAFMVKLTFCADKLVNHYMCDILPLLERSCTSTYVN |
| CafaOR5.2.5 | LGVYVMGFAGAMAHTVCMVRLTFCANNLVDHYMCDILPLLERSCTSTYVN |
| HsOR11.18.36 | LGVYGMGFAGAMAHTACMMGVTFCANNLVNHYMCDILPLLECACTSTYVN |
|  | 210 220 230 240 250 |
| CatG10 | ELVVFVVVGIDIGVPTVTIFISYALILTSILHIRSTEGRSKAFSTCSSHI |
| Olfr145 | ELVVFIVVGIDIGVPTVTIFISYALILSSILRISSTEGRSKAFSTCSSHI |
| CafaOR5.2.5 | ELVVFIVVGIDIGVPTVTIFISYALILSSILRIHSTKGRSKAFSTCSSHI |
| HsOR11.18.36 | ELVVFVVVGIDIGVPTVTIFISYALILSSIFHIDSTEGRSKAFSTCSSHI |
|  | 260 270 280 290 300 |
| CatG10 | IAVSLFFGSGAFMYLKPSSLLPMNQGKVSSLFYTTVVPMLNPLIYSLRNK |
| Olfr145 | IAVSLFFGSGAFMYLKPSSLLPMNQGKVSSLFYTIVVPMLNPLIYSLRNK |
| CafaOR5.2.5 | IAVSLFFGSGAFMYLKPSSLLPMNQGKVSSLFYTIVVPMLNPLIYSLRNK |
| HsOR11.18.36 | IAVSLFFGSGAFMYLKPFSLLAMNQGKVSSLFYTTVVPMLNPLIYSLRNK |
|  | 310 320 330 340 350 |
| CatG10 | DVKVALKKSLSKKTFS |
| Olfr145 | DVKVALRKTLSRSSFS |
| CafaOR5.2.5 | DVKIALKKTLSKKPFS |
| HsOR11.18.36 | DVKVALKKILNKNAFS |

FIG. 11A

| Dog OR | | Odorant | Response | EC$_{50}$ | Emax | Assay |
|---|---|---|---|---|---|---|
| OR_2 | OR6P1 | p-Anisaldehyde | Active | 30μM | 63.5 | CRE-NanoLuc |
| | | 4-Ethoxybenzaldehyde | Active | 35μM | 39 | CRE-NanoLuc |
| OR_3 | OR51E1 | Isovaleric acid | Active | 30μM | 91 | CNG |
| | | 4-Methylvaleric acid | Active | 35μM | 90 | CNG |
| | | Hexanoic acid | Active | 90μM | 74 | CNG |
| | | 3-Methyl-2-hexanoic acid | Low activity | >100μM | 8 | CNG |
| OR_4 | OR51L1 | Hexanoic acid | Inactive | — | 1.6 | CRE-NanoLuc |
| | | Allyl phenylacetate | Active | >100μM | 2.9 | CRE-NanoLuc |
| OR_8 | OR2C1 | Nonanethiol | Active | 2μM | 6.3 | CNG |
| | | Isovaleric acid | Active | n.d. | 6.8 | CRE-NanoLuc |
| OR_9 | OR5A1 | Citral | Active | 1μM | 3.6 | CRE-NanoLuc |
| | | Amyl acetate | Active | 2μM | 6.1 | CRE-NanoLuc |
| | | β-Ionone | Active | 1μM | 6.1 | CRE-NanoLuc |
| OR_10 | OR8B8 | Acetophenone | Active | 110μM | 33 | CRE-NanoLuc |
| | | Propriophenone | Active | 75μM | 9.6 | CRE-NanoLuc |
| | | Coumarin | Active | 125μM | 44 | CRE-NanoLuc |

Inactive | Doubtful response, very low activity | Active, but low activity and/or EC$_{50}$ cannot be determined | Active

FIG. 16

| Cat OR | | Odorant | Response | EC$_{50}$ | Emax | Assay |
|---|---|---|---|---|---|---|
| OR_2 | OR6P1 | p-Anisaldehyde | Active | ~100μM | 17.3 | CRE-NanoLuc |
| | | 4-Ethoxybenzaldehyde | Active | 165μM | 13.1 | CRE-NanoLuc |
| OR_3 | OR51E1 | Isovaleric acid | Active | 45μM | 93 | CNG |
| | | 4-Methylvaleric acid | Active | 45μM | 78 | CNG |
| | | Hexanoic acid | Active | 125μM | 41 | CNG |
| | | 3-Methyl-2-hexanoic acid | Low activity | >100μM | 3 | CNG |
| OR_4 | OR51L1 | Hexanoic acid | Active | >50μM | 3 | CRE-NanoLuc |
| | | Allyl phenylacetate | Active | >100μM | 8.6 | CRE-NanoLuc |
| OR_8 | OR2C1 | Nonanethiol | Active | 2μM | 4.5 | CNG |
| OR_9 | OR5A1 | Isovaleric acid | Active | 20μM | 78 | CRE-NanoLuc |
| | | Citral | Active | 4μM | 43 | CRE-NanoLuc |
| | | Amyl acetate | Active | 5μM | 64 | CRE-NanoLuc |
| | | β-Ionone | Active | 3μM | 84 | CRE-NanoLuc |
| OR_10 | OR8B8 | Acetophenone | Inactive | — | 1.4 | CRE-NanoLuc |
| | | Propriophenone | Inactive | — | 1.1 | CRE-NanoLuc |
| | | Coumarin | Active | n.d. | 2.7 | CRE-NanoLuc |

Inactive | Doubtful response, very low activity | Active, but low activity and/or EC$_{50}$ cannot be determined | Active

FIG. 17

SCREENING METHODS USING OLFACTORY RECEPTORS AND NOVEL COMPOUNDS IDENTIFIED USING THE SAME

CROSS-REFERENCE TO RELATED APPLICATION

This application is a U.S. National Stage Patent Application under 35 U.S.C. § 371 of International Application No. PCT/US2017/054620, filed on Sep. 29, 2017, which claims priority to U.S. Provisional Application No. 62/402,823 filed on Sep. 30, 2016, the contents of each of which are incorporated by reference in their entireties, and to which priority is claimed.

SEQUENCE LISTING

The application contains a Sequence Listing which has been filed electronically in ASCII format and is hereby incorporated by reference in its entirety. Said ASCII copy, created on Mar. 15, 2019, is named 0692690314SL.txt and is 7,123,648 bytes in size. The Sequence Listing, electronically filed herewith, does not extend beyond the scope of the specification and thus does not contain new matter.

FIELD

The presently disclosed subject matter relates to the use of olfactory receptors (ORs) for the identification of olfactory modulators. The presently disclosed subject matter further relates to the use of olfactory receptors to screen raw materials for making pet food products, as well as screening finished pet food products, for the presence of olfactory modulating compounds.

BACKGROUND

Olfactory profiles for edible compositions can be characterized by a set of psychophysical descriptors, such as, for example, one or more of a fruity, floral, honey, fatty, minty and metallic smell. In certain embodiments, a combination of different odorants can be perceived as a new odor object. Chemical compounds that elicit these odor senses are often referred to as odorants. Without being bound by theory, it is hypothesized that odors are sensed by olfactory receptors in the nasal cavity and throat which transmit signals to the brain where the odorants and resulting olfactory profiles are registered. Olfactory receptors comprise a large class of G-protein coupled receptors (GPCR) that detect compounds associated with odor sensory perception.

Pet food manufacturers have a long-standing desire to provide pet food products that have high nutritional value. In addition, and with particular regard to cat and dog foods, pet food manufacturers desire a high degree of palatability so that pets can receive the full nutritional benefit from their food. Domestic animals are notoriously finicky in their food preferences, and often refuse to eat a pet food product that it has accepted over time or refuse to eat any more than a minimal amount of a pet food product. This phenomenon may be, in part, due to the subtle differences in the sensory profiles of the raw material, which can be perceived by the domestic animals because of their gustatory and olfactory systems. As a result, pet owners frequently change types and brands of pet food in order to maintain their pets in a healthy and contented condition.

While there have been recent advances in odor and flavor technologies, there remains a need for methods of screening raw materials that are used to make pet food product, and for screening finished pet food products, to ensure that the most palatable products and processes for making the pet food products are used. There also remains a need for compounds that can enhance or modify the palatability of pet food products by enhancing or modifying the odor, texture and/or flavor profiles of the pet food products. The enhancement or modification can be used to increase the intensity of a desirable attribute, to replace a desirable attribute that is not present or somehow lost in the pet food product, or to decrease the intensity of an undesirable attribute. In particular, it is desirable to decrease the presence or intensity of undesirable repellant odors in a pet food product. Similarly, there is a need to increase the acceptance of pet medications by enhancing or modifying the palatability of the medications.

The pet care industry is also concerned with developing odor deterrents that can effectively discourage a pet from scratching, chewing, licking, or ingesting things that harm the health of the animal or the property of the owners. While it is known that certain odorants can be effective to deter pets, there is a significant variation in pets' reactions to these odor deterrents. Thus, there exists a need for compounds that effectively impart an undesirable odor to harmful or toxic objects.

Therefore, there remains a need in the art for methods to screen raw pet food materials (e.g. new protein sources), as well as final pet food products, to provide fragrant, palatable and nutritious pet food. There also remains a need to identify compounds that enhance, decrease, or otherwise modulate the palatability and/or deterrence of pet food products, or objects, and for odor compositions comprising these compounds.

SUMMARY OF THE INVENTION

The presently disclosed subject matter provides methods for identifying compounds that enhance, increase, decrease and/or modulate the activity and/or expression of an olfactory receptor. In certain embodiments, the methods entail screening for compounds that modulate the olfactory receptor activity and/or expression in a pet food product or medicine, or in raw materials used to make the pet food product or medicine. The presently disclosed subject matter also provides compounds that enhance, increase, decrease and/or modulate the activity and/or expression of an olfactory receptor identified by said methods. In certain embodiments, the olfactory receptor is a canine or feline receptor.

In certain embodiments, the method for identifying compounds that enhance, increase, decrease and/or modulate the activity and/or expression of an olfactory receptor comprises expressing an olfactory receptor having a nucleotide sequence set forth in any one or more of SEQ ID NOs:11-30, or any one or more of the nucleotide sequences set forth in SEQ ID NOs:61-3808, or a fragment or variant thereof, in a cell. The method can further comprise contacting the cell expressing the olfactory receptor with a sample (e.g., pet food raw material, finished pet food, or a test compound) and determining the activity and/or expression of the olfactory receptor in the presence of the sample as compared to the activity and/or expression of the receptor in the absence of the sample. In certain embodiments, the activity and/or expression of the olfactory receptor is determined in the presence of the sample and an olfactory receptor agonist.

In certain embodiments, a method for identifying compounds that enhance, increase, decrease and/or modulate the activity and/or expression of an olfactory receptor comprises expressing an olfactory receptor having an amino acid sequence set forth in any one or more of SEQ ID NOs:41-60, or any one or more of amino acid sequence set forth in SEQ ID NOs:61-3808, or a fragment or variant thereof, in a cell. The method can further comprise contacting the cell expressing the olfactory receptor with a sample (e.g., pet food raw material, finished pet food, or a test compound) and determining the activity and/or expression of the olfactory receptor in the presence of the sample as compared to the activity and/or expression of the receptor in the absence of the sample. In certain embodiments, the activity and/or expression of the olfactory receptor is determined in the presence of the sample and an olfactory receptor agonist.

In certain embodiments, the present disclosure provides a method for identifying a composition that modulates the activity of an olfactory receptor comprising (a) contacting an olfactory receptor agonist with an olfactory receptor, (b) determining the activity of the olfactory receptor, (c) contacting a test agent with the olfactory receptor, (d) determining the activity of the olfactory receptor, and (e) selecting the test agent as the composition when the activity of (d) is greater than or less than the activity of (b).

In certain embodiments, the olfactory receptor agonist is selected from the group consisting of trifernal, isovaleric acid, 3-methyl-2-hexanoic acid, alpha-ionone, hexyl acetate, amyl mercaptan, helional, para-anisaldehyde, 4-ethoxybenzaldehyde, menthol, methyl-eugenol, methyl-salicylate, phenylacetaldehyde, beta-ionone, amyl acetate, nonanethiol, acetophenone, coumarin, lilial, meta-anisaldehyde, 4-methyl-valeric acid, pentanol, allyl-phenylacetate, hexanoic acid, alpha-ionone, citral, isoamylacetate, octanethiol, propiophenone, 7-methoxycoumarin and combinations thereof.

In certain non-limiting embodiments, the methods for identifying a compound that modulates the activity of an olfactory receptor described herein utilize cells expressing an olfactory receptor that is native to the cells. Examples of such cells expressing a native olfactory receptor include, for example but not limited to, human, dog and/or cat olfactory cells (e.g., olfactory receptor cells). In certain embodiments, the human, dog and/or cat olfactory cells expressing an olfactory receptor are isolated from a human, dog and/or cat and cultured in vitro. In certain embodiments, the olfactory receptor cells can be immortalized, for example, such that the cells isolated from a human, dog and/or cat can be propagated in culture.

In certain embodiments, the cell expresses a calcium-binding photoprotein, a cyclic nucleotide gated (CNG) channel, a cAMP response element (CRE)-containing luciferase reporter, a GloSensor luciferase, or a PKA-NanoBiT system. In certain embodiments, the calcium-binding photoprotein is selected from the group consisting of clytin, aequorin, obelin, any recombinant or isolated versions thereof, and any combinations thereof. In certain embodiments, an intracellular calcium level is monitored by luminescence detection or fluorescence detection. In certain embodiments, the fluorescence detection comprises a calcium sensitive fluorescent dye selected from the group consisting of Fura-2 AM, Fura-2 pentapotassium, Fura Red AM, Indo-1 AM, Indo-1 pentapotassium, Fluo-3, Fluo-4, Fluo-8, Calcium Green-1, Calcium 3, Calcium 4, Calcium 5, Rhod-2, derivatives thereof and combinations thereof.

In certain embodiments, the test agent has an EC50 value of no more than about 200 µM. In certain embodiments, the test agent has an Emax value of no less than about 2.0.

The present disclosure also provides for methods for identifying compounds that enhance, increase, decrease and/or modulate the activity and/or expression of an olfactory receptor, wherein the assay is conducted using a cell-free assay, for example, wherein the olfactory receptor is bound to or otherwise attached to a substrate.

The present disclosure also provides for methods for identifying compounds that enhance, increase, decrease and/or modulate the activity and/or expression of an olfactory receptor, wherein the assay is conducted using an in silico model of the olfactory receptor, for example, wherein the olfactory receptor is modeled using a computer program and binding of the compound to the receptor is predicted through docking algorithms.

The presently disclosed subject matter further provides a method for making a palatable pet food product, wherein the raw materials used to generate the pet food product are screened to determine if they contain compounds that enhance, increase, decrease and/or modulate the activity and/or expression of an olfactory receptor. In certain embodiments, the raw material is a novel protein source. In certain embodiments the raw material is a protein source that is not commonly consumed in the human food chain. In certain embodiments, a raw pet food product that comprises a compound that increases the activity and/or expression of an olfactory receptor (for example, as compared to an olfactory receptor not contacted with the raw material) is not selected for use in generating a finished pet food product. In certain embodiments, a raw pet food product that comprises a compound that increases the activity and/or expression of an olfactory receptor (for example, as compared to an olfactory receptor not contacted with the raw material) is selected for use in generating a finished pet food product. In other embodiments, a raw pet food material that does not increase the activity and/or expression of an olfactory receptor (or that reduces the activity of an olfactory receptor, for example, in the presence of an olfactory receptor agonist) is selected for generating a finished pet food product. In other embodiments, a raw pet food material that does not increase the activity and/or expression of an olfactory receptor (or that reduces the activity of an olfactory receptor, for example, in the presence of an olfactory receptor agonist) is not selected for generating a finished pet food product.

The presently disclosed subject matter further provides a method for making a palatable pet food product, wherein the finished pet food product is screened to determine if it contains compounds that enhance, increase, decrease and/or modulate the activity and/or expression of an olfactory receptor. In certain embodiments, the compounds are formed during the manufacturing process. In one embodiment, a finished pet food product that comprises a compound that increases the activity and/or expression of an olfactory receptor (for example, as compared to an olfactory receptor not contacted with the finished pet food product) is supplemented with one or more compounds that decrease the activity and/or expression of an olfactory receptor (for example, an antagonist compound). In one embodiment, a finished pet food product that comprises a compound that decreases the activity and/or expression of an olfactory receptor (for example, as compared to an olfactory receptor not contacted with the finished pet food product, or as compared to an olfactory receptor contacted with an agonist) is supplemented with one or more compounds that increases the activity and/or expression of an olfactory receptor (for example, an agonist compound).

The presently disclosed subject matter further provides a method for making a palatable pet medicine product, wherein the finished pet medicine product is screened to determine if it contains compounds that enhance, increase, decrease and/or modulate the activity and/or expression of an olfactory receptor. In certain embodiments, the compounds are formed during the manufacturing process. In one embodiment, a finished pet medicine product that comprises a compound that increases the activity and/or expression of an olfactory receptor (for example, as compared to an olfactory receptor not contacted with the finished pet medicine product) is supplemented with one or more compounds that decrease the activity and/or expression of an olfactory receptor (for example, an antagonist compound). In one embodiment, a finished pet medicine product that comprises a compound that decreases the activity and/or expression of an olfactory receptor (for example, as compared to an olfactory receptor not contacted with the finished pet medicine product, or as compared to an olfactory receptor contacted with an agonist) is supplemented with one or more compounds that increases the activity and/or expression of an olfactory receptor (for example, an agonist compound).

The presently disclosed subject matter further provides flavor compositions that comprise a modulator of an olfactory receptor, e.g., an agonist and/or an antagonist and/or an allosteric modulator and/or an inverse agonist, identified according to the methods described herein.

In certain embodiments, said compounds can be used in methods for maintaining the health of an animal by imparting a repellant odor and/or decreasing the palatability of an object or surface. In certain embodiments, the method comprises applying an odor deterrent product comprising a compound as described herein to the object or surface. In certain embodiments, the object is harmful to the health of the animal or toxic to the animal.

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

BRIEF DESCRIPTION OF THE DRAWINGS

FIG. 1 shows human, canine and feline olfactory receptor (OR) nucleotide sequences (SEQ ID NOs:1-30) along with their corresponding amino acid sequences (SEQ ID NOs: 31-60). The sequences include the human olfactory receptor HsOR17.1.11 (hOR3A1), HsOR1.4.8 (hOR6P1), HsOR11.3.14 (hOR51E1), HsOR11.3.40 (hOR51L1), HsOR14.1.27 (hOR11H6), HsOR11.13.7 (hOR4D6), HsOR14.2.5 (hOR4E2), HsOR16.1.3 (hOR2C1), HsOR11.13.6 (hOR5A1), and HsOR11.18.36 (hOR8B8); the canine olfactory receptor CafaOR9.2.9, CafaOR38.1.21, CafaOR21.2.15, CafaOR21.2.43, CafaOR15.2.20, CafaOR18.3.11, CafaOR15.3.1, CafaOR6.3.1, CafaOR18.3.12, and CafaOR5.2.5; and the feline olfactory receptor E1:13347030-13347977, F1:65134904-65135858, D1:62955839-62956792, D1:63312327-63313289, B3:72908295-72909287, D1:105486528-105487493, B3:74116955-74117893, E3:40237904-40238842, D1:105462554-105463512, and D1:21266824-21267768.

FIGS. 2A-2E. A) Alignment of canine, feline, and human olfactory receptor sequences as labeled (SEQ ID NOs:41, 51 and 31, respectively, in order of appearance). The active site, defined as those residues within 9 Å(1 Å=$10^{-10}$ m) of any heavy atom in the ligand, is highlighted by black boxes over the sequence alignment. Residues N-terminal to the seven-transmembrane domain are included for ease of identifying residues by number within the protein sequence. Residues C-terminal to the seven-transmembrane domain are not included in the alignments. B) Chemical structure of the ligand (Lilial) used in the modeling. C) A near view of the ligand bound to the canine receptor CafaOR9.2.9. The figure illustrates where the compound binds within the seven-helical transmembrane-domain (7TM) of the chosen receptor. D) A near view of the ligand bound to the receptor that illustrates residues defining the environment of the bound ligand. A smaller number of residues is chosen relative to those highlighted in A) for ease of viewing. E) An interaction map of the ligand bound the receptor that illustrates residues defining the environment of the bound ligand. Residues that can contact the ligand are shown as circles. Dark circles are those that interact primarily through van der Waals or hydrophobic contacts. Lighter circles are those that interact with ligand via other interaction types such as hydrogen bonds, ring stacking, salt bridges. When present, a halo around a circle indicates that there is significant loss of water-accessible surface area for that residue on ligand binding. When present, hydrogen bonds are indicated by dotted lines. Residues that can potentially make hydrogen bond with the ligand include Gln103. Additional residues that can potentially make ring stacking, salt bridges, hydrogen bonding, pi interactions, charged interactions, van der Waals interactions, or hydrophobic interactions with the ligand include Leu104, Lys275, Arg87, Val81, Met84, Val279, Tyr262, Met209, Gly258, Val111, Tyr255, Thr282, Phe107 and Thr80.

FIGS. 3A-3E. A) Alignment of canine, feline, and human olfactory receptor sequences as labeled (SEQ ID NOs: 52, 32 and 42, respectively, in order of appearance). The active site, defined as those residues within 9 Å(1 Å=$10^{-10}$ m) of any heavy atom in the ligand, is highlighted by black boxes over the sequence alignment. Residues N-terminal to the seven-transmembrane domain are included for ease of identifying residues by number within the protein sequence. Residues C-terminal to the seven-transmembrane domain are not included in the alignments. B) Chemical structure of the ligand (p-Anisaldehyde) used in the modeling. C) A near view of the ligand bound to the canine receptor CafaOR38.1.21. The figure illustrates where the compound binds within the seven-helical transmembrane-domain (7TM) of the chosen receptor. D) A near view of the ligand bound to the receptor that illustrates residues defining the environment of the bound ligand. A smaller number of residues is chosen relative to those highlighted in A) for ease of viewing. E) An interaction map of the ligand bound the receptor that illustrates residues defining the environment of the bound ligand. Residues that can contact the ligand are shown as circles. Dark circles are those that interact primarily through van der Waals or hydrophobic contacts. Lighter circles are those that interact with ligand via other interaction types such as hydrogen bonds, ring stacking, salt bridges. When present, a halo around a circle indicates that there is significant loss of water-accessible surface area for that residue on ligand binding. When present, hydrogen bonds are indicated by dotted lines. Residues that can potentially make hydrogen bond with the ligand include Lys273. Additional residues that can potentially make ring stacking, salt bridges, hydrogen bonding, pi interactions, charged interactions, van der Waals, or hydrophobic interactions with the ligand include Thr78, Leu82, Tyr260, Thr256, Tyr253 and Phe105.

FIGS. 4A-4E. A) Alignment of canine, feline, and human olfactory receptor sequences as labeled (SEQ ID NOs: 43, 53 and 33, respectively, in order of appearance). The active site, defined as those residues within 9 Å(1 Å=$10^{-10}$ m) of any heavy atom in the ligand, is highlighted by black boxes over the sequence alignment. Residues N-terminal to the seven-transmembrane domain are included for ease of identifying residues by number within the protein sequence. Residues C-terminal to the seven-transmembrane domain are not included in the alignments. B) Chemical structure of the ligand ((+)-menthol) used in the modeling. C) A near view of the ligand bound to the canine receptor CafaOR21.2.15. The figure illustrates where the compound binds within the seven-helical transmembrane-domain (7TM) of the chosen receptor. D) A near view of the ligand bound to the receptor that illustrates residues defining the environment of the bound ligand. A smaller number of residues is chosen relative to those highlighted in A) for ease of viewing. E) An interaction map of the ligand bound the receptor that illustrates residues defining the environment of the bound ligand. Residues that can contact the ligand are shown as circles. Dark circles are those that interact primarily through van der Waals or hydrophobic contacts. Lighter circles are those that interact with ligand via other interaction types such as hydrogen bonds, ring stacking, salt bridges. When present, a halo around a circle indicates that there is significant loss of water-accessible surface area for that residue on ligand binding. When present, hydrogen bonds are indicated by dotted lines. Residues that can potentially make ring stacking, salt bridges, hydrogen bonding, pi interactions, charged interactions, van der Waals, or hydrophobic interactions with the ligand include Met83, His107, Ile106, Leu182, Asn197, Gly201, Val204, Ser260, Phe256 and Leu273. Additional residues that can potentially make van der Waals or hydrophobic interaction with the ligand include Met103.

FIGS. 5A-5E. A) Alignment of canine, feline, and human olfactory receptor sequences as labeled (SEQ ID NOs:34, 44 and 54, respectively, in order of appearance). The active site, defined as those residues within 9 Å(1 Å=$10^{-10}$ m) of any heavy atom in the ligand, is highlighted by black boxes over the sequence alignment. Residues N-terminal to the seven-transmembrane domain are included for ease of identifying residues by number within the protein sequence. Residues C-terminal to the seven-transmembrane domain are not included in the alignments. B) Chemical structure of the ligand (Androstadienone) used in the modeling. C) A near view of the ligand bound to the canine receptor CafaOR21.2.43. The figure illustrates where the compound binds within the seven-helical transmembrane-domain (7TM) of the chosen receptor. D) A near view of the ligand bound to the receptor that illustrates residues defining the environment of the bound ligand. A smaller number of residues is chosen relative to those highlighted in A) for ease of viewing. E) An interaction map of the ligand bound the receptor that illustrates residues defining the environment of the bound ligand. Residues that can contact the ligand are shown as circles. Dark circles are those that interact primarily through van der Waals or hydrophobic contacts. Lighter circles are those that interact with ligand via other interaction types such as hydrogen bonds, ring stacking, salt bridges. When present, a halo around a circle indicates that there is significant loss of water-accessible surface area for that residue on ligand binding. When present, hydrogen bonds are indicated by dotted lines. Residues that can potentially make ring stacking, salt bridges, hydrogen bonding, pi interactions, charged interactions, van der Waals, or hydrophobic interactions with the ligand include Met80, Met88, Leu108, Ile111, His112, Thr115, Val209, Val210, Thr213, Leu214, Val262, Ile263, Ser266, Ile281, Ala284, and Leu288. Additional residues that can potentially make van der Waals or hydrophobic interaction with the ligand include Asp285.

FIGS. 6A-6E. A) Alignment of canine, feline, and human olfactory receptor sequences as labeled (SEQ ID NOs:35, 45 and 55, respectively, in order of appearance). The active site, defined as those residues within 9 Å(1 Å=$10^{-10}$ m) of any heavy atom in the ligand, is highlighted by black boxes over the sequence alignment. Residues N-terminal to the seven-transmembrane domain are included for ease of identifying residues by number within the protein sequence. Residues C-terminal to the seven-transmembrane domain are not included in the alignments. B) Chemical structure of the ligand (isobuteric acid) used in the modeling. C) A near view of the ligand bound to the feline receptor catGr5 (B3: 72908295-72909287). The figure illustrates where the compound binds within the seven-helical transmembrane-domain (7TM) of the chosen receptor. D) A near view of the ligand bound the receptor that illustrates residues defining the environment of the bound ligand. A smaller number of residues is chosen relative to those highlighted in A) for ease of viewing. E) An interaction map of the ligand bound to the receptor that illustrates residues defining the environment of the bound ligand. Residues that can contact the ligand are shown as circles. Dark circles are those that interact primarily through van der Waals or hydrophobic contacts. Lighter circles are those that interact with ligand via other interaction types such as hydrogen bonds, ring stacking, salt bridges. When present, a halo around a circle indicates that there is significant loss of water-accessible surface area for that residue on ligand binding. When present, hydrogen bonds are indicated by dotted lines. Residues that can potentially make hydrogen bond with the ligand include Tyr277. Additional residues that can potentially make ring stacking, salt bridges, hydrogen bonding, pi interactions, charged interactions, van der Waals, or hydrophobic interactions with the ligand include Phe119, Pro177, Leu180, Ile181, Pro199, Cys217, and Phe220. Additional residues that can potentially make van der Waals or hydrophobic interaction with the ligand include Tyr277 and Lys290.

FIGS. 7A-7E. A) Alignment of canine, feline, and human olfactory receptor sequences as labeled (SEQ ID NOs:36, 56 and 46, respectively, in order of appearance). The active site, defined as those residues within 9 Å(1 Å=$10^{-10}$ m) of any heavy atom in the ligand, is highlighted by black boxes over the sequence alignment. Residues N-terminal to the seven-transmembrane domain are included for ease of identifying residues by number within the protein sequence. Residues C-terminal to the seven-transmembrane domain are not included in the alignments. B) Chemical structure of the ligand (β-ionone) used in the modeling. C) A near view of the ligand bound to the feline receptor catGr6 (D1:

Figure 2B:
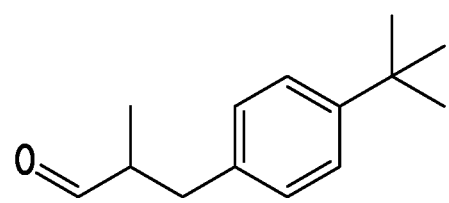
Figure 2C:
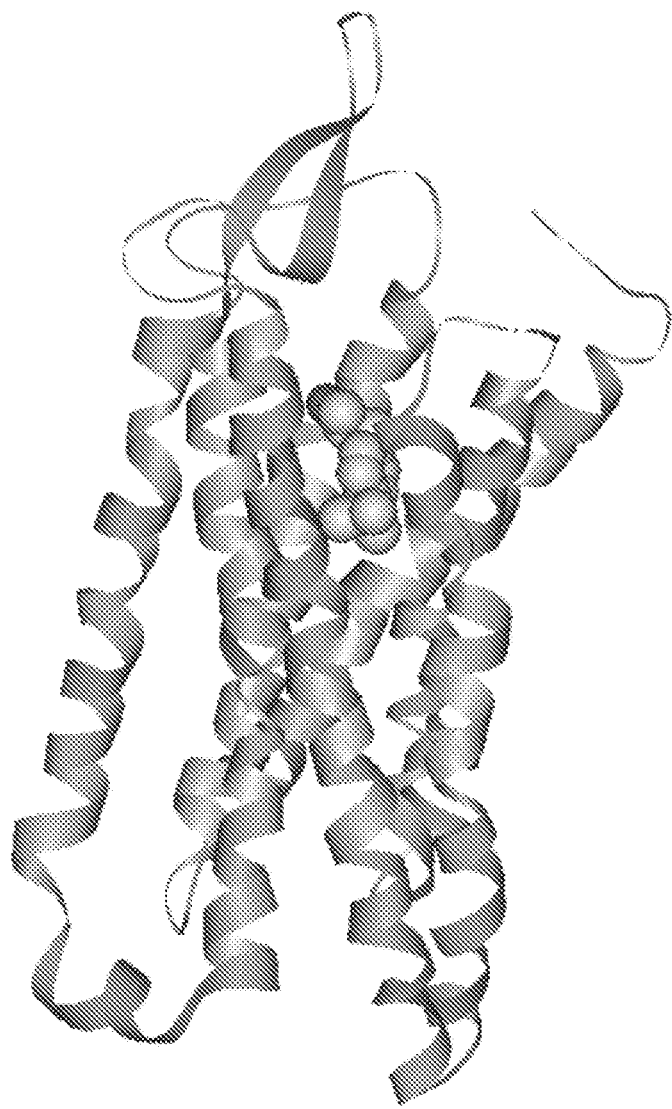
Figure 2D:
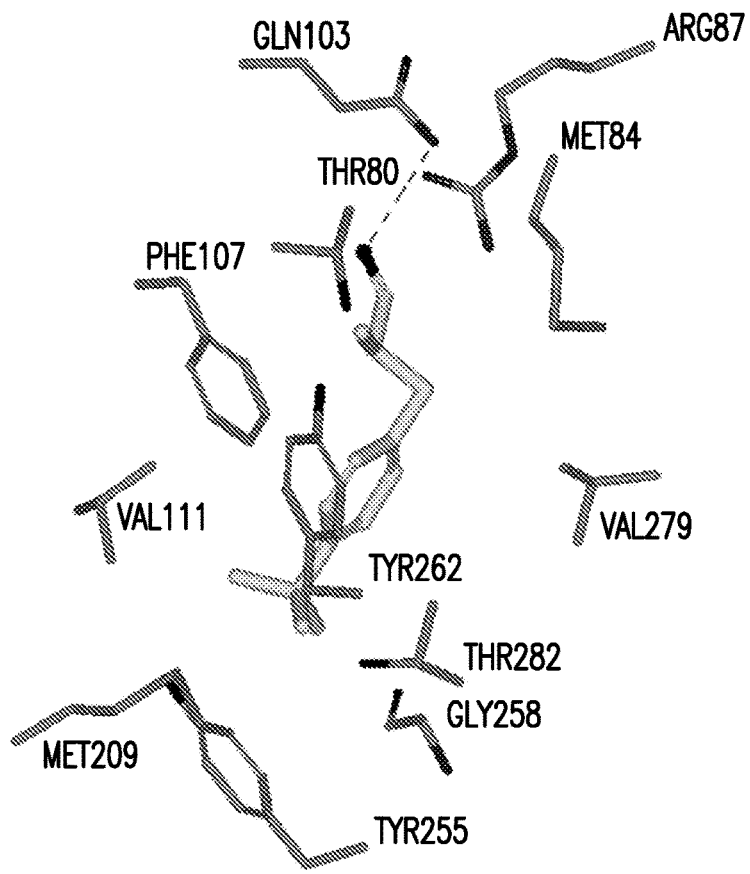
Figure 2E:
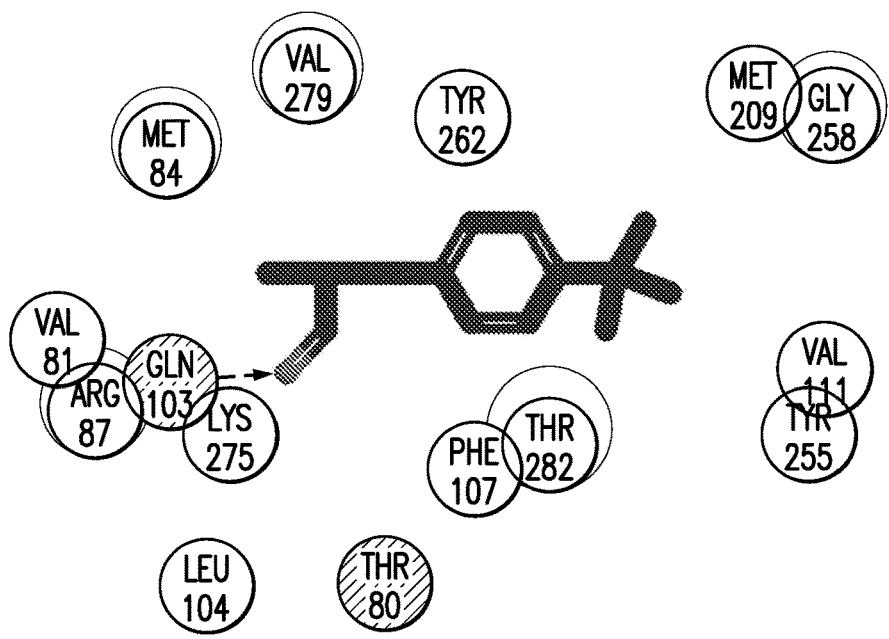
Figure 3B:
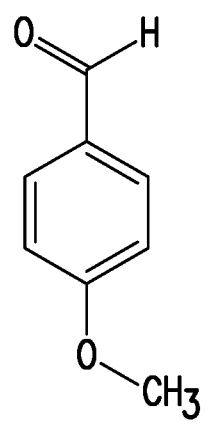
Figure 3C:
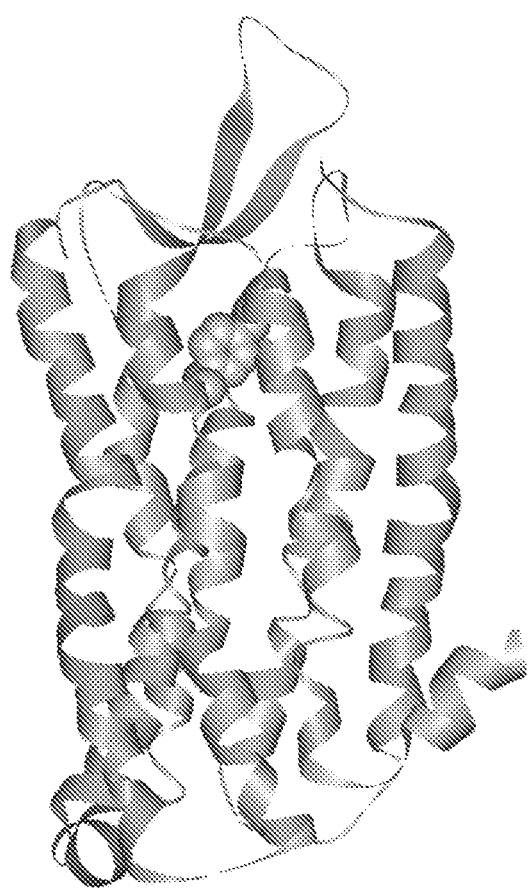
Figure 3D:
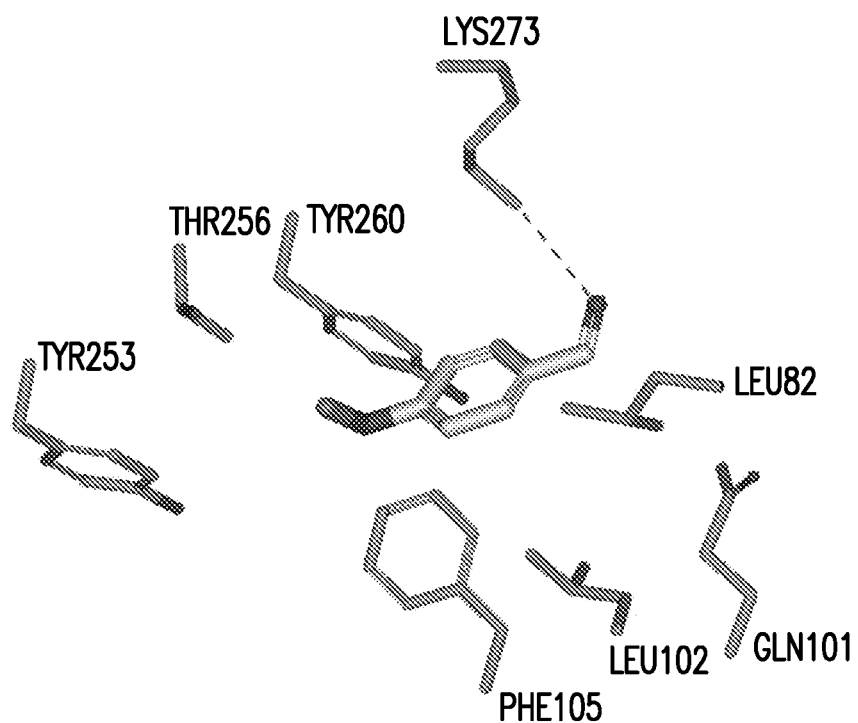
Figure 3E:
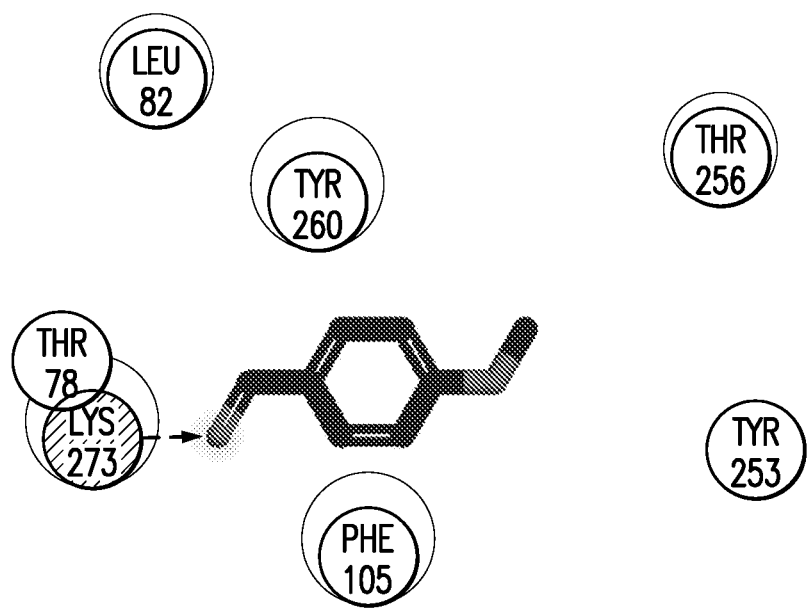
Figure 4B:
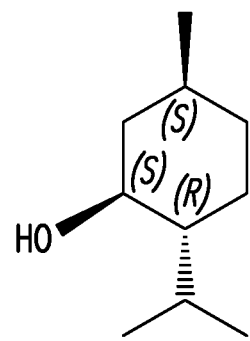
Figure 4C:
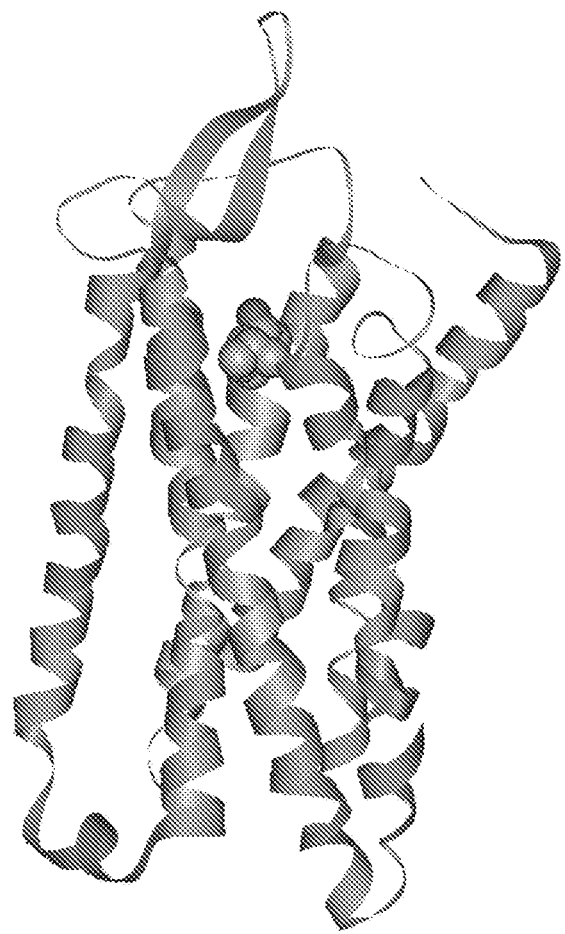
Figure 4D:
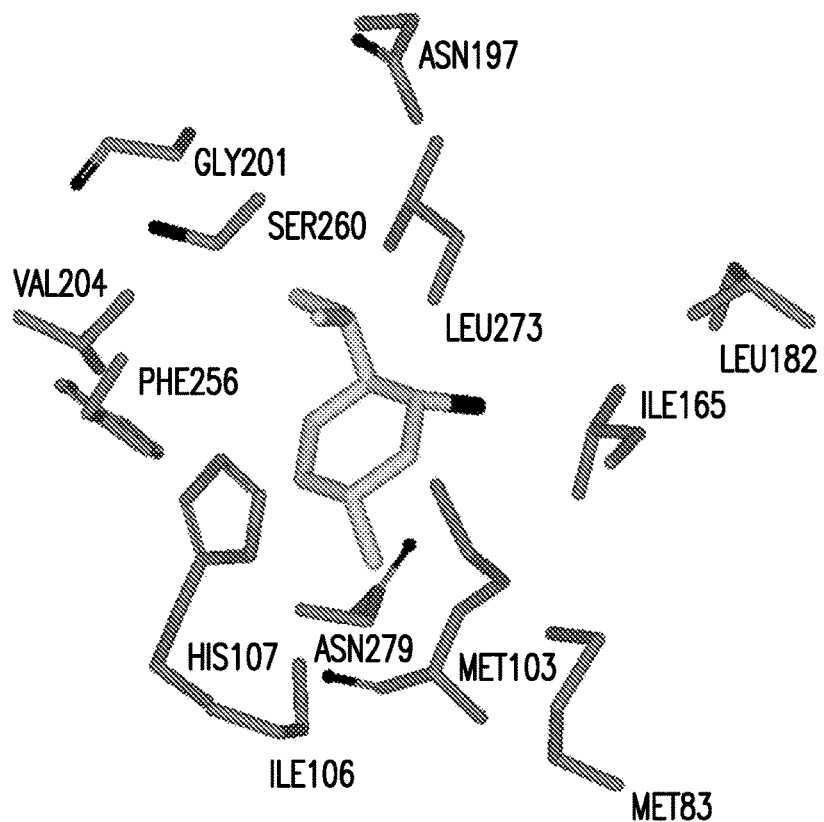
Figure 4E:
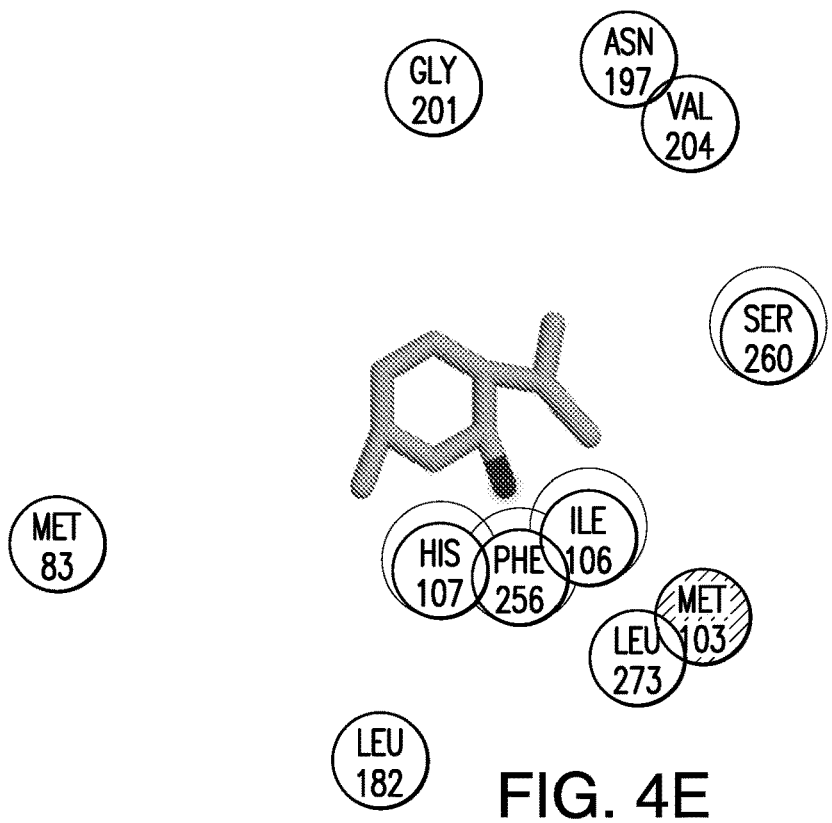
Figure 5B:
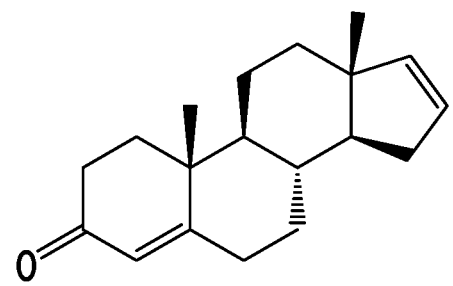
Figure 5C:
Figure 5D:
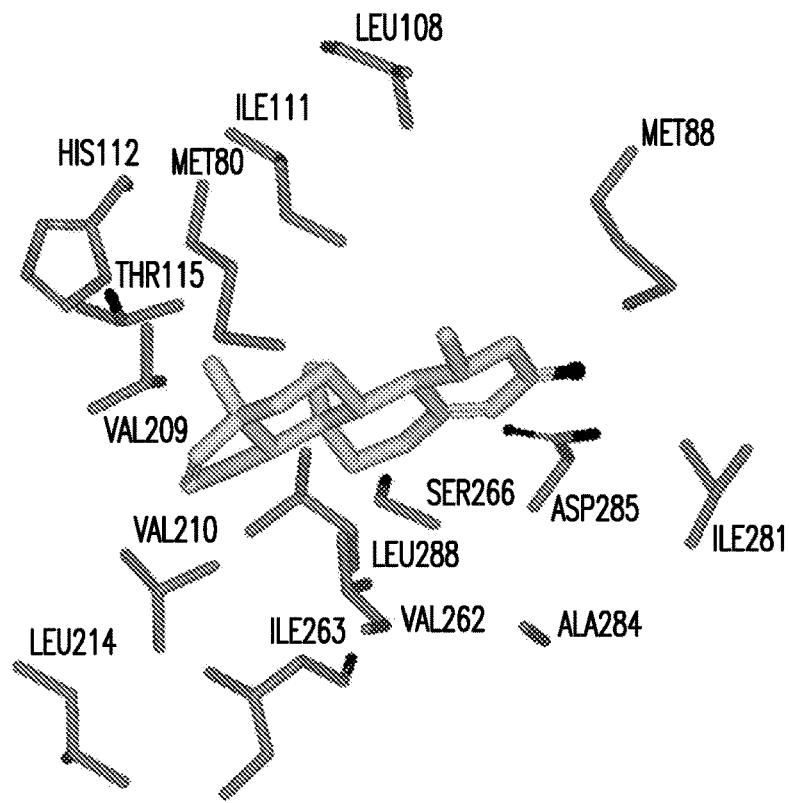
Figure 5E:
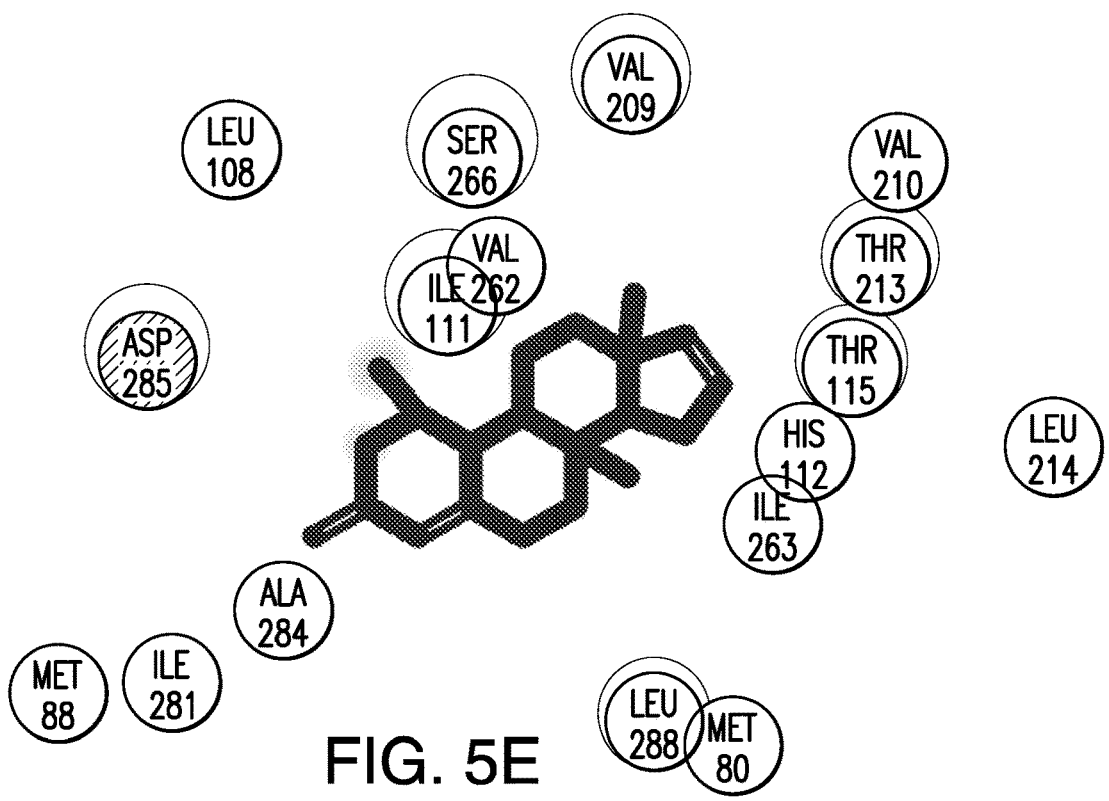
Figure 6B:
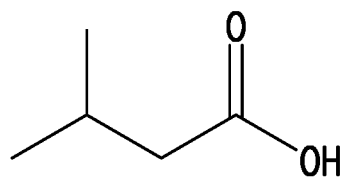
Figure 6C:
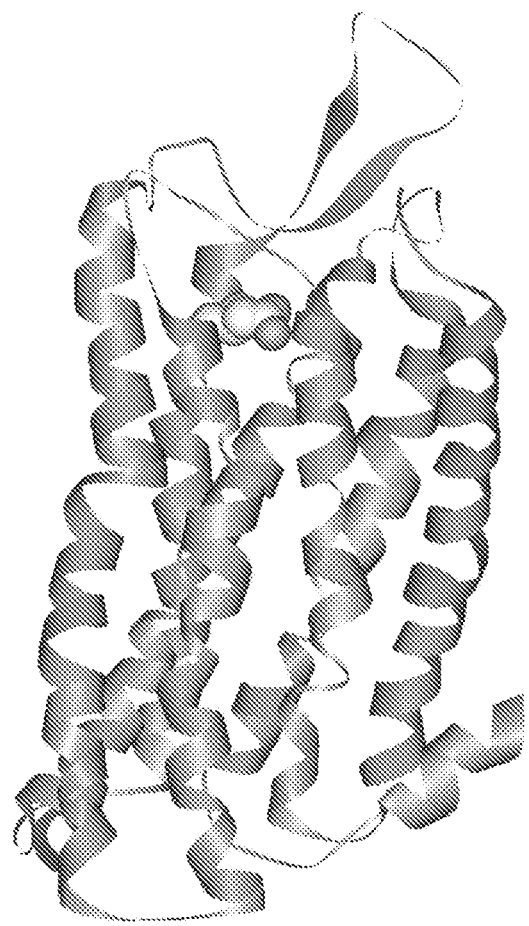
Figure 6D:
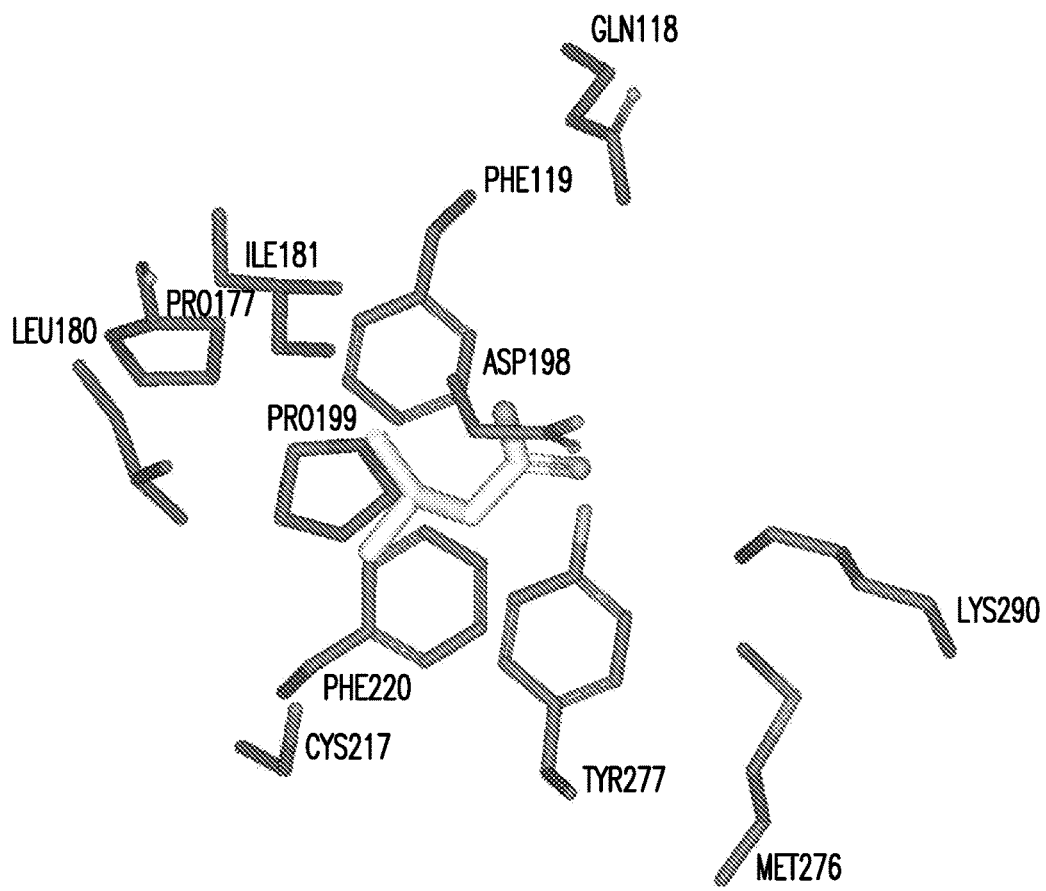
Figure 6E:
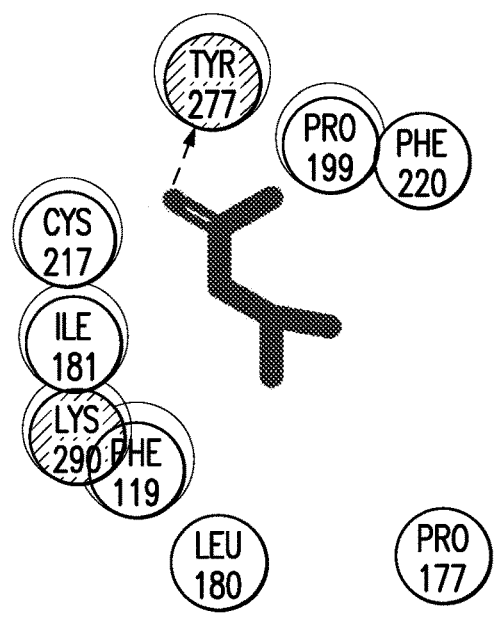
Figure 7B:
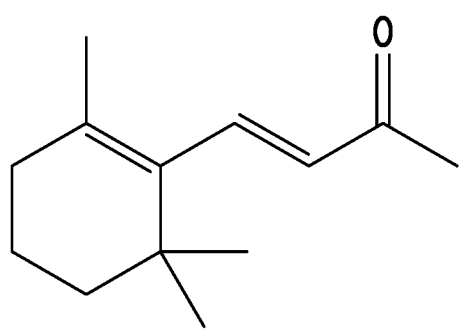
Figure 7C:
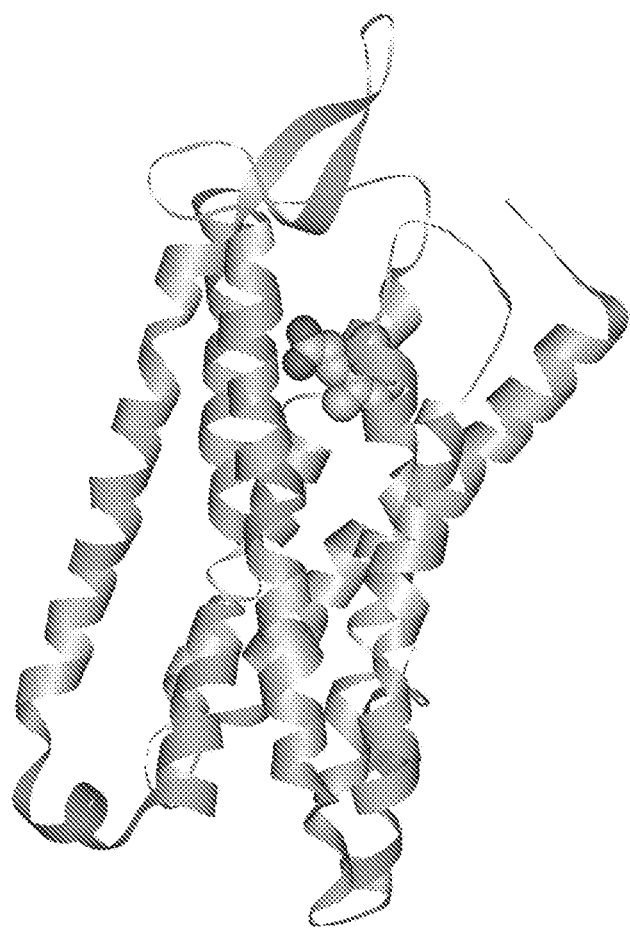
Figure 7D:
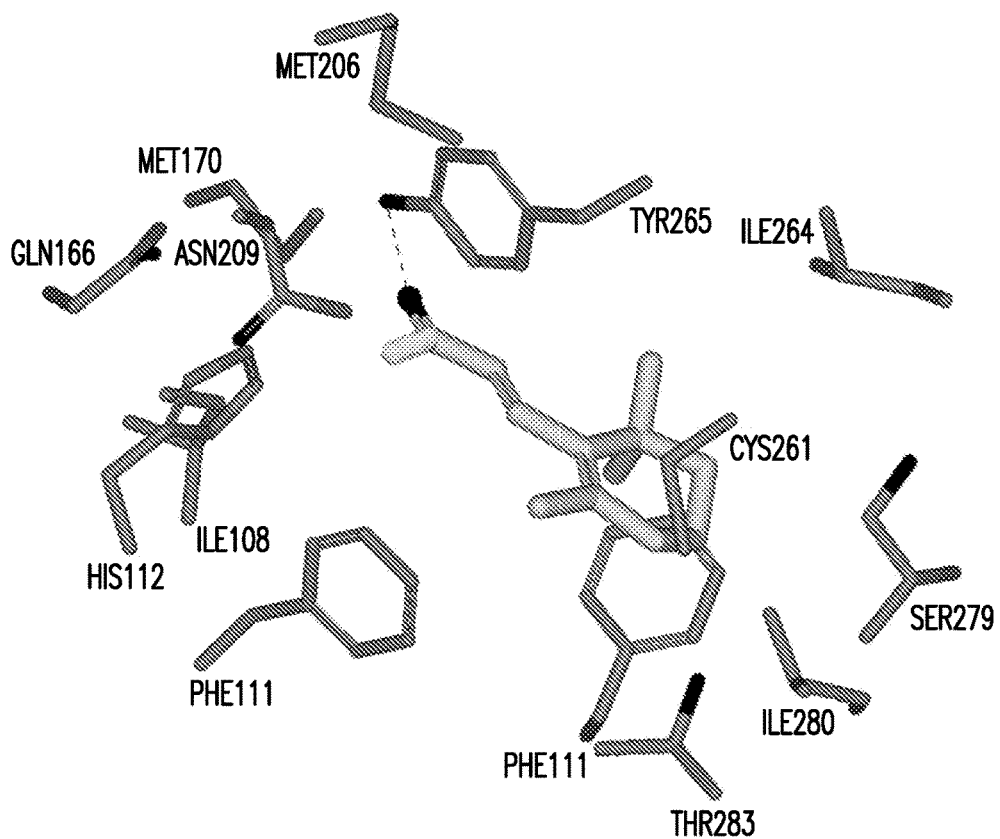
Figure 7E:
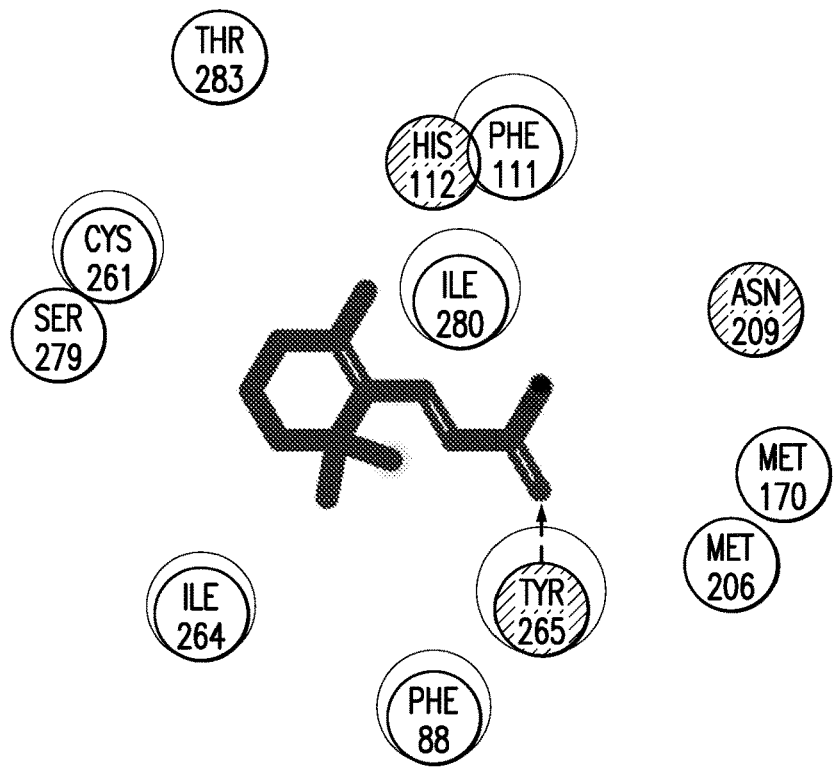
Figure 8B:
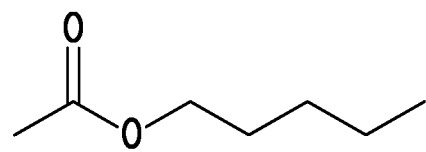
Figure 8C:
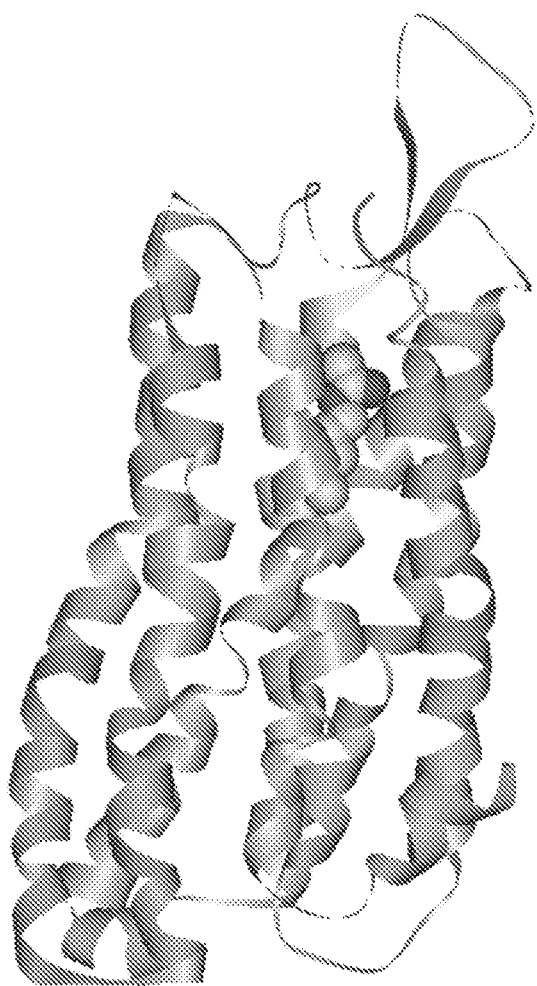
Figure 8D:
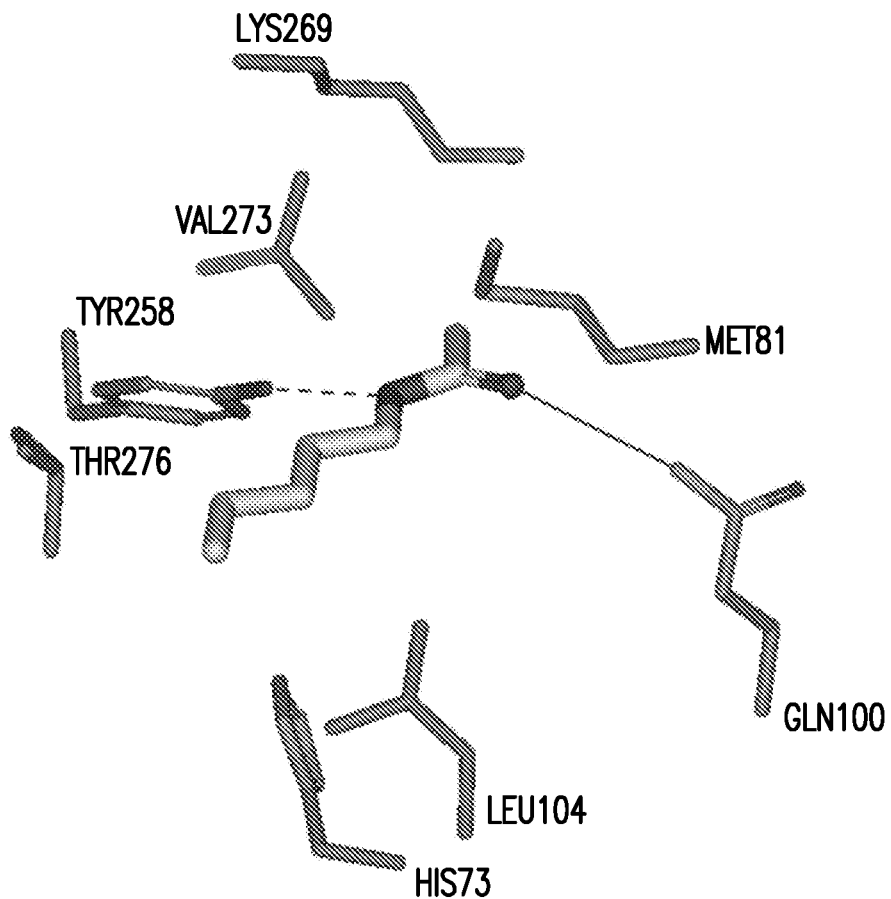
Figure 8E:
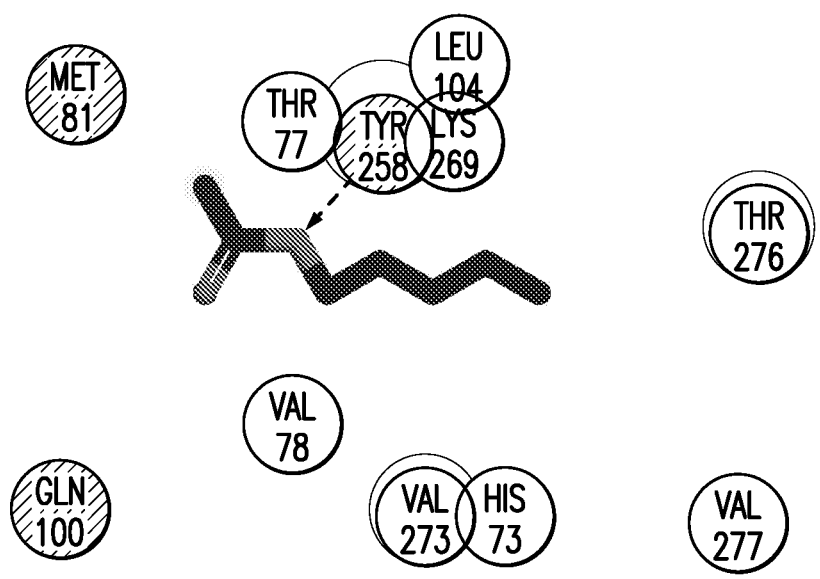
Figure 9B:
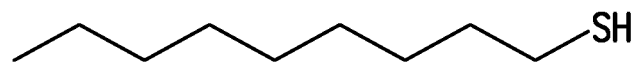
Figure 9C:
Figure 9D:
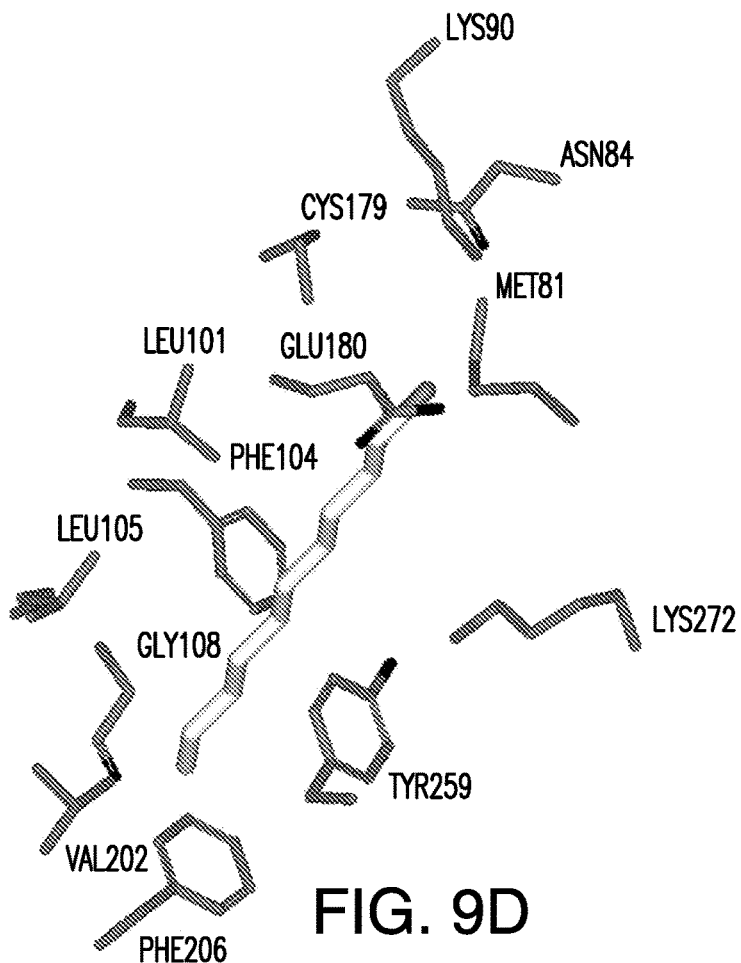
Figure 9E:
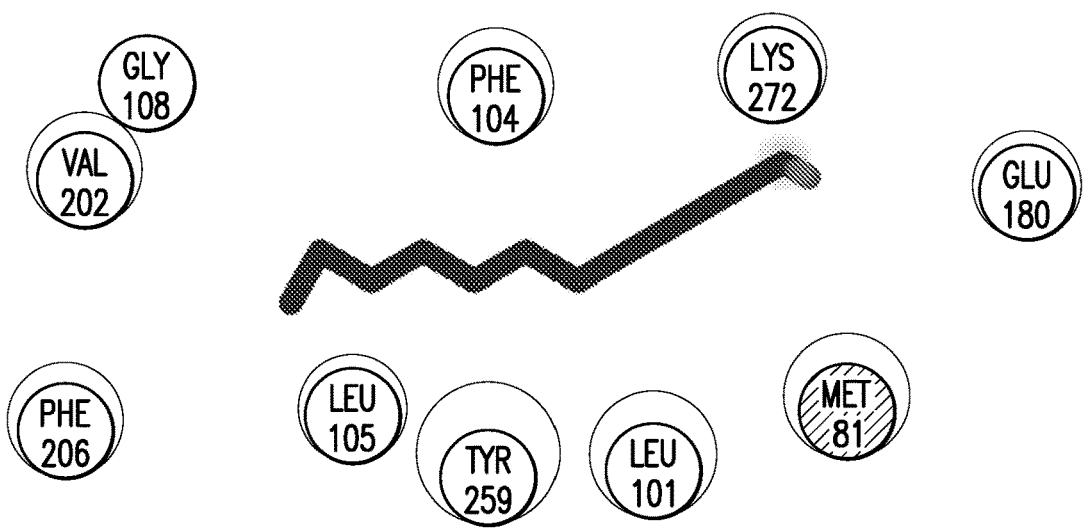
Figure 10B:
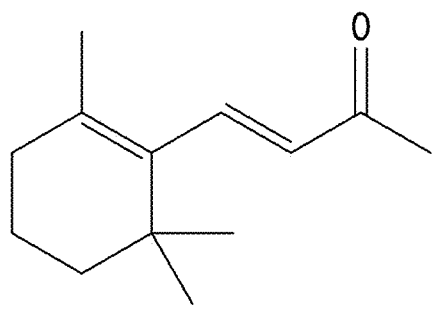
Figure 10C:
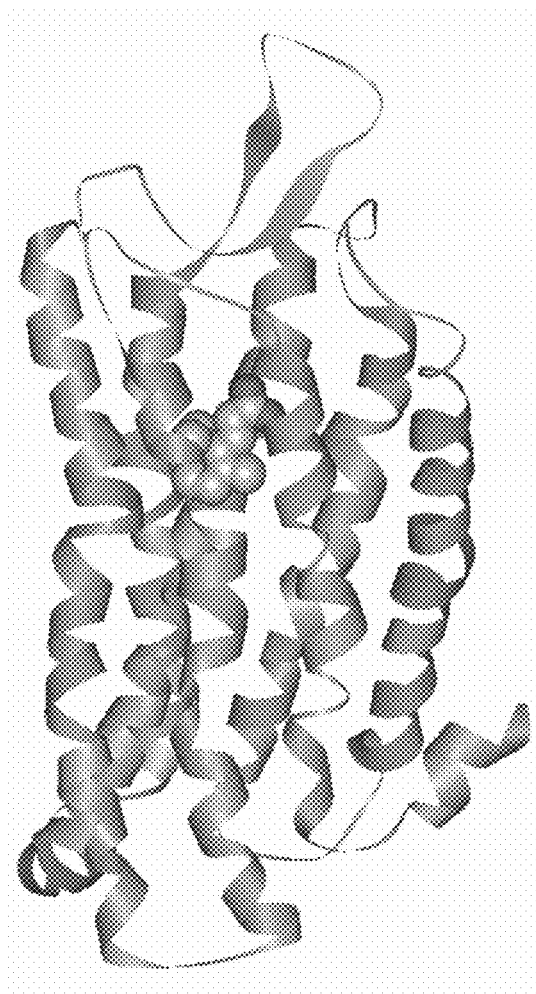
Figure 10D:
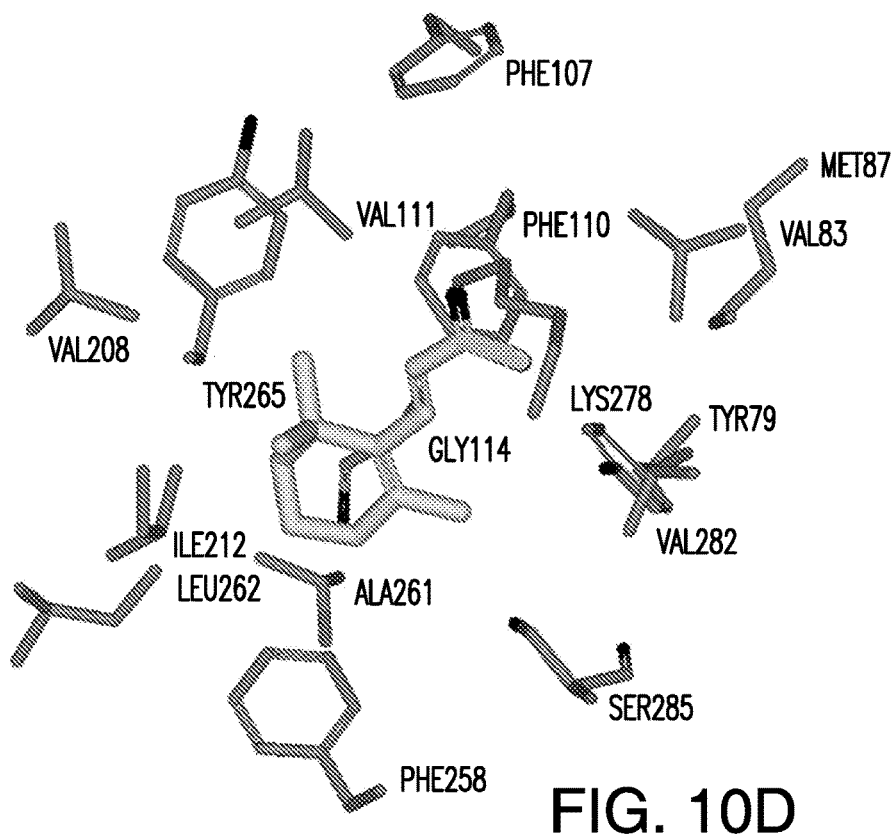
Figure 10E:
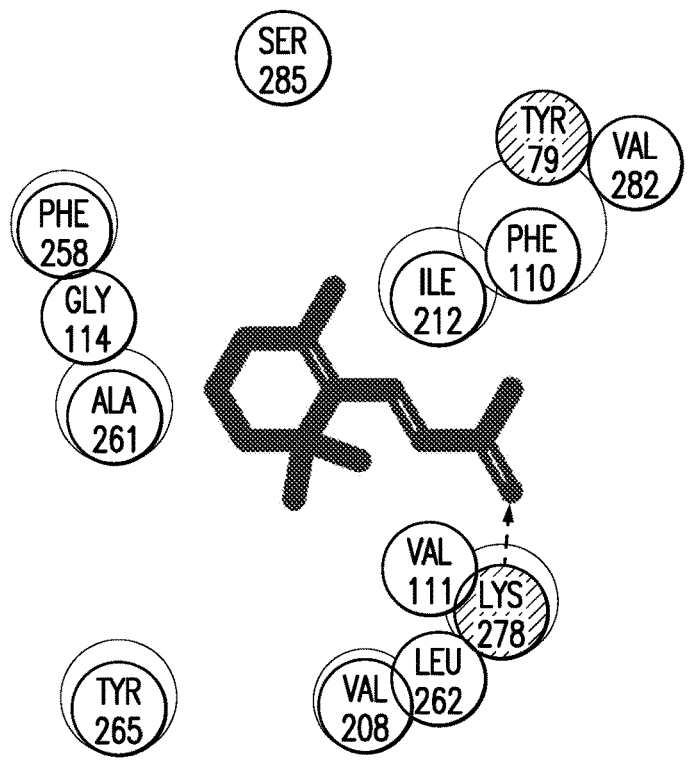
Figure 11B:
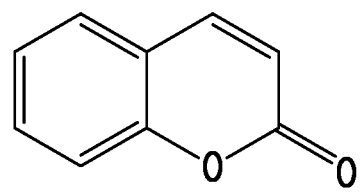
Figure 11C:
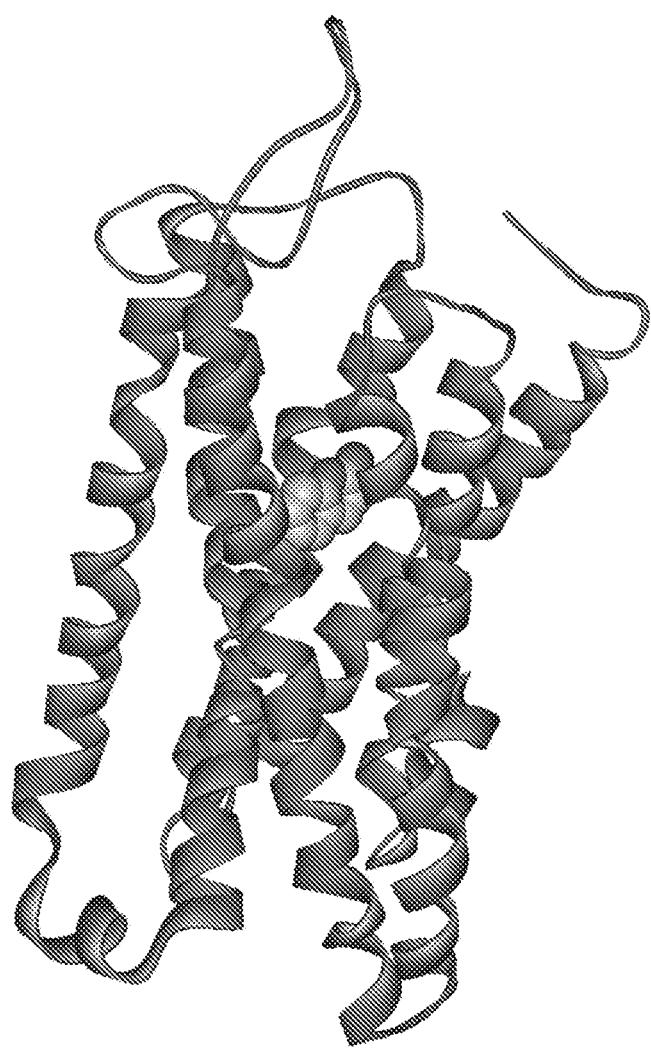
Figure 11D:
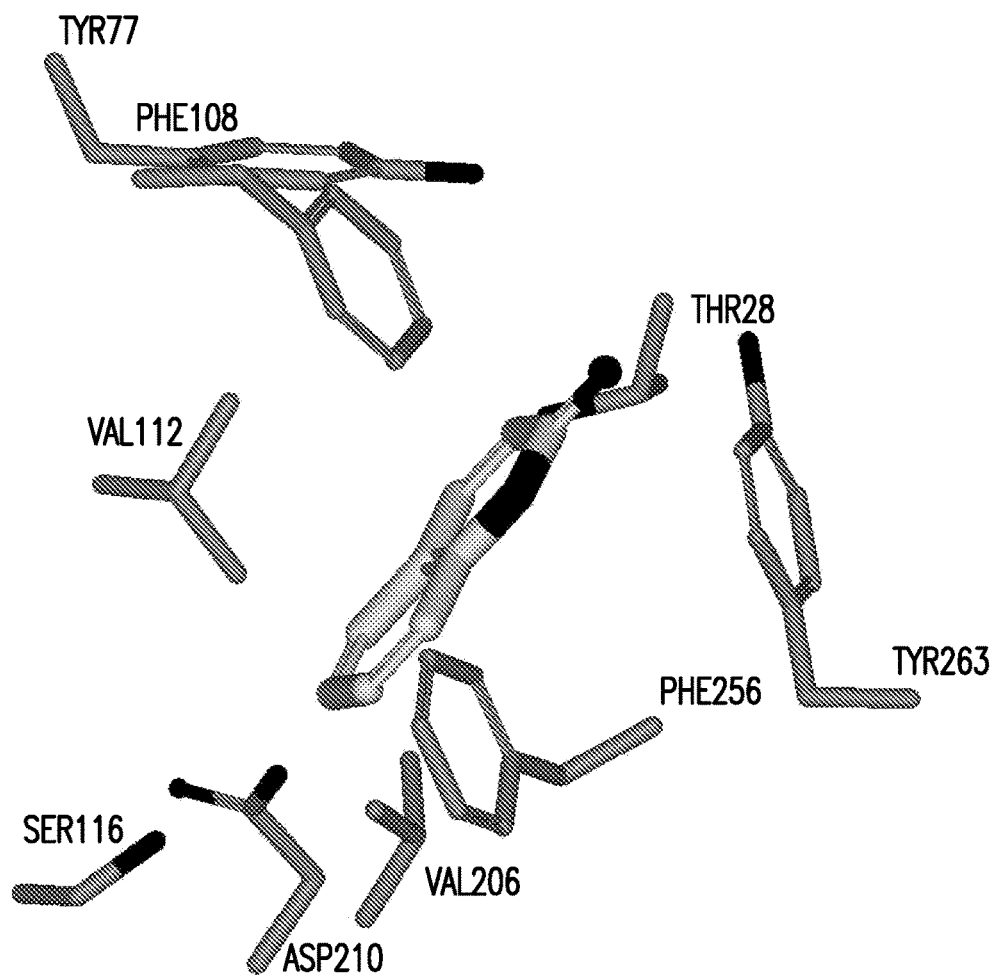
Figure 11E:
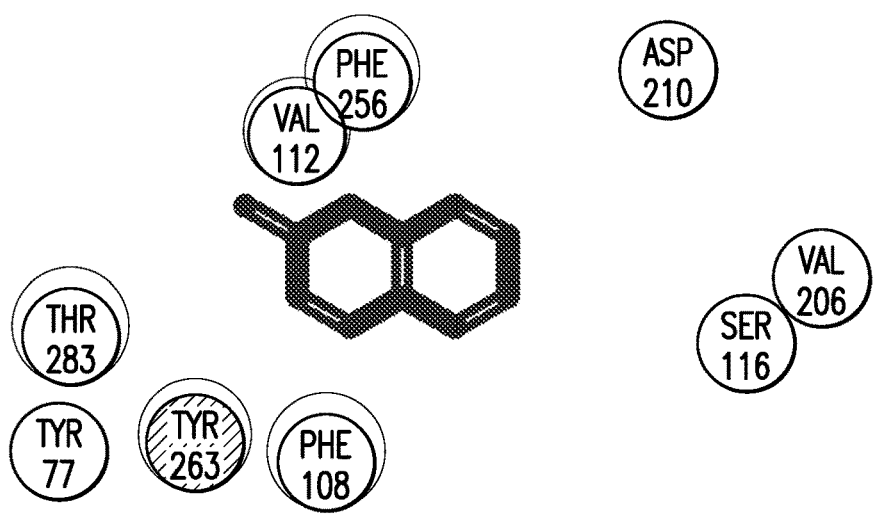

105486528-105487493). The figure illustrates where the compound binds within the seven-helical transmembrane-domain (7TM) of the chosen receptor. D) A near view of the ligand bound to the receptor that illustrates residues defining the environment of the bound ligand. A smaller number of residues is chosen relative to those highlighted in A) for ease of viewing. E) An interaction map of the ligand bound the receptor that illustrates residues defining the environment of the bound ligand. Residues that can contact the ligand are shown as circles. Dark circles are those that interact primarily through van der Waals or hydrophobic contacts. Lighter circles are those that interact with ligand via other interaction types such as hydrogen bonds, ring stacking, salt bridges. When present, a halo around a circle indicates that there is significant loss of water-accessible surface area for that residue on ligand binding. When present, hydrogen bonds are indicated by dotted lines. Residues that can potentially make hydrogen bond with the ligand include Tyr265. Additional residues that can potentially make ring stacking, salt bridges, hydrogen bonding, pi interactions, charged interactions, van der Waals, or hydrophobic interactions with the ligand include Phe88, Phe111, Met170, Met206, Cys261, Ile264, Ser279, Ile280, and Thr283. Additional residues that can potentially make van der Waals or hydrophobic interaction with the ligand include His112, Asn209 and Tyr265.

FIGS. 8A-8E. A) Alignment of canine, feline, and human olfactory receptor sequences as labeled (SEQ ID NOs:47, 37 and 57, respectively, in order of appearance). The active site, defined as those residues within 9 Å(1 Å=10$^{-10}$ m) of any heavy atom in the ligand, is highlighted by black boxes over the sequence alignment. Residues N-terminal to the seven-transmembrane domain are included for ease of identifying residues by number within the protein sequence. Residues C-terminal to the seven-transmembrane domain are not included in the alignments. B) Chemical structure of the ligand (Amyl acetate) used in the modeling. C) A near view of the ligand bound to the feline receptor catG7 (B3: 74116955-74117893). The figure illustrates where the compound binds within the seven-helical transmembrane-domain (7TM) of the chosen receptor. D) A near view of the ligand bound to the receptor that illustrates residues defining the environment of the bound ligand. A smaller number of residues is chosen relative to those highlighted in A) for ease of viewing. E) An interaction map of the ligand bound the receptor that illustrates residues defining the environment of the bound ligand. Residues that can contact the ligand are shown as circles. Dark circles are those that interact primarily through van der Waals or hydrophobic contacts. Lighter circles are those that interact with ligand via other interaction types such as hydrogen bonds, ring stacking, salt bridges. When present, a halo around a circle indicates that there is significant loss of water-accessible surface area for that residue on ligand binding. When present, hydrogen bonds are indicated by dotted lines. Residues that can potentially make hydrogen bond with the ligand include Met81, Tyr258, and Gln100. Additional residues that can potentially make ring stacking, salt bridges, hydrogen bonding, pi interactions, charged interactions, van der Waals, or hydrophobic interactions with the ligand Thr77, Lys269, Leu104, Thr276, Val277, His73, Val273 and Val78.

FIGS. 9A-9E. A) Alignment of canine, feline, and human olfactory receptor sequences as labeled (SEQ ID NOs:38, 58 and 48, respectively, in order of appearance). The active site, defined as those residues within 9 Å(1 Å=10$^{-10}$ m) of any heavy atom in the ligand, is highlighted by black boxes over the sequence alignment. Residues N-terminal to the seven-transmembrane domain are included for ease of identifying residues by number within the protein sequence. Residues C-terminal to the seven-transmembrane domain are not included in the alignments. B) Chemical structure of the ligand (1-nonanethiol) used in the modeling. C) A near view of the ligand bound to the feline receptor catG8 (E3: 40237904-40238842). The figure illustrates where the compound binds within the seven-helical transmembrane-domain (7TM) of the chosen receptor. D) A near view of the ligand bound to the receptor that illustrates residues defining the environment of the bound ligand. A smaller number of residues is chosen relative to those highlighted in A) for ease of viewing. E) An interaction map of the ligand bound the receptor that illustrates residues defining the environment of the bound ligand. Residues that can contact the ligand are shown as circles. Dark circles are those that interact primarily through van der Waals or hydrophobic contacts. Lighter circles are those that interact with ligand via other interaction types such as hydrogen bonds, ring stacking, salt bridges. When present, a halo around a circle indicates that there is significant loss of water-accessible surface area for that residue on ligand binding. When present, hydrogen bonds are indicated by dotted lines. Residues that can potentially make ring stacking, salt bridges, hydrogen bonding, pi interactions, or charged interactions with the ligand include Leu101, Phe104, Leu105, Gly108, Glu180, Val202, Phe206, Tyr259, and Lys272. Additional residues that can potentially make van der Waals or hydrophobic interaction with the ligand include Met81.

FIGS. 10A-10E. A) Alignment of canine, feline, and human olfactory receptor sequences as labeled (SEQ ID NOs:49, 59 and 39, respectively, in order of appearance). The active site, defined as those residues within 9 Å(1 Å=10$^{-10}$ m) of any heavy atom in the ligand, is highlighted by black boxes over the sequence alignment. Residues N-terminal to the seven-transmembrane domain are included for ease of identifying residues by number within the protein sequence. Residues C-terminal to the seven-transmembrane domain are not included in the alignments. B) Chemical structure of the ligand (β-ionone) used in the modeling. C) A near view of the ligand bound to the feline receptor catG9 (D1:105462554-105463512). The figure illustrates where the compound binds within the seven-helical transmembrane-domain (7TM) of the chosen receptor. D) A near view of the ligand bound to the receptor that illustrates residues defining the environment of the bound ligand. A smaller number of residues is chosen relative to those highlighted in A) for ease of viewing. E) An interaction map of the ligand bound the receptor that illustrates residues defining the environment of the bound ligand. Residues that can contact the ligand are shown as circles. Dark circles are those that interact primarily through van der Waals or hydrophobic contacts. Lighter circles are those that interact with ligand via other interaction types such as hydrogen bonds, ring stacking, salt bridges. When present, a halo around a circle indicates that there is significant loss of water-accessible surface area for that residue on ligand binding. When present, hydrogen bonds are indicated by dotted lines. Residues that can potentially make hydrogen bond with the ligand include Lys278. Additional residues that can potentially make ring stacking, salt bridges, hydrogen bonding, pi interactions, or charged interactions with the ligand include Phe110, Val111, Gly114, Val208, Ile212, Phe258, Ala261, Leu262, Tyr265, Val282, and Ser285. Additional residues that can potentially make van der Waals or hydrophobic interaction with the ligand include Tyr79 and Lys278.

FIGS. 11A-11E. A) Alignment of canine, murine, feline, and human olfactory receptor sequences as labeled (SEQ ID NOs:60, 3,809, 50 and 40, respectively, in order of appearance). The active site, defined as those residues within 9 Å (1 Å=$10^{-10}$ m) of any heavy atom in the ligand, is highlighted by black boxes over the sequence alignment. Residues N-terminal to the seven-transmembrane domain are included for ease of identifying residues by number within the protein sequence. Residues C-terminal to the seven-transmembrane domain are not included in the alignments. B) Chemical structure of the ligand (Coumarin) used in the modeling. C) A near view of the ligand bound to the canine receptor CafaOR5.2.5. The figure illustrates where the compound binds within the seven-helical transmembrane-domain (7TM) of the chosen receptor. D) A near view of the ligand bound to the receptor that illustrates residues defining the environment of the bound ligand. A smaller number of residues is chosen relative to those highlighted in A) for ease of viewing. E) An interaction map of the ligand bound the receptor that illustrates residues defining the environment of the bound ligand. Residues that can contact the ligand are shown as circles. Dark circles are those that interact primarily through van der Waals or hydrophobic contacts. Lighter circles are those that interact with ligand via other interaction types such as hydrogen bonds, ring stacking, salt bridges. When present, a halo around a circle indicates that there is significant loss of water-accessible surface area for that residue on ligand binding. When present, hydrogen bonds are indicated by dotted lines. Residues that can potentially make ring stacking, salt bridges, hydrogen bonding, pi interactions, or charged interactions with the ligand include Tyr77, Phe108, Val112, Ser116, Val206, Asp210, Phe256, and Thr283. Additional residues that can potentially make van der Waals or hydrophobic interaction with the ligand include Tyr263.

Figure 12:
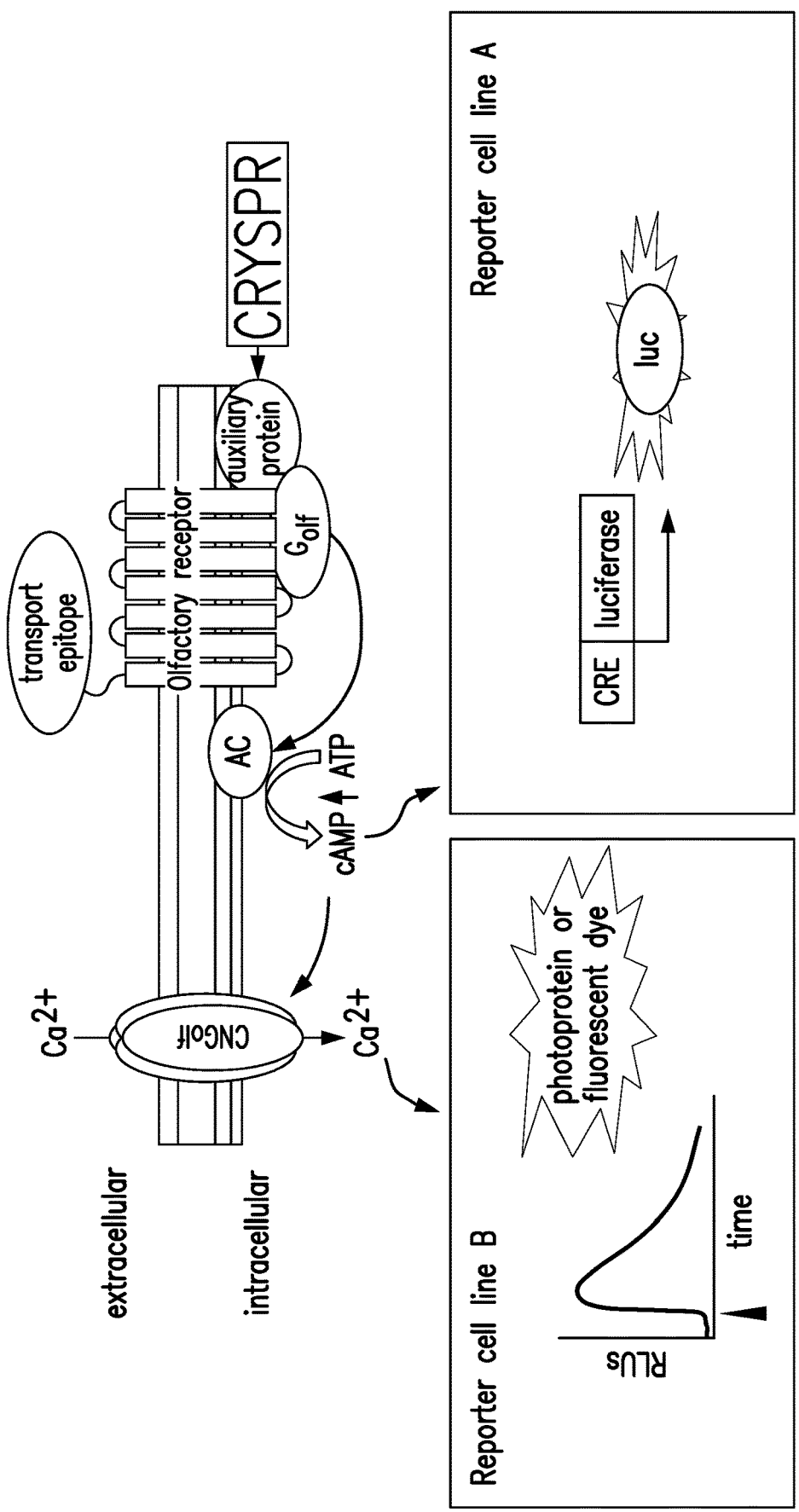

FIG. 12 shows native olfactory receptor signaling pathway and possible functional assays.

Figure 13:
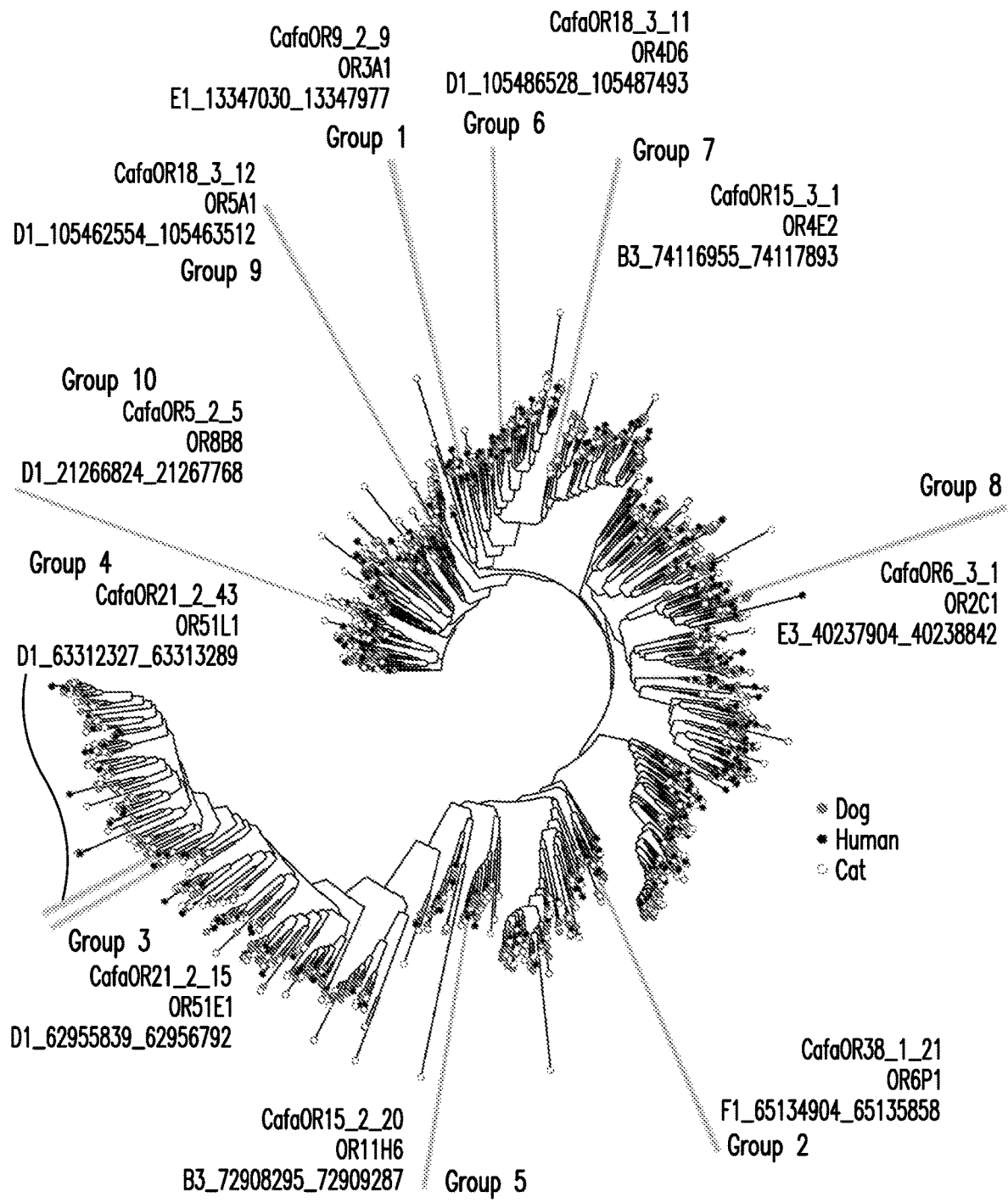

FIG. 13 shows a phylogenetic tree for multi-species (human/canine/feline) covering the olfactory genetic space. The phylogenetic tree shows all olfactory receptors and highlighted the 30 selected olfactory receptors (10 human receptors, 10 canine receptors, 10 feline receptors).

Figure 14:
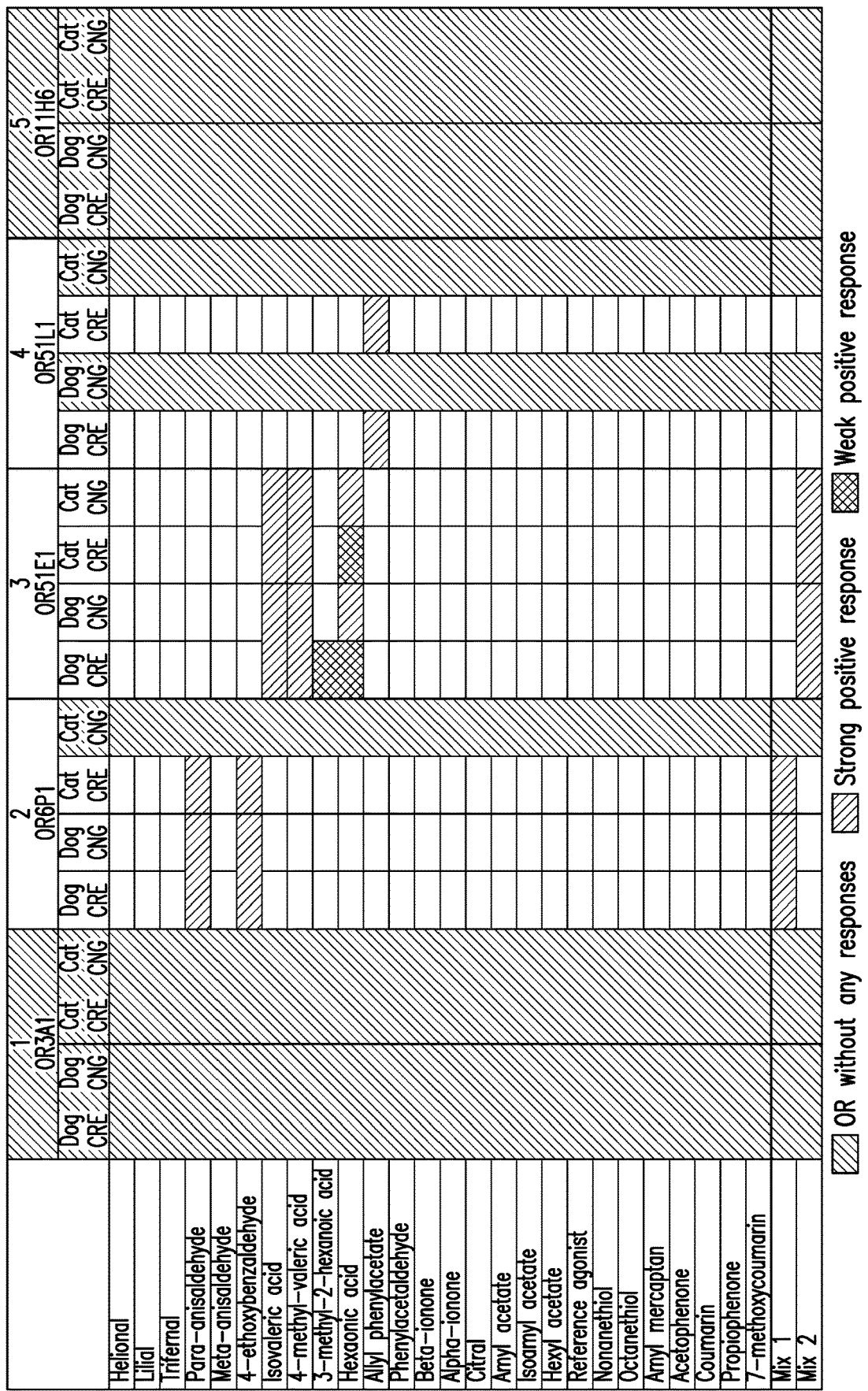

FIG. 14 shows the summarized results of phase 2 testing of OR_1 to OR_5 in Example 4.

Figure 15:
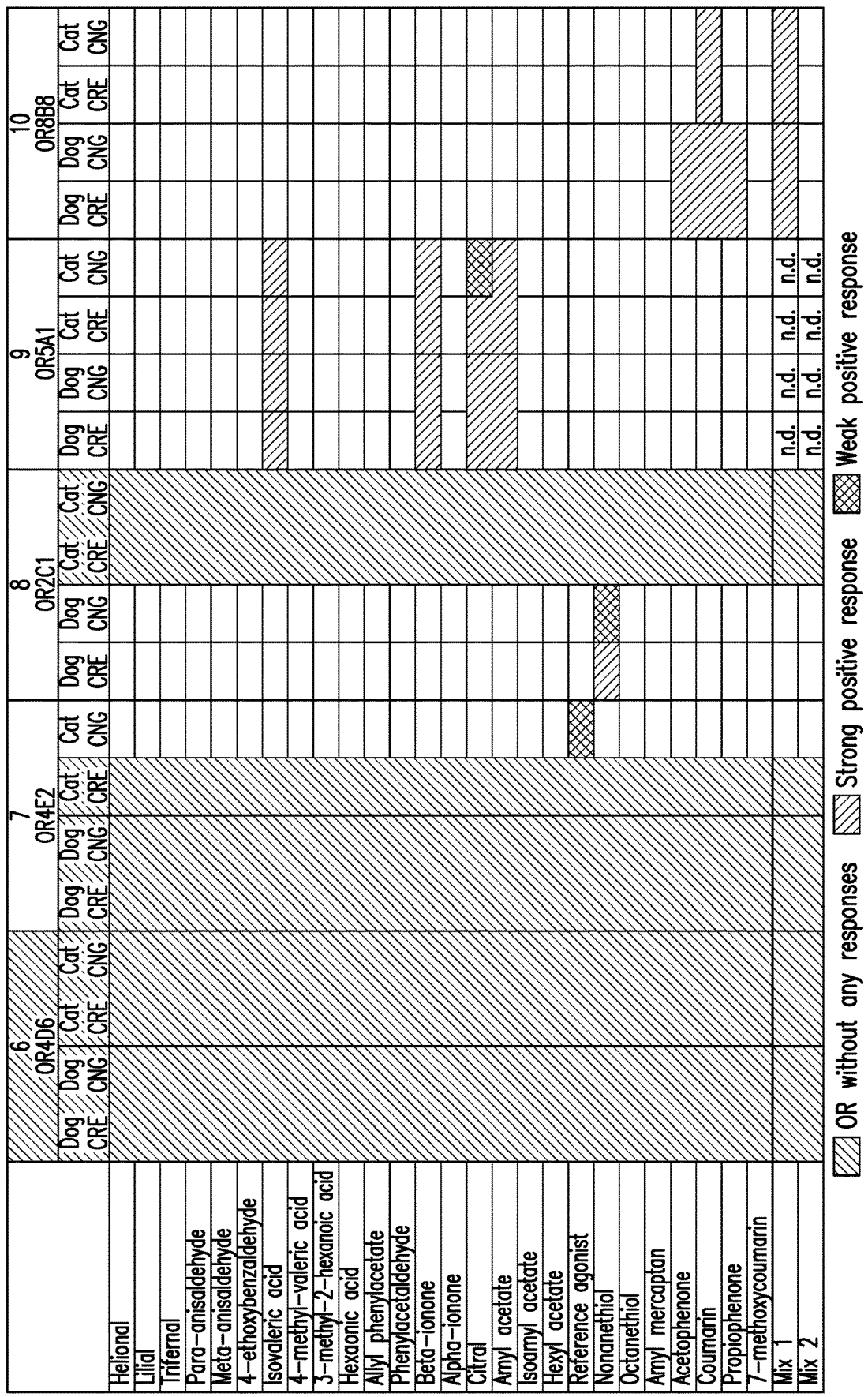

FIG. 15 shows the summarized results of phase 2 testing of OR_6 to OR_10 in Example 4.

FIG. 16 shows the summarized results of phase 3 testing of dog ORs in Example 4.

FIG. 17 shows the summarized results of phase 3 testing of cat ORs in Example 4.

Figure 18:
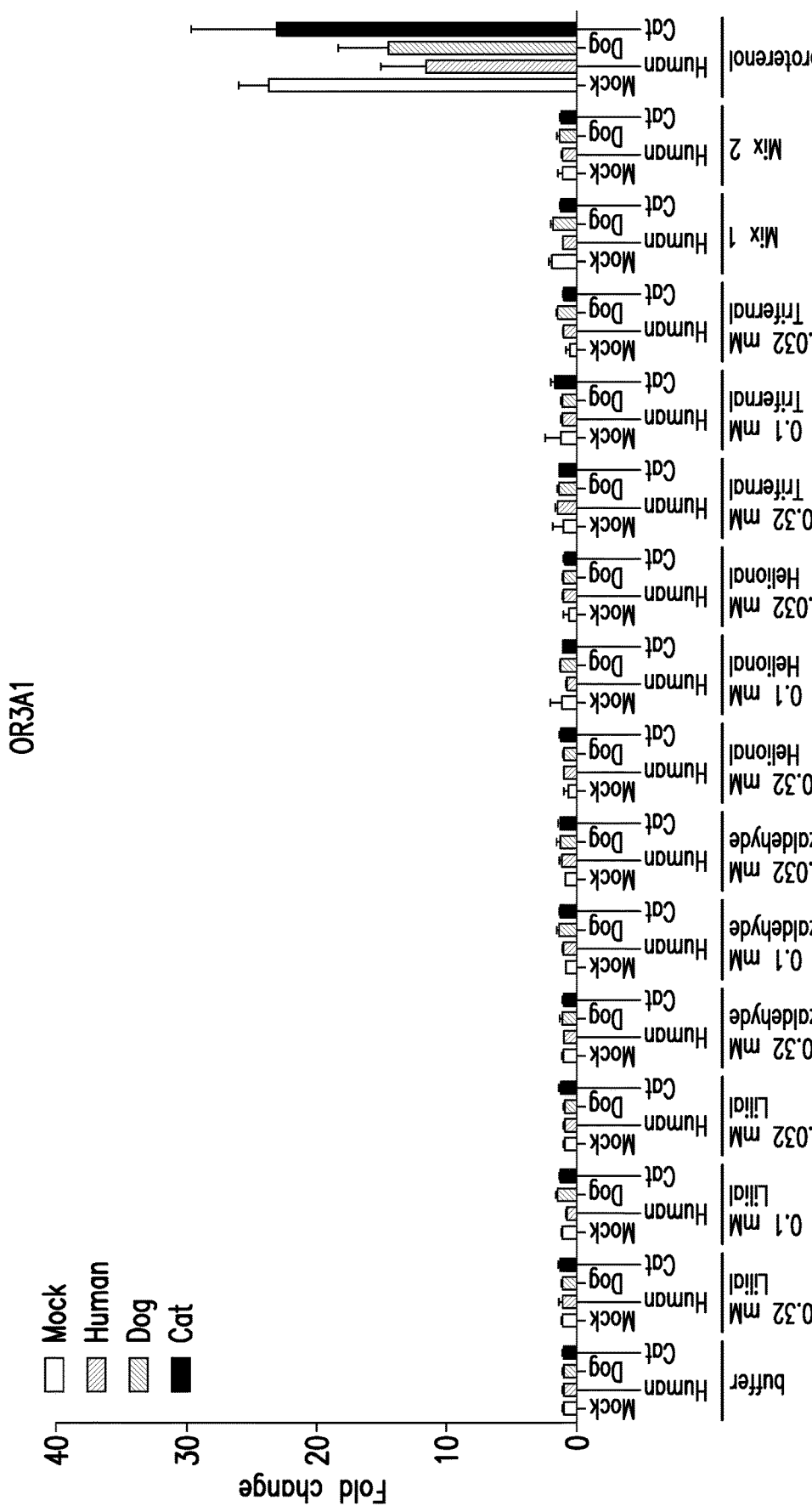

FIG. 18 shows the results of the CRE-NanoLuc luciferase assay using OR_1 (OR3A1).

Figure 19:
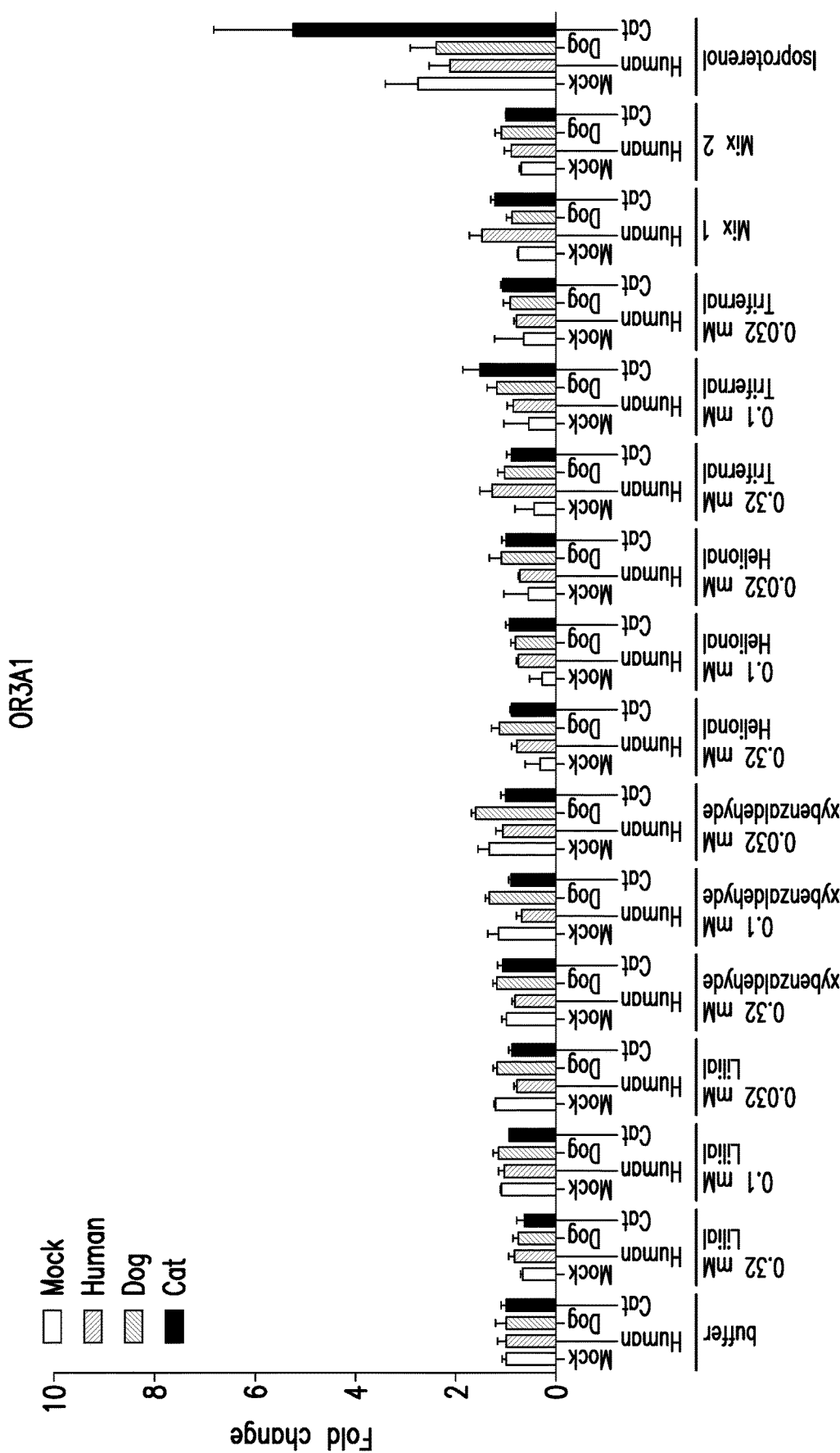

FIG. 19 shows the results of the chAMPion assay using OR_1 (OR3A1).

Figure 20:
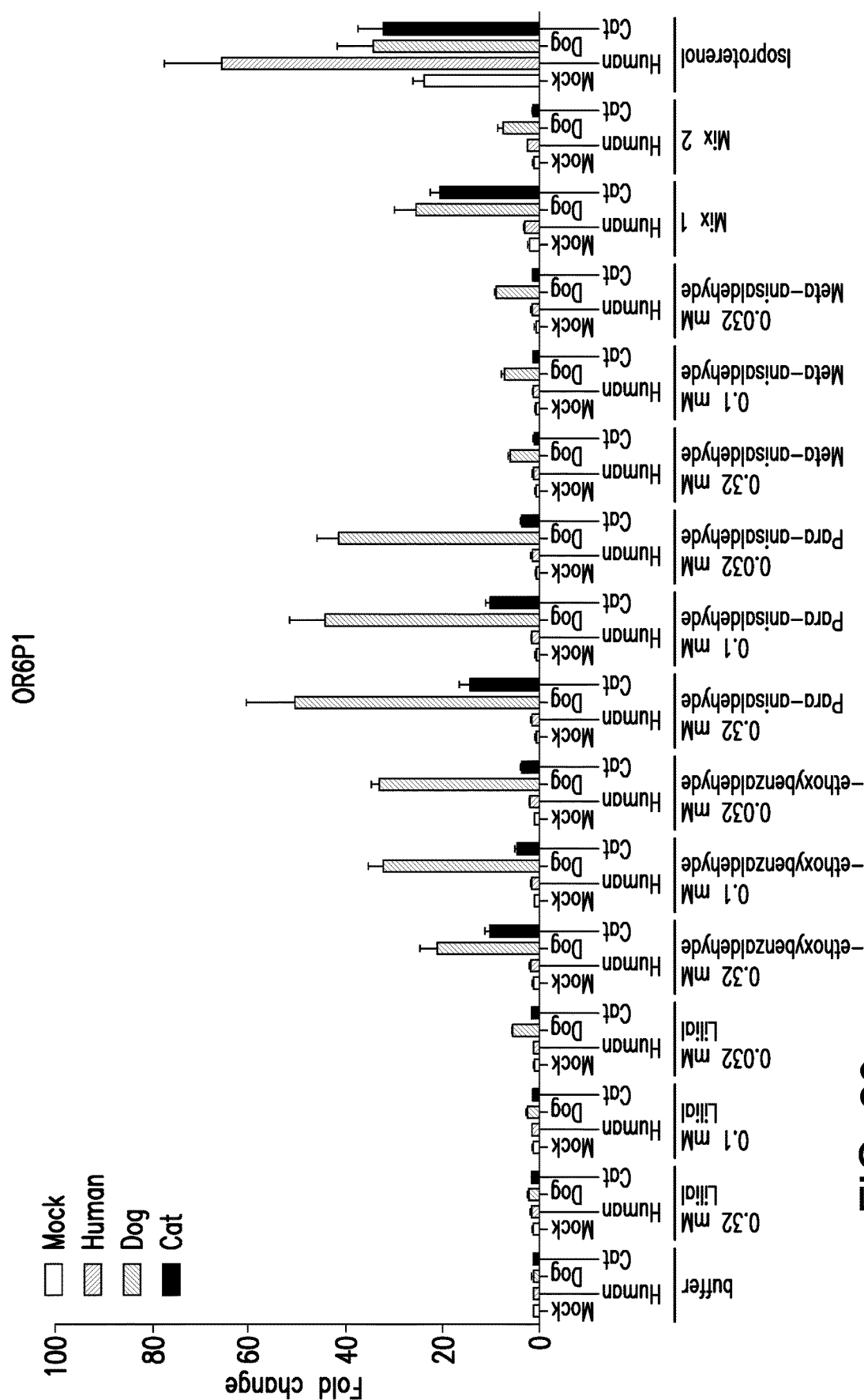

FIG. 20 shows the results of the CRE-NanoLuc luciferase assay using OR_2 (OR6P1).

Figure 21:
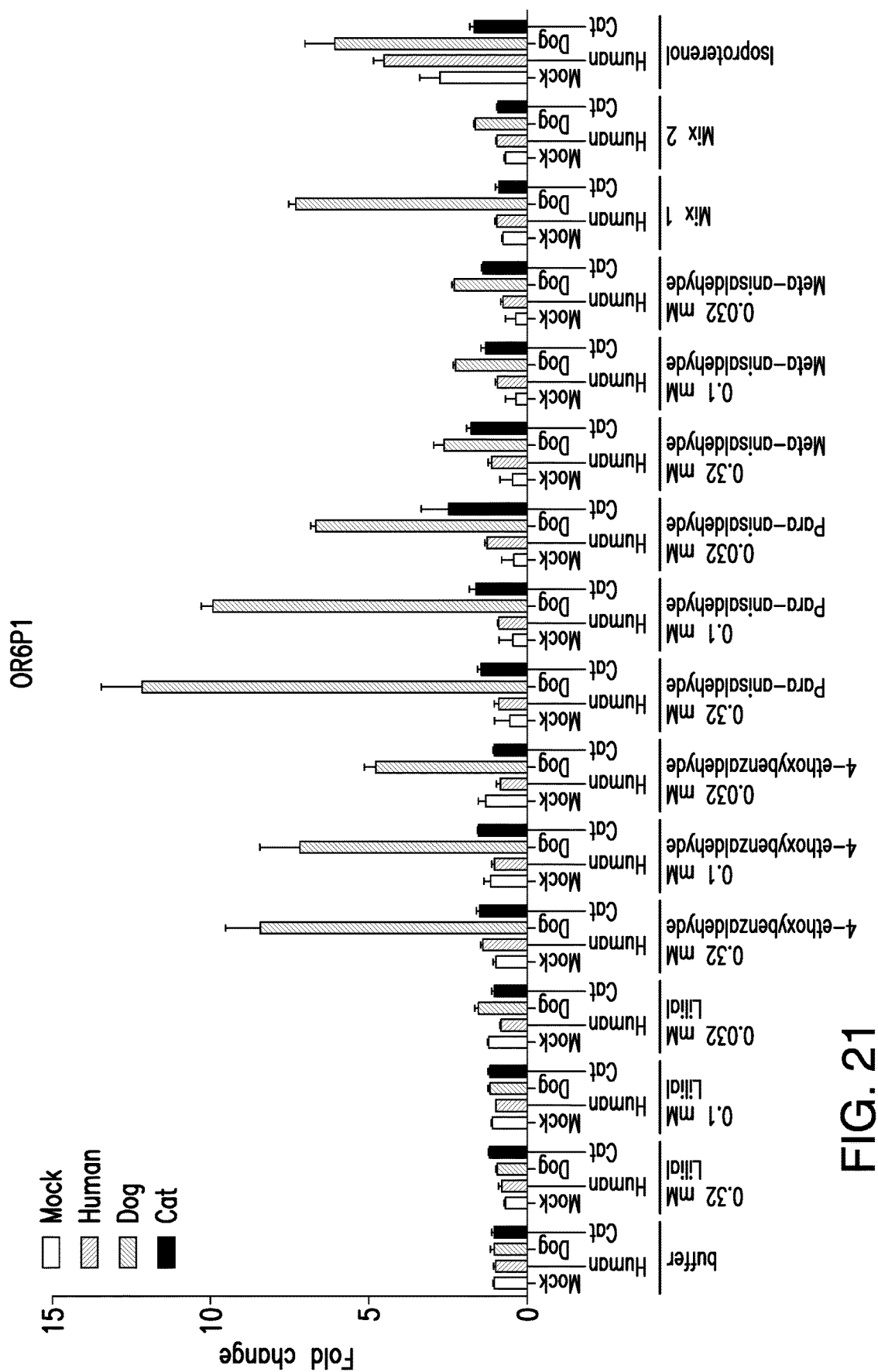

FIG. 21 shows the results of the chAMPion assay using OR_2 (OR6P1).

Figure 22:
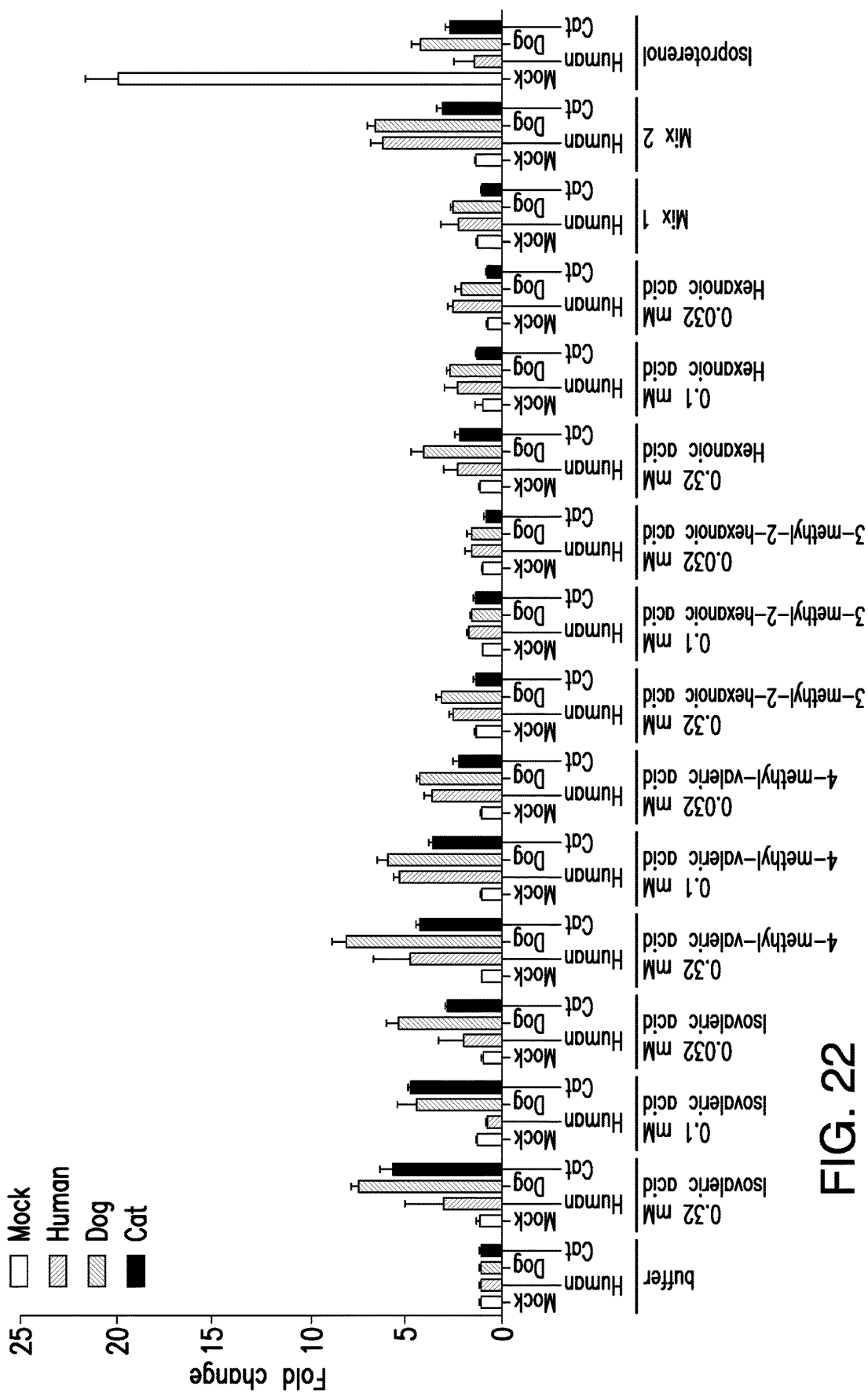

FIG. 22 shows the results of the CRE-NanoLuc luciferase assay using OR_3 (OR51E1).

Figure 23:
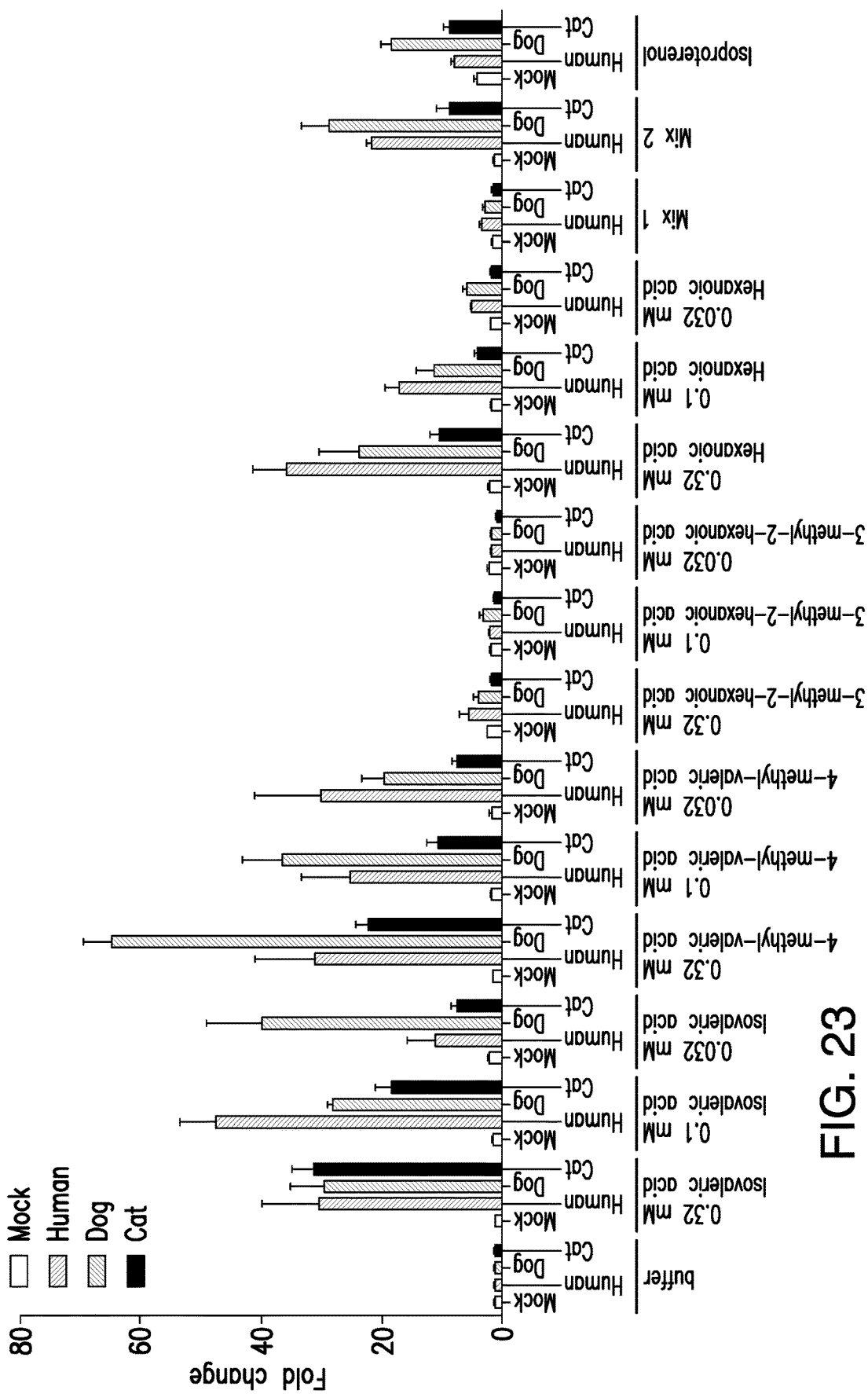

FIG. 23 shows the results of the chAMPion assay using OR_3 (OR51E1).

Figure 24:
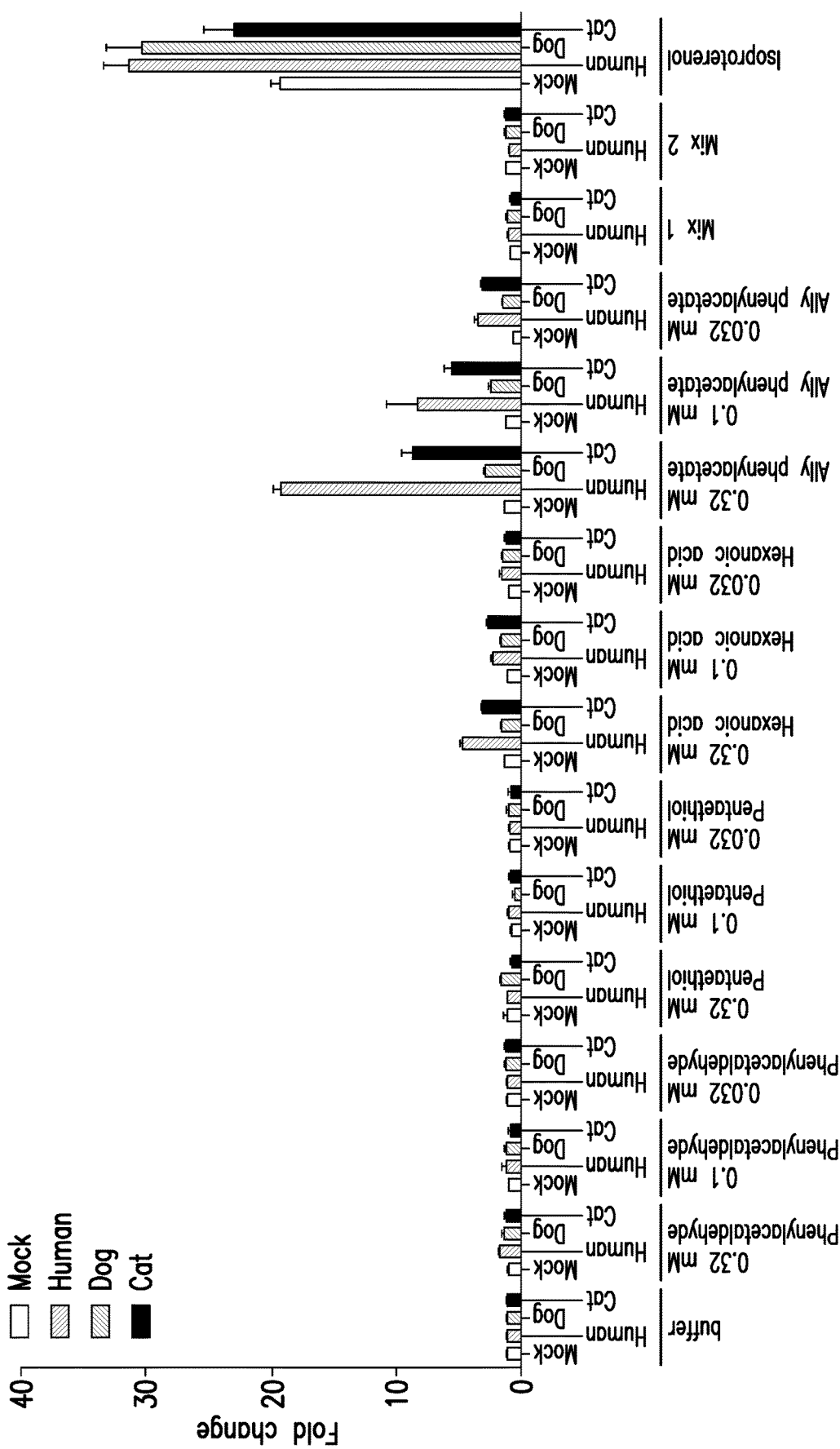

FIG. 24 shows the results of the CRE-NanoLuc luciferase assay using OR_4 (OR51L1).

Figure 25:
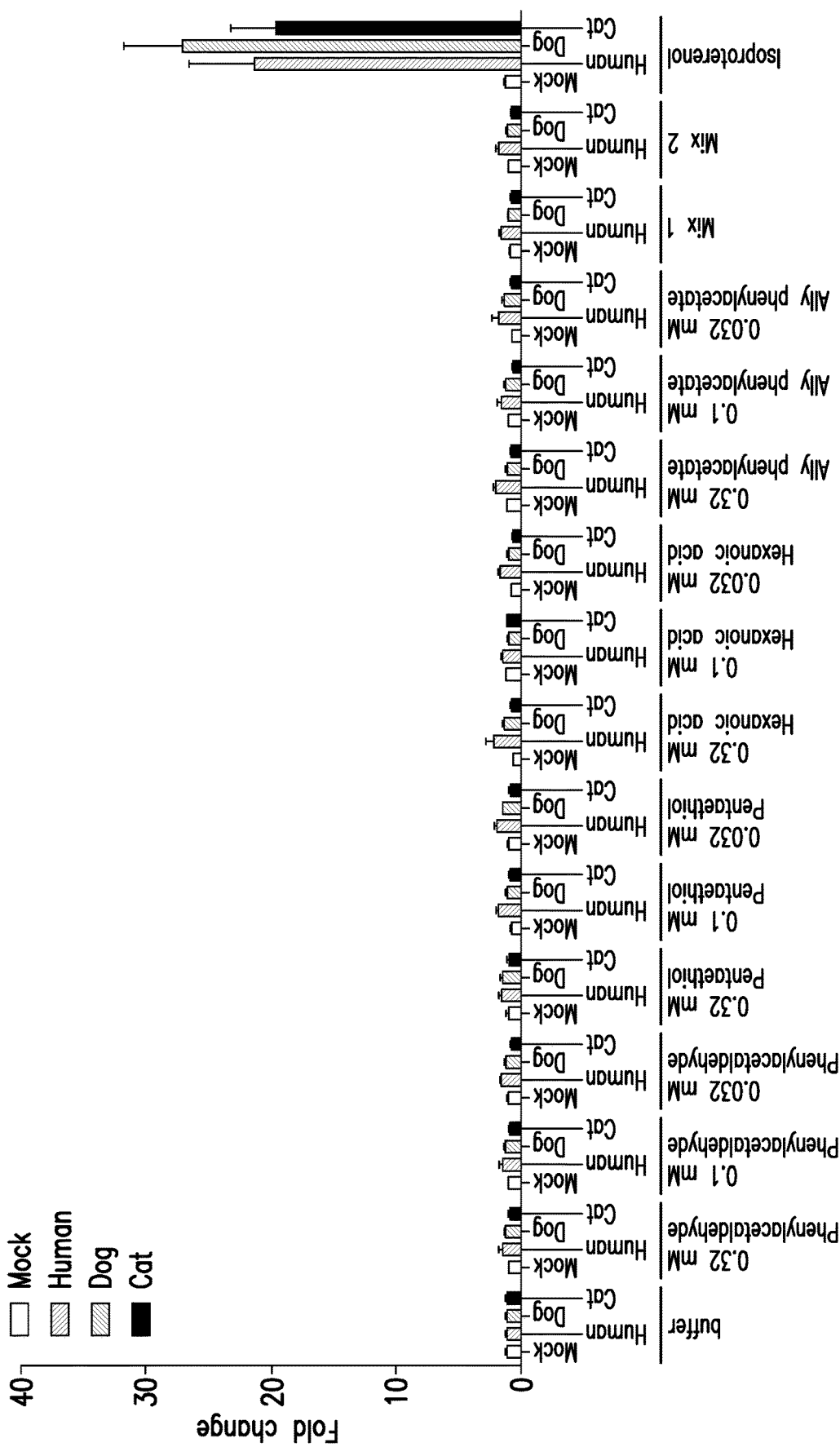

FIG. 25 shows the results of the chAMPion assay using OR_4 (OR51L1).

Figure 26:
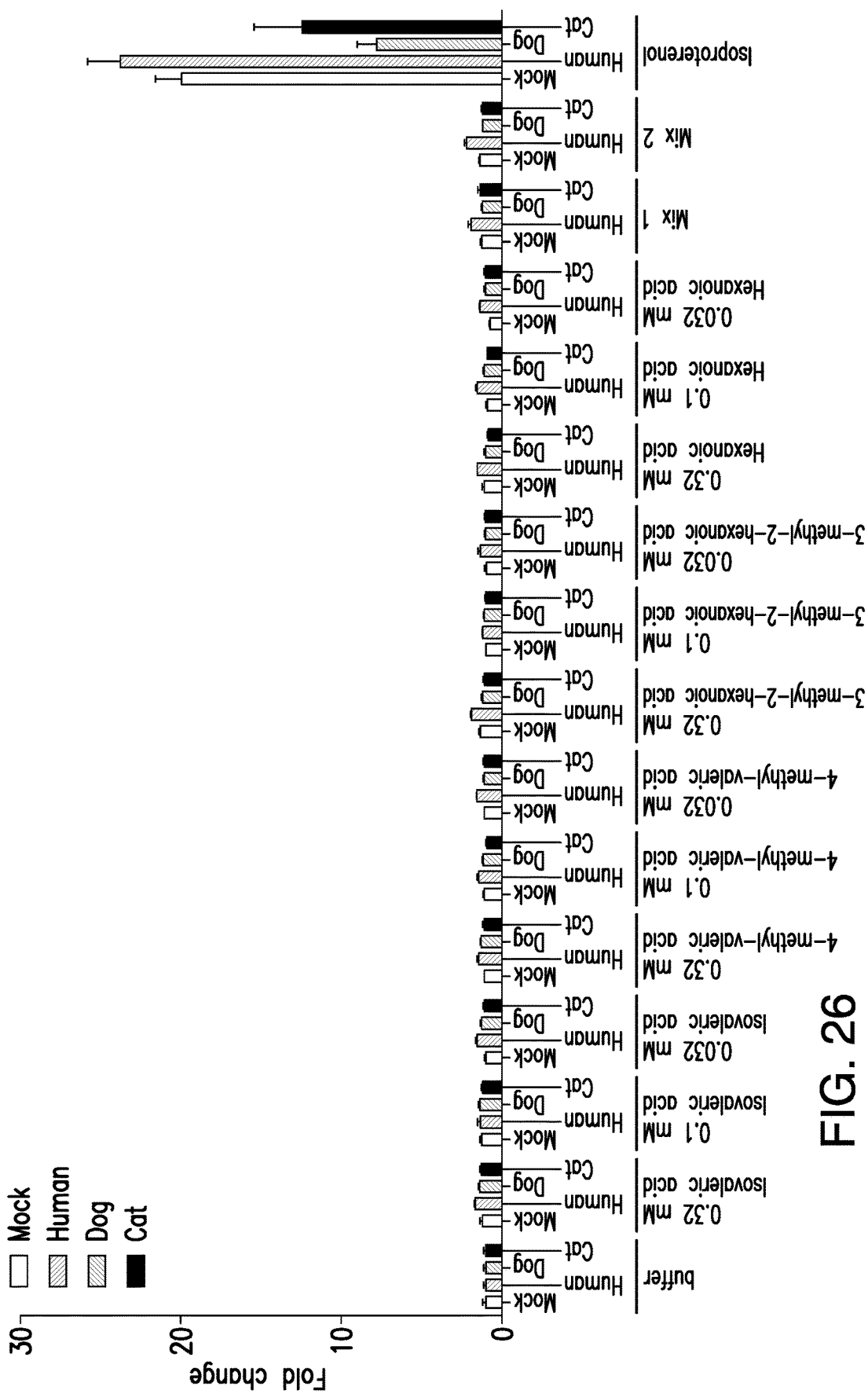

FIG. 26 shows the results of the CRE-NanoLuc luciferase assay using OR_5 (OR11H6).

Figure 27:
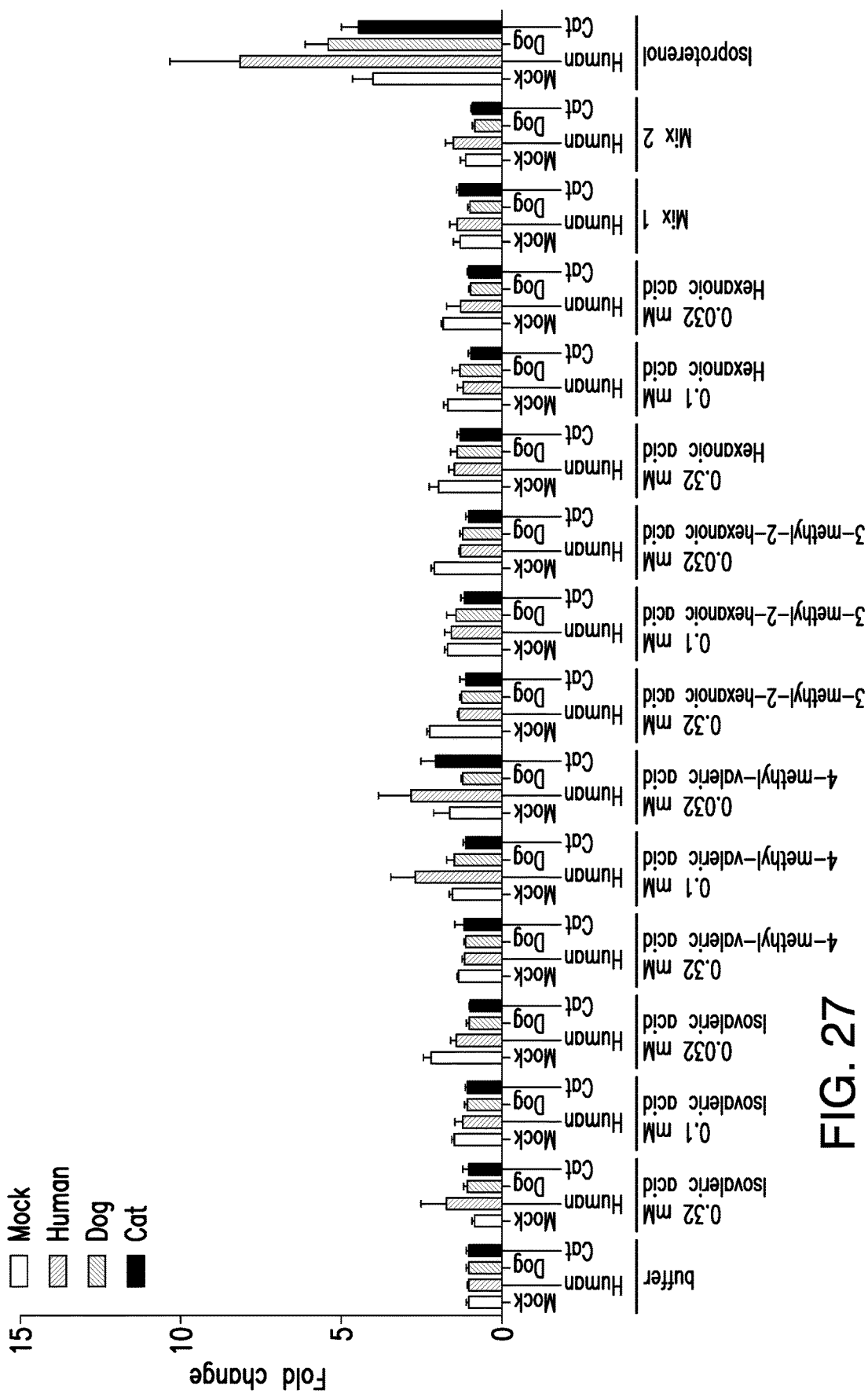

FIG. 27 shows the results of the chAMPion assay using OR_5 (OR11H6).

Figure 28:
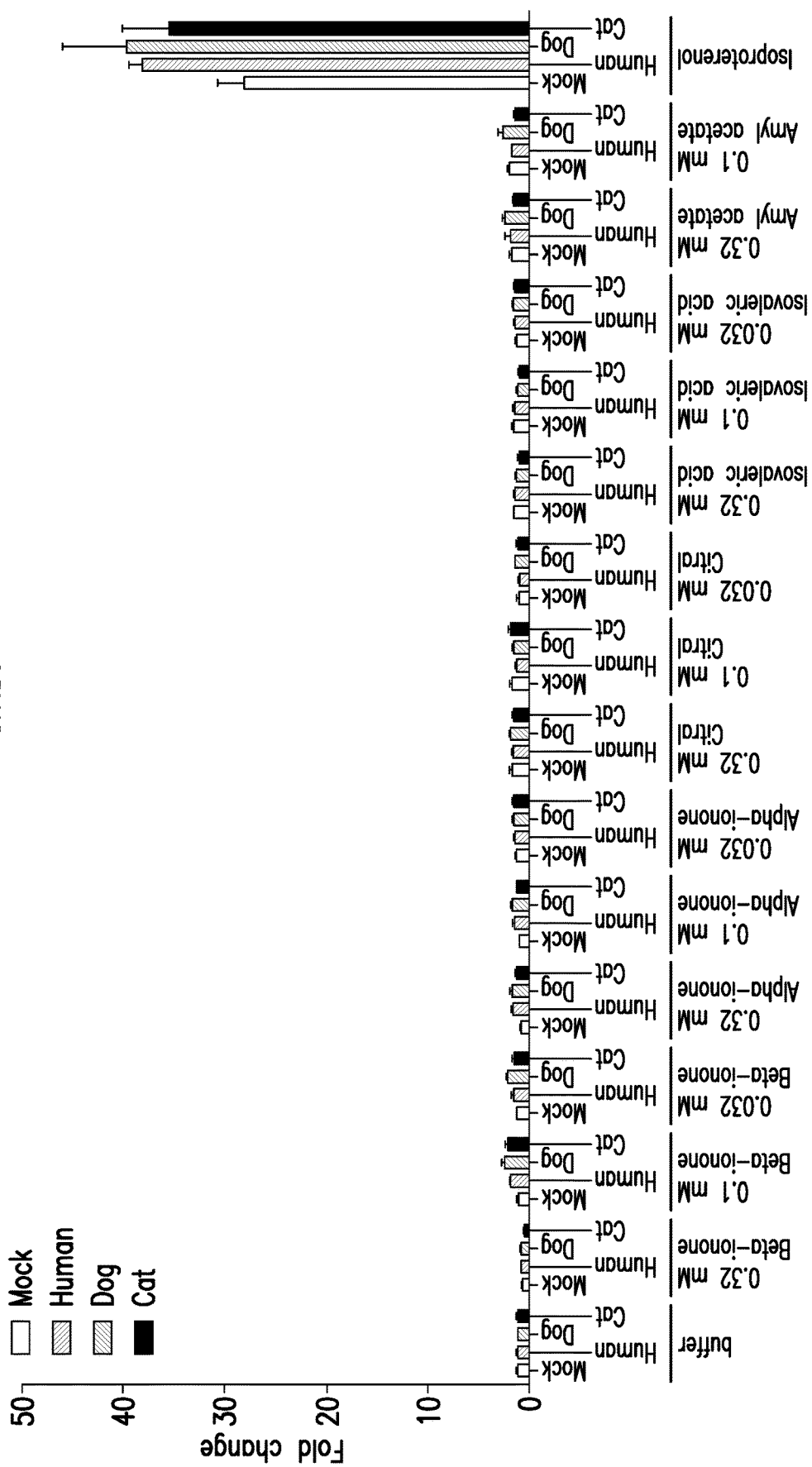

FIG. 28 shows the results of the CRE-NanoLuc luciferase assay using OR_6 (OR4D6).

Figure 29:
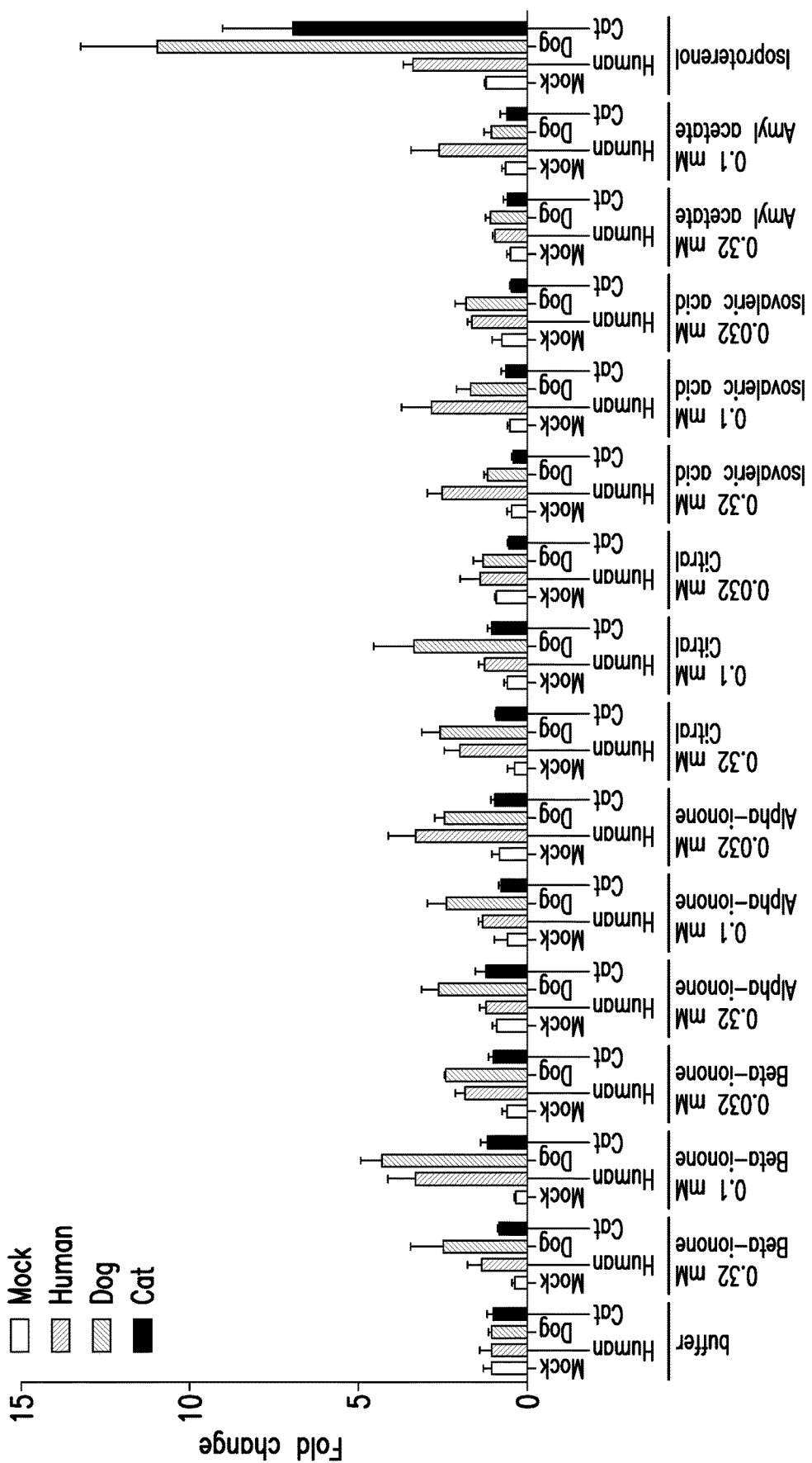

FIG. 29 shows the results of the chAMPion assay using OR_6 (OR4D6).

Figure 30:
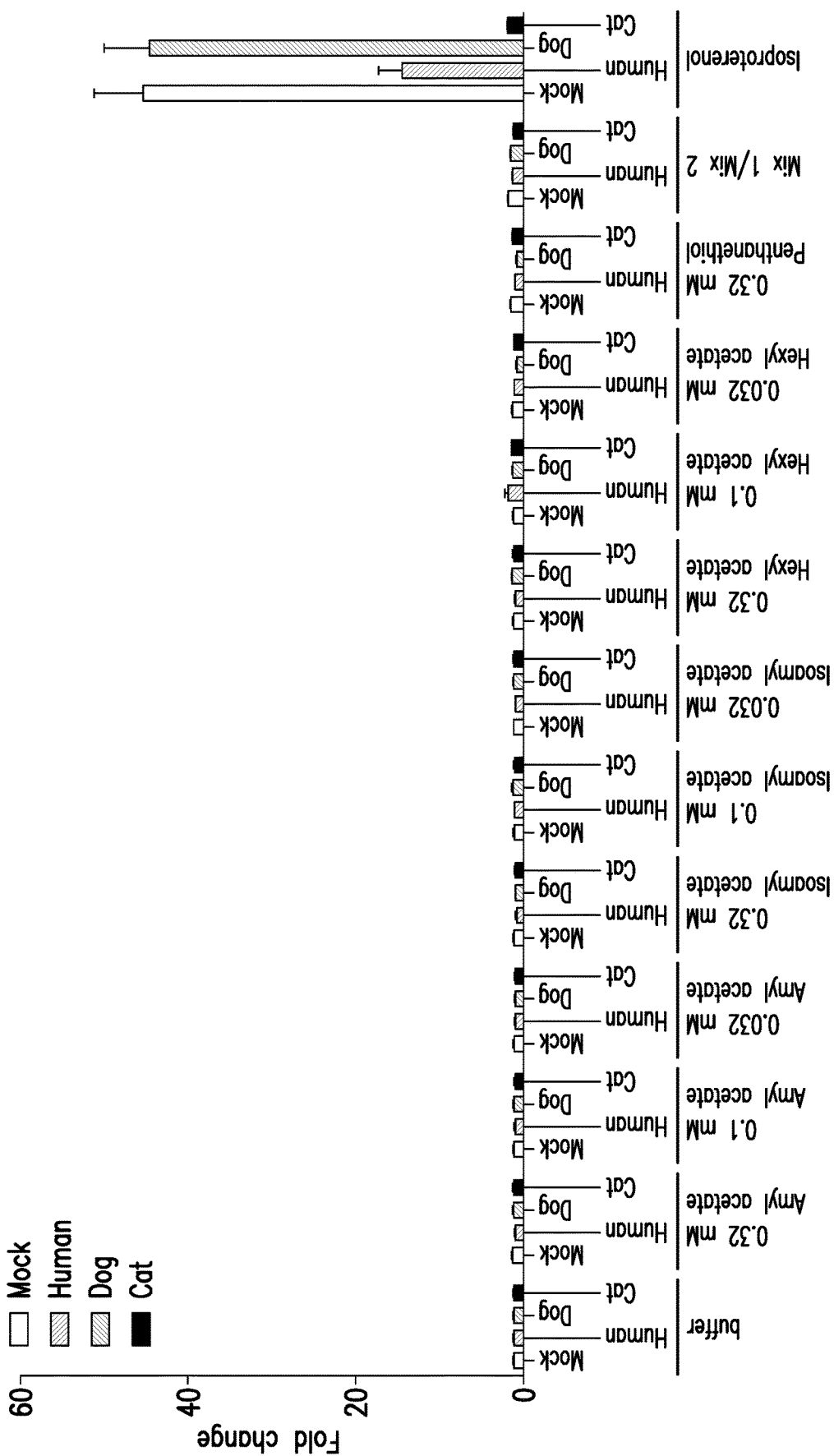

FIG. 30 shows the results of the CRE-NanoLuc luciferase assay using OR_7 (OR4E2).

Figure 31:
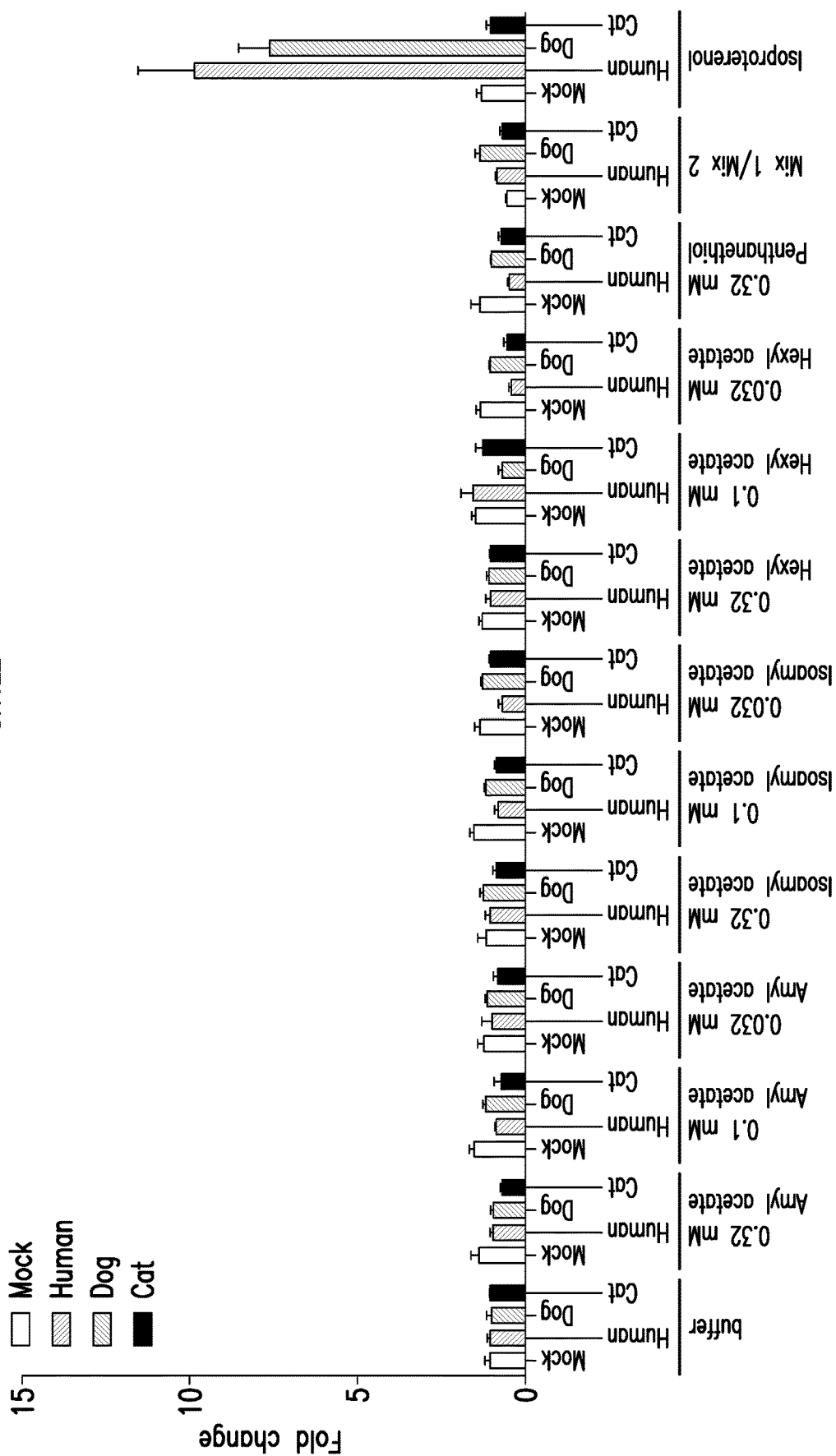

FIG. 31 shows the results of the chAMPion assay using OR_7 (OR4E2).

Figure 32:
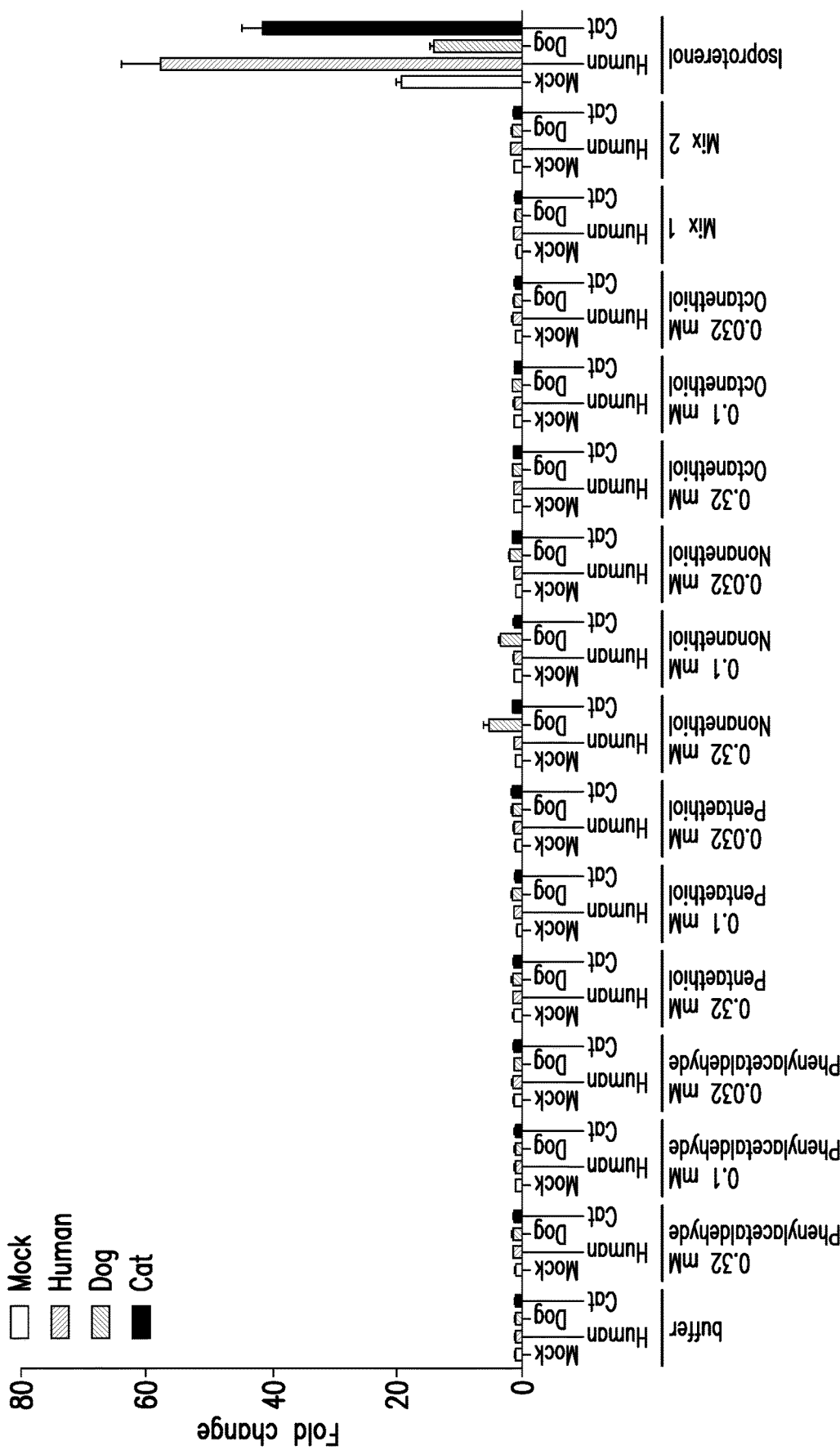

FIG. 32 shows the results of the CRE-NanoLuc luciferase assay using OR_8 (OR2C1).

Figure 33:
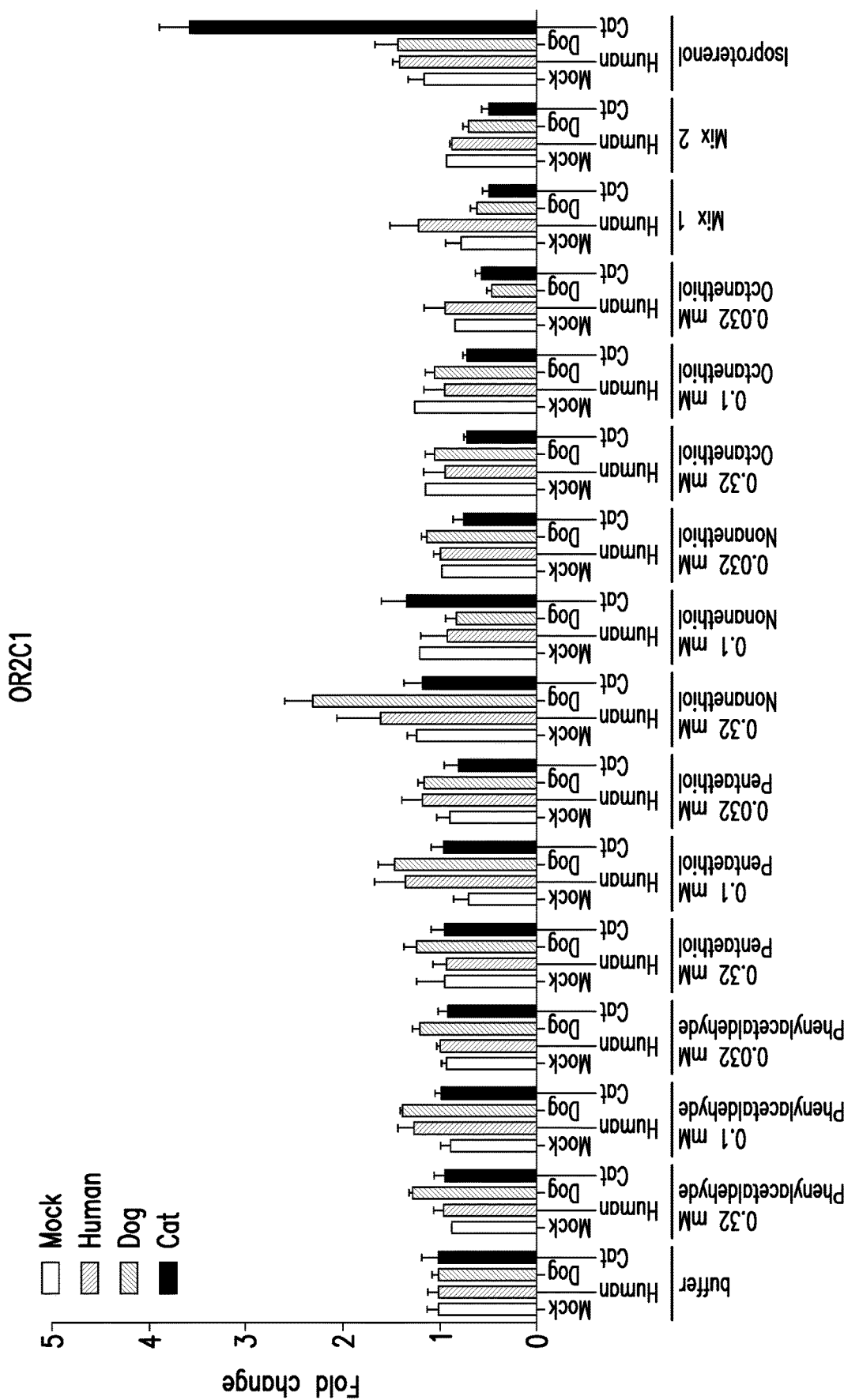

FIG. 33 shows the results of the chAMPion assay using OR_8 (OR2C1).

Figure 34:
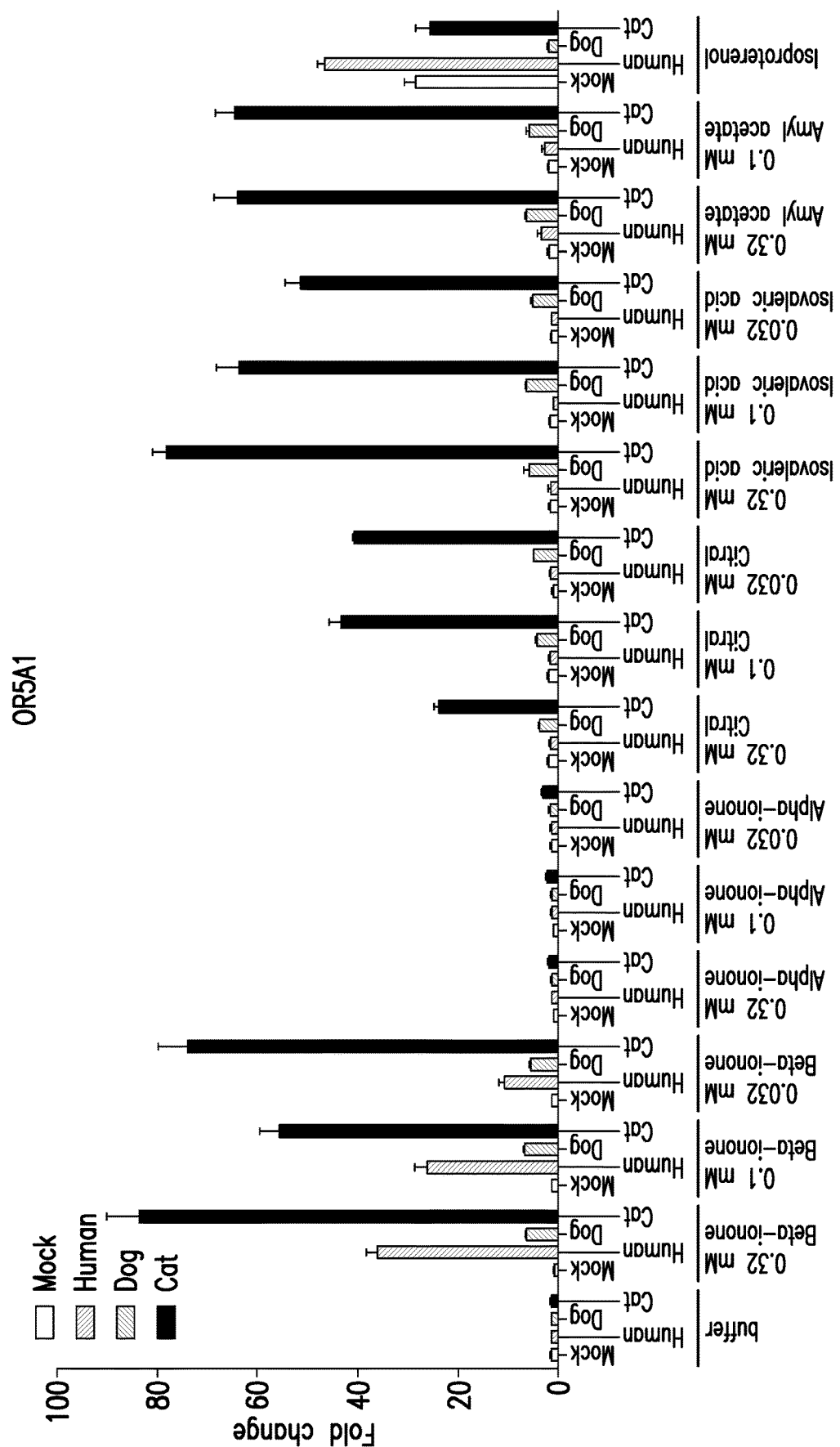

FIG. 34 shows the results of the CRE-NanoLuc luciferase assay using OR_9 (OR5A1).

Figure 35:
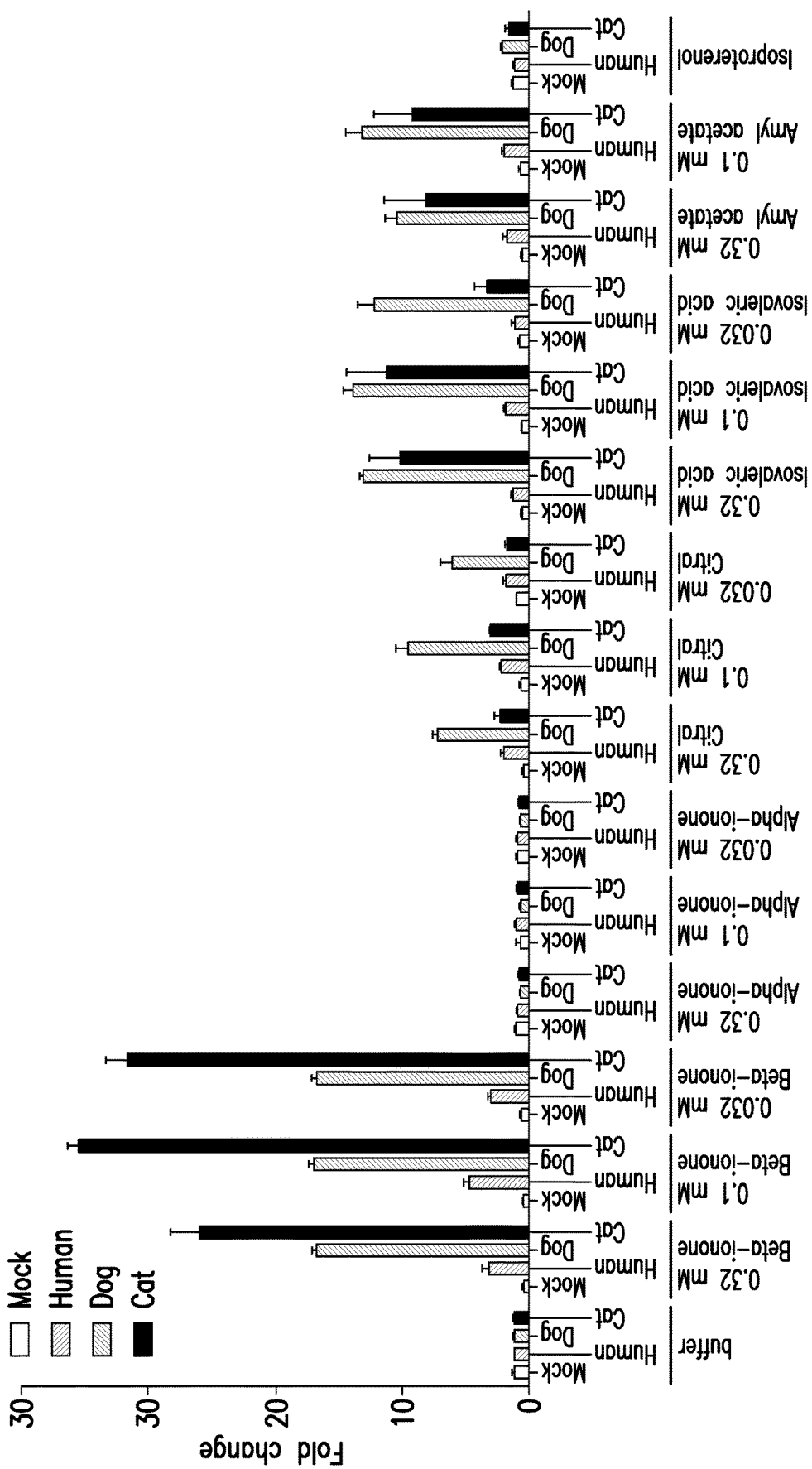

FIG. 35 shows the results of the chAMPion assay using OR_9 (OR5A1).

Figure 36:
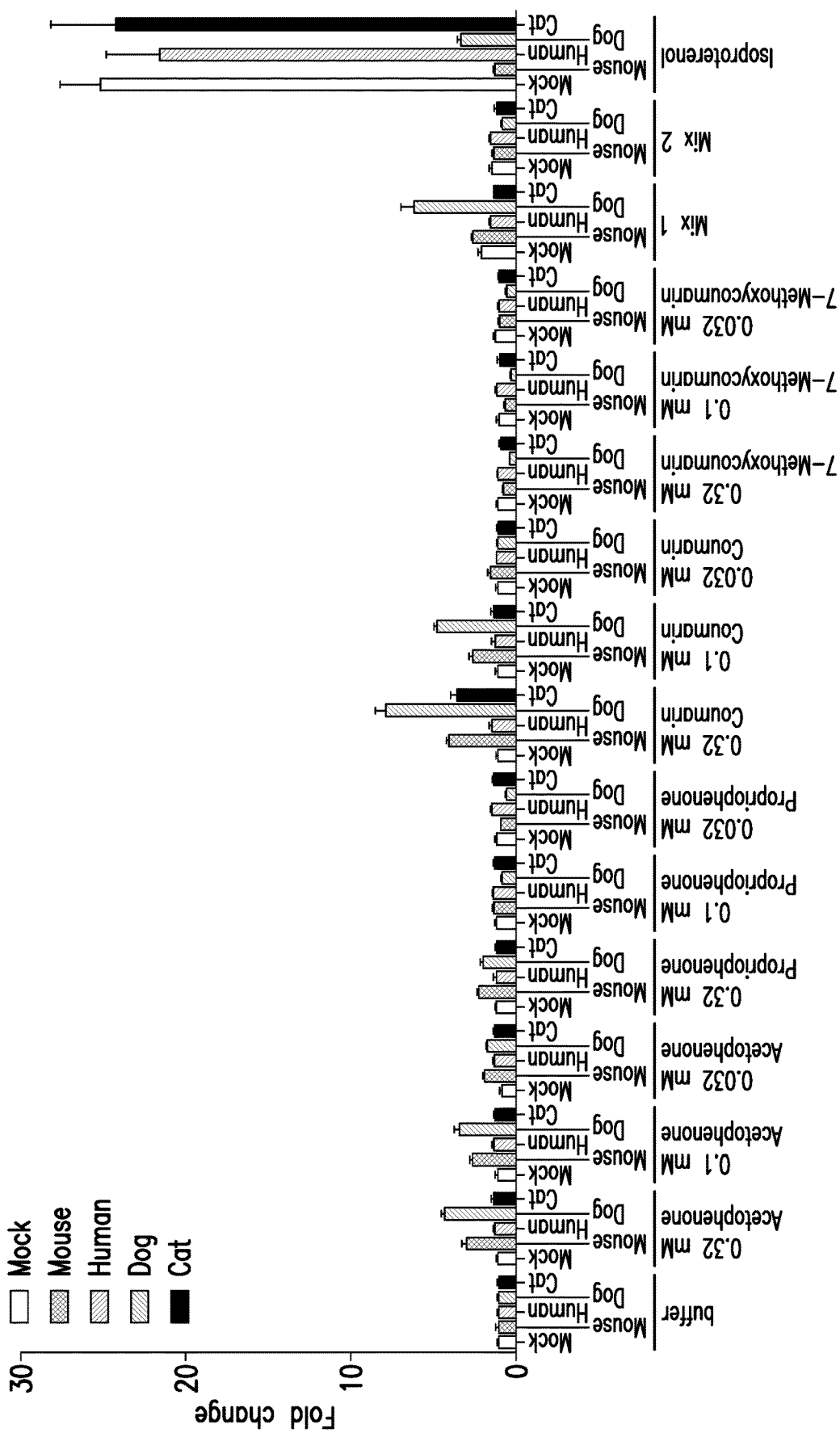

FIG. 36 shows the results of the CRE-NanoLuc luciferase assay using OR_10 (OR8B8).

Figure 37:
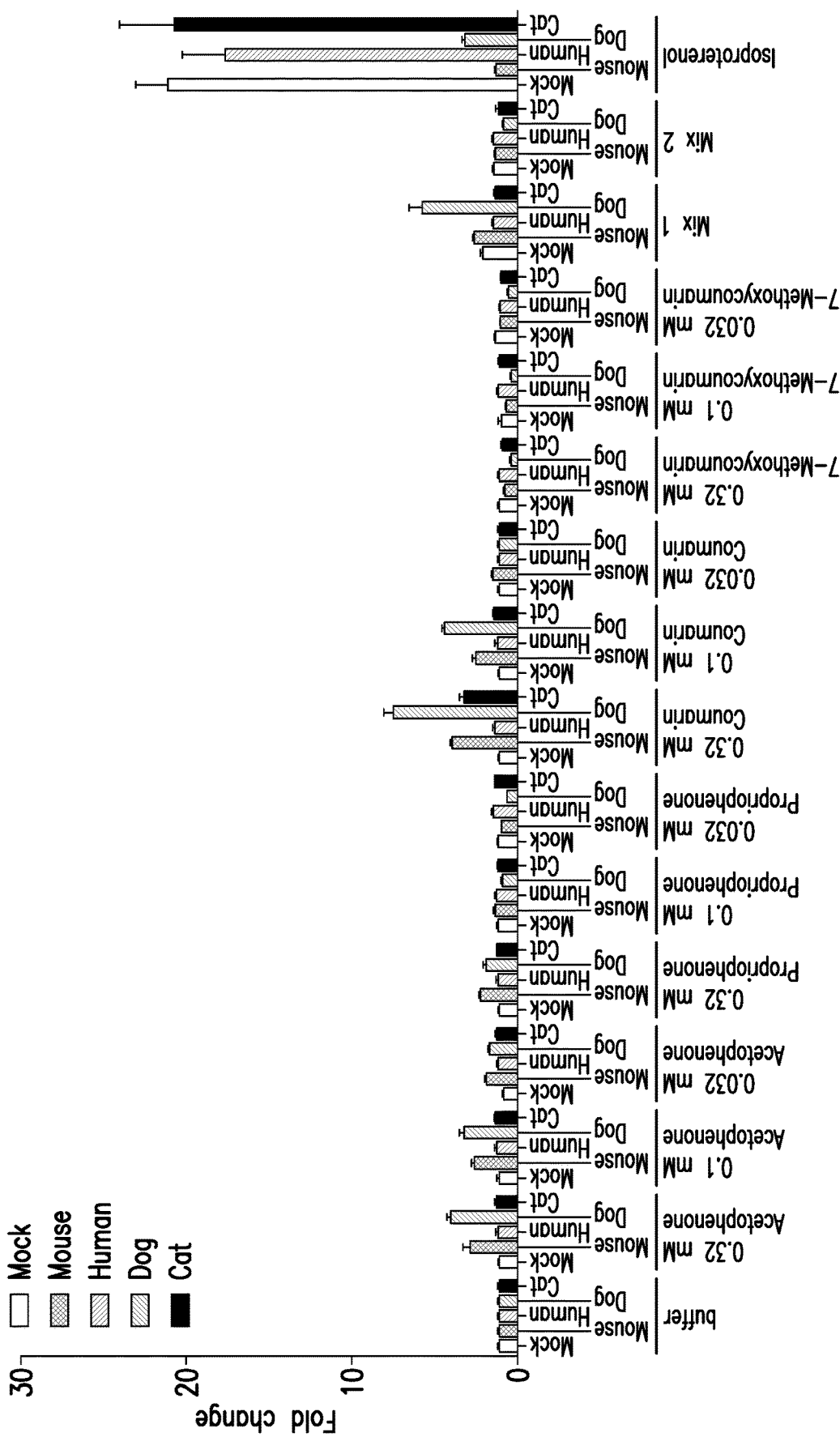

FIG. 37 shows the results of the chAMPion assay using OR_10 (OR8B8).

Figure 38A:
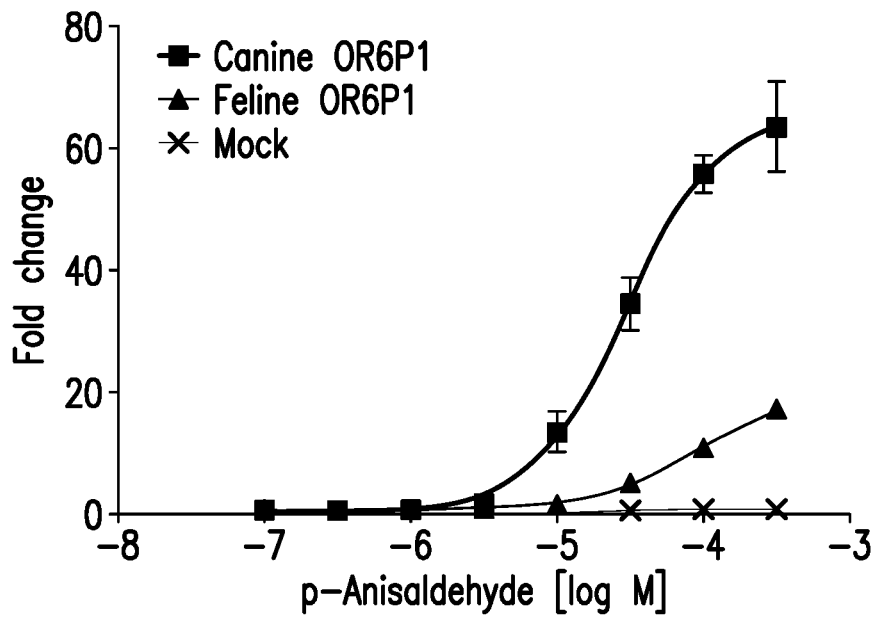
Figure 38B:
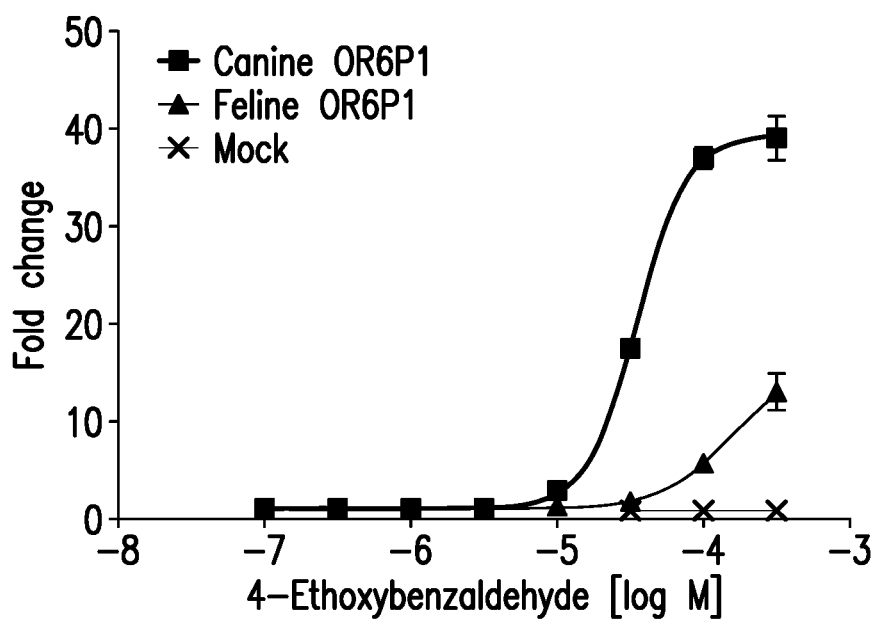
Figure 39A:
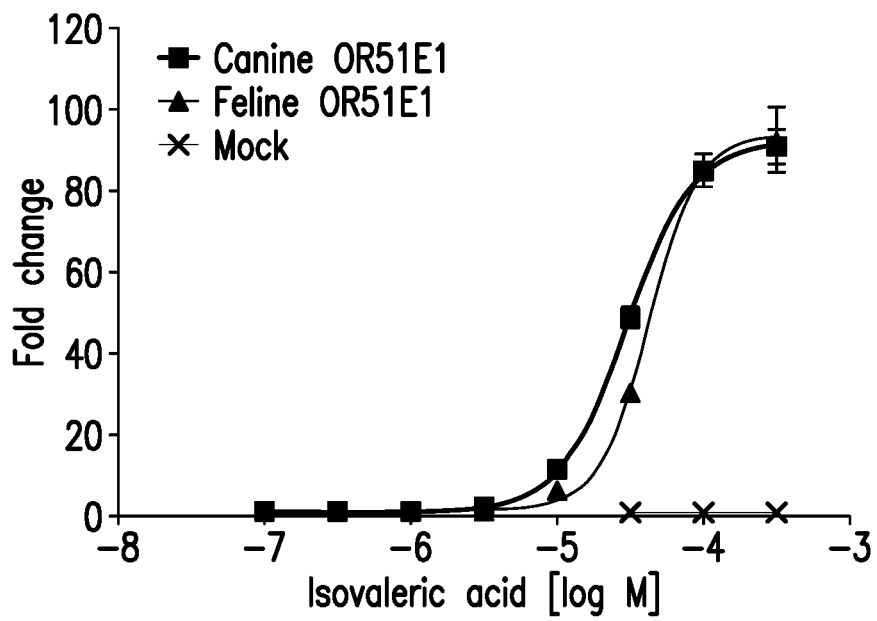
Figure 39B:
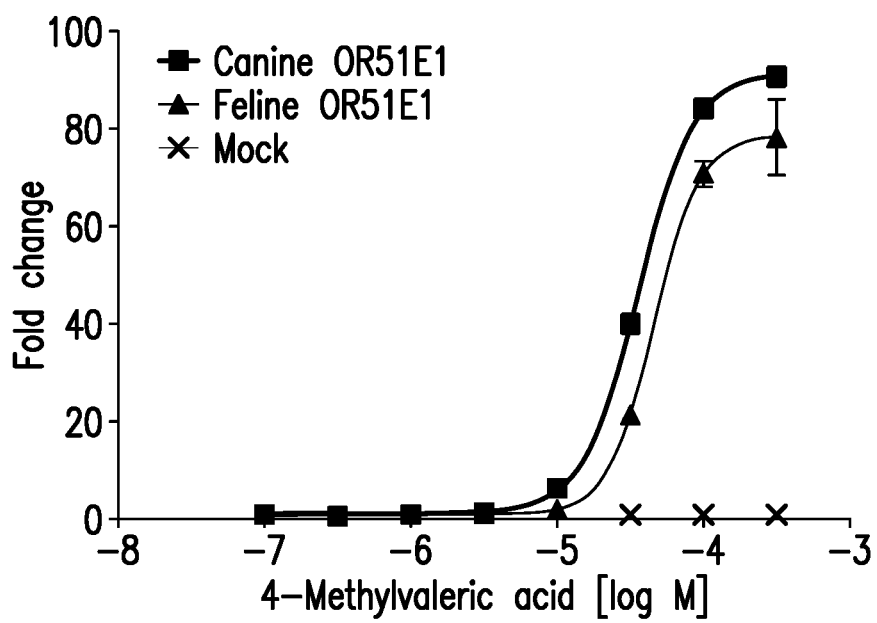
Figure 39C:
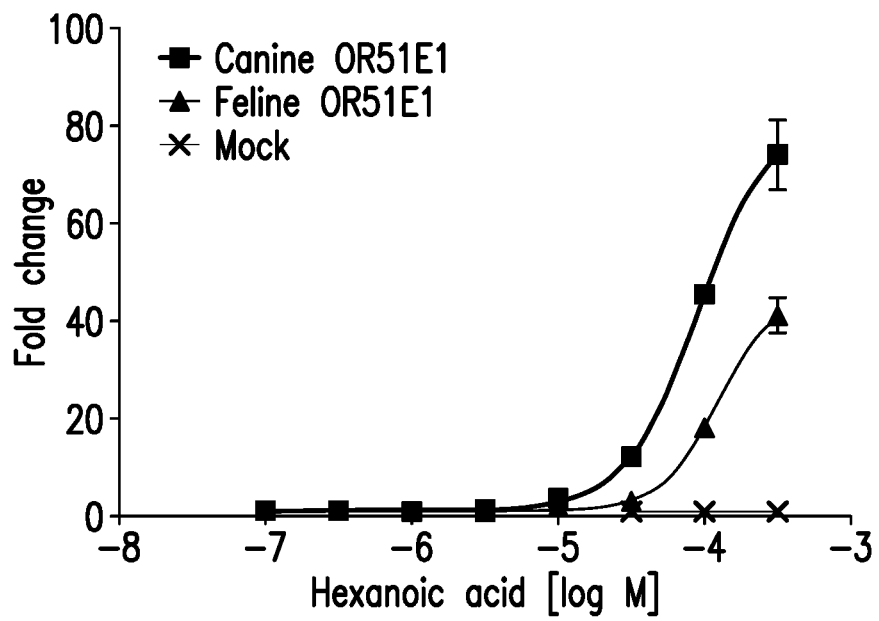
Figure 39D:
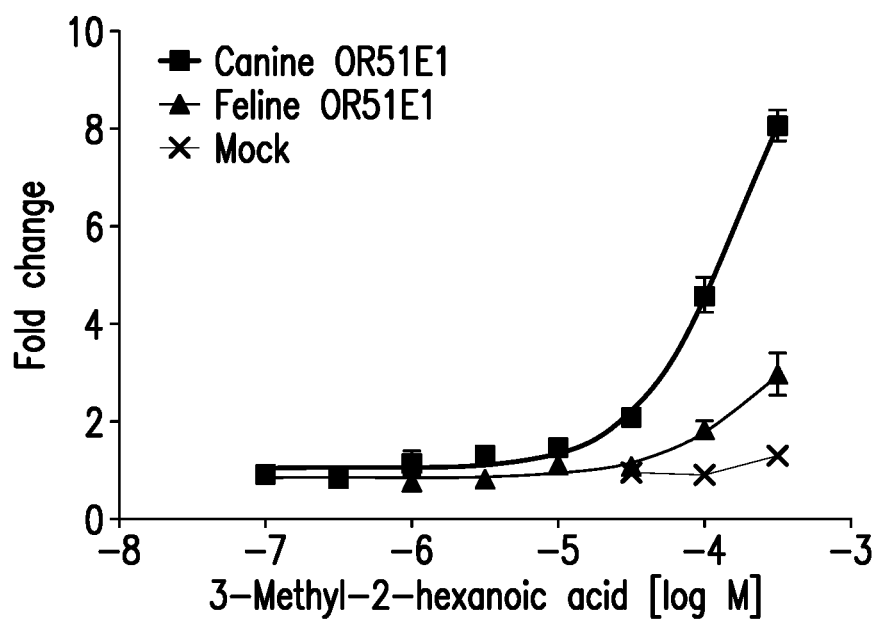

FIGS. 38A-38B show the dose-response curves of the positive ligands for OR_2 (OR6P1). A) The dose-response curves of para-anisaldehyde using mock, feline and canine receptors. B) The dose-response curves of 4-ethoxybenzaldehyde using mock, feline and canine receptors.

FIGS. 39A-39D show the dose-response curves of the positive ligands for OR_3 (OR51E1). A) The dose-response curves of isovaleric acid using mock, feline and canine receptors. B) The dose-response curves of 4-methyl-valeric acid using mock, feline and canine receptors. C) The dose-response curves of hexanoic acid using mock, feline and canine receptors. D) The dose-response curves of 3-methyl-2-hexanoic acid using mock, feline and canine receptors.

Figure 40A:
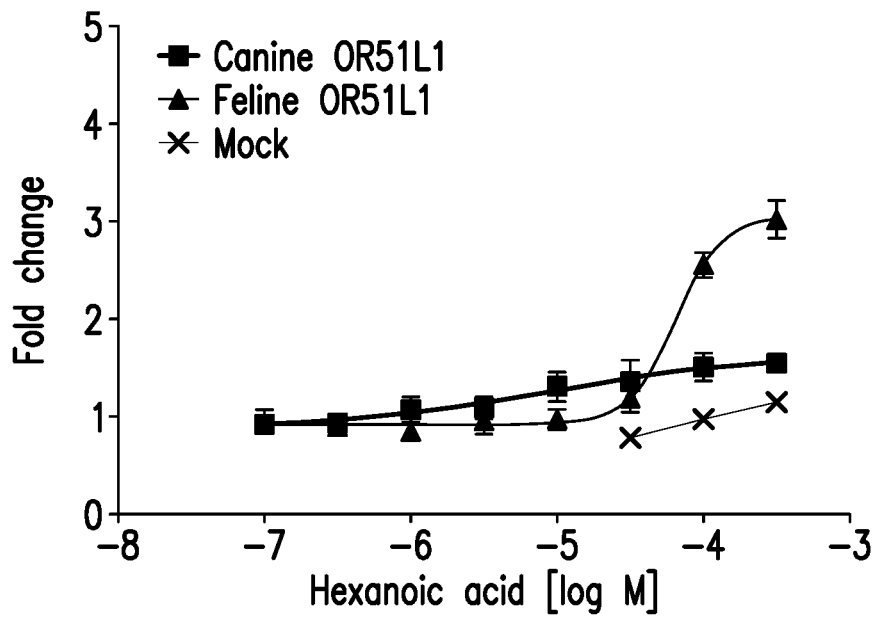
Figure 40B:
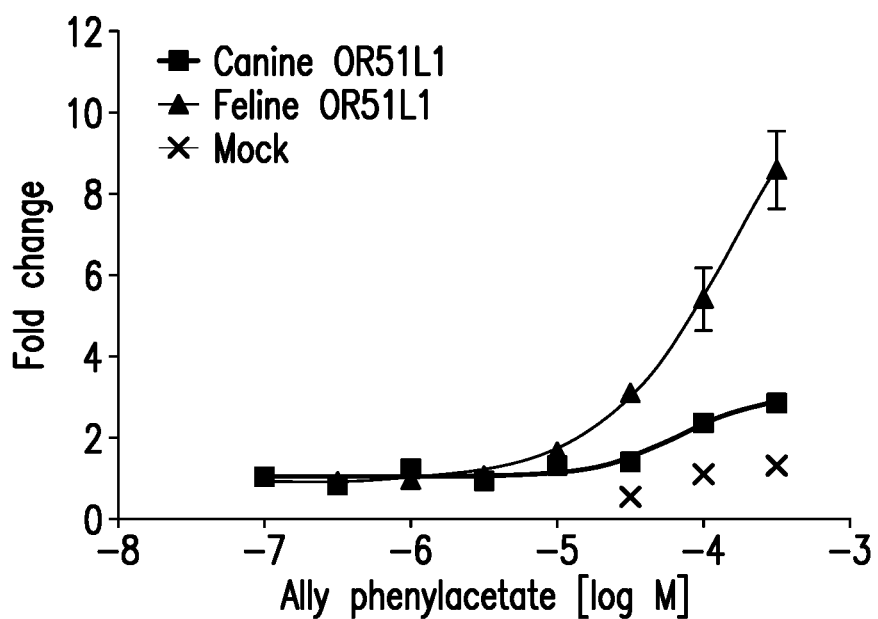

FIGS. 40A-40B show the dose-response curves of the positive ligands for OR_4 (OR51L1). A) The dose-response curves of hexanoic acid using mock, feline and canine receptors. B) The dose-response curves of allyl-phenylacetate using mock, feline and canine receptors.

Figure 41A:
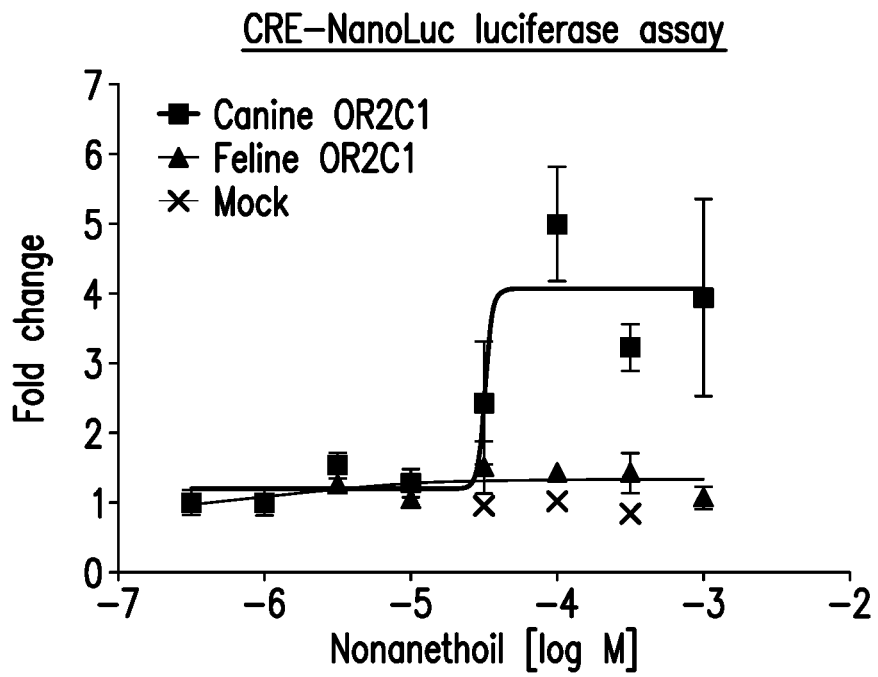
Figure 41B:
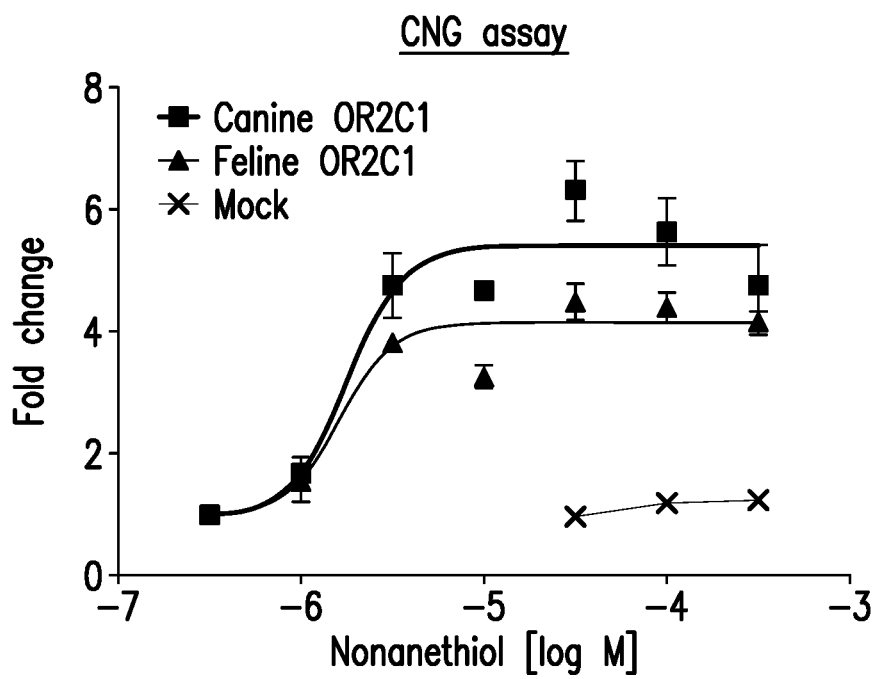
Figure 42A:
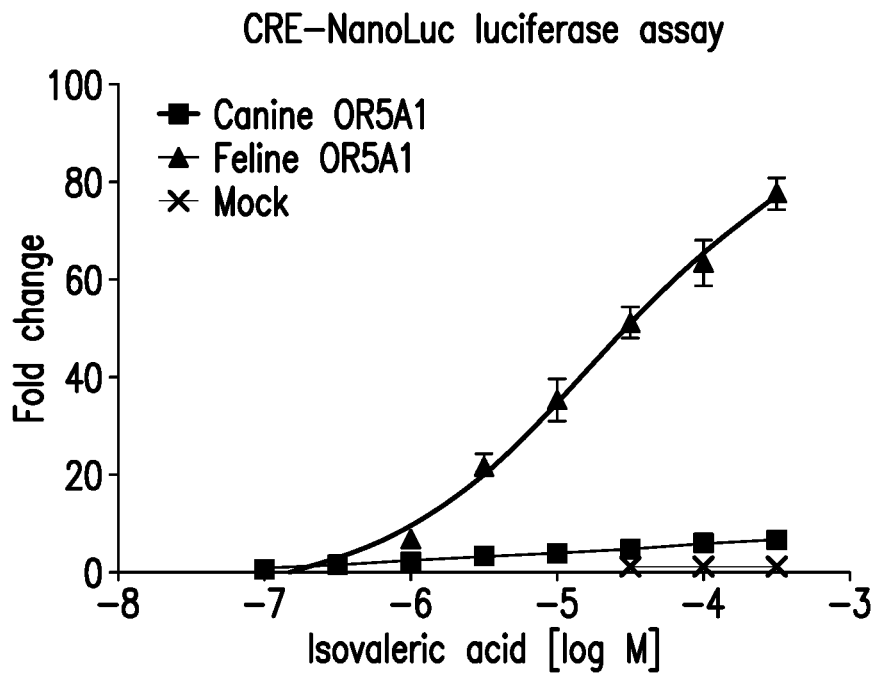
Figure 42B:
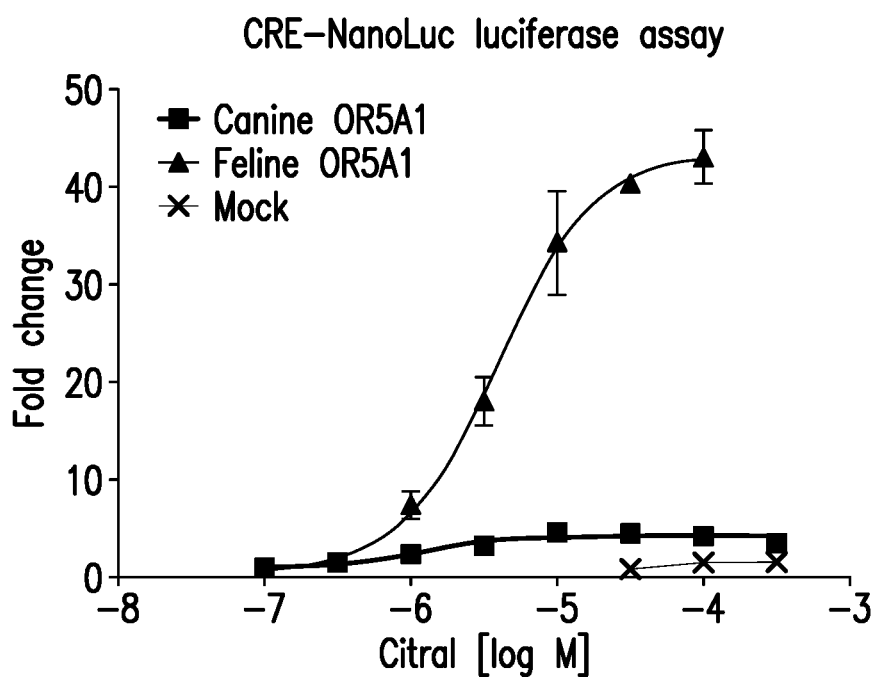
Figure 42C:
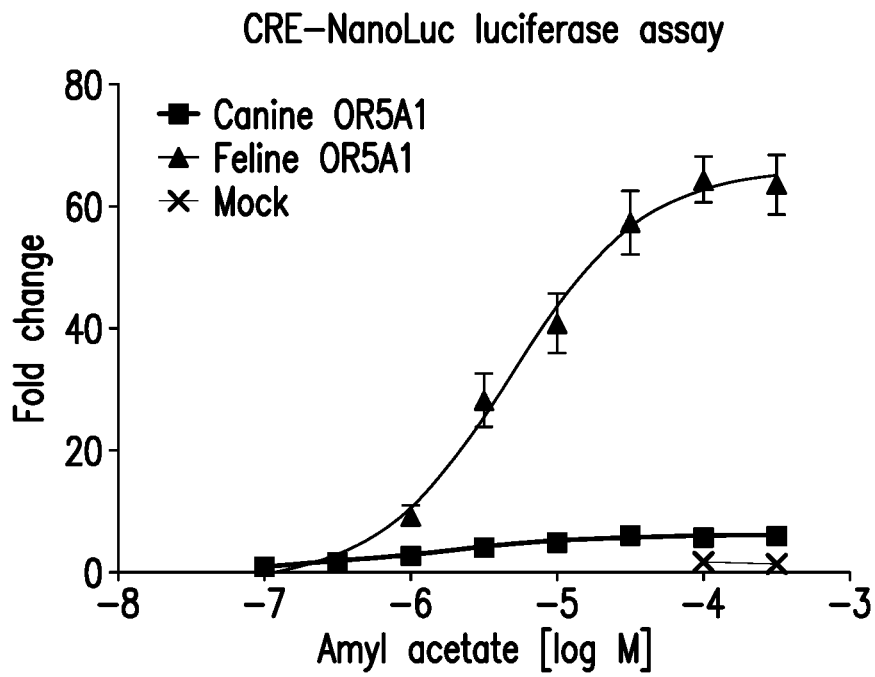
Figure 42D:
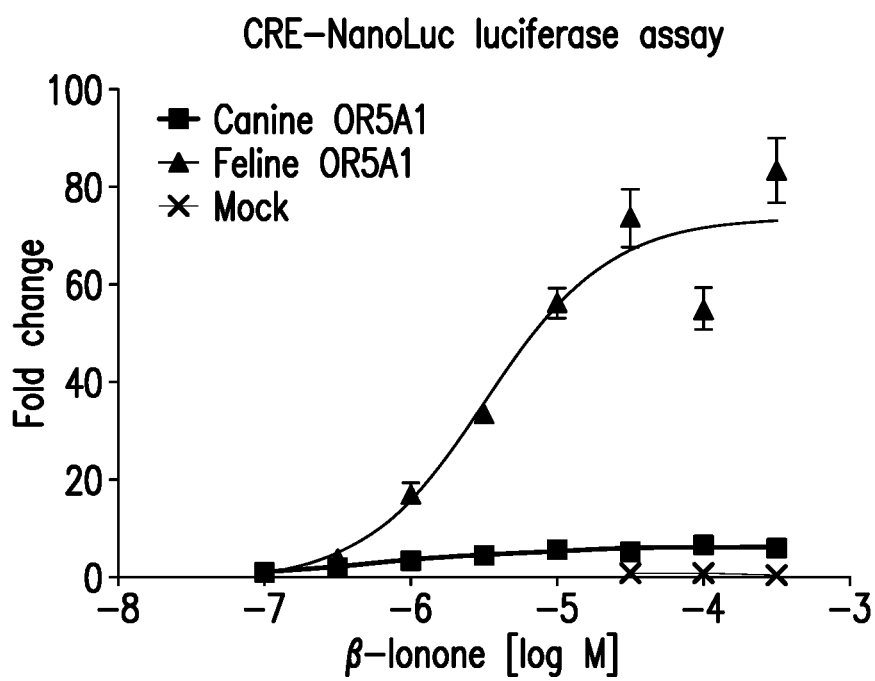
Figure 42E:
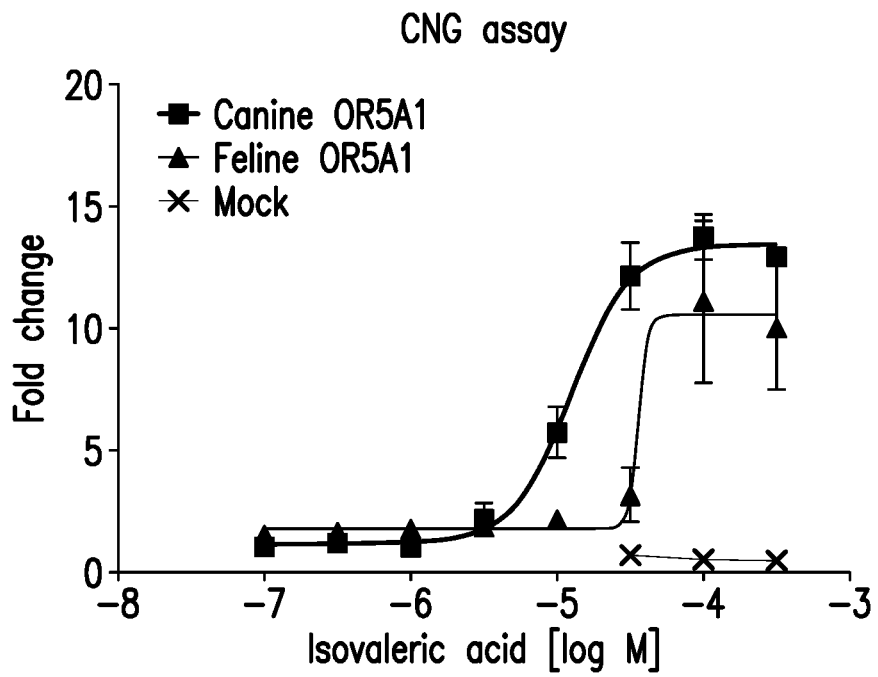
Figure 42F:
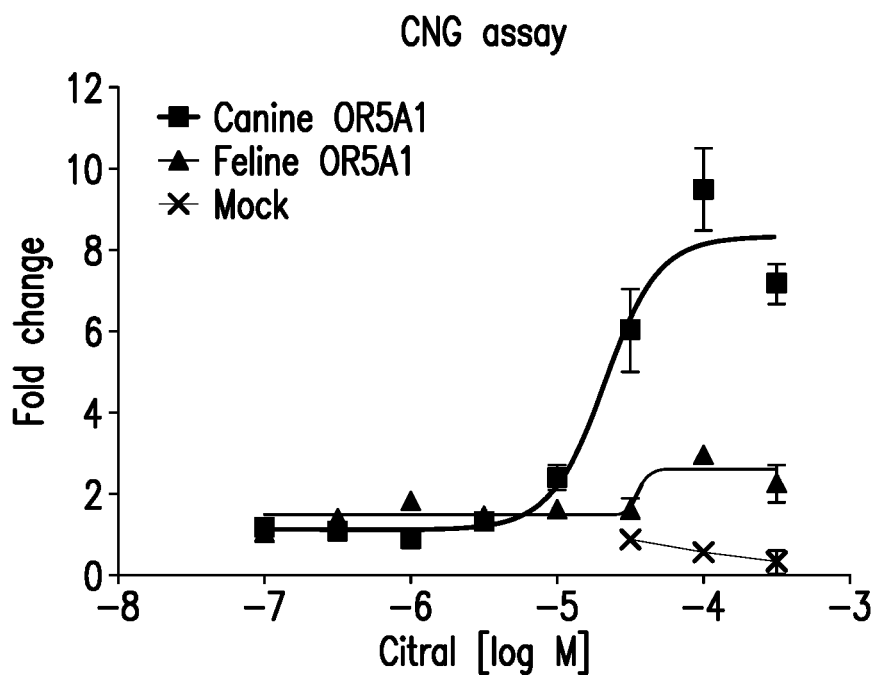
Figure 42G:
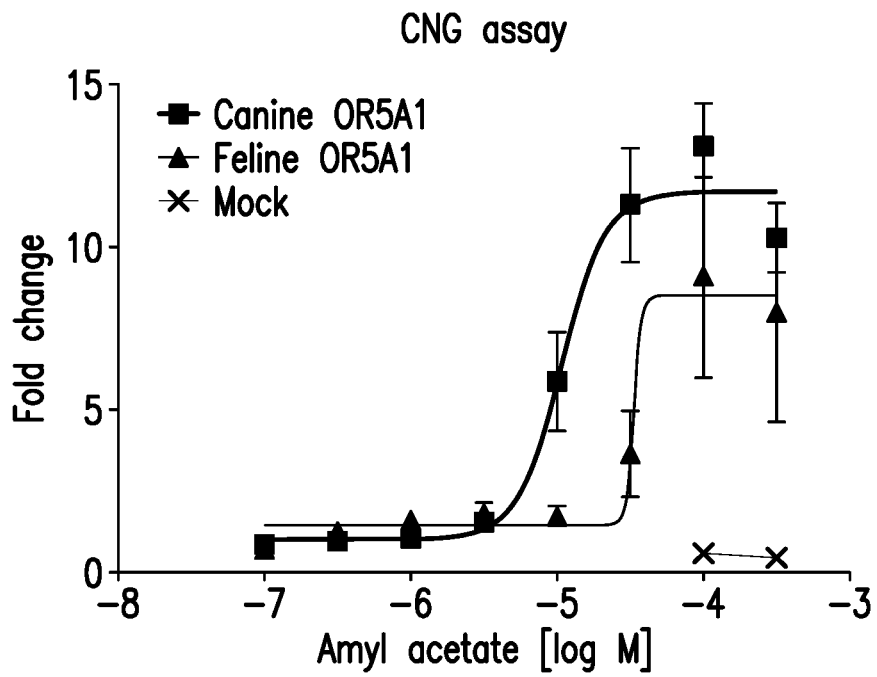
Figure 42H:
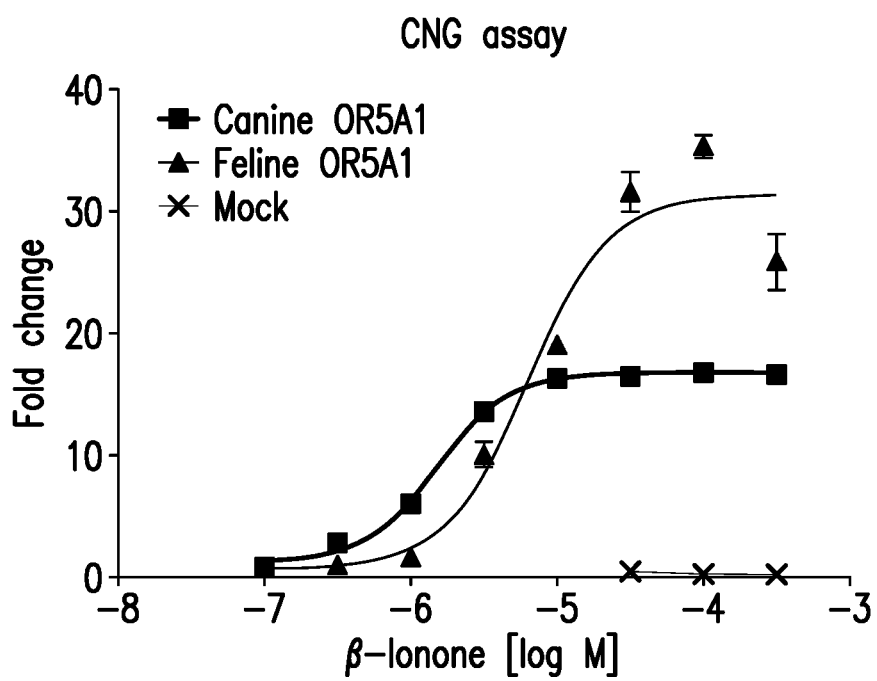

FIGS. 41A-41B show the dose-response curves of the positive ligands for OR_8 (OR2C1). A) The dose-response curves of nonanethiol using mock, feline and canine receptors and using the CRE-NanoLuc luciferase assay. B) The dose-response curves of nonanethiol using mock, feline and canine receptors and using the CNG assay.

FIGS. 42A-42H show the dose-response curves of the positive ligands for OR_9 (OR5A1). A) The dose-response curves of isovaleric acid using mock, feline and canine receptors and using the CRE-NanoLuc luciferase assay. B) The dose-response curves of citral using mock, feline and canine receptors and using the CRE-NanoLuc luciferase assay. C) The dose-response curves of amyl acetate using mock, feline and canine receptors and using the CRE-NanoLuc luciferase assay. D) The dose-response curves of beta-ionone using mock, feline and canine receptors and using the CRE-NanoLuc luciferase assay. E) The dose-response curves of isovaleric acid using mock, feline and canine receptors and using the CNG assay. F) The dose-response curves of citral using mock, feline and canine receptors and using the CNG assay. G) The dose-response curves of amyl acetate using mock, feline and canine receptors and using the CNG assay. H) The dose-response curves of beta-ionone using mock, feline and canine receptors and using the CNG assay. Human OR5A1 is only responsive in CRE-Nanoluc assay, which responds only to β-ionone. Dog OR5A1 has slightly different response profile in both assays: in CRE-NanoLuc assay the receptor responds to all four compounds with similar EC50 and Emax; in CNG assay the receptor responds to all four compounds, but the response to β-ionone has the lowest EC50 and the highest Emax. Cat OR5A1 has different response profile in both assays: in CRE-NanoLuc assay the receptor responds to all four compounds with similar EC50 and Emax; in CNG assay the receptor has strong response only to β-ionone, but has weaker responses for isovaleric acid and amyl acetate, and no response to citral. The difference in response profiles in both assays might be due to different assay protocols and longer incubation times in the CRE-NanoLuc assay.

Figure 43A:
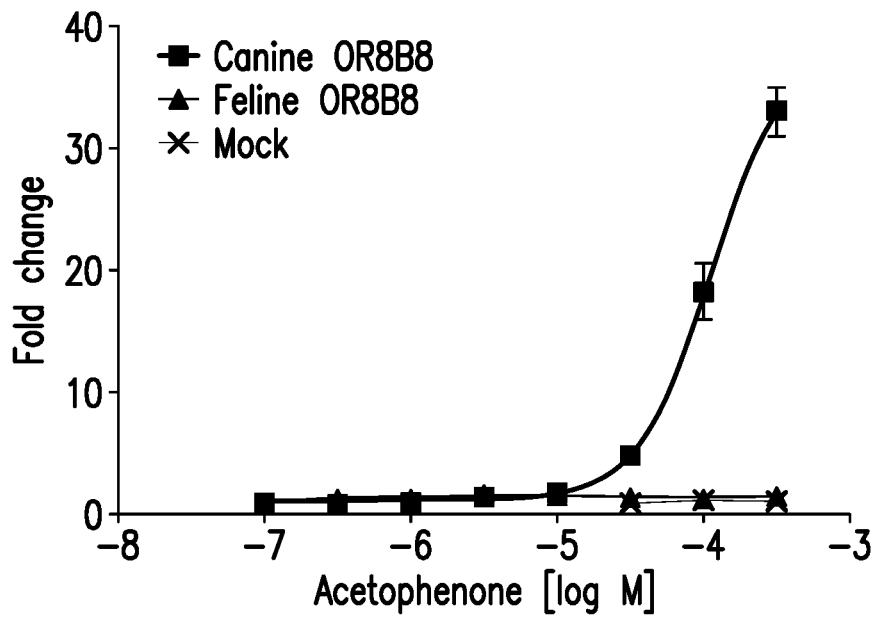
Figure 43B:
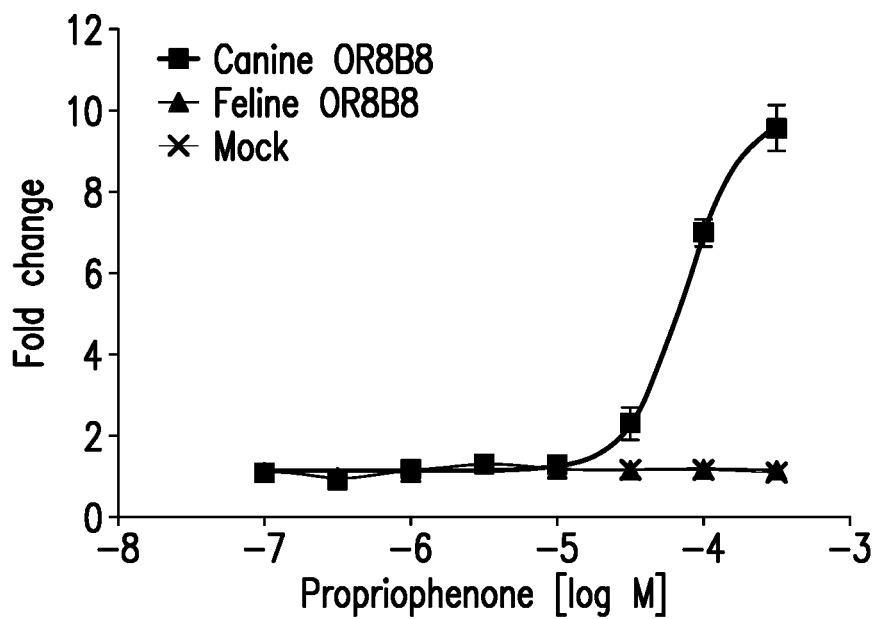
Figure 43C:
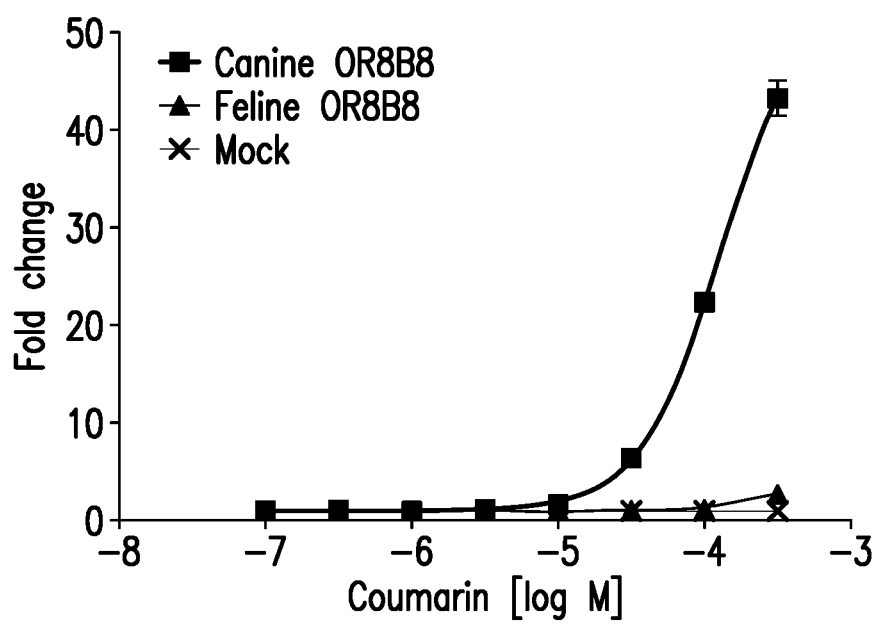

FIGS. 43A-43C show the dose-response curves of the positive ligands for OR_10 (OR8B8). A) The dose-response curves of acetophenone using mock, feline and canine receptors. B) The dose-response curves of propriophenone using mock, feline and canine receptors. C) The dose-response curves of coumarin using mock, feline and canine receptors.

DETAILED DESCRIPTION

The presently disclosed subject matter relates to methods for screening and identifying compounds that modulate the activity and/or expression of olfactory receptors. The presently disclosed subject matter further relates to making fragrant, palatable, nutritionally-complete pet food products, medicines, as well as non-nutritionally-complete pet food products (e.g., snack, care and treats), wherein the raw materials of the pet food and/or finalized pet food product or medicine is screened to determine if it contains compounds that modulate the olfactory receptors. Furthermore, such screening methods can be used to select raw materials and/or finalized pet food products that do not comprise repellant compounds. Compounds identified through said methods can be used to modify the fragrance and/or palatability of pet food products and medicines by increasing or decreasing an attractive or repellant odor. Said compounds can also be used to increase a repellant odor of an object, and thereby reduce contact, palatability and ingestion by a cat or a dog.

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the methods and compositions of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used interchangeably herein, "odor", "smell" and "aroma" refer to a sensation caused by activation of receptor cells in a subject's olfactory system. In certain embodiments, odor can be characterized by a set of psychophysical descriptors, such as, for example, one or more of a fruity, floral, honey, fatty, minty and metallic smell. See, e.g., Dravnieks, Atlas of Odor Character Profiles, American Society for Testing and Materials, 1985; Castro et al., PLOS ONE, 0073289, 2014, the contents of which are incorporated herein by reference. In certain embodiments, an olfactory sense is elicited in a subject by an "odorant." In certain embodiments, combination of different odorants can be perceived as a new odor object. In certain embodiments, an odorant can be a synthetic odorant. In certain embodiments, the odorant is obtained or prepared from a natural source.

As used herein, "olfactory profile" refers to a combination of odor senses, each of which can be characterized by a set of psychophysical descriptors, such as, for example, one or more of a fruity, floral, honey, fatty, minty and metallic smell. In certain embodiments, a combination of different odorants can be perceived as a new odor sensory experience. In certain embodiments, an olfactory profile is produced by one or more odorant that is present in a composition at the same or different concentrations. In certain embodiments, an olfactory profile refers to the intensity of an odor or combination of odors, for example, a fruity, floral, honey, fatty, minty and metallic smell, as detected by a subject or any assay known in the art. In certain embodiments, modifying, changing or varying the combination of odorants in an olfactory profile can change the sensory experience of a subject.

As used herein, "flavor" refers to one or more sensory stimuli, such as, for example, one or more of taste (gustatory), smell (olfactory), touch (tactile) and temperature (thermal) stimuli. In certain non-limiting embodiments, the sensory experience of a subject exposed to a flavor can be classified as a characteristic experience for the particular flavor. For example, a flavor can be identified by the subject as being, but not limited to, a floral, citrus, berry, nutty, caramel, chocolate, peppery, smoky, cheesy, meaty, etc., flavor. As used herein, a flavor composition can be selected from a liquid, solution, dry powder, spray, paste, suspension and any combination thereof. The flavor can be a natural composition, an artificial composition, a nature identical, or any combination thereof.

As used herein, "flavor profile" refers to a combination of sensory stimuli, for example, tastes, olfactory, tactile and/or thermal stimuli. In certain embodiments, the flavor profile comprises one or more flavors which contribute to the sensory experience of a subject. In certain embodiments, modifying, changing or varying the combination of stimuli in a flavor profile can change the sensory experience of a subject.

As used herein "admixing," for example, "admixing the flavor composition or combinations thereof of the present application with a food product," refers to the process where the flavor composition, or individual components of the flavor composition, is mixed with or added to the completed product or mixed with some or all of the components of the product during product formation or some combination of these steps. When used in the context of admixing, the term "product" refers to the product or any of its components. This admixing step can include a process selected from the step of adding the flavor composition to the product, spraying the flavor composition on the product, coating the flavor composition on the product, suspending the product in the flavor composition, painting the flavor composition on the product, pasting the flavor composition on the product, encapsulating the product with the flavor composition, mixing the flavor composition with the product and any combination thereof. The flavor composition can be a solution, liquid, dry powder, spray, paste, suspension and any combination thereof.

As used herein, "palatability" can refer to the overall willingness of a human or non-human animal, for example, a companion animal, to eat a certain food product. Increasing the "palatability" of a food product can lead to an increase in the enjoyment and acceptance of the food by the human or non-human animal to ensure the human or non-human animal eats a "healthy amount" of the food. Decreasing the "palatability" of a food product can lead to a decrease in the enjoyment and acceptance of the food by the human or non-human animal. The term "healthy amount" of a food as used herein refers to an amount that enables the human or non-human animal to maintain or achieve an intake contributing to its overall general health in terms of micronutrients, macronutrients and calories, for example, such as set out in the "Mars Petcare Essential Nutrient Standards." In certain embodiments, "palatability" can mean a relative preference of a human or non-human animal for one food product over another. For example, when a human or non-human animal shows a preference for one of two or more food products, the preferred food product is more "palatable," and has "enhanced palatability." In certain embodiments, the relative palatability of one food product compared to one or more other food products can be determined, for example, in side-by-side, free-choice comparisons, e.g., by relative consumption of the food products, or other appropriate measures of preference indicative of palatability. Palatability can be determined by a standard testing protocol in which the animal has equal access to both food products such as a test called "two-bowl test" or "versus test." Such preference can arise from any of the animal's senses, but can be related to, inter alia, taste, aftertaste, smell, mouth feel and/or texture.

The term "pet food" or "pet food product" or "final pet food product" means a product or composition that is intended for consumption by a companion animal, such as cats, dogs, guinea pigs, rabbits, birds and horses. For example, but not by way of limitation, the companion animal can be a "domestic" dog, e.g., *Canis lupus familiaris*. In certain embodiments, the companion animal can be a "domestic" cat such as *Felis domesticus*. A "pet food" or "pet food product" includes any food, feed, snack, food supplement, liquid, beverage, treat, toy (chewable and/or consumable toys), meal substitute or meal replacement.

The term "human food" or "human food product" or "final human food product" means a product or composition that is intended for consumption by a human. A "human food" or "human food product" includes any food, feed, snack, food supplement, liquid, beverage, treat, meal substitute or meal replacement.

In certain embodiments, a "food product" includes human and/or pet food products.

As used herein "nutritionally-complete" refers to pet food product that contains all known required nutrients for the intended recipient of the pet food product, in appropriate amounts and proportions based, for example, on recommendations of recognized or competent authorities in the field of companion animal nutrition. Such foods are therefore capable of serving as a sole source of dietary intake to maintain life, without the addition of supplemental nutritional sources.

The term "raw material" means a plant and/or animal material before being processed or manufactured into a final pet food product. In certain embodiments, a "raw material" is not significantly processed in order to separate it into individual elements prior to analysis (e.g., by extraction, purification, fractionation and/or concentration). A "raw material" includes a protein source for a pet food product. In certain embodiments, the raw material is a novel protein source that does not compete with the human food sources (i.e., a protein source that is not commonly eaten by humans). In certain embodiments, the raw material is a by-product of the human food chain. In certain non-limiting embodiments, the "raw material" is processed, for example, in order to separate it into individual elements prior to analysis (e.g., by extraction, purification, fractionation and/or concentration), prior to being analyzed according to the methods described herein.

As used herein "flavor composition" refers to at least one compound or biologically acceptable salt thereof that modulates, including enhancing, multiplying, potentiating, decreasing, suppressing, or inducing, the tastes, smells, flavors and/or textures of a natural or synthetic tastant, flavoring agent, taste profile, flavor profile and/or texture profile in an animal or a human. In certain embodiments, the flavor composition comprises a combination of compounds or biologically acceptable salts thereof. In certain embodiments, the flavor composition includes one or more excipients.

As used herein, "odor deterrent," "odor deterrent product," or "odor deterrent composition" refers to a product or composition containing at least one compound or biologically acceptable salt thereof that provides a repellant odor to an object. In certain embodiments, the odor deterrent discourages an animal from contacting, approaching, chewing, licking, or consuming an object, for example, a food or liquid product. In certain embodiments, the object is, for example but not limited to, clothing, shoes, carpet, furniture, household items, pesticides, herbicides, or poisonous compounds. In certain embodiments, the object is another animal or the animal itself. In other embodiment, the object is toxic to the animal, or would be detrimental to the animal's health upon contact or ingestion.

As used herein, the terms "modulates" or "modifies" refers to an increase or decrease in the amount, quality or effect of a particular activity of a receptor and/or an increase or decrease in the expression, activity or function of a receptor. "Modulators," as used herein, refer to any inhibitory or activating compounds identified using in silico, in vitro and/or in vivo assays for, e.g., agonists, antagonists, allosteric modulators and their homologs, including fragments, variants and mimetics.

"Inhibitors" or "antagonists," as used herein, refer to modulating compounds that reduce, decrease, block, prevent, delay activation, inactivate, desensitize or down regulate the biological activity and/or expression of a receptor or pathway of interest. The term "antagonist" includes full, partial, and neutral antagonists as well as inverse agonists.

"Inducers," "activators" or "agonists," as used herein, refer to modulating compounds that increase, induce, stimulate, open, activate, facilitate, enhance activation, sensitize or upregulate a receptor or pathway of interest. The term "agonist" includes full and partial agonists.

"Allosteric modulators" as used herein, refer to "positive allosteric modulators" and "negative allosteric modulators." "Positive allosteric modulators" refer to modulating compounds that increase, induce, stimulate, open, activate, facilitate, enhance activation, sensitize or up regulate a receptor or pathway of interest caused by the binding of a different compound to the receptor. "Negative allosteric modulators" refer to modulating compounds that reduce, decrease, block, prevent, delay activation, inactivate, desensitize or down regulate the biological activity and/or expression of a receptor or pathway of interest caused by the binding of a different compound to the receptor.

As used herein, the terms "vector" and "expression vector" refer to DNA molecules that are either linear or circular, into which another DNA sequence fragment of appropriate size can be integrated. Such DNA fragment(s) can include additional segments that provide for transcription of a gene encoded by the DNA sequence fragment. The additional segments can include and are not limited to: promoters, transcription terminators, enhancers, internal ribosome entry sites, untranslated regions, polyadenylation signals, selectable markers, origins of replication and such like. Expression vectors are often derived from plasmids, cosmids, viral vectors and yeast artificial chromosomes. Vectors are often recombinant molecules containing DNA sequences from several sources.

The term "operably linked," when applied to DNA sequences, for example in an expression vector, indicates that the sequences are arranged so that they function cooperatively in order to achieve their intended purposes, i.e., a promoter sequence allows for initiation of transcription that proceeds through a linked coding sequence as far as the termination signal.

The term "nucleic acid molecule" and "nucleotide sequence," as used herein, refers to a single or double stranded covalently-linked sequence of nucleotides in which the 3' and 5' ends on each nucleotide are joined by phosphodiester bonds. The nucleic acid molecule can include deoxyribonucleotide bases or ribonucleotide bases, and can be manufactured synthetically in vitro or isolated from natural sources.

The terms "polypeptide," "peptide," "amino acid sequence" and "protein," used interchangeably herein, refer to a molecule formed from the linking of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis or enzymatic synthesis. The terms can apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid," as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate and O-phosphoserine. Amino acid analogs and derivatives can refer to compounds that have the same basic chemical structure as a naturally occurring amino acid, i.e., a carbon that is bound to a hydrogen, a carboxyl group, an amino group and an R group, e.g., homoserine, norleucine, methionine sulfoxide and methionine methyl sulfonium. Such analogs can have modified R groups (e.g., norleucine) or modified peptide backbones, but retain the same basic chemical structure as a naturally occurring amino acid. Amino acid mimetics means chemical compounds that have a structure that is different from the general chemical structure of an amino acid, but that function in a manner similar to a naturally occurring amino acid.

The terms "isolated" or "purified", used interchangeably herein, refers to a nucleic acid, a polypeptide, or other biological moiety that is removed from components with which it is naturally associated. The term "isolated" can refer to a polypeptide that is separate and discrete from the whole organism with which the molecule is found in nature or is present in the substantial absence of other biological macromolecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome.

As used herein, the term "recombinant" can be used to describe a nucleic acid molecule and refers to a polynucleotide of genomic, RNA, DNA, cDNA, viral, semisynthetic or synthetic origin which, by virtue of its origin or manipulation is not associated with all or a portion of the polynucleotide with which it is associated in nature.

The term "fusion," as used herein, refers to joining of different peptide or protein segments by genetic or chemical methods wherein the joined ends of the peptide or protein segments may be directly adjacent to each other or may be separated by linker or spacer moieties such as amino acid residues or other linking groups.

2. Olfactory Receptors

The presently disclosed subject matter provides olfactory receptors for use in the disclosed methods. The olfactory receptors of the present disclosure can include mammalian olfactory receptors such as, but not limited to, human, canine and feline olfactory receptors.

In certain non-limiting embodiments, the olfactory receptor is a human olfactory receptor, for example, human olfactory receptor HsOR17.1.11 (hOR3A1), HsOR1.4.8 (hOR6P1), HsOR11.3.14 (hOR51E1), HsOR11.3.40 (hOR51L1), HsOR14.1.27 (hOR11H6), HsOR11.13.7 (hOR4D6), HsOR14.2.5 (hOR4E2), HsOR16.1.3 (hOR2C1), HsOR11.13.6 (hOR5A1), HsOR11.18.36 (hOR8B8), or combinations thereof.

In certain non-limiting embodiments, the olfactory receptor is a canine olfactory receptor, for example, canine olfactory receptor CafaOR9.2.9, CafaOR38.1.21, CafaOR21.2.15, CafaOR21.2.43, CafaOR15.2.20, CafaOR18.3.11, CafaOR15.3.1, CafaOR6.3.1, CafaOR18.3.12, CafaOR5.2.5, or combinations thereof. In certain non-limiting embodiments, the olfactory receptor is a canine olfactory receptor having a nucleotide sequence or an amino acid sequence set forth in SEQ ID NOs:61-2260.

In certain non-limiting embodiments, the olfactory receptor is a feline olfactory receptor, for example, feline olfactory receptor E1:13347030-13347977, F1:65134904-65135858, D1:62955839-62956792, D1:63312327-63313289, B3:72908295-72909287, D1:105486528-105487493, B3:74116955-74117893, E3:40237904-40238842, D1:105462554-105463512, D1:21266824-21267768, or combinations thereof. In certain non-limiting embodiments, the olfactory receptor is a feline olfactory receptor having a nucleotide sequence or an amino acid sequence set forth in SEQ ID NOs:2261-3808.

The olfactory receptors tested in the working examples, along with their synonyms and group designations are listed in Table 1.

TABLE 1

| OR Orthologue Group | OR Orthologue Name | Human OR | Canine OR | Feline OR |
|---|---|---|---|---|
| OR_1 | OR3A1 | HsOR17.1.11 (hOR3A1) (SEQ ID NOs: 1 and 31) | CafaOR9.2.9 (canine OR3A1) (SEQ ID NOs: 11 and 41) | E1: 13347030-13347977 (feline OR3A1) (SEQ ID NOs: 21 and 51) |
| OR_2 | OR6P1 | HsOR1.4.8 (11OR6P1) (SEQ ID NOs: 2 and 32) | CafaOR38.1.21 (canine OR6P1) (SEQ ID NOs: 12 and 42) | F1: 65134904-65135858 (feline OR6P1) (SEQ ID NOs: 22 and 52) |
| OR_3 | OR51E1 | HsOR11.3.14 (hOR51E1) (SEQ ID NOs: 3 and 33) | CafaOR21.2.15 (canine OR51E1) (SEQ ID NOs: 13 and 43) | D1: 62955839-62956792 (feline OR51E1) (SEQ ID NOs: 23 and 53) |
| OR_4 | OR51L1 | HsOR11.3.40 (hOR51L1) (SEQ ID NOs: 4 and 34) | CafaOR21.2.43 (canine OR51L1) (SEQ ID NOs: 14 and 44) | D1: 63312327-63313289 (feline OR51L1) (SEQ ID NOs: 24 and 54) |
| OR_5 | OR11H6 | HsOR14.1.27 (hOR11H6) (SEQ ID NOs: 5 and 35) | CafaOR15.2.20 (canine OR11H6) (SEQ ID NOs: 15 and 45) | B3: 72908295-72909287 (feline OR11H6) (SEQ ID NOs: 25 and 55) |
| OR_6 | OR4D6 | HsOR11.13.7 (hOR4D6) (SEQ ID NOs: 6 and 36) | CafaOR18.3.11 (canine OR4D6) (SEQ ID NOs: 16 and 46) | D1: 105486528-105487493 (feline OR4D6) (SEQ ID NOs: 26 and 56) |
| OR_7 | OR4E2 | HsOR14.2.5 (hOR4E2) (SEQ ID NOs: 7 and 37) | CafaOR15.3.1 (canine OR4E2) (SEQ ID NOs: 17 and 47) | B3: 74116955-74117893 (feline OR4E2) (SEQ ID NOs: 27 and 57) |
| OR_8 | OR2C1 | HsOR16.1.3 (hOR2C1) (SEQ ID NOs: 8 and 38) | CafaOR6.3.1 (canine OR2C1) (SEQ ID NOs: 18 and 48) | E3: 40237904-40238842 (feline OR2C1) (SEQ ID NOs: 28 and 58) |
| OR_9 | OR5A1 | HsOR11.13.6 (hOR5A1) (SEQ ID NOs: 9 and 39) | CafaOR18.3.12 (canine OR5A1) (SEQ ID NOs: 19 and 49) | D1: 105462554-105463512 (feline OR5A1) (SEQ ID NOs: 29 and 59) |
| or_10 | OR8B8 | HsOR11.18.36 (hOR8B8) (SEQ ID NOs: 10 and 40) | CafaOR5.2.5 (canine OR8B8) (SEQ ID NOs: 20 and 50) | D1: 21266824-21267768 (feline OR8B8) (SEQ ID NOs: 30 and 60) |

In certain embodiments, an olfactory receptor for use in the presently disclosed methods encompasses a canine olfactory receptor comprising a nucleotide sequence set forth in SEQ ID NO: 11, 12, 13, 14, 15, 16, 17, 18, 19, or 20, an amino acid sequence set forth in SEQ ID NO:41, 42, 43, 44, 45, 46, 47, 48, 49, or 50, and/or a nucleotide sequence or an amino acid sequence set forth in SEQ ID NOs:61-2260, including fragments thereof (e.g., functional fragments thereof) and variants thereof.

In certain embodiments, an olfactory receptor for use in the presently disclosed methods encompasses a feline olfactory receptor comprising a nucleotide sequence set forth in SEQ ID NO:21, 22, 23, 24, 25, 26, 27, 28, 29, or 30, an amino acid sequence set forth in SEQ ID NO:51, 52, 53, 54, 55, 56, 57, 58, 59, or 60, and/or a nucleotide sequence or an amino acid sequence set forth in SEQ ID NOs:2261-3808, including fragments thereof (e.g., functional fragments thereof) and variants thereof.

In certain embodiments, the olfactory receptor for use in the presently disclosed subject matter can include a receptor encoded by a nucleotide sequence that is at least 85%, at least 90%, at least 91%, at least 92%, at least 93%, at least 94%, at least 95%, at least 96%, at least 97%, at least 98% or at least 99% homologous to any one of SEQ ID NOs: 11-30 and/or a nucleotide sequence set forth in SEQ ID NOs:61-3808, (homology, as that term is used herein, may be measured using standard software such as BLAST or FASTA), including fragments thereof (e.g., functional fragments thereof).

In certain embodiments, the olfactory receptor for use in the presently disclosed methods can include a receptor comprising an amino acid sequence that is between about 33 and 99%, between about 34 and 99%, between about 35 and 99%, between about 40 and 99%, between about 45 and 99%, between about 50 and 99%, between about 55 and 99%, between about 60 and 99%, between about 61 and 99%, between about 65 and 99%, between about 70 and 99%, between about 72 and 99%, between about 75 and 99%, between about 79 and 99%, between about 80 and 99%, between about 84 and 99%, between about 85 and 99%, between about 87 and 99%, between about 89 and 99%, between about 90 and 99%, between about 95 and 99%, or between about 97 and 99% homologous to any one of SEQ ID NOs: 41-60 and/or an amino acid sequence set forth in SEQ ID NOs:61-3808, (homology, as that term is used herein, may be measured using standard software such as BLAST or FASTA), including fragments thereof (e.g., functional fragments thereof).

In certain embodiments, the olfactory receptor for use in the presently disclosed methods can include a receptor comprising an amino acid sequence that is at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% homologous to any one of SEQ ID NOs:41-60 and/or an amino acid sequence set forth in SEQ ID NOs:61-3808, (homology, as that term is used herein, may be measured using standard software such as BLAST or FASTA), including fragments thereof (e.g., functional fragments thereof).

In certain embodiments, the olfactory receptor is a canine CafaOR9.2.9 comprising an amino acid sequence as set forth in SEQ ID NO:41, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO: 11, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a canine CafaOR38.1.21 comprising an amino acid sequence as set forth in SEQ ID NO:42, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO: 12, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a canine CafaOR21.2.15 comprising an amino acid sequence as set forth in SEQ ID NO:43, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO: 13, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a canine CafaOR21.2.43 comprising an amino acid sequence as set forth in SEQ ID NO:44, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO: 14, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a canine CafaOR15.2.20 comprising an amino acid sequence as set forth in SEQ ID NO:45, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:15, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a canine CafaOR18.3.11 comprising an amino acid sequence as set forth in SEQ ID NO:46, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO: 16, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a canine CafaOR15.3.1 comprising an amino acid sequence as set forth in SEQ ID NO:47, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:17, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a canine CafaOR6.3.1 comprising an amino acid sequence as set forth in SEQ ID NO:48, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO: 18, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a canine CafaOR18.3.12 comprising an amino acid sequence as set forth in SEQ ID NO:49, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO: 19, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a canine CafaOR5.2.5 comprising an amino acid sequence as set forth in SEQ ID NO:50, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:20, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a feline E1:13347030-13347977 comprising an amino acid sequence as set forth in SEQ ID NO:51, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:21, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a feline F1:65134904-65135858 comprising an amino acid sequence as set forth in SEQ ID NO:52, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:22, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a feline D1:62955839-62956792 comprising an amino acid sequence as set forth in SEQ ID NO:53, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:23, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a feline D1:63312327-63313289 comprising an amino acid sequence as set forth in SEQ ID NO:54, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:24, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a feline B3:72908295-72909287 comprising an amino acid sequence as set forth in SEQ ID NO:55, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:25, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a feline D1:105486528-105487493 comprising an amino acid sequence as set forth in SEQ ID NO:56, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:26, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a feline B3:74116955-74117893 comprising an amino acid sequence as set forth in SEQ ID NO:57, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:27, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a feline E3:40237904-40238842 comprising an amino acid sequence as set forth in SEQ ID NO:58, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:28, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a feline D1:105462554-105463512 comprising an amino acid sequence as set forth in SEQ ID NO:59, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:29, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, the olfactory receptor is a feline D1:21266824-21267768 comprising an amino acid sequence as set forth in SEQ ID NO:60, or a sequence at least 99, 98, 97, 96, 95, 90, 85 or 80 percent homologous thereto (homology, as that term is used herein, may be measured using standard software such as BLAST or FASTA), and is encoded, for example, by a nucleic acid comprising a sequence as set forth in SEQ ID NO:30, or a sequence at least 99, 98, 97, 96, 95, 90, 85 or 80 percent homologous thereto (homology, as that term is used herein, may be measured using standard software such as BLAST or FASTA), including fragments thereof (e.g., functional fragments thereof).

In certain embodiments, homology is described as a percent identity between two sequences. The percent identity of two amino acid sequences or of two nucleotide sequences can be determined by aligning the sequences for optimal comparison purposes (e.g., gaps can be introduced in the first sequence for best alignment with the sequence) and comparing the amino acid residues or nucleotides at corresponding positions. The percent identity can be determined by the number of identical amino acid residues or nucleotides in the sequences being compared (e.g., % identity=number of identical positions/total number of positions ×100).

In certain embodiments, a fragment of an olfactory receptor (e.g., functional fragments thereof) comprises at least about 5, about 10, about 15, about 20, about 25, about 30, about 40, about 50, about 60, about 70, about 80, about 90, about 100, about 125, about 150, about 175, about 200, about 250, about 300 or more amino acid residues, or any intermediate value or range thereof. In certain embodiments, the fragment comprises between about 5 to about 10, about 5 to about 20, about 5 to about 30, about 5 to about 40, about 5 to about 50, about 10 to about 50, about 10 to about 60, about 10 to about 70, about 10 to about 80, about 10 to about 90, about 10 to about 100, about 20 to about 100, about 50 to about 100, about 50 to about 150, about 50 to about 200, about 50 to about 250, about 100 to about 250, or about 100 to about 300 amino acid residues, or any intermediate range thereof.

The determination of percent identity between two sequences can be determined using a mathematical algorithm known to those of skill in the art. A non-limiting example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877, the disclosures of which are incorporated herein by reference in their entireties. The NBLAST and XBLAST programs of Altschul, et al. (1990) J. Mol. Biol. 215:403-410 have incorporated such an algorithm. BLAST nucleotide searches can be performed with the NBLAST program, for example, score=100, word length=12, to obtain nucleotide sequences homologous to nucleotide sequences of the invention. BLAST protein searches can be performed with the XBLAST program, for example, score=50, word length=3, to obtain amino acid sequences homologous to amino acid sequence of the invention. To obtain gapped alignments for comparison purposes, Gapped BLAST can be utilized as described in Altschul et al. (1997) Nucleic Acids Res. 25:3389-3402, the disclosure of which is incorporated herein by reference in its entirety. Alternatively, PSI-Blast can be used to perform an iterated search, which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. An additional non-limiting example of a mathematical algorithm utilized for the comparison of sequences is the algorithm of Myers and Miller, CABIOS (1989), the disclosure of which is incorporated herein by reference in its entirety. The ALIGN program (version 2.0), which is part of the CGC sequence alignment software package, has incorporated such an algorithm. Other non-limiting examples of algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8, the disclosures of which are incorporated herein by reference in their entireties. Within FASTA, ktup is a control option that sets the sensitivity and speed of the search.

In certain embodiments, the disclosed subject matter provides for the use of an isolated or purified olfactory receptor and/or variants and fragments thereof. The disclosed subject matter also encompasses the use of sequence variants. In certain embodiments, variation can occur in either or both the coding and non-coding regions of a nucleotide sequence of an olfactory receptor. Variants can include a substantially homologous protein encoded by the same genetic locus in an organism, i.e., an allelic variant. Variants also encompass proteins derived from other genetic loci in an organism, e.g., human, canine and feline but having substantial homology to the olfactory receptor, i.e., a homolog. Variants can also include proteins substantially homologous to the olfactory receptor but derived from another organism, i.e., an ortholog. Variants also include proteins that are substantially homologous to the olfactory receptor that are produced by chemical synthesis. Variants also include proteins that are substantially homologous to the olfactory receptor that are produced by recombinant methods.

Orthologs, homologs and allelic variants can be identified using methods well known in the art. These variants can include a nucleotide sequence encoding a receptor that is at least about 60-65%, about 65-70%, about 70-75, about 80-85%, about 90-95%, about 95-99% or more homologous to the nucleotide sequence shown in any one of SEQ ID NOs:11-30, or any one of nucleotide sequences in SEQ ID NOs:61-3808, or fragments thereof. Such nucleic acid molecules can readily be identified as being able to hybridize under stringent conditions, to the nucleotide sequence shown in any one of SEQ ID NOs:11-30, or any one of nucleotide sequences in SEQ ID NOs:61-3808, or a fragment thereof. In certain embodiments, two polypeptides (or regions thereof) are substantially homologous when the amino acid sequences are at least about 60-65%, about 65-70%, about 70-75, about 80-85%, about 90-95%, about 95-99% or more homologous to the amino acid sequences shown in any one of SEQ ID NOs:41-60, or any one of amino acid sequences in SEQ ID NOs:61-3808, or a fragment thereof. A substantially homologous amino acid sequence, according to the disclosed subject matter, will be encoded by a nucleic acid sequence hybridizing to the nucleic acid sequence, or portion thereof, of the nucleotide sequence shown in any one of SEQ ID NOs:41-60, or any one of amino acid sequences in SEQ ID NOs:61-3808, under stringent conditions.

The olfactory receptors for use in the methods of the disclosed subject matter include olfactory receptors having additions, deletions or substitutions of amino acid residues (variants) which do not substantially alter the biological activity of the receptor. Those individual sites or regions of the olfactory receptors which may be altered without affecting biological activity can be determined by examination of the structure of the olfactory receptor extracellular domain, for example. Alternatively and/or additionally, one can empirically determine those regions of the receptor which would tolerate amino acid substitutions by alanine scanning mutagenesis (Cunningham et al., Science 244, 1081-1085 (1989), the disclosure of which is hereby incorporated by reference in its entirety). In the alanine scanning mutagenesis method, selected amino acid residues are individually substituted with a neutral amino acid (e.g., alanine) in order to determine the effects on biological activity.

It is generally recognized that conservative amino acid changes are least likely to perturb the structure and/or function of a polypeptide. Accordingly, the disclosed subject matter encompasses one or more conservative amino acid changes within an olfactory receptor. Conservative amino acid changes generally involve substitution of one amino acid with another that is similar in structure and/or function (e.g., amino acids with side chains similar in size, charge and shape). Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within an olfactory receptor can be replaced with other amino acid residues from the same side chain family and the altered protein can be tested for retained function using the functional assays described herein. Modifications can be introduced into an olfactory receptor of the present disclosure by standard techniques known in the art, such as site-directed mutagenesis and PCR-mediated mutagenesis. If such substitutions result in retention in biological activity, then more substantial changes can be introduced and/or other additions/deletions may be made and the resulting products screened. In certain embodiments, deletions or additions can be from 5-10 residues, alternatively from 2-5 amino acid residues or from 1-2 residues, and values in between.

The presently disclosed subject matter also provides isolated nucleic acids encoding olfactory receptors, including fragments thereof (e.g., functional fragments thereof). The olfactory receptors of the present disclosure can include mammalian olfactory receptors such as, but not limited to, human, canine and feline olfactory receptors. The isolated nucleic acids can be genomic DNAs, cDNAs and RNAs (e.g., mRNAs)

In certain non-limiting embodiments, the olfactory receptor is a canine olfactory receptor, for example, canine olfactory receptor CafaOR9.2.9, CafaOR38.1.21, CafaOR21.2.15, CafaOR21.2.43, CafaOR15.2.20, CafaOR18.3.11, CafaOR15.3.1, CafaOR6.3.1, CafaOR18.3.12, CafaOR5.2.5, including fragments thereof (e.g., functional fragments thereof), or combinations thereof. In certain embodiments, the olfactory receptor comprises a nucleotide sequence set forth in SEQ ID NO: 11, 12, 13, 14, 15, 16, 17, 18, 19, or 20, including fragments thereof (e.g., functional fragments thereof). In certain embodiments, the olfactory receptor comprises a nucleotide sequence set forth in SEQ ID NOs:61-2260, including fragments thereof (e.g., functional fragments thereof).

In certain non-limiting embodiments, the olfactory receptor is a feline olfactory receptor, for example, feline olfactory receptor E1:13347030-13347977, F1:65134904-65135858, D1:62955839-62956792, D1:63312327-63313289, B3:72908295-72909287, D1:105486528-105487493, B3:74116955-74117893, E3:40237904-40238842, D1:105462554-105463512, D1:21266824-21267768, including fragments thereof (e.g., functional fragments thereof), or combinations thereof. In certain embodiments, the olfactory receptor comprises a nucleotide sequence set forth in SEQ ID NO: 21, 22, 23, 24, 25, 26, 27, 28, 29, or 30, including fragments thereof (e.g., functional fragments thereof). In certain embodiments, the olfactory receptor comprises a nucleotide sequence set forth in SEQ ID NOs:2261-3808, including fragments thereof (e.g., functional fragments thereof).

The disclosed subject matter also provides for fusion proteins that comprise an olfactory receptor, or fragment thereof. In certain embodiments, the disclosed subject matter provides for fusion proteins of an olfactory receptor, or functional fragments thereof, and an immunoglobulin heavy chain constant region. In certain embodiments, a fusion protein of the present disclosure can include a detectable marker, a functional group such as a carrier, a label, a stabilizing sequence or a mechanism by which olfactory receptor agonist binding can be detected. Non-limiting embodiments of a label include a FLAG tag, a His tag, a MYC tag, a maltose binding protein and others known in the art. The presently disclosed subject matter also provides nucleic acids encoding such fusion proteins, vectors containing fusion protein-encoding nucleic acids and host cells comprising such nucleic acids or vectors. In certain embodiments, fusions can be made at the amino terminus (N-terminus) of an olfactory receptor or at the carboxy terminus (C-terminus) of an olfactory receptor.

In certain embodiments, the olfactory receptors disclosed herein can contain additional amino acids at the N-terminus and/or at the C-terminus end of the sequences, e.g., when used in the methods of the disclosed subject matter. In certain embodiments, the additional amino acids can assist with immobilizing the polypeptide for screening purposes, or allow the polypeptide to be part of a fusion protein, as disclosed above, for ease of detection of biological activity.

3. Methods for Identifying Olfactory Receptor Modulating Compounds

The present disclosure further provides methods for identifying compounds that modulate the activity and/or expression of an olfactory receptor. For example, and not by way of limitation, the modulator can be an agonist (for example, a full or partial agonist), or an antagonist, or an inverse agonist, or an allosteric modulator. The presently disclosed subject matter provides in silico and in vitro methods for identifying compounds that modulate the activity and/or expression of an olfactory receptor, disclosed above.

3.1 in Silico Methods

The presently disclosed subject matter further provides in silico methods for identifying compounds that can potentially interact with an olfactory receptor and/or modulate the activity and/or expression of an olfactory receptor.

In certain embodiments, the method can include predicting the three-dimensional structure (3D) of an olfactory receptor and screening the predicted 3D structure with putative olfactory receptor modulating compounds (i.e., test compounds). The method can further include predicting whether the putative compound would interact with the binding site of the receptor by analyzing the potential interactions with the putative compound and the amino acids of the receptor. The method can further include identifying a test compound that can bind to and/or modulate the biological activity of the olfactory receptor by determining whether the 3D structure of the compound fits within the binding site of the 3D structure of the receptor.

In certain embodiments, the olfactory receptor for use in the disclosed method can be a canine receptor CafaOR9.2.9, CafaOR38.1.21, CafaOR21.2.15, CafaOR21.2.43, CafaOR15.2.20, CafaOR18.3.11, CafaOR15.3.1, CafaOR6.3.1, CafaOR18.3.12, CafaOR5.2.5, or combinations thereof. In certain non-limiting embodiments, the olfactory receptor is a canine olfactory receptor described in SEQ ID NOs:61-2260.

In certain embodiments, the olfactory receptor for use in the disclosed method can be a feline receptor E1:13347030-13347977, F1:65134904-65135858, D1:62955839-

62956792, D1:63312327-63313289, B3:72908295-72909287, D1:105486528-105487493, B3:74116955-74117893, E3:40237904-40238842, D1:105462554-105463512, and D1:21266824-21267768, or combinations thereof. In certain non-limiting embodiments, the olfactory receptor is a feline olfactory receptor described in SEQ ID NOs:2261-3808.

In other embodiments, the olfactory receptor for use in the disclosed method can have the amino acid sequence of any one of SEQ ID NO:41-60, or any one of amino acid sequences in SEQ ID NOs:61-3808, or a fragment or variant thereof. In certain embodiments, the olfactory receptor for use in the presently disclosed subject matter can include a receptor comprising an amino acid sequence having at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% identity to any one of SEQ ID NO:41-60, or any one of amino acid sequences in SEQ ID NOs:61-3808, or a fragment or variant thereof. In certain embodiments, the olfactory receptor for use in the disclosed method can be encoded by a nucleotide sequence of any one of SEQ ID NO: 11-30, or any one of nucleotide sequences in SEQ ID NOs:61-3808, or a fragment or variant thereof. In certain embodiments, the olfactory receptor for use in the presently disclosed subject matter can include a receptor encoded by a nucleotide sequence having at least 85%, at least 90%, at least 91%, at least 92%, at least 93%, at least 94%, at least 95%, at least 96%, at least 97%, at least 98% or at least 99% identity to any one of SEQ ID NO: 11-30, or any one of nucleotide sequences in SEQ ID NOs:61-3808, or a fragment or variant thereof.

Non-limiting examples of compounds (e.g., potential olfactory receptor modulators) that can be tested using the disclosed methods include any small chemical compound, or any biological entity, such as peptides, salts, amino acids and odor compound known in the art, e.g. androstenone. In certain embodiments, the test compound can be a small chemical molecule.

In certain embodiments, structural models of an olfactory receptor can be built using crystal structures of other GPCRs as templates for homology modeling. For example, and not by way of limitation, structural models can be generated using the crystal structures of GPCRs. In certain embodiments, a structural model of an olfactory receptor can be based on a known or a combination of known crystal structures of GPCRs. (See, e.g., Lee et al., Eur J Pharmacol. 2015 May 14. pii: S0014-2999(15)30012-1, which is incorporated by reference in its entirety herein). In certain embodiments, a structural model of an olfactory receptor can be generated based on the crystal structure of a P2 adrenergic receptor, 3SN6 from Protein Data Bank (PDB). (See, e.g., Rasmussen et al., Nature. 2011 Jul. 19; 477(7366):549-55, which is incorporated by reference in its entirety herein). In certain embodiments, a structural model of the 7 transmembrane domain (7TM) of an olfactory receptor can be generated based on the crystal structures of existing GPCR crystal structure 3SN6 from PDB. In certain embodiments structural models of an olfactory receptor can be built using the I-TASSER Suite of programs (Yang et al., Nat Methods, 12: 7-8 (2015), which is incorporated by reference in its entirety herein) and Modeller (Eswar et al., Curr Protoc Bioinformatics, 15:5.6.1-5.6.30 (2006), which is incorporated by reference in its entirety herein), which is part of the DiscoveryStudio (DS) suite of programs from Accelrys (DiscoveryStudio (DS) is a suite of interactive modeling and simulation programs from the Accelrys corporation).

Any suitable modelling software known in the art can be used. In certain embodiments, the Modeller software package can be used to generate the three-dimensional protein structure.

In certain embodiments, the in silico methods of identifying a compound that binds to an olfactory receptor comprises determining whether a test compound interacts with one or more amino acids of an olfactory receptor binding pocket, as described herein.

Compounds that are identified by the disclosed in silico methods can be further tested using the in vitro and in vivo methods disclosed herein.

3.2 Olfactory Receptor Transmembrane Compound Binding Site

The present application provides for methods of screening for compounds that modulate the activity of an olfactory receptor, for example, a canine or feline olfactory receptor, wherein the compounds interact with one or more amino acids of the olfactory receptor. In certain embodiments, the binding site of an olfactory receptor comprises amino acids within the 7TM domain of the receptor, and can be identified by generating an interaction map of the receptor using in silico modeling, as described herein. In one non-limiting example, the presence of an amino acid in the 7TM interaction map means that the residue is in the vicinity of the ligand binding environment, an interacts with the ligand.

In certain embodiments, the interaction between a compound and one or more amino acids of the olfactory receptor described herein can comprise one or more hydrogen bond, covalent bond, non-covalent bond, salt bridge, physical interaction, and combinations thereof. The interactions can also be any interaction characteristic of a ligand receptor interaction known in the art. Such interactions can be determined by, for example, site directed mutagenesis, x-ray crystallography, x-ray or other spectroscopic methods, Nuclear Magnetic Resonance (NMR), cross-linking assessment, mass spectroscopy or electrophoresis, cryo-microscopy, displacement assays based on known agonists, structural determination and combinations thereof. In certain embodiments, the interactions are determined in silico, for example, by theoretical means such as docking a compound into a feline or canine olfactory receptor binding pocket as described herein, for example, using molecular docking, molecular modeling, molecular simulation, or other means known to persons of ordinary skill in the art.

In certain embodiments, the interaction between an amino acid in the 7TM interaction map and the ligand is a pi-pi interaction.

In certain embodiments, the interaction between an amino acid in the 7TM interaction map and the ligand is a hydrogen bond interaction.

In certain embodiments, the interaction between an amino acid in the 7TM interaction map and the ligand is a hydrophobic interaction.

In certain embodiments, the interaction between an amino acid in the 7TM interaction map and the ligand is a van de Waals interaction.

In certain embodiments, the amino acid in the 7TM interaction map is a polar amino acid, wherein the amino acid interacts with the ligand as a hydrogen bond donor and/or acceptor.

In certain embodiments, the interaction between a compound and one or more amino acids of the olfactory receptors described herein can comprises one or more hydrogen bond, covalent bond, non-covalent bond, salt bridge, physical interaction, and combinations thereof. The interactions can also be any interaction characteristic of a ligand receptor interaction known in the art. Such interactions can be determined by, for example, site directed mutagenesis, x-ray crystallography, x-ray or other spectroscopic methods, Nuclear Magnetic Resonance (NMR), cross-linking assessment, mass spectroscopy or electrophoresis, cryo-microscopy, displacement assays based on known agonists, structural determination and combinations thereof. In certain embodiments, the interactions are determined in silico, for example, by theoretical means such as docking a compound into an olfactory receptor binding pocket using molecular docking, molecular modeling, molecular simulation, or other means known to persons of ordinary skill in the art.

In certain embodiments, the olfactory receptor is a canine olfactory receptor, for example, but not limited to, CafaOR9.2.9, CafaOR38.1.21, CafaOR21.2.15, CafaOR21.2.43, CafaOR15.2.20, CafaOR18.3.11, CafaOR15.3.1, CafaOR6.3.1, CafaOR18.3.12, or CafaOR5.2.5. In certain non-limiting embodiments, the olfactory receptor is a canine olfactory receptor described in SEQ ID NOs:61-2260.

In certain embodiments, the olfactory receptor is a feline olfactory receptor, for example, but not limited to, E1:13347030-13347977, F1:65134904-65135858, D1:62955839-62956792, D1:63312327-63313289, B3:72908295-72909287, D1:105486528-105487493, B3:74116955-74117893, E3:40237904-40238842, D1:105462554-105463512, or D1:21266824-21267768. In certain non-limiting embodiments, the olfactory receptor is a feline olfactory receptor described in SEQ ID NOs:2261-3808.

In certain embodiments, the compounds interact with one or more olfactory receptors described herein according to any combination of interactions described herein, for example, one, two, three or more of the interactions.

In certain embodiments, the compounds bind to at least one of the receptors described herein. In certain embodiment, the compounds bind selectively to only one of the receptors described herein.

In one embodiment, the olfactory receptor is a canine CafaOR9.2.9. In certain embodiments, the amino acid residues that the compounds interact with comprises CafaOR9.2.9 residue Gln103, for example, by hydrogen bonding or salt bridge interactions, as exemplified by in silico modeling of Lilial in CafaOR9.2.9 (FIG. 2). Alternatively, or in addition, in certain embodiments, the amino acids that the compounds interact with comprise CafaOR9.2.9 residues Leu104, Lys275, Arg87, Val81, Met84, Val279, Tyr262, Met209, Gly258, Val111, Tyr255, Thr282, Phe107 and/or Thr80, either alone or in conjunction with interactions to Gln103 listed above, for example, by polar, ring stacking, salt bridges, hydrogen bonding, pi interactions, charged interactions, van der Waals interactions, or hydrophobic interactions, as exemplified by in silico modeling of Lilial in CafaOR9.2.9 (FIG. 2). Alternatively, or in addition, in certain embodiments, the amino acids that the compounds interact with comprise any one, two, three or more of the CafaOR9.2.9 residues Gln103, Leu104, Lys275, Arg87, Val81, Met84, Val279, Tyr262, Met209, Gly258, Val111, Tyr255, Thr282, Phe107 and Thr80, for example, by polar, ring stacking, salt bridges, hydrogen bonding, pi interactions, or charged interactions, van der Waals, hydrophobic interaction or other interactions, as exemplified by in silico modeling of Lilial in CafaOR9.2.9 (FIG. 2).

In one embodiment, the olfactory receptor is a canine CafaOR38.1.21. In certain embodiments, the amino acid residues that the compounds interact with comprises CafaOR38.1.21 residue Lys273, for example, by hydrogen bonding or salt bridge interactions, as exemplified by in silico modeling of p-Anisaldehyde in CafaOR38.1.21 (FIG. 3). Alternatively, or in addition, in certain embodiments, the amino acids that the compounds interact with comprise CafaOR38.1.21 residues Thr78, Leu82, Tyr260, Thr256, Tyr253 and/or Phe105, either alone or in conjunction with interactions to Lys273 listed above, for example, by polar, ring stacking, salt bridges, hydrogen bonding, pi interactions, charged interactions, van der Waals interactions, or hydrophobic interactions, as exemplified by in silico modeling of p-Anisaldehyde in CafaOR38.1.21 (FIG. 3). Alternatively, or in addition, in certain embodiments, the amino acids that the compounds interact with comprise any one, two, three or more of the CafaOR38.1.21 residues Lys273, Thr78, Leu82, Tyr260, Thr256, Tyr253 and Phe105, for example, by polar, ring stacking, salt bridges, hydrogen bonding, pi interactions, or charged interactions, van der Waals, hydrophobic interaction or other interactions, as exemplified by in silico modeling of p-Anisaldehyde in CafaOR38.1.21 (FIG. 3).

In one embodiment, the olfactory receptor is a canine CafaOR21.2.15. In certain embodiments, the amino acids that the compounds interact with comprise CafaOR21.2.15 residues Met83, His107, Ile106, Leu182, Asn197, Gly201, Val204, Ser260, Phe256 and/or Leu273, for example, by polar, ring stacking, salt bridges, hydrogen bonding, pi interactions, charged interactions, van der Waals interactions, or hydrophobic interactions, as exemplified by in silico modeling of (+)-menthol in CafaOR21.2.15 (FIG. 4). Alternatively, or in addition, in certain embodiments, the amino acids that the compounds interact with comprise any one, two, three or more of the CafaOR21.2.15 residues Met103, Met83, His107, Ile106, Leu182, Asn197, Gly201, Val204, Ser260, Phe256 and Leu273, for example, by polar, ring stacking, salt bridges, hydrogen bonding, pi interactions, or charged interactions, van der Waals, hydrophobic interaction or other interactions, as exemplified by in silico modeling of (+)-menthol in CafaOR21.2.15 (FIG. 4).

In one embodiment, the olfactory receptor is a canine CafaOR21.2.43. In certain embodiments, the amino acids that the compounds interact with comprise CafaOR21.2.43 residues Met80, Met88, Leu108, Ile111, His112, Thr115, Val209, Val210, Thr213, Leu214, Val262, Ile263, Ser266, Ile281, Ala284, and/or Leu288, for example, by polar, ring stacking, salt bridges, hydrogen bonding, pi interactions, charged interactions, van der Waals interactions, or hydrophobic interactions, as exemplified by in silico modeling of Androstadienone in CafaOR21.2.43 (FIG. 5). Alternatively, or in addition, in certain embodiments, the amino acids that the compounds interact with comprise any one, two, three or more of the CafaOR21.2.43 residues Asp285, Met80, Met88, Leu108, Ile111, His112, Thr115, Val209, Val210, Thr213, Leu214, Val262, Ile263, Ser266, Ile281, Ala284, and Leu288, for example, by polar, ring stacking, salt bridges, hydrogen bonding, pi interactions, or charged interactions, van der Waals, hydrophobic interaction or other interactions, as exemplified by in silico modeling of Androstadienone in CafaOR21.2.43 (FIG. 5).

In one embodiment, the olfactory receptor is a feline catGr5 (B3:72908295-72909287). In certain embodiments, the amino acid residues that the compounds interact with comprises catGr5 (B3:72908295-72909287) residue Tyr277, for example, by hydrogen bonding or salt bridge interactions, as exemplified by in silico modeling of isobuteric acid in catGr5 (B3:72908295-72909287) (FIG. 6). Alternatively, or in addition, in certain embodiments, the amino acids that the compounds interact with comprise catGr5 (B3:72908295-72909287) residues Phe119, Pro177, Leu180, Ile181, Pro199, Cys217, and/or Phe220, either alone or in conjunction with interactions listed above, for example, by polar, ring stacking, salt bridges, hydrogen bonding, pi interactions, charged interactions, van der Waals interactions, or hydrophobic interactions, as exemplified by in silico modeling of isobuteric acid in catGr5 (B3: 72908295-72909287) (FIG. 6). Alternatively, or in addition, in certain embodiments, the amino acids that the compounds interact with comprise any one, two, three or more of the CafaOR9.2.9 residues Tyr277, Lys290, Phe119, Pro177, Leu180, Ile181, Pro199, Cys217, and Phe220, for example, by polar, ring stacking, salt bridges, hydrogen bonding, pi interactions, or charged interactions, van der Waals, hydrophobic interaction or other interactions, as exemplified by in silico modeling of isobuteric acid in catGr5 (B3:72908295-72909287) (FIG. 6).

In one embodiment, the olfactory receptor is a feline catGr6 (D1:105486528-105487493). In certain embodiments, the amino acid residues that the compounds interact with comprises catGr6 (D1:105486528-105487493) residue Tyr265, for example, by hydrogen bonding or salt bridge interactions, as exemplified by in silico modeling of β-ionone in catGr6 (D1:105486528-105487493) (FIG. 7). Alternatively, or in addition, in certain embodiments, the amino acids that the compounds interact with comprise catGr6 (D1:105486528-105487493) residues Phe88, Phe111, Met170, Met206, Cys261, Ile264, Ser279, Ile280, and/or Thr283, either alone or in conjunction with interactions listed above, for example, by polar, ring stacking, salt bridges, hydrogen bonding, pi interactions, charged interactions, van der Waals interactions, or hydrophobic interactions, as exemplified by in silico modeling of β-ionone in catGr6 (D1:105486528-105487493) (FIG. 7). Alternatively, or in addition, in certain embodiments, the amino acids that the compounds interact with comprise any one, two, three or more of the catGr6 (D1:105486528-105487493) residues His112, Asn209, Tyr265, Phe88, Phe111, Met170, Met206, Cys261, Ile264, Ser279, Ile280, and Thr283, for example, by polar, ring stacking, salt bridges, hydrogen bonding, pi interactions, or charged interactions, van der Waals, hydrophobic interaction or other interactions, as exemplified by in silico modeling of β-ionone in catGr6 (D1:105486528-105487493) (FIG. 7).

In one embodiment, the olfactory receptor is a feline catG7 (B3:74116955-74117893). In certain embodiments, the amino acid residues that the compounds interact with comprises catG7 (B3:74116955-74117893) residues Met81, Tyr258, and Gln100, for example, by hydrogen bonding or salt bridge interactions, as exemplified by in silico modeling of Amyl acetate in catG7 (B3:74116955-74117893) (FIG. 8). Alternatively, or in addition, in certain embodiments, the amino acids that the compounds interact with comprise catG7 (B3:74116955-74117893) residues Thr77, Lys269, Leu104, Thr276, Val277, His73, Val273 and/or Val78, either alone or in conjunction with interactions listed above, for example, by polar, ring stacking, salt bridges, hydrogen bonding, pi interactions, charged interactions, van der Waals interactions, or hydrophobic interactions, as exemplified by in silico modeling of Amyl acetate in catG7 (B3:74116955-74117893) (FIG. 8). Alternatively, or in addition, in certain embodiments, the amino acids that the compounds interact with comprise any one, two, three or more of the catG7 (B3:74116955-74117893) residues Met81, Tyr258, Gln100, Thr77, Lys269, Leu104, Thr276, Val277, His73, Val273 and Val78, for example, by polar, ring stacking, salt bridges, hydrogen bonding, pi interactions, or charged interactions, van der Waals, hydrophobic interaction or other interactions, as exemplified by in silico modeling of Amyl acetate in catG7 (B3:74116955-74117893) (FIG. 8).

In one embodiment, the olfactory receptor is a feline catG8 (E3:40237904-40238842). In certain embodiments, the amino acids that the compounds interact with comprise catG8 (E3:40237904-40238842) residues Leu101, Phe104, Leu105, Gly108, Glu180, Val202, Phe206, Tyr259, and/or Lys272, for example, by polar, ring stacking, salt bridges, hydrogen bonding, pi interactions, charged interactions, van der Waals interactions, or hydrophobic interactions, as exemplified by in silico modeling of 1-nonanethiol in catG8 (E3:40237904-40238842) (FIG. 9). Alternatively, or in addition, in certain embodiments, the amino acids that the compounds interact with comprise any one, two, three or more of the catG8 (E3:40237904-40238842) residues Met81, Leu101, Phe104, Leu105, Gly108, Glu180, Val202, Phe206, Tyr259, and Lys272, for example, by polar, ring stacking, salt bridges, hydrogen bonding, pi interactions, or charged interactions, van der Waals, hydrophobic interaction or other interactions, as exemplified by in silico modeling of 1-nonanethiol in catG8 (E3:40237904-40238842) (FIG. 9).

In one embodiment, the olfactory receptor is a feline catG9 (D1:105462554-105463512). In certain embodiments, the amino acid residues that the compounds interact with comprises catG9 (D1:105462554-105463512) residue Lys278, for example, by hydrogen bonding or salt bridge interactions, as exemplified by in silico modeling of β-ionone in catG9 (D1:105462554-105463512) (FIG. 10). Alternatively, or in addition, in certain embodiments, the amino acids that the compounds interact with comprise catG9 (D1:105462554-105463512) residues Phe110, Val111, Gly114, Val208, Ile212, Phe258, Ala261, Leu262, Tyr265, Val282, and/or Ser285, either alone or in conjunction with interactions listed above, for example, by polar, ring stacking, salt bridges, hydrogen bonding, pi interactions, charged interactions, van der Waals interactions, or hydrophobic interactions, as exemplified by in silico modeling of β-ionone in catG9 (D1:105462554-105463512) (FIG. 10). Alternatively, or in addition, in certain embodiments, the amino acids that the compounds interact with comprise any one, two, three or more of the catG9 (D1:105462554-105463512) residues Tyr79, Lys278, Phe110, Val111, Gly114, Val208, Ile212, Phe258, Ala261, Leu262, Tyr265, Val282, and Ser285, for example, by polar, ring stacking, salt bridges, hydrogen bonding, pi interactions, or charged interactions, van der Waals, hydrophobic interaction or other interactions, as exemplified by in silico modeling of β-ionone in catG9 (D1:105462554-105463512) (FIG. 10).

In one embodiment, the olfactory receptor is a canine CafaOR5.2.5. In certain embodiments, the amino acids that the compounds interact with comprise CafaOR5.2.5 residues Tyr77, Phe108, Val112, Ser116, Val206, Asp210, Phe256, and/or Thr283, for example, by polar, ring stacking, salt bridges, hydrogen bonding, pi interactions, charged interactions, van der Waals interactions, or hydrophobic interactions, as exemplified by in silico modeling of Coumarin in CafaOR5.2.5 (FIG. 11). Alternatively, or in addition, in certain embodiments, the amino acids that the compounds interact with comprise any one, two, three or more of the CafaOR5.2.5 residues Tyr263, Tyr77, Phe108, Val112, Ser116, Val206, Asp210, Phe256, and Thr283, for example, by polar, ring stacking, salt bridges, hydrogen bonding, pi interactions, or charged interactions, van der Waals, hydrophobic interaction or other interactions, as exemplified by in silico modeling of Coumarin in CafaOR5.2.5 (FIG. 11).

In certain embodiments, the compounds interact with any one or more of the human, canine, or feline olfactory receptors described herein, wherein the compounds interact with one or more amino acid residues present in the 7TM domains of said receptors. The EC2 loop of said receptors is at the entrance to the active site pocket of the receptors. In certain embodiments, amino acid residues present in the EC2 loop of the olfactory receptors interact with the compounds described herein.

3.3 In Vitro Methods

The presently disclosed subject matter further provides in vitro methods for identifying raw materials for generating pet food, food products, or compounds that can modulate the activity and/or expression of an olfactory receptor.

Olfactory receptors for use in the presently disclosed methods can include isolated or recombinant olfactory receptors or cells expressing an olfactory receptor, disclosed herein. In certain embodiments, the olfactory receptor for use in the disclosed methods can comprise the amino acid sequence of any one of SEQ ID NO:41-60, or any one of amino acid sequences in SEQ ID NOs:61-3808, or a fragment or variant thereof. In certain embodiments, the olfactory receptor for use in the disclosed method can have at least about 33%, 34%, 35%, 40%, 45%, 50%, 55%, 60%, 61%, 65%, 70%, 72%, 75%, 79%, 80%, 84%, 85%, 87%, 89%, 90%, 91%, 92%, 93%, 94%, 95%, 96%, 97%, 98%, or 99% identity to the amino acid sequence of any one of SEQ ID NO:41-60, or any one of amino acid sequences in SEQ ID NOs:61-3808, or a fragment or variant thereof. In certain embodiments, the olfactory receptor for use in the disclosed method can be encoded by a nucleotide sequence comprising any one of SEQ ID NO: 11-30, or any one of nucleotide sequences in SEQ ID NOs:61-3808, or a fragment or variant thereof. In certain embodiments, the olfactory receptor for use in the presently disclosed subject matter can include a receptor encoded by a nucleotide sequence having at least 85%, at least 90%, at least 91%, at least 92%, at least 93%, at least 94%, at least 95%, at least 96%, at least 97%, at least 98% or at least 99% identity to any one of SEQ ID NO: 11-30, or any one of nucleotide sequences in SEQ ID NOs:61-3808, or a fragment or variant thereof.

In certain embodiments, the method for identifying compounds that modulate the activity and/or expression of an olfactory receptor comprises measuring the biological activity of an olfactory receptor in the absence and/or presence of a test compound. In certain embodiments, the method can include measuring the biological activity of an olfactory receptor in the presence of varying concentrations of the test compound. The method can further include identifying the test compounds that result in a modulation of the activity and/or expression of the olfactory receptor compared to the activity and/or expression of the olfactory receptor in the absence of the test compound.

In certain embodiments, the method can further include analyzing two or more, three or more or four or more test compounds in combination. In certain embodiments, the two or more, three or more or four or more test compounds can be from different classes of compounds, e.g., amino acids and small chemical compounds. For example, and not by way of limitation, the method can include analyzing the effect of one or more small chemical test compounds on the biological activity and/or expression of an olfactory receptor in the presence of one or more amino acid test compounds. In certain embodiments, the method for identifying the effect of a compound on the activity and/or expression of an olfactory receptor comprises analyzing the effect of a test compound on the biological activity and/or expression of an olfactory receptor in the presence of an olfactory receptor ligand, for example, an odorant or olfactory receptor agonist/antagonist.

In certain embodiments, the method for identifying compounds that can modulate the activity and/or expression of an olfactory receptor comprises expressing an olfactory receptor in a cell line and measuring the biological activity of the receptor in the presence and/or absence of a test compound. The method can further comprise identifying test compounds that modulate the activity of the receptor by determining if there is a difference in receptor activation in the presence of a test compound compared to the activity of the receptor in the absence of the test compound. In certain embodiments, the method can include measuring the biological activity of the olfactory receptor in the presence of varying concentrations of the test compound. In certain embodiments, the selectivity of the putative olfactory receptor modulator can be evaluated by comparing its effects on other GPCRs or olfactory receptors.

In certain embodiments, the compounds identified according to the methods described herein increase or decrease the biological activity of an olfactory receptor by at least about 5%, 10%, 15%, 20%, 25%, 30%, 35%, 40%, 45%, 50%, 55%, 60%, 65%, 70%, 75%, 80%, 85%, 90%, 95%, 100%, or more, compared to the biological activity of the olfactory receptor when the compound is not present.

In certain embodiments, the method for identifying compounds that modulate the activity and/or expression of an olfactory receptor comprises determining whether a compound modulates the receptor directly, for example, as an agonist or antagonist. In certain embodiments, the method comprises determining whether a compound indirectly modulates the activity of the receptor (e.g., as an allosteric modulator), for example, by enhancing or decreasing the effect of other compounds on activating or inhibiting receptor activity.

In certain embodiments, the test agent that can modulate the activity and/or expression of an olfactory receptor has an EC50 value of no more than about 200 PM. In certain embodiments, the test agent has an EC50 value of no more than about 1 µM, 2 µM, 3 µM, 4 µM, 5 µM, 6 µM, 7 µM, 8 µM, 9 µM, 10 µM, 20 µM, 30 µM, 40 µM, 50 µM, 60 µM, 70 µM, 80 µM, 90 µM, 100 µM, 110 µM, 120 µM, 130 µM, 140 µM, 150 µM, 160 µM, 170 µM, 180 µM, 190 µM or 200 µM. In certain embodiments, the test agent has an EC50 value of no more than about 250 µM, 300 µM, 400 µM, 500 µM, 600 µM, 700 µM, 800 µM, 900 µM or 1 M. In certain embodiments, the test agent has an EC50 value of at least 1 µM, 10 µM, 100 µM, 1 nM, 10 nM, or 100 nM, but no more than about 1 µM, 2 µM, 3 µM, 4 µM, 5 µM, 6 µM, 7 µM, 8 µM, 9 µM, 10 µM, 20 µM, 30 M, 40 µM, 50 M, 60 µM, 70 M, 80 M, 90 M, 100 µM, 110 µM, 120 µM, 130 µM, 140 µM, 150 µM, 160 µM, 170 µM, 180 µM, 190 µM or 200 µM.

In certain embodiments, the test agent that can modulate the activity and/or expression of an olfactory receptor has an Emax value of no less than about 2.0. In certain embodiments, the test agent has an Emax value of no less than about 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 40, 50, 60, 70, 80, 90, 100, 110, 120, 130, 140. 150 or 200. In certain embodiments, the test agent has an Emax value of more than about 200.

Activation of the receptor in the presently disclosed methods can be detected through the use of a labelling compound and/or agent. In certain embodiments, the activity of the olfactory receptor can be determined by the detection of secondary messengers such as, but not limited to, cAMP, cGMP, IP3, DAG or calcium. In certain embodiments, the activity of the olfactory receptor can be determined by the detection of the intracellular calcium levels. Monitoring can be by way of, but not limited to, luminescence or fluorescence detection, such as by a calcium sensitive fluorescent dye or luminescent photoprotein. In certain embodiments, monitoring can be by way of luminescence. In certain embodiments, the intracellular calcium levels can be determined using a cellular dye, e.g., a fluorescent calcium indicator such as Calcium 4. In certain embodiments, the intracellular calcium levels can be determined by measuring the level of calcium binding to a calcium-binding protein, for example, calmodulin. Alternatively and/or additionally, the activity of the olfactory receptor can be determined by the detection of the phosphorylation, transcript levels and/or protein levels of one or more downstream protein targets of the olfactory receptor. In certain embodiments, the GloSensor™ and/or protein kinase A (PKA)-NanoBiT™ technologies are used to determine the activity of an olfactory receptor. In certain embodiments, chAMPion assay system are used to determine the activity of an olfactory receptor, which measures cAMP levels indirectly via calcium influx through cyclic nucleotide gated (CNG) channels. In certain embodiments, GloSensor assay comprises transient co-transfection of OR plasmid and GloSensor plasmid and detection of cAMP by GloSensor (permutated luciferase, luminescence activity depends on binding of cAMP); luminescence read-out. In certain embodiments, PKA-NanoBiT assay comprises transient co-transfection of OR plasmid with PKA-NanoBiT plasmids and detection of a decrease of fluorescence and/or luminescence read-out (OFF signal) resulting from cAMP-dependent dissociation of PKA subunits which disrupts split-luciferase complementation. In certain embodiments, chAMPion assay comprises transient transfection of OR plasmid and detection of calcium through photoprotein or fluorescent dye, resulting from increased cAMP level which leads to opening of CNG channel and calcium influx.

The cell line used in the presently disclosed methods can include any cell type that is capable of expressing an olfactory receptor (e.g., stable or transient expression). Non-limiting examples of cells that can be used in the disclosed methods include HeLa cells, Chinese hamster ovary cells (CHO cells), African green monkey kidney cells (COS cells), *Xenopus* oocytes, HEK-293 cells and murine 3T3 fibroblasts. In certain embodiments, the method can include expressing an olfactory receptor in HEK-293 cells. In certain embodiments, the method can include expressing an olfactory receptor in COS cells. In certain embodiments, the cells constitutively express the olfactory receptor. In certain embodiments, the cells transiently express the olfactory receptor. In another embodiment, expression of the olfactory receptor by the cells is inducible.

In certain embodiments, the cell expresses a calcium-binding photoprotein, a cyclic nucleotide gated (CNG) channel, a cAMP response element (CRE)-containing luciferase reporter, a GloSensor luciferase, or a PKA-NanoBiT system. In certain embodiments, the cell expresses a calcium-binding photoprotein, wherein the photoprotein luminesces upon binding calcium. In certain embodiments, the calcium-binding photoprotein comprises a compound selected from the group consisting of clytin, aequorin, obelin, any recombinant or isolated versions thereof, and combinations thereof. In certain embodiments, the calcium binding photoprotein comprises the protein clytin. In certain embodiments the clytin is a recombinant clytin. In certain embodiments, the clytin comprises an isolated clytin, for example, a clytin isolated from *Clytia gregarium*. In certain embodiments, the calcium-binding photoprotein comprises the protein aequorin, for example, a recombinant aequorin or an isolated aequorin, such as an aequorin isolated from *Aequorea victoria*. In certain embodiments, the calcium-binding photoprotein comprises the protein obelin, for example, a recombinant obelin or an isolated obelin, such as an obelin isolated from *Obelia longissima*.

In certain embodiments, an intracellular calcium level is monitored by luminescence detection or fluorescence detection. In certain embodiments, the fluorescence detection comprises a calcium sensitive fluorescent dye selected from the group consisting of Fura-2 AM, Fura-2 pentapotassium, Fura Red AM, Indo-1 AM, Indo-1 pentapotassium, Fluo-3, Fluo-4, Fluo-8, Calcium Green-1, Calcium 3, Calcium 4, Calcium 5, Rhod-2, derivatives thereof and combinations thereof.

In certain embodiments, expression of an olfactory receptor in a cell can be performed by introducing a nucleic acid encoding an olfactory receptor into the cell. For example, and not by way of limitation, a nucleic acid having the nucleotide sequence set forth in any one of SEQ ID NO: 11-30, or any one of nucleotide sequences in SEQ ID NOs:61-3808, or a fragment thereof, can be introduced into a cell. In certain embodiments, the introduction of a nucleic acid into a cell can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92 (1985), the disclosures of which are hereby incorporated by reference in their entireties) and can be used in accordance with the disclosed subject matter. In certain embodiments, the technique can provide for the stable transfer of the nucleic acid to the cell, so that the nucleic acid is expressible by the cell and inheritable and expressible by its progeny. In certain embodiments, the technique can provide for a transient transfer of the nucleic acid to the cell, so that the nucleic acid is expressible by the cell, wherein the concentration of the nucleic acid and the expression decrease in subsequent generations of the cell's progeny.

In certain embodiments, the methods can include identifying compounds that bind to an olfactory receptor. The methods can comprise contacting an olfactory receptor with a test compound and measuring binding between the compound and the olfactory receptor. For example, and not by way of limitation, the methods can include providing an isolated or purified olfactory receptor in a cell-free system, and contacting the receptor with a test compound in the cell-free system to determine if the test compound binds to the olfactory receptor. In certain embodiments, the method can comprise contacting an olfactory receptor expressed on the surface of a cell with a candidate compound and detecting binding of the candidate compound to the olfactory receptor. The binding can be measured directly, e.g., by using a labeled test compound, or can be measured indirectly. In certain embodiments, the detection comprises detecting a physiological event in the cell caused by the binding of the compound to the olfactory receptor, e.g., an increase in the intracellular calcium levels. For example, and not by way of limitation, detection can be performed by way of fluorescence detection, such as a calcium sensitive fluorescent dye, by detection of luminescence, or any other method of detection known in the art.

In other non-limiting embodiments, the in vitro assay comprises cells expressing an olfactory receptor that is native to the cells. Examples of such cells expressing a native olfactory receptor include, for example but not limited to, human, dog and/or cat olfactory cells (e.g., olfactory receptor cells). In certain embodiments, the human, dog and/or cat olfactory cells expressing an olfactory are isolated from a human dog and/or cat and cultured in vitro. In certain embodiments, the olfactory receptor cells can be immortalized, for example, such that the cells isolated from a human, dog and/or cat can be propagated in culture.

In certain embodiments, expression of an olfactory receptor in a cell can be induced through gene editing, for example, through use of the CRISPR gene editing system to incorporate an olfactory receptor gene into the genome of a cell, or to edit or modify an olfactory receptor gene native to the cell.

In certain embodiments, the in vitro methods of identifying a compound that binds to an olfactory receptor comprises determining whether a test compound interacts with one or more amino acids of an olfactory receptor binding pocket, as described herein.

In certain embodiments, compounds identified as modulators of an olfactory receptor can be further tested in other analytical methods including, but not limited to, in vivo assays, to confirm or quantitate their modulating activity.

In certain embodiments, the methods of identifying an olfactory receptor modulator can comprise comparing the effect of a test compound to an olfactory receptor agonist or antagonist. For example, a test compound that increases or decreases the activity of the receptor in the presence of an agonist when compared to the activity of the receptor when contacted with an olfactory receptor agonist alone can be selected as an olfactory receptor modulating compound.

Olfactory receptor agonists that can be used according to said methods can comprise one or more compounds described by Table 1.

TABLE 2

Compounds for Human (H) or Mouse (M) Olfactory Receptors

| Olfactory Receptor Orthologues | | | |
|---|---|---|---|
| Human | Canine | Feline | Compounds |
| HsOR17.1.11 (hOR3A1) | CafaOR9.2.9 | E1: 13347030-13347977 (CatG1) | aldehyde TPM (H), cyclosa (H), foliaver (H), helional (H), lilial (H), methyl-hydrocinnamaldehyde (H), methyl-phenyl-pentanal (H), trifemal (H) |
| HsOR1.4.8 (hOR6P1) | CafaOR38.1.21 | F1: 65134904-65135858 (CatG2) | anisaldehyde (H) |
| HsOR11.3.14 (hOR51E1) | CafaOR21.2.15 | D1: 62955839-62956792 (CatG3) | (+)-menthol (H), 2,4-DNT (H), 3-methyl-valeric acid (H), 4-methyl-valeric acid (H), butyl butyryl lactate (H), butyl butyryllactate (H), butyric acid (H), DMDS (H), eugenol methyl (H), eugenyl acetate (H), isovaleric acid (H), methyl furfuryl disulfide (H), methyl salicylate (H), nonanoic acid (H), pentanol (H), propanal (H), pyrazine (H) |
| HsOR11.3.40 (hOR51L1) | CafaOR21.2.43 | D1: 63312327-63313289 (CatG4) | allyl phenylacetate (H), androstadienone (H), caproic acid (H), hexanoic acid (H), phenyl acetaldehyde (H) |
| HsOR14.1.27 (hOR11H6) | CafaOR15.2.20 | B3: 72908295-72909287 (CatG5) | isovaleric acid (H) |
| HsOR11.13.7 (hOR4D6) | CafaOR18.3.11 | D1: 105486528-105487493 (CatG6) | beta-ionone (H) |
| HsOR14.2.5 (hOR4E2) | CafaOR15.3.1 | B3: 74116955-74117893 (CatG7) | amyl acetate (H) |
| HsOR16.1.3 (hOR2C1) | CafaOR6.3.1 | E3: 40237904-40238842 (CatG8) | nonanethiol (H), octanethiol (H) |
| HsOR11.13.6 (hOR5A1) | CafaOR18.3.12 | D1: 105462554-105463512 (CatG9) | beta-ionone (H) |
| HsOR11.18.36 (hOR8B8) | CafaOR5.2.5 | D1: 21266824-21267768 (CatG10) | acetophenone (M), coumarin (M) |

In certain embodiments, the olfactory receptor agonist is selected from the group consisting of trifernal, isovaleric acid, 3-methyl-2-hexanoic acid, alpha-ionone, hexyl acetate, amyl mercaptan, helional, para-anisaldehyde, 4-ethoxybenzaldehyde, menthol, methyl-eugenol, methyl-salicylate, phenylacetaldehyde, beta-ionone, amyl acetate, nonanethiol, acetophenone, coumarin, lilial, meta-anisaldehyde, 4-methyl-valeric acid, pentanol, allyl-phenylacetate, hexanoic acid, alpha-ionone, citral, isoamylacetate, octanethiol, propiophenone, 7-methoxycoumarin and combinations thereof.

In certain embodiments, the olfactory receptor modulators of the present disclosure comprise a salt of the olfactory receptor modulator, for example, but not limited to, an acetate salt or a formate salt. In certain embodiments, the olfactory receptor modulator salt comprises an anion (−) (for example, but not limited to, $Cl^-$, $O^{2-}$, $CO_3^{2-}$, $HCO_3^-$, $OH^-$, $NO_3^-$, $PO_4^{3-}$, $SO_4^{2-}$, $CH_3COO^-$, $HCOO^-$ and $C_2O_4^{2-}$) bonded via an ionic bond with a cation (+) (for example, but not limited to, $Al^{3+}$, $Ca^{2+}$, $Na^+$, $K^+$, $Cu^{2+}$, $H^+$, $Fe^{3+}$, $Mg^{2+}$, $NH_4^+$ and $H_3O^+$). In other embodiments, the olfactory receptor agonist salt comprises a cation (+) bonded via an ionic bond with an anion (−).

In certain embodiments, the olfactory receptor modulators of the present application are identified through in silico modeling of an olfactory receptor, e.g., a canine and/or feline olfactory receptor, wherein the olfactory receptor modulators of the present application comprise a structure that fits within a binding site of the olfactory receptor. In certain embodiments, the in silico method comprises the in silico methods described above and in the Examples section of the present application.

In certain embodiments, the olfactory receptor modulators of the present application are identified through an in vitro method, wherein the olfactory receptor modulator compounds modulate an olfactory receptor, disclosed herein, expressed by cells in vitro. In certain embodiments, the in vitro method comprises the in vitro methods described above and in the Examples section of the present application.

4. Pet Food Products

The present application provides for screening methods that can be used to identify suitable raw materials to produce a palatable and nutritious pet food product. The presently disclosed screening methods can also be used to determine if a finished pet food product would be palatable to the pet (e.g., a dog or a cat). For example, the in vitro methods described herein can be used to screen raw materials and finished pet food products to identify whether the raw materials or finished pet food products comprise compounds that increase, decrease, or modulate olfactory receptor activity and/or expression. In certain embodiments, raw materials and finished pet food products that do not increase the activity and/or expression of an olfactory receptor can be selected for use in, or as, a pet food product for consumption. In certain embodiments, raw materials and finished pet food products that do increase the activity and/or expression of an olfactory receptor can be selected for use in, or as, a pet food product for consumption.

Non-limiting examples of suitable pet food products include wet food products, dry food products, moist food products, pet food supplements (e.g., vitamins), pet beverage products, snack and treats and pet food categories described herein.

One of the goals of the pet care industry is to identify sustainable protein sources for pets that do not compete with the human food chain. As such, there is an ongoing search for novel protein sources that fit these criteria. The presently disclosed screening method can be used to identify which of the novel protein sources would be considered palatable to the pet, or at least have no effect on the palatability of the other ingredients of the pet food. In certain embodiments, the novel protein source (i.e., raw material) is meat, fish, cheese, beans, yeast, yeast extracts, bacteria, algae, fungi, nuts, seeds or other plant material, or combinations thereof. In certain embodiments, the raw material is meat.

In certain embodiments, the protein source can be derived from a variety of plant sources. Non-limiting examples of plant sources include corn, maize, rice, soy, wheat, etc. For example, and not by way of limitation, the plant-derived protein can include lupin protein, wheat protein, soy protein and combinations thereof. Alternatively or additionally, the protein source can be derived from a variety of animal sources, for example, a multicellular eukaryotic organism from the kingdom animalia. Non-limiting examples of animal protein include beef, pork, poultry, lamb or fish including, for example, muscle meat, meat byproduct, meat meal or fish meal. Other non-limiting examples of animal sources include insects, or other organism from the phylum arthropoda.

In certain embodiments, the protein source can be derived from yeast or any other single-cell eukaryotic organisms, mold, mushroom or fungi.

In certain embodiments, the protein source can be derived from bacteria, archaea, or any other archaebacteria, eubacteria, or prokaryotic organism.

In certain embodiments, the protein source can be derived from algae, kelp, seaweed, or any other single or multicellular photosynthetic organism or protist.

In certain embodiments, the presently disclosed subject matter includes accepting or rejecting a raw material for the production of pet food based on the raw material's ability to enhance, increase, decrease and/or modulate the activity and/or expression of an olfactory receptor.

In certain embodiments, the raw material is rejected if the raw material results in the enhancement or increase in the activity and/or expression of at least one olfactory receptor. In certain embodiments, the raw material is rejected if the raw material results in the enhancement or increase in the activity and/or expression of at least two, at least three, at least four, at least five, at least six, at least seven, at least eight, at least nine, at least ten, at least eleven, at least twelve, at least thirteen, at least fourteen, at least fifteen, and/or at least sixteen olfactory receptors.

In certain embodiments, the raw material is accepted if the raw material results in the enhancement or increase in the activity and/or expression of at least one olfactory receptor. In certain embodiments, the raw material is accepted if the raw material results in the enhancement or increase in the activity and/or expression of at least two, at least three, at least four, at least five, at least six, at least seven, at least eight, at least nine, at least ten, at least eleven, at least twelve, at least thirteen, at least fourteen, at least fifteen, and/or at least sixteen olfactory receptors.

In certain embodiments, the raw material is accepted if it does not modulate the activity of at least one olfactory receptor. In certain embodiments, the raw material is selected if it inhibits or blocks the activity and/or expression of at least one olfactory receptor.

In certain embodiments, the raw material is rejected if it does not modulate the activity of at least one olfactory receptor. In certain embodiments, the raw material is rejected if it inhibits or blocks the activity and/or expression of at least one olfactory receptor.

In certain embodiments, the olfactory receptor is selected from any one or more of canine receptors CafaOR9.2.9, CafaOR38.1.21, CafaOR21.2.15, CafaOR21.2.43, CafaOR15.2.20, CafaOR18.3.11, CafaOR15.3.1, CafaOR6.3.1, CafaOR18.3.12, and/or CafaOR5.2.5. In certain non-limiting embodiments, the olfactory receptor is selected from one or more of canine olfactory receptors described in SEQ ID NOs:61-2260.

In certain embodiments, the olfactory receptor is selected from any one or more of feline receptors E1:13347030-13347977, F1:65134904-65135858, D1:62955839-62956792, D1:63312327-63313289, B3:72908295-72909287, D1:105486528-105487493, B3:74116955-74117893, E3:40237904-40238842, D1:105462554-105463512, and/or D1:21266824-21267768. In certain non-limiting embodiments, the olfactory receptor is selected from one or more of feline olfactory receptors described in SEQ ID NOs:2261-3808.

In certain non-limiting embodiments, a raw material that results in the enhancement or increase in the activity and/or expression of at least one olfactory receptor can be admixed with a compound that inhibits or reduces the activity and/or expression of the at least one olfactory receptor, wherein the admixture is accepted for the production of pet food.

During the production of pet food, some of the materials may change form due to mechanical forces, thermal forces, or chemical reactions. The presently disclosed screening method can be used to identify pet food products that form compounds that are unpalatable to an animal, for example, a canine or a feline, for example, a compound that enhances or increases the activity and/or expression of an olfactory receptor.

In certain embodiments, the presently disclosed subject matter includes accepting or rejecting a pet food product based on the product's ability to enhance, increase, decrease and/or modulate the activity and/or expression of an olfactory receptor.

In certain embodiments, the pet food product is rejected if the product results in the enhancement or increase in the activity and/or expression of at least one olfactory receptor. In certain embodiments, the pet food product is rejected if the product results in the enhancement or increase in the activity and/or expression of at least two, at least three, at least four, at least five, at least six, at least seven, at least eight, at least nine, at least ten, at least eleven, at least twelve, at least thirteen, at least fourteen, at least fifteen, and/or at least sixteen olfactory receptors. In certain embodiments, the pet food product is accepted if it does not modulate the activity of at least one olfactory receptor. In certain embodiments, the pet food product is selected if it inhibits or blocks the activity and/or expression of at least one olfactory receptor.

In certain embodiments, the pet food product is accepted if the product results in the enhancement or increase in the activity and/or expression of at least one olfactory receptor. In certain embodiments, the pet food product is accepted if the product results in the enhancement or increase in the activity and/or expression of at least two, at least three, at least four, at least five, at least six, at least seven, at least eight, at least nine, at least ten, at least eleven, at least twelve, at least thirteen, at least fourteen, at least fifteen, and/or at least sixteen olfactory receptors. In certain embodiments, the pet food product is rejected if it does not modulate the activity of at least one olfactory receptor. In certain embodiments, the pet food product is rejected if it inhibits or blocks the activity and/or expression of at least one olfactory receptor.

The flavor compositions of the present disclosed subject matter can also be used in a wide variety of pet food products. The combination of the flavoring composition(s) of the presently disclosed subject matter together with a pet food product and optional ingredients, when desired, provides a flavoring agent that possesses unexpected odor and imparts, for example, a desirable olfactory sensory experience. The flavor compositions disclosed herein can be added prior to, during or after formulation processing or packaging of the pet food product, and the components of the flavor composition can be added sequentially or simultaneously.

In certain embodiments, the pet food product is a nutritionally complete dry, wet or semi-moist food product. A dry or low moisture-containing nutritionally-complete pet food product can comprise less than about 15% moisture. A wet or high moisture-containing nutritionally-complete pet food product can comprise greater than about 50% moisture. Such food products can include from about 10% to about 90% fat, from about 10% to about 70% protein and from about 5% to about 80% carbohydrates, e.g., dietary fiber and ash, on a percent energy basis.

In certain embodiments, the pet food product is a nutritionally complete dry, wet or semi-moist food product. In certain embodiments, the pet food product includes from about 60% fat, from about 30% protein and from about 10% carbohydrates, e.g., dietary fiber and ash, on a percent energy basis.

In certain embodiments, the pet food product is a nutritionally complete moist food product. A moist, e.g., semi-moist or semi-dry or soft dry or soft moist or intermediate or medium moisture containing nutritionally-complete pet food product comprises from about 15 to about 50% moisture.

In certain embodiments, the pet food product is a non-nutritionally-complete pet food products (e.g., snack, care and treats). In certain embodiments, the pet food product is a pet food snack product. Non-limiting examples of pet food snack products include snack bars, pet chews, crunchy treats, cereal bars, snacks, biscuits and sweet products.

In certain embodiments of the present disclosure, the odor and/or palatability attributes of a pet food product or medicine prepared according to the methods described herein can be measured by an in vivo smelling method that uses a panelist of odor testers. For example, but not by way of limitation, the panel can contain canine and/or feline panelists. In certain embodiments, the palatability of a pet food product containing, for example, a screened raw material or a screened pet food product can be determined by the consumption of the pet food product alone (e.g., the one bowl test, monadic ranking). In certain embodiments, the palatability of a screened raw material or a screened pet food product can be determined by the preferential consumption of the pet food product or raw material, versus a pet food product that is known to be palatable to the animal (e.g., the two bowl test for testing preference, difference and/or choice).

In certain embodiments, the palatability and/or repellant blocking odor of a compound identified according to the methods described herein can be determined by the preferential consumption of a water solution containing said compound versus a water solution that does not contain the compound or contains a different flavor composition, for example, an olfactory receptor agonist (e.g., the two bottle test). The intake ratio for each pet food product or water solution can be determined by measuring the amount of one ration consumed divided by the total consumption. The consumption ratio (CR) can then be calculated to compare the consumption of one ration in terms of the other ration to determine the preferential consumption of one food product or water solution over the other. Alternatively or additionally, the difference in intake (g) can be used to assess the average difference in intake between the two solutions in a two bottle test or between two pet food products in a two bowl test at a selected significance level, for example, at the 5% significance level to determine an average difference in intake with a 95% confidence interval. In certain embodiments, the confidence interval can be about 90%. However, any significance level may be used, for example, a 1, 2, 3, 4, 5, 10, 15, 20, 25 or 50% significance level.

In certain embodiments, percentage preference scores, e.g., the percentage preference for one solution or food product by an animal, is the percentage of the total liquid or food product ingested during the test that that solution or food product accounts for, can also be calculated.

5. Odor Deterrents

The present disclosure provides methods for maintaining the health of an animal by imparting a repellant odor and/or decreasing the palatability of an object or surface. In certain embodiments, the method comprises applying, coating or contacting an odor deterrent product comprising a compound identified according to the methods described herein to the object or surface, and thereby preventing contact and/or ingestion of said object or surface by an animal. Accordingly, detrimental effects on the animal's health that could result from contact and/or ingestion of said object or surface are avoided. In certain embodiments, the object or surface is harmful to the health of the animal or toxic to the animal.

EXAMPLES

The presently disclosed subject matter will be better understood by reference to the following Examples, which are provided as exemplary of the invention, and not by way of limitation.

Example 1—In Silico Model of Interactions Between Olfactory Receptors and Putative Binding Compounds The present example describes the computational modeling of canine/feline olfactory receptors (ORs) to identify putative olfactory receptor modulators.

Homology models of canine/feline olfactory receptors were based on crystal structure of 3SN6 from Protein Data Bank (PDB). 3SN6 is the crystal structure of β2 adrenergic receptor from Group A GPCR with bound agonist (BI-167107 from Boehringer Ingelheim). (Rasmussen et al., Nature, 477: 549-555 (2011)). The models were built using the I-TASSER Suite of programs (Yang et al., Nat Methods, 12: 7-8 (2015)) and Modeller (Eswar et al., Curr Protoc Bioinformatics, 15:5.6.1-5.6.30 (2006)), which is part of the DiscoveryStudio (DS) suite of programs from Accelrys (DiscoveryStudio (DS) is a suite of interactive modeling and simulation programs from the Accelrys corporation).

The odor compounds were docked into the active site of canine/feline olfactory receptors. The docking program Bio-Dock from BioPredict, Inc., was used but other state of the art docking programs could be used for this purpose.

The results of in silico modeling are presented in FIGS. 2-11. FIG. 13 shows a phylogenetic tree for multi-species (human/canine/feline) covering the olfactory genetic space. The phylogenetic tree shows all olfactory receptors, and that the 30 selected olfactory receptors (10 human receptors, 10 canine receptors, 10 feline receptors, highlighted, SEQ ID NO: 1-60) are evenly distributed around the olfactory genetic space. FIG. 13 further shows the 10 pairs of canine/feline olfactory receptors (SEQ ID NO: 11-30 and SEQ ID NO:41-60) were chosen because they cover an optimal breadth and range of the potential OR receptors.

Example 2—Identification of Canine and Feline Olfactory Receptors

The dog olfactory receptor sequences and methods for detection were previously described by Niimura & Nei (2007) from which the 1,100 dog olfactory receptor sequences were obtained. The 774 putative cat olfactory receptor sequences were identified using a combination of previous annotations and similarity searches. The sequences for gene annotations containing "olfactory receptor" were extracted from the ensemble cat genome (Felis_catus_6.2 (GCA 000181335.2)). In addition Dog, Human, Mouse, Elephant, Cow, Horse, Rabbit and Guinea Pig nucleotide sequences (Niimura et al., 2015) were used to search against the cat genome. The cat reference sequence was extracted for all unique alignments with >=65 percent identity and >=650 bp length. Redundant sequences (>=95% identity) were removed using longest first sequence clustering (Fu et al., 2012) retaining only representatives. The amino acid translations for these representatives were identified using sixpack from the emboss package (Rice et al., 2000), selecting the longest amino acid sequence within an open reading frame.

The nucleic acid and amino acid sequences of the 1,100 dog olfactory receptors and 774 putative cat olfactory receptors are set forth in SEQ ID NOs:61-3808.

Example 3—Identification of Canine and Feline Olfactory Receptor Modulators Using In Vitro Assays This example refers to the functional expression of different feline and canine olfactory receptors (ORs). 20 OR sequences were selected, where 10 sequences have feline origins and the remaining 10 have canine origins. These ORs were subcloned into a modified expression vector suitable for the transient, functional expression of ORs. The transiently expressed receptors were then stimulated with various concentrations of different odorants aiming to deorphanize the feline and canine ORs. As illustrated in FIG. 12, OR responsiveness was detected in either one or both of the following cell lines and assays: 1) HEK293 PEAKrapid/RTP1s endo (reporter cell line A) and a CRE-NanoLuc luciferase reporter assay; and 2) HEK293/NatClytin/CNG/RTPIs (reporter cell line B) endo and a CNG chAMPion assay. Functional expression of the different OR sets were transient in reporter cell line A or B. The transiently transfected ORs were stimulated with 3 concentrations (n=4) of different odorants (at least 3).

Material and Methods

Cell lines. The following cell lines were used for this project:
- Reporter cell line A (for CRE-Luciferase, GloSensor, and PKA-NanoBiT assays): HEK293 PEAKrapid/RTP1s endo
- Reporter cell line B (for chAMPion assay): HEK293/CNG/nat-Clytin/RTP1s endo Cell culture media. Cells were maintained in DMEM High Glucose (Lonza BioWhittaker cat. BE12-604F/U1; 500 mL) supplemented with fetal bovine serum (Sigma cat. F7524; final concentration 10%), penicillin-streptomycin (BioWhittaker cat. DE17-602E; 5 mL of 100× solution) and the following selection antibiotics:
- HEK293 PEAKrapid/RTP1s endo: 0.1 mg/mL G418, 0.2 mg/mL hygromycin, 0.1 mg/mL zeocin.
- HEK293/CNG/nat-Clytin/RTP1s endo: 0.8 mg/mL G418, 50 μg/mL zeocin, 0.6 μg/mL puromycin.

Cell culture conditions. Cell lines were maintained in their respective complete culture media at 37° C., 5% $CO_2$, and 90% humidity. Cells were split twice a week. Under standard propagation conditions, approx. $4 \times 10^6$ cells were seeded in a T225 flask recovering about $30 \times 10^6$ cells/flask. For splitting, cells were gently washed with PBS and then incubated with trypsin for 5 min at RT or 37° C. Media were added and cells were resuspended.

Buffers. Tyrode buffer with 0 mM calcium: in-house solution (130 mM NaCl, 5 mM KCl, 1 mM $MgCl_2$, 5 mM $NaHCO_3$, 20 mM HEPES in water at pH 7.4; sterile filtered and autoclaved). Tyrode buffer: in-house solution (130 mM NaCl, 5 mM KCl, 1 mM $MgCl_2$, 5 mM $NaHCO_3$, 2 mM $CaCl_2$, 20 mM HEPES in water at pH 7.4; sterile filtered and autoclaved). Tyrode buffer with 10 mM calcium: Tyrode buffer 0 mM calcium plus 10 mM $CaCl_2$. Calcium chloride (dihydrate): Sigma, 223506, 1 M stock solution, prepared in water and stored at RT. Coelenterazine: stock solution: 5 mg/mL in DMSO (11.8 mM) with 30 μM glutathione; aliquoted and stored at −20° C.; diluted 1:1000 in tyrode buffer for experiments (final concentration: 11.8 μM).

OR sequences. The canine OR sequences SEQ ID NOs: 11-20 and the feline OR sequences SEQ ID NOs: 21-30 were used. These sequences were synthesized and cloned into a pcDNA5 expression vector with an N-terminal SSTR3 transport tag.

OR ligands. OR and odorant combinations test in phase 2 are provided in Table 3.

TABLE 3

| ORs - human, dog, cat, (mouse) | Odorant | Structure |
|---|---|---|
| OR_1 (OR3A1) | Helional | 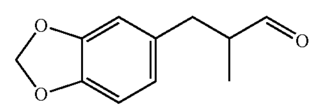 |
| | Lilial | |
| | Trifernal | |
| OR_2 (OR6P1) | para-Anisaldehyde | 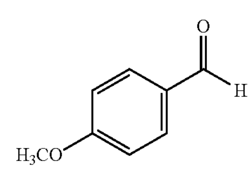 |
| | meta-Anisaldehyde | |

TABLE 3-continued

| ORs - human, dog, cat, (mouse) | Odorant | Structure |
|---|---|---|
| | 4-Ethoxybenzaldehyde | |
| OR_3 (OR51E1) (Odorants in gray shade were present in mixes but not tested individually) | Isovaleric acid | 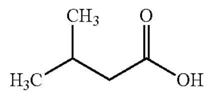 |
| | 4-Methyl-valeric acid | |
| | 3-Methyl-2-hexanoic acid | |
| | Hexaonic acid | |
| | (+)-Menthol | |
| | Methyl eugenol | |
| | Methyl salicylate | |
| | Pentanol | $CH_3(CH_2)_3CH_2OH$ |
| OR_4 (OR51L1) | Allyl phenylacetate | 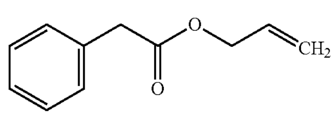 |
| | Hexanoic acid | |

TABLE 3-continued

| ORs - human, dog, cat, (mouse) | Odorant | Structure |
|---|---|---|
| | Phenylacetaldehyde | benzyl-CH$_2$-CHO |
| OR_5 (OR11H6) | Isovaleric acid | (CH$_3$)$_2$CHCH$_2$COOH |
| | 4-Methyl-valeric acid | CH$_3$(CH$_2$)$_3$CH$_2$COOH |
| | 3-Methyl-2-hexanoic acid | CH$_3$CH$_2$CH=CH-CH(CH$_3$)COOH |
| OR_6 (OR4D6), OR_9 (OR5A1) | beta-Ionone | (structure shown) |
| | alpha-Ionone | (structure shown) |
| | Citral | (CH$_3$)$_2$C=CHCH$_2$CH$_2$C(CH$_3$)=CHCHO |
| OR_7 (OR4E2) | Amyl acetate | CH$_3$COO-C$_5$H$_{11}$ |
| | Isoamyl acetate | CH$_3$COOCH$_2$CH$_2$CH(CH$_3$)$_2$ |
| | Hexyl acetate | CH$_3$COO-C$_6$H$_{13}$ |
| OR_8 (OR2C1) | Nonanethiol | CH$_3$(CH$_2$)$_7$CH$_2$SH |
| | Octanethiol | CH$_3$(CH$_2$)$_6$CH$_2$SH |
| | Amyl mercaptan | CH$_3$(CH$_2$)$_3$CH$_2$SH |
| OR_10 (OR8B8) | Acetophenone | C$_6$H$_5$COCH$_3$ |

TABLE 3-continued

| ORs - human, dog, cat, (mouse) | Odorant | Structure |
|---|---|---|
| | Coumarin | (structure) |
| | Propiophenone | (structure) |
| | 7-Methoxycoumarin | (structure) |

Four of the compounds for OR_3 (highlighted in bold) were not tested individually on the receptors but were included in the mixes. All compounds were purchased from Sigma-Aldrich. In addition to individual compounds, mixes were tested in phase 2 of the project on some ORs. The composition of the mixes tested on some ORs in phase 2 are provided in Table 4.

TABLE 4

| Mix 1 | Mix 2 |
|---|---|
| Helional | Lilial |
| para-Anisaldehyde | meta-Anisaldehyde |
| 4-Ethoxybenzaldehyde | 4-Methyl-valeric acid |
| Menthol | Pentanol |
| Methyl-eugenol | Allyl-phenylacetate |
| Methyl-salicylate | Hexanoic acid |
| Phenylacetaldehyde | alpha-Ionone |
| beta-Ionone | Citral |
| Amyl acetate | Isoamylacetate |
| Nonanethiol | Octanethiol |
| Acetophenone | Propiophenone |
| Coumarin | 7-Methoxycoumarin |

In phase 3, all positive combinations of ORs (always including human, dog, and cat ORs) and odorants were tested in full dose-response curves. OR and odorant combinations tested in phase 3 are provided in Table 5.

TABLE 5

| OR | Odorant |
|---|---|
| OR_2 OR6P1 | p-Anisaldehyde |
| | 4-Ethoxybenzaldehyde |
| OR_3 OR51E1 | Isovaleric acid |
| | 4-Methylvaleric acid |
| | Hexanoic acid |
| | 3-Methyl-2-hexanoic acid |
| OR_4 OR51L1 | Hexanoic acid |
| | Allyl phenylacetate |
| OR_8 OR2C1 | Nonanethiol |
| OR_9 OR5A1 | Isovaleric acid |
| | Citral |
| | Amyl acetate |
| | β-Ionone |
| OR_10 OR8B8 | Acetophenone |
| | Propriophenone |
| | Coumarin |

Assay kits. The following kit were used according to the manufacterer's instructions:
nano-Glo® Luciferase Assay System (Promega) for the CRE-NanoLuc luciferase assay.

Assay Protocols

CRE-NanoLuc luciferase assay. HEK293 PEAKrapid/RTP1s endo cells were transiently transfected with plasmids encoding the respective OR together with a CRE-NanoLuc luciferase plasmid (Promega) in a 1:1 ratio and were seeded at 20,000 cells/well in 25 µL/well complete growth medium in poly-D-lysine coated black, clear-bottom 384 MTPs.

Twenty-four hours later, the cell medium was removed manually and cells were incubated with 20 µL/well Tyrode buffer. Compounds prepared in Tyrode buffer with 0 mM calcium were added to cells (10 µL/well of 3× solutions). Cells were then incubated at 37° C. for 3-4 h. The plates were read in a luminescence plate reader (FLIPR$^{TETRA}$, Molecular Devices). Luminescence (camera settings: exposure time: 0.99 s; maximum gain) was recorded for 90 s after addition of 20 µL/well of the NanoGlo reagent.

Data were analyzed with the Screenworks® software (Molecular Devices, version 4.0.0.30). Luminescence values (in RLU) were exported as averages from 20 s-75 s. In addition to using raw values, the data were also normalized to background signals (wells containing buffer only) and expressed as "Fold change" (mean value (n=2)/mean value of buffer wells (n=2)). Data analysis and plotting of graphs was carried out using Excel (Microsoft) and GraphPad Prism (GraphPad Software, Inc.).

chAMPion (CNG channel) assay. HEK293/CNG/nat-Clytin/RTP1 s endo cells were transiently transfected with plasmids encoding the respective OR and were seeded at 20,000 cells/well in 25 µL/well complete growth medium in poly-D-lysine coated black, clear-bottom 384 MTPs.

Twenty-four hours later, the cell medium was removed manually and cells were incubated in 20 µL/well coelenterazine (11 µM) in Tyrode buffer with 0 mM calcium for 3.5 h at 37° C. Plates were then read in a luminescence plate reader (FLIPR$^{TETRA}$, Molecular Devices) with the following camera settings: exposure time: 0.533 s, maximum gain. Luminescence was recorded for 1 min after addition of 10 µL/well compounds (3× solutions prepared in Tyrode buffer with 0 mM calcium), followed by an incubation period of 30 min at 37° C. Luminescence was again recorded for 1 min after addition of 20 µL/well Tyrode buffer with 10 mM CaCl$_2$. The first reading after compound addition monitors the receptor-Gα$_q$ signaling pathway—as expected, no signals were observed here. The second reading after addition of calcium monitors OR-Gas signaling; these data were analyzed.

Data were analyzed with the Screenworks® software (Molecular Devices, version 4.0.0.30). Luminescence values (in RLU) were exported as maximum RLU between 10 s and 40 s. In addition to using raw values, the data were also normalized to background signals (wells containing buffer only) and expressed as "Fold change" (mean value (n=2)/mean value of buffer wells (n=2)). Data analysis and plotting of graphs was carried out using Excel (Microsoft) and GraphPad Prism (GraphPad Software, Inc.).

Results

In phase 1 of the project, twenty OR sequences, ten canine and ten feline sequences, to be analyzed in this project, were submitted by Mars Petcare. The OR sequences were synthesized and subcloned into an expression vector adding a transport epitope tag to the N-terminus of the OR proteins to facilitate their expression and plasma membrane localization.

A first functional test of the canine and feline ORs was carried out in phase 2. Sets of ORs, each consisting of human, cat, and dog orthologs (and in case of OR_10, OR8B8, also the mouse ortholog), were tested with three concentrations of a minimum of three odorants, pre-selected on the basis of published activity on the human ortholog or predicted potential activity. Most sets of ORs were also challenged with two mixes consisting of 12 odorants each. All sets of ORs were tested in parallel in two cell-based assays, CRE-NanoLuc luciferase assay and CNG chAMPion assay. These two assays were found to be the two best assays for the ten human ORs, which were tested in a previous study.

Of the ten sets of ORs that were tested in phase 2, seven sets showed responses of at least one receptor ortholog to at least one compound (FIGS. 14 and 15). Several ORs responded to more than one compound. For four sets of ORs, both dog and cat ORs showed activity; these include the set of OR_2 (OR6P1) for which the human ortholog did not respond to the same set of ligands as did the dog and cat receptors. For three other sets of ORs only the dog ortholog or the cat ortholog, respectively, responded.

In phase 3 of the project, six positive OR sets, including all available orthologs, were re-tested with their positive ligands in eight concentrations and dose-response curves were calculated. The results of phase 3 are summarized FIGS. 16 and 17. Briefly, six dog ORs were shown to be active (with numbers of ligands): OR6P1 (2); OR51E1 (3-4); OR51L1 (1); OR2C1 (1); OR5A1 (4); OR8B8 (3). In addition, six cat ORs showed activity: OR6P1 (2); OR51E1 (3-4); OR51L1 (2); OR4E2 (1); OR2C1 (1); OR5A1 (4); OR8B8 (1).

All data are presented in full detail in FIGS. 18-43. FIGS. 18-37 represent the results obtained in phase 2 assays. FIGS. 38-43 represent the dose-response curves of the positive ligands in phase 3 assays. The following data were exported: CRE-Luciferase: Average 15 s-60 s; chAMPion assay: Maximum 10 s-30 s. Data were normalized as "Fold Change" (compared to mean of buffer values). The base of all logarithm is 10.

Example 4—Identification of Canine and Feline Olfactory Receptor Modulators Using In Vitro Assays The present example describes an in vitro assay for identifying compounds that modulate the activation of a canine or feline olfactory receptor by an olfactory receptor ligand.

Compounds identified by in silico modeling with an olfactory receptor, as detailed above in Example 1, as putative olfactory receptor modulators are selected for further testing in vitro. In vitro functional characterization of the selected modulators is used to evaluate the effectiveness of a putative modulator compound in modulating the activation of the olfactory receptor by an olfactory receptor ligand.

HEK293 cells (or other suitable expression system) that stably or transiently express a canine or feline olfactory receptor (e.g., canine CafaOR9.2.9, CafaOR38.1.21, CafaOR21.2.15, CafaOR21.2.43, CafaOR15.2.20, CafaOR18.3.11, CafaOR15.3.1, CafaOR6.3.1, CafaOR18.3.12, CafaOR5.2.5, or feline E1:13347030-13347977, F1:65134904-65135858, D1:62955839-62956792, D1:63312327-63313289, B3:72908295-72909287, D1:105486528-105487493, B3:74116955-74117893, E3:40237904-40238842, D1:105462554-105463512, D1:21266824-21267768, or any one of the receptors having a nucleotide sequence or an amino acid sequence set forth in SEQ ID NOs:61-3808) are exposed to putative modulator compounds and an olfactory receptor ligand (e.g., an agonist) to modulate the activity and/or expression of the olfactory receptor.

An exemplary method of an in vitro assay is as follows. All transient transfections are performed with, for example, Lipofectamine2000 (Invitrogen) according to the manufactures protocol. 10 µl Lipofectamine2000 is diluted in 500 µl DMEM (Life Technologies) and incubated for 5 minutes at room temperature. 3 µg of plasmid DNA (1 µg/µl) is diluted in 500 µl DMEM and added to the Lipofectamine2000 mix to obtain a final volume of 1000 µl. After additional 30 minutes of incubation at room temperature, the DNA-Lipofectamine complex is added to 1000 µl of a cell suspension containing 1,400,000 cells/ml. Subsequently, 25 µl of the complete mixture is seeded into each well of a black 384 well polystyrene assay plate. At 3 hours post-transfection the transfection mix is removed from the cells and fresh DMEM containing 10% FBS and 1% P/S is added. At 27 to 30 hours post-transfection the medium is removed from the cells and 20 µl loading buffer that includes a calcium sensitive fluorescent dye or luminescent substrate (Tyrode's buffer+2 µM Fluo4-AM (Invitrogen)+2.5 mM probenecid (Invitrogen) for fluorescence or Coelenterazine (Biosynth)+Tyrode's buffer for luminescence) is added for 1 hour (fluorescence) or 3 hours (luminescence) at 37° C. The cells are then washed 2 times every 20 minutes with Tyrode's buffer using an automated plate washer (Biochrom Asys Plate Washer) for the fluorescent protocol. No wash step is required for the luminescent protocol.

Activation of the olfactory receptor is then detected, for example, by detecting a change in intracellular calcium levels using the calcium sensitive fluorescent dye, the calcium sensitive luminescent photoprotein, or by any detection system known in the art. Cells that do not express the olfactory receptor (MOCK control) are used as a control. Examples of such data capturing systems include FLIPR® Tetra or a FlexStation® 3 system. However, other imaging techniques and systems can be used, for example, microscopic imaging of the treated cells.

For each putative olfactory receptor modulator, dose response curves are generated with at least 8 concentrations in triplicate and the $EC_{50}$ value of the putative olfactory receptor modulator is determined. Graphs are plotted, for example, in SigmaPlot V12 (Systat Software) with error bars representing standard error.

REFERENCES

Niimura, Y., & Nei, M. (2007). Extensive Gains and Losses of Olfactory Receptor Genes in Mammalian Evolution. PLoS ONE, 2(8), e708. http://doi.org/10.1371/journal.pone.0000708

Niimura, Y., Matsui, A., & Touhara, K. (2015). Corrigendum: Extreme expansion of the olfactory receptor gene repertoire in African elephants and evolutionary dynamics of orthologous gene groups in 13 placental mammals. Genome Research, 25(6), 926.

Fu L, Niu B, Zhu Z, Wu S, Li W. CD-HIT: accelerated for clustering the next-generation sequencing data. Bioinformatics. 2012 Dec. 1; 28(23):3150-2. doi:10.1093/bioinformatics/bts565. Epub 2012 Oct. 11. PubMed PMID: 23060610; PubMedCentral PMCID: PMC3516142.

Rice P, Longden I, Bleasby A. EMBOSS: the European Molecular Biology Open Software Suite. Trends Genet. 2000 June; 16(6):276-7. PubMed PMID: 10827456.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11237155B2). An electronic copy of the "Sequence Listing" will also be available from the USPTO upon request and payment of the fee set forth in 37 CFR 1.19(b)(3).

We claim:

1. A method for identifying a compound capable of modifying palatability of a pet food product, the method comprising:
   a. measuring a first activity of a feline olfactory receptor,
   b. contacting a test agent with the feline olfactory receptor,
   c. measuring a second activity of the feline olfactory receptor after contacting the test agent, and
   d. determining that the test agent is a compound capable of modifying palatability of a pet food product when the second activity of the feline olfactory receptor is increased or decreased compared to the first activity; wherein the feline olfactory receptor comprises an amino acid sequence selected from the group consisting of SEQ ID Nos: 51-60, wherein the first and second activities are measured by detecting a secondary messenger.

2. A method for identifying a compound capable of modifying palatability of a pet food product, the method comprising
   a. contacting a test agent with a feline olfactory receptor,
   b. detecting binding between the test agent and one or more amino acids of the feline olfactory receptor, and
   c. determining that the test agent is a compound capable of modifying olfactory profile of a pet food product when the test agent binds one or more amino acids of the-feline olfactory receptor wherein the feline olfactory receptor comprises an amino acid sequence selected from the group consisting of SEQ ID Nos: 51-60.

3. The method of claim 2, wherein the method comprises detecting a binding between the test agent and one or more amino acids in a 7 transmembrane domain (7TM) domain of the olfactory receptor.

4. The method of claim 2, further comprising measuring a first activity of the feline olfactory receptor before contacting the test agent, and measuring a second activity of the feline olfactory receptor after contacting the test agent, wherein the first and second activities are measured by detecting a secondary messenger.

5. The method of claim 2, further comprising contacting an olfactory receptor ligand to the feline olfactory receptor.

6. The method of claim 2, wherein the feline olfactory receptor is a feline catGr5 olfactory receptor comprising the amino acid sequence described by SEQ ID NO: 55, and wherein the one or more amino acids of the feline olfactory receptor are selected from the group consisting of Tyr277, Lys290, Phe119, Pro177, Leu180, Ile181, Pro199, Cys217, and Phe220.

7. The method of claim 2, wherein the feline olfactory receptor is a feline catGr6 olfactory receptor comprising the amino acid sequence described by SEQ ID NO: 56, and wherein the one or more amino acids of the feline olfactory receptor are selected from the group consisting of His112, Asn209, Tyr265, Phe88, Phe111, Met170, Met206, Cys261, Ile264, Ser279, Ile280, and Thr283.

8. The method of claim 2, wherein the feline olfactory receptor is a feline catG7 olfactory receptor comprising the amino acid sequence described by SEQ ID NO: 57, and wherein the one or more amino acids of the feline olfactory receptor are selected from the group consisting of Met81, Tyr258, Gln100, Thr77, Lys269, Leu104, Thr276, Val277, His73, Val273 and Val78.

9. The method of claim 2, wherein the feline olfactory receptor is a feline catG8 olfactory receptor comprising the amino acid sequence described by SEQ ID NO: 58, and wherein the one or more amino acids of the feline olfactory receptor are selected from the group consisting of Met81, Leu101, Phe104, Leu105, Gly108, Glu180, Val202, Phe206, Tyr259, and Lys272.

10. The method of claim 2, wherein the feline olfactory receptor is a feline catG9 olfactory receptor comprising the amino acid sequence described by SEQ ID NO: 59, and wherein the one or more amino acids of the feline olfactory receptor are selected from the group consisting of Tyr79, Lys278, Phe110, Val111, Gly114, Val208, Ile212, Phe258, Ala261, Leu262, Tyr265, Val282, and Ser285.

11. The method of claim 2, wherein the binding is determined by site directed mutagenesis, x-ray crystallography, x-ray spectroscopy, Nuclear Magnetic Resonance (NMR), cross-linking assessment, mass spectroscopy, electrophoresis, displacement assay, and combinations thereof.

12. The method of claim 1, wherein the test agent has an $EC_{50}$ value of no more than 200 µM.

13. The method of claim 1, wherein the test agent has an Emax value of no less than 2.0.

14. A method for identifying a compound capable of modifying olfactory profile of a pet food product, the method comprising
    a. contacting an olfactory receptor agonist with a feline olfactory receptor,
    b. measure a first activity of the feline olfactory receptor,
    c. contacting a test agent with the feline olfactory receptor,
    d. measure a second activity of the feline olfactory receptor, and
    e. determining that the test agent is a compound capable of modifying palatability of a pet food product when the first activity is lesser than the second activity;
    wherein the feline olfactory receptor comprises an amino acid sequence selected from the group consisting of SEQ ID Nos: 51-60, wherein the first and second activities are measured by detecting a secondary messenger.

15. The method of claim 14, wherein the olfactory receptor agonist is selected from the group consisting of trifernal, isovaleric acid, 3-methyl-2-hexanoic acid, alpha-ionone, hexyl acetate, amyl mercaptan, helional, para-anisaldehyde, 4-ethoxybenzaldehyde, menthol, methyl-eugenol, methyl-salicylate, phenylacetaldehyde, beta-ionone, amyl acetate, nonanethiol, acetophenone, coumarin, lilial, meta-anisaldehyde, 4-methyl-valeric acid, pentanol, allyl-phenylacetate, hexanoic acid, alpha-ionone, citral, isoamylacetate, octanethiol, propiophenone, 7-methoxycoumarin and combinations thereof.

16. A method for selecting a pet food product or component thereof, comprising
    a. measuring a first activity of a feline olfactory receptor,
    b. contacting a test agent with the feline olfactory receptor,
    c. measuring a second activity of the feline olfactory receptor after contacting the test agent, and
    d. selecting the test agent as a pet food product, or component thereof, when the second activity of the feline olfactory receptor is increased or decreased compared to the first activity;
    wherein the feline olfactory receptor comprises an amino acid sequence selected from the group consisting of SEQ ID Nos: 51-60, wherein the first and second activities are measured by detecting a secondary messenger.

* * * * *